US011131671B2

(12) United States Patent
Eden et al.

(10) Patent No.: US 11,131,671 B2
(45) Date of Patent: Sep. 28, 2021

(54) PROTEIN SIGNATURES FOR DISTINGUISHING BETWEEN BACTERIAL AND VIRAL INFECTIONS

(71) Applicant: MeMed Diagnostics Ltd., Tirat HaCarmel (IL)

(72) Inventors: Eran Eden, Haifa (IL); Kfir Oved, Hof HaCarmel (IL); Assaf Cohen-Dotan, Natania (IL); Roy Navon, Tel-Aviv (IL); Olga Boico, Haifa (IL); Gali Kronenfeld, Tirat Carmel (IL); Meital Paz, Haifa (IL); Ellen Bamberger, Haifa (IL)

(73) Assignee: MeMed Diagnostics Ltd., Tirat HaCarmel (IL)

( * ) Notice: Subject to any disclaimer, the term of this patent is extended or adjusted under 35 U.S.C. 154(b) by 0 days.

(21) Appl. No.: 16/238,582

(22) Filed: Jan. 3, 2019

(65) Prior Publication Data

US 2019/0120837 A1 Apr. 25, 2019

Related U.S. Application Data

(63) Continuation of application No. PCT/IL2017/050780, filed on Jul. 10, 2017.

(60) Provisional application No. 62/360,418, filed on Jul. 10, 2016.

(51) Int. Cl.
| | |
|---|---|
| *C07K 14/525* | (2006.01) |
| *C07K 14/555* | (2006.01) |
| *C07K 14/575* | (2006.01) |
| *G01N 33/52* | (2006.01) |
| *G01N 33/53* | (2006.01) |
| *G01N 33/535* | (2006.01) |
| *G01N 33/547* | (2006.01) |
| *G01N 33/68* | (2006.01) |
| *G01N 33/569* | (2006.01) |
| *G01N 33/50* | (2006.01) |
| *C07K 14/54* | (2006.01) |
| *C07K 16/12* | (2006.01) |
| *C07K 16/24* | (2006.01) |
| *C07K 16/26* | (2006.01) |
| *G01N 33/577* | (2006.01) |
| *G16B 20/00* | (2019.01) |
| *G16B 40/00* | (2019.01) |

(52) U.S. Cl.
CPC ...... *G01N 33/56911* (2013.01); *C07K 14/525* (2013.01); *C07K 14/5412* (2013.01); *C07K 14/555* (2013.01); *C07K 14/57527* (2013.01); *C07K 16/12* (2013.01); *C07K 16/248* (2013.01); *C07K 16/249* (2013.01); *C07K 16/26* (2013.01); *G01N 33/5091* (2013.01); *G01N 33/52* (2013.01); *G01N 33/53* (2013.01); *G01N 33/535* (2013.01); *G01N 33/547* (2013.01); *G01N 33/577* (2013.01); *G01N 33/6863* (2013.01); *G01N 33/6869* (2013.01); *G01N 33/6893* (2013.01); *G01N 2333/525* (2013.01); *G01N 2333/5412* (2013.01); *G01N 2333/555* (2013.01); *G01N 2333/5753* (2013.01); *G01N 2333/585* (2013.01); *G01N 2333/70578* (2013.01); *G01N 2333/70596* (2013.01); *G01N 2333/7155* (2013.01); *G01N 2469/00* (2013.01); *G01N 2800/122* (2013.01); *G01N 2800/26* (2013.01); *G16B 20/00* (2019.02); *G16B 40/00* (2019.02)

(58) Field of Classification Search
CPC .............. C07K 14/525; C07K 14/5412; C07K 14/57527; G01N 33/53; G01N 2333/525; G01N 2333/5753; G01N 2333/70578; G01N 2333/5412; G01N 2333/70596; G01N 2333/7155; G01N 33/52; G01N 33/535; G01N 33/68; G01N 22/56911; G01N 33/6863; G01N 33/547; G01N 33/6869; G01N 33/56911; G01N 2333/555; G01N 2333/585
See application file for complete search history.

(56) References Cited

U.S. PATENT DOCUMENTS

| | | |
|---|---|---|
| 5,639,617 A | 6/1997 | Bohuon |
| 5,910,421 A | 6/1999 | Small, Jr. et al. |
| 6,077,665 A | 6/2000 | Welrich et al. |
| 6,136,526 A | 10/2000 | Venge |
| 6,210,661 B1 | 4/2001 | Enssle et al. |
| 6,709,855 B1 | 3/2004 | Stanton et al. |
| 6,756,483 B1 | 6/2004 | Bergmann et al. |
| 7,115,717 B2 | 10/2006 | Mori et al. |
| 7,132,246 B2 | 11/2006 | Bergmann et al. |

(Continued)

FOREIGN PATENT DOCUMENTS

| | | |
|---|---|---|
| CN | 1656378 | 8/2005 |
| CN | 101208602 | 6/2008 |

(Continued)

OTHER PUBLICATIONS

Ali et al. Reliability of serum procalcitonin concentrations for the diagnosis of sepsis in neonates. Egypt J Immunol 15(1): 75-84, 2008;; Abstract Only.*

(Continued)

*Primary Examiner* — Bridget E Bunner

(57) ABSTRACT

Methods of diagnosing infections are disclosed. In one embodiment, the method comprises measuring the amount of each of the polypeptides TRAIL, CRP, IP10 and at least one additional polypeptide selected from the group consisting of IL-6 and PCT.

3 Claims, 30 Drawing Sheets

Specification includes a Sequence Listing.

(56) References Cited

U.S. PATENT DOCUMENTS

| | | | |
|---|---|---|---|
| 7,153,662 | B2 | 12/2006 | Bergmann et al. |
| 7,157,081 | B2 | 1/2007 | Bergmann et al. |
| 7,598,031 | B2 | 10/2009 | Lew |
| 7,629,116 | B2 | 12/2009 | Ott |
| 7,892,539 | B2 | 2/2011 | Winoto et al. |
| 8,021,836 | B2 | 9/2011 | Kolopp-Sarda et al. |
| 8,465,951 | B2 | 6/2013 | Rao et al. |
| 8,507,210 | B2 | 8/2013 | Bergmann et al. |
| 8,563,476 | B2 | 10/2013 | Lillard, Jr. |
| 8,697,370 | B2 | 4/2014 | Kas et al. |
| 8,821,876 | B2 | 9/2014 | Ginsburg et al. |
| 9,034,328 | B2 | 5/2015 | Takahashi |
| 9,709,565 | B2 | 7/2017 | Eden et al. |
| 9,726,668 | B2 | 8/2017 | Oved et al. |
| 9,850,539 | B2 | 12/2017 | Tsalik et al. |
| 10,209,260 | B2 | 2/2019 | Oved et al. |
| 10,303,846 | B2 | 5/2019 | Eden et al. |
| 10,502,739 | B2* | 12/2019 | Oved ............... G01N 33/56911 |
| 10,859,574 | B2 | 12/2020 | Oved et al. |
| 2004/0038201 | A1 | 2/2004 | Nau et al. |
| 2004/0043379 | A1 | 3/2004 | Hashimoto et al. |
| 2004/0171013 | A1 | 9/2004 | Lilius et al. |
| 2005/0227223 | A1 | 10/2005 | Miyawaki |
| 2005/0233395 | A1 | 10/2005 | Weiser et al. |
| 2006/0052278 | A1 | 3/2006 | Powell |
| 2006/0099628 | A1 | 5/2006 | Ching et al. |
| 2006/0246495 | A1 | 11/2006 | Garrett et al. |
| 2007/0015172 | A1 | 1/2007 | Zhang et al. |
| 2007/0184460 | A1 | 8/2007 | Ching et al. |
| 2007/0231816 | A1 | 10/2007 | Chaussabel et al. |
| 2007/0281319 | A1 | 12/2007 | Kolopp-Sarda et al. |
| 2008/0020379 | A1 | 1/2008 | Agan et al. |
| 2008/0064113 | A1 | 3/2008 | Goix et al. |
| 2008/0171323 | A1 | 7/2008 | Banchereau et al. |
| 2009/0155180 | A1 | 6/2009 | Jump et al. |
| 2009/0203534 | A1 | 8/2009 | Hossain et al. |
| 2010/0028874 | A1 | 2/2010 | Ramachandran et al. |
| 2010/0068147 | A1 | 3/2010 | Hibberd et al. |
| 2010/0143372 | A1 | 6/2010 | Yao et al. |
| 2010/0297611 | A1 | 11/2010 | Sambursky et al. |
| 2011/0059858 | A1 | 3/2011 | Kas et al. |
| 2011/0117563 | A1 | 5/2011 | Filipowicz et al. |
| 2011/0183856 | A1 | 7/2011 | Agan et al. |
| 2011/0275542 | A1 | 11/2011 | Eden et al. |
| 2011/0312534 | A1 | 12/2011 | Kayser et al. |
| 2013/0309168 | A1 | 11/2013 | Ho |
| 2014/0127827 | A1 | 5/2014 | Kim et al. |
| 2014/0206016 | A1 | 7/2014 | Lozano Sanchez et al. |
| 2014/0227324 | A1 | 8/2014 | Robinson et al. |
| 2015/0017630 | A1 | 1/2015 | Oved et al. |
| 2016/0153993 | A1 | 6/2016 | Eden et al. |
| 2017/0030909 | A1 | 2/2017 | Oved et al. |
| 2017/0234873 | A1 | 8/2017 | Oved et al. |
| 2017/0235871 | A1 | 8/2017 | Eden et al. |
| 2017/0269081 | A1 | 9/2017 | Oved et al. |
| 2018/0074057 | A1 | 3/2018 | Eden et al. |
| 2019/0011456 | A1 | 1/2019 | Oved et al. |
| 2019/0041388 | A1 | 2/2019 | Oved et al. |
| 2019/0085378 | A1 | 3/2019 | Eden et al. |
| 2019/0161813 | A1 | 5/2019 | Oved et al. |
| 2019/0237156 | A1 | 8/2019 | Eden et al. |
| 2019/0242894 | A1 | 8/2019 | Oved et al. |
| 2019/0242895 | A1 | 8/2019 | Eden et al. |
| 2019/0271709 | A1 | 9/2019 | Eden et al. |
| 2019/0339189 | A1 | 11/2019 | Takeda et al. |
| 2020/0088728 | A1 | 3/2020 | Oved et al. |
| 2020/0124593 | A1 | 4/2020 | Oved et al. |
| 2020/0388347 | A1 | 12/2020 | Eden et al. |
| 2020/0393463 | A1 | 12/2020 | Oved et al. |
| 2020/0400668 | A1 | 12/2020 | Eden et al. |

FOREIGN PATENT DOCUMENTS

| | | |
|---|---|---|
| CN | 101479389 | 7/2009 |
| CN | 101541976 | 9/2009 |
| CN | 101611314 | 12/2009 |
| CN | 101617056 | 12/2009 |
| CN | 101617230 | 12/2009 |
| CN | 101622364 | 1/2010 |
| CN | 101790687 | 7/2010 |
| CN | 102301002 | 12/2011 |
| CN | 103119444 | 5/2013 |
| CN | 104204803 | 12/2014 |
| EP | 1489416 | 12/2004 |
| JP | 2005-106694 | 4/2005 |
| JP | 2008-502908 | 1/2008 |
| JP | 2011-069696 | 4/2011 |
| KR | 10-2016-0072626 | 6/2016 |
| WO | WO 95/29404 | 11/1995 |
| WO | WO 2004/108899 | 12/2004 |
| WO | WO 2006/009702 | 1/2006 |
| WO | WO 2007/011412 | 1/2007 |
| WO | WO 2007/088355 | 8/2007 |
| WO | WO 2007/127801 | 11/2007 |
| WO | WO 2008/024642 | 2/2008 |
| WO | WO 2009/015821 | 2/2009 |
| WO | WO 2009/021521 | 2/2009 |
| WO | WO 2009/025743 | 2/2009 |
| WO | WO 2009/077864 | 6/2009 |
| WO | WO 2009/130176 | 10/2009 |
| WO | WO 2009/158521 | 12/2009 |
| WO | WO 2010/056637 | 5/2010 |
| WO | WO 2011/008349 | 1/2011 |
| WO | WO 2011/017682 | 2/2011 |
| WO | WO 2011/132086 | 10/2011 |
| WO | WO 2013/117746 | 8/2013 |
| WO | WO 2014/006408 | 1/2014 |
| WO | WO 2014049255 | 4/2014 |
| WO | WO 2014/117873 | 8/2014 |
| WO | WO 2015/048098 | 4/2015 |
| WO | WO 2016/024278 | 2/2016 |
| WO | WO 2016/059636 | 4/2016 |
| WO | WO 2016/079219 | 5/2016 |
| WO | WO 2016/092554 | 6/2016 |
| WO | WO 2017/149547 | 9/2017 |
| WO | WO 2017/149548 | 9/2017 |
| WO | WO 2017/221255 | 12/2017 |
| WO | WO 2018/011795 | 1/2018 |
| WO | WO 2018/011796 | 1/2018 |
| WO | WO 2018/060998 | 4/2018 |
| WO | WO 2018/060999 | 4/2018 |

OTHER PUBLICATIONS

Becker et al. Procalcitonin in sepsis and systemic inflammation: a harmful biomarker and a therapeutic target. Brit J Pharmacol 159: 253-264, 2010.*
Herzig et al. The role of CXCL10 in the pathogenesis of experimental septic shock. Critical Care 18: R113, 2014; 18 total page.*
Ng et al. IP-10 is an early diagonistic marker for identification of late-onset bacterial infection in preterm infants. Pediatric Res 61(1): 93-98, 2007.*
Povoa et al. C-reactive protein, an early marker of community-acquired sepsis resolution: a multi-center prospective observational study. Critical Care 15: R169, 2011; 10 total page.*
Tian et al. Soluble tumor necerosis factor related apoptosis inducing ligand level as a predictor of severity of sepsis and the risk of mortality in septic patients. PLoS One 8(12): e82204, 2013; 5 total page.*
Bloos et al. Rapid diagnosis of sepsis. Virulence 5(1): 154-160, 2014.*
Henriquez-Camacho et al. Biomarkers for sepsis. Biomed Res Int 2014: 547818, 2014 (6 pages).*
Official Action dated Apr. 23, 2019 From the US Patent and Trademark Office Re. U.S. Appl. No. 16/157,193. (47 pages).
Dirke et al. "TRAIL and DeR1 Expressions Are Differentially Regulated in the Pancreatic Islets of STZ- Versus CY-AppHed NOD Mice", Experimental Diabetes Research, Article ID 625813, pp. 1-11, 2011.
Kichev et al. "Tumor Necrosis Factor-Related Apoptosis-Inducing Ligand (TRAiL) Signaling and Cell Death in the Immature Central

(56) References Cited

OTHER PUBLICATIONS

Nervous System after Hypoxia-Ischemia and Inflammation", Journal of Biological Chemistry 289(13): 9430-9439, 2014.
Notification of Office Action and Search Report dated Jan. 11, 2019 From the State intellectual Property Office of the People's Republic of China Re. Application No. 201580055946.0. (5 Pages).
Applicant-Initiated Interview Summary dated Feb. 10, 2020 From the US Patent and Trademark Office Re. U.S. Appl. No. 16/157,193. (3 pages).
Supplementary European Search Report and the European Search Opinion dated Feb. 18, 2020 From the European Patent Office Re. Application No. 17827121.9. (5 Pages).
Hearing Notice Dated Jul. 16, 2019 From the Government of India, Patent Office, Intellectual Property Building Re. Application No. 1780/MUMNP/2014. (3 Pages).
Notice of Allowance dated Jul. 29, 2019 From the US Patent and Trademark Office Re. U.S. Appl. No. 15/237,728. (21 pages).
Advisory Action Before the Filing of an Appeal Brief dated Dec. 23, 2019 From the US Patent and Trademark Office Re. U.S. Appl. No. 16/157,193. (3 pages).
Restriction Official Action dated Dec. 5, 2019 From the US Patent and Trademark Office Re. U.S. Appl. No. 16/081,906. (9 pages).
Official Action dated Oct. 15, 2019 From the US Patent and Trademark Office Re. Application No. 151713,722. (57 Pages).
Official Action dated Sep. 16, 2019 From the US Patent and Trademark Office Re. U.S. Appl. No. 16/355,984. (44 pages).
Official Action dated Sep. 18, 2019 From the US Patent and Trademark Office Re. U.S. Appl. No. 16/157,193. (30 pages).
Official Action dated Oct. 24, 2019 From the US Patent and Trademark Office Re. U.S. Appl. No. 15/531,747. (37 Pages).
Requisition by the Examiner dated Oct. 4, 2019 From the Innovation, Science and Economic Development Canada, Canadian Intellectual Property Office Re. Application No. 2,863,819. (3 pages).
Supplementary European Search Report and the European Search Opinion dated Sep. 30, 2019 From the European Patent Office Re. Application No. 17759388.6. (11 Pages).
Supplementary Partial European Search Report and the European Provisional Opinion dated Oct. 24, 2019 From the European Patent Office Re. Application No. 17759389.4. (15 pages).
Translation dated Sep. 22, 2019 of Search Report and Opinion dated Aug. 20, 2019 From the Servico Publico Federal, Ministerio da Economia, Instituto Nacional da Propriedade Industrial do Brasil Re. Application No. BR112014 019733-4 and Its Summary in English. (4 Pages).
Barnhart et al. "Changes in Cellular mRNA Stability, Splicing, and Polyadenylation Through HuR Protein Sequestration by a Cytoplasmic RNA Virus", Cell Reports, XP055621573, 5(4): 909-917, Nov. 27, 2013.
Consiglio et al. "BEAT: Bioinformatics Exon Array Tool to Store, Analyze and Visualize Affymetrix GeneChip Human Exon Array Data From Disease Experiments", BMC Bioinformatics, XP021117755, 13(Suppl.4): S21-1-S21-14, Mar. 28, 2012.
UCSC "UCSC Browser on Human Feb. 2009 (GRCh37/hg19) Assembly: Showing Location of Probes on the Affymetrix ExonChip Binding to Exons of ANKRD22", UCSC Browser, XP055621243, Retrieved From the Internet, 7 P., Jan. 2009.
UCSC "UCSC Genome Browser on Human Feb. 2009 (GRCh37/hg19) Assembly: Showing Location of Probes on the Affymetrix ExonChip Binding to Exons of AIM2", UCSC Browser, XP055621240, Retrieved From the Internet, 8 P., Jan. 2009.
Zaas et al. "The Current Epidemiology and Clinical Decisions Surrounding Acute Respiratory Infections", Trends in Molecular Medicine, XP055522333, 20(10): 579-588, Published Online Sep. 5, 2014.
Notification of Office Action and Search Report dated Feb. 19, 2019 From the State Intellectual Property of the People's Republic of China Re. Application No. 201580075265.0 and A Summary of the Notification of Office Action Into English. (7 Pages).
Search Report and Opinion dated Aug. 20, 2019 From the Servico Publico Federal, Ministerio da Economia, institute Nacional da Propriedade industrial do Brasil Re. Application No. BR112014 019733-4 and Its Summary in English. (4 Pages).
Translation dated Sep. 11, 2019 of Notification of Office Action dated Aug. 22, 2019 From the State Intellectual Property Office of the People's Republic of China Re. Application No. 201580055946.0. (1 Page).
Communication Pursuant to Article 94(3) EPC dated May 7, 2019 From the European Patent Office Re. Application No. 15831781.8. (3 Pages).
Examination Report dated May 29, 2019 From the Australian Government, IP Australia Re. Application No. 2018202302. (5 Pages).
Notification of Office Action dated Jun. 3, 2019 From the China National Intellectual Property Administration Re. Application No. 201610817276.8 and Its Translation Into English. (10 Pages).
Examination Report Under Sections 12 & 13 of the Patents Act, 1970 and the Patents Rules, 2003 dated Oct. 21, 2019 From the Government of India, Intellectual Property India, Patents, Designs, Trade Marks, Geographical Indications Re. Application No. 9122/DELNP/2012 (5 Pages).
Notice of Reason for Rejection dated Nov. 12, 2019 From the Japan Patent Office Re. Application No. 2017-126712 and an English Summary. (3 Pages).
Supplementary European Search Report and the European Search Opinion dated Jan. 28, 2020 From the European Patent Office Re. Application No. 17759389.4. (11 Pages).
Official Action dated Feb. 3, 2020 From the US Patent and Trademark Office Re. U.S. Appl. No. 16/355,984. (24 pages).
Search Report and Opinion dated Dec. 10, 2019 From the Servico Publico Federal, Ministerio da Economia, Instituto Nacional da Propriedade Industrial do Brasil Re. Application No. BR112017002884-0 and Its Translation Into English. (7 Pages).
Supplementary European Search Report and the European Search Opinion dated Jan. 21, 2020 From the European Patent Office Re. Application No. 17827122.7.
Notification of Office Action dated Jul. 2, 2019 From the State Intellectual Property Office of the People's Republic of China Re. Application No. 201580075265.0. (3 Pages).
Request for Examination dated Jun. 18, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (11 Pages).
Translation dated Jul. 10, 2019 of Notification of Office Action dated Jul. 2, 2019 From the State Intellectual Property Office of the People's Republic of China Re. Application No. 201580075265.0. (1 Page).
Office Action dated Nov. 28, 2019 From the Israel Patent Office Re. Application No. 254095 and Its Translation Into English. (7 Pages).
Translation of Reason for Rejection dated Nov. 21, 2019 of OA of Nov. 12, 2019 From the Japanese Patent Office Re. Application No. 2017126712. (2 Pages).
Notification of Office Action dated Aug. 22, 2019 From the State Intellectual Property Office of the People's Republic of China Re. Application No. 201580055946.0. (3 Pages).
Applicant-Initiated Interview Summary dated Jul. 6, 2016 From the US Patent and Trademark Office Re. U.S. Appl. No. 14/377,887.
Applicant-Initiated Interview Summary dated Jul. 17, 2015 From the US Patent and Trademark Office Re. U.S. Appl. No. 13/090,893.
Applicant-Initiated Interview Summary dated Feb. 22, 2017 From the US Patent and Trademark Office Re. U.S. Appl. No. 14/377,887. (3 Pages).
Applicant-Initiated Interview Summary dated Oct. 26, 2017 From the US Patent and Trademark Office Re. U.S. Appl. No. 15/237,728. (3 pages).
Applicant-Initiated Interview Summary dated Jul. 30, 2018 From the US Patent and Trademark Office Re. U.S. Appl. No. 15/641,400. (3 pages).
Communication Pursuant to Article 94(3) EPC dated Dec. 9, 2016 From the European Patent Office Re. Application No. 13703112.6. (4 Pages).

(56) References Cited

OTHER PUBLICATIONS

Communication Pursuant to Article 94(3) EPC dated Oct. 9, 2018 From the European Patent Office Re. Application No. 11748712.4. (8 Pages).
Communication Pursuant to Article 94(3) EPC dated Jun. 17, 2016 From the European Patent Office Re. Application No. 11748712.4.
European Search Report and the European Search Opinion dated May 16, 2018 From the European Patent Office Re. Application No. 18162713.4. (7 Pages).
Examination Report dated Oct. 6, 2017 From the Australian Government, IP Australia Re. Application No. 2013217935. (2 Pages).
Examination Report Under Sections 12 & 13 of the Patents Act, 1970 and the Patents Rules, 2003 dated Mar. 26, 2018 From the Government of India, Intellectual Property India, Patents, Designs, Trade Marks, Geographical Indications Re. Application No. 9122/DELNP/2012. (7 Pages).
Examination Report Under Sections 12 & 13 of the Patents Act, 1970 and the Patents Rules, 2003 Dated 30 Nov. 2018 From the Government of India, Intellectual Property India, Patents, Designs, Trade Marks, Geographical Indications Re. Application No. 1780/MUMNP/2014. (7 Pages).
Examiner-Initiated Interview Summary dated Nov. 27, 2017 From the US Patenet and Trademark Office Re. U.S. Appl. No. 15/518,491. (2 pages).
International Preliminary Report on Patentability dated Sep. 13, 2018 From the International Bureau of WIPO Re. Application No. PCT/IL2017/050270. (7 Pages).
International Preliminary Report on Patentability dated Sep. 13, 2018 From the International Bureau of WIPO Re. Application No. PCT/IL2017/050271. (9 Pages).
International Preliminary Report on Patentability dated Jun. 22, 2017 From the International Bureau of WIPO Re. Application No. PCT/IL2015/051201. (7 Pages).
International Preliminary Report on Patentability dated Feb. 23, 2017 From the International Bureau of WIPO Re. Application No. PCT/IL2015/050823. (7 Pages).
International Preliminary Report on Patentability dated Apr. 27, 2017 From the International Bureau of WIPO Re. Application No. PCT/IL2015/051024. (7 Pages).
International Search Report and the Written Opinion dated Mar. 12, 2012 From the International Searching Authority Re. Application No. PCT/IB2011/001299.
International Search Report and the Written Opinion dated Sep. 14, 2017 From the International Searching Authority Re. Application No. PCT/IL2017/050781. (12 Pages).
International Search Report and the Written Opinion dated Jun. 15, 2017 From the International Searching Authority Re. Application No. PCT/IL2017/050270. (13 Pages).
International Search Report and the Written Opinion dated Jun. 15, 2017 From the International Searching Authority Re. Application No. PCT/IL2017/050271. (16 Pages).
International Search Report and the Written Opinion dated Sep. 18, 2017 From the International Searching Authority Re. Application No. PCT/IL2017/050780. (15 Pages).
International Search Report and the Written Opinion dated Jan. 20, 2016 From the International Searching Authority Re. Application No. PCT/IL2015/051024.
International Search Report and the Written Opinion dated Feb. 22, 2016 From the International Searching Authority Re. Application No. PCT/IL2015/051201.
International Search Report and the Written Opinion dated Dec. 25, 2017 From the International Searching Authority Re. Application No. PCT/IL2017/051088. (9 Pages).
International Search Report and the Written Opinion dated Dec. 28, 2017 From the International Searching Authority Re. Application No. PCT/IL2017/051089. (10 Pages).
International Search Report and the Written Opinion dated Nov. 29, 2015 From the International Searching Authority Re. Application No. PCT/IL2015/050823.

International Search Report dated Apr. 5, 2013 From the International Searching Authority Re. Application No. PCT/EP2013/052619.
Notice of Allowance dated Apr. 10, 2017 From the US Patent and Trademark Office Re. U.S. Appl. No. 14/377,887. (14 pages).
Notice of Non-Compliant Amendment dated Aug. 4, 2015 From the US Patent and Trademark Office Re. U.S. Appl. No. 13/090,893.
Notice of Reasons for Rejection dated Nov. 1, 2016 From the Japan Patent Office Re. Application No. 2014-556086 and Its Translation Into English. (12 Pages).
Notice of Reasons for Rejection dated Jun. 19, 2018 From the Japan Patent Office Re. Application No. 2017-126712 and Its Translation Into English. (9 Pages).
Notice on Office Action and the Search Report dated Feb. 25, 2015 From the State Intellectual Property Office of the People's Republic of China Re. Application No. 201180030792.1 and Its Translation Into English.
Notification of Office Action and Search Report dated Mar. 4, 2016 From the State Intellectual Property Office of the People's Republic of China Re. Application No. 201380019055.0.
Notification of Office Action and Search Report dated Feb. 13, 2017 From the State Intellectual Property Office of the People's Republic of China Re. Application No. 201380019055.0 and Its Translation of Office Action Into English. (10 Pages).
Notification of Office Action and Search Report dated Jun. 19, 2018 From the State Intellectual Property Office of the People's Republic of China Re. Application No. 201580075265.0 and its English Summary (14 Pages).
Notification of Office Action and Search Report dated Oct. 30, 2017 From the State Intellectual Property Office of the People's Republic of China Re. Application No. 201610817276.8. (10 Pages).
Notification of Office Action dated Jul. 3, 2015 From the State Intellectual Property Office of the People's Republic of China Re. Application No. 201380019055.0.
Notification of Office Action dated Aug. 4, 2016 From the State Intellectual Property Office of the People's Republic of China Re. Application No. 201380019055.0 and Its Translation Into English.
Notification of Office Action dated May 6, 2014 From the State Intellectual Property Office of the People's Republic of China Re. Application No. 201180030792.1 and Its Translation Into English.
Notification of Office Action dated Jan. 21, 2016 From the State Intellectual Property Office of the People's Republic of China Re. Application No. 201180030792.1 and Its Translation Into English.
Notification of Office Action dated Aug. 25, 2017 From the State Intellectual Property Office of the People's Republic of China Re. Application No. 201380019055.0. (6 Pages).
Notification of Office Action dated Aug. 28, 2015 From the State Intellectual Property Office of the People's Republic of China Re. Application No. 201180030792.1 and its Translation into English.
Notification of Office Action dated Aug. 30, 2018 From the State Intellectual Property Office of the People's Republic of China Re. Application No. 201610817276.8 and Its Translation Into English. (22 Pages).
Notification of Reexamination dated Jan. 12, 2018 From the State Intellectual Property Office of the People's Republic of China Re. Application No. 2013800190and Its MachineTranslation into English.
Office Action dated Jun. 20, 2018 From the State Intellectual Property Office of the People's Republic of China Re. Application No. 201580055946.0 and Its Summary of the Notification of Office Action Into English.).(5 Pages).
Office Action dated Feb. 29, 2016 From the Israel Patent Office Re. Application No. 233998 and Its Translation Into English.
Official Action dated Sep. 1, 2015 From the US Patent and Trademark Office Re. U.S. Appl. No. 13/090,893.
Official Action dated Apr. 4, 2016 From the US Patent and Trademark Office Re. U.S. Appl. No. 13/090,893.
Official Action dated Jan. 4, 2019 From the US Patent and Trademark Office Re. U.S. Appl. No. 15/713,722. (72 pages).
Official Action dated Feb. 6, 2018 From the US Patent and Trademark Office Re. U.S. Appl. No. 15/503,439. (63 pages).
Official Action dated Nov. 7, 2016 From the US Patent and Trademark Office Re. U.S. Appl. No. 13/090,893. (26 pages).

(56) References Cited

OTHER PUBLICATIONS

Official Action dated Jun. 10, 2013 From the US Patent and Trademark Office Re. U.S. Appl. No. 13/090,893.
Official Action dated Apr. 12, 2018 From the US Patent and Trademark Office Re. U.S. Appl. No. 15/518,491. (59 pages).
Official Action dated Aug. 12, 2015 From the US Patent and Trademark Office Re. U.S. Appl. No. 14/377,887.
Official Action dated May 12, 2017 From the US Patent and Trademark Office Re. U.S. Appl. No. 15/237,728. (27 pages).
Official Action dated Apr. 13, 2016 From the US Patent and Trademark Office Re. U.S. Appl. No. 14/377,887.
Official Action dated Mar. 13, 2014 From the US Patent and Trademark Office Re. U.S. Appl. No. 13/090,893.
Official Action dated Dec. 15, 2016 From the US Patent and Trademark Office Re. U.S. Appl. No. 14/377,887. (22 pages).
Official Action dated May 15, 2018 From the US Patent and Trademark Office Re. U.S. Appl. No. 15/237,728. (55 pages).
Official Action dated Nov. 16, 2018 From the US Patent and Trademark Office Re. U.S. Appl. No. 15/503,439. (41 pages).
Official Action dated Dec. 17, 2018 From the US Patent and Trademark Office Re. U.S. Appl. No. 15/237,728. (39 pages).
Official Action dated Nov. 18, 2016 From the US Patent and Trademark Office Re. U.S. Appl. No. 15/237,728. (33 pages).
Official Action dated Jan. 26, 2017 From the US Patent and Trademark Office Re. U.S. Appl. No. 15/015,309. (45 pages).
Official Action dated Mar. 26, 2015 From the US Patent and Trademark Office Re. U.S. Appl. No. 13/090,893.
Official Action dated Apr. 30, 2018 From the US Patent and Trademark Office Re. U.S. Appl. No. 15/641,400. (62 pages).
Official Action dated Mar. 30, 2018 From the US Patent and Trademark Office Re. U.S. Appl. No. 15/531,747. (67 pages).
Requisition by the Examiner dated Nov. 9, 2018 From the Innovation, Science and Economic Development Canada, Canadian Intellectual Property Office Re. Application No. 2,796,666. (3 pages).
Requisition by the Examiner dated Jan. 18, 2018 From the Innovation, Science and Economic Development Canada, Canadian Intellectual Property Office Re. Application No. 2,796,666. (5 Pages).
Restriction Official Action dated Nov. 2, 2017 From the US Patent and Trademark Office Re. U.S. Appl. No. 15/531,747. (9 pages).
Restriction Official Action dated Nov. 8, 2018 From the US Patent and Trademark Office Re. U.S. Appl. No. 16/157,193. (5 pages).
Restriction Official Action dated May 10, 2018 From the US Patent and Trademark Office Re. U.S. Appl. No. 15/713,722. (6 Pages).
Restriction Official Action dated Feb. 13, 2013 From the US Patent and Trademark Office Re. U.S. Appl. No. 13/090,893.
Restriction Official Action dated May 15, 2015 From the US Patent and Trademark Office Re. U.S. Appl. No. 14/377,887.
Restriction Official Action dated Aug. 31, 2017 From the US Patent and Trademark Office Re. U.S. Appl. No. 15/518,491. (6 pages).
Search Report dated May 6, 2014 From the State Intellectual Property Office of the People's Republic of China Re. Application No. 201180030792.1 and Its Translation Into English.
Second Notice of Allowance dated Dec. 12, 2018 From the US Patent and Trademark Office Re. U.S. Appl. No. 15/641,400. (7 pages).
Supplementary European Search Report and the European Search Opinion dated Mar. 15, 2018 From the European Patent Office Re. Application No. 15831781.8. (11 pages).
Supplementary European Search Report and the European Search Opinion dated Sep. 17, 2018 From the European Patent Office Re. Application No. 15868614.7. (18 Pages).
Supplementary Partial European Search Report and the European Provisional Opinion dated Jun. 1, 2018 From the European Patent Office Re. Application No. 15868614.7. (23 Pages).
Translation dated Sep. 4, 2017 of Notification of Office Action dated Aug. 25, 2017 From the State Intellectual Property Office of the People's Republic of China Re. Application No. 201380019055.0.
Translation dated Apr. 5, 2016 of Notification of Office Action dated Mar. 4, 2016 From the State Intellectual Property Office of the People's Republic of China Re. Application No. 201380019055.0.
Translation dated Sep. 21, 2015 of Office Action dated Jul. 3, 2015 From the State Intellectual Property Office of the People's Republic of China Re. Application No. 201380019055.0.
Translation of Notification of Office Action and Search Report dated Oct. 30, 2017 From the State Intellectual Property Office of the People's Republic of China Re. Application No. 201610817276.8. (16 Pages).
Alexander et al. "*Staphylococcus aureus* and *Salmonella enterica* Serovar Dublin Induce Tumor Necrosis Factor-Related Apoptosis-Inducing Ligand Expression by Normal 1\1ouse and Human Osteoblasts", Infection and Immunity, 69(3): 1581-1586, Mar. 2001.
Biezeveld et al. "Sustained Activation of Neutrophils in the Course of Kawasaki Disease: An Association with Matrix Metalloproteinases", Clinical & Experimental Immunology 141(1): 183-188, Jul. 2005.
Boldrick et al. "Stereotyped and Specific Gene Expression Programs in Human Innate immune Responses to Bacteria", Proc. Natl. Acad. Sci. USA, PNAS, 99(2): 972-977, Jan. 22, 2002.
Borjesson et al. "Insights Into Pathogen Immune Evasion Mechanisms: Anaplasma Phagocytophilum Fails to Induce an Apoptosis Differentiation Program in Human Neutrophils", The Jurnal of Immunology, 174: 6364-6372, 2005.
Boser et al. "A Training Algorithm for Optimal Margin Classifiers", Proceedings of the 5th Annual ACM Workshop on Computational Learning Theory, COLT'92, Pittsburgh, PA, USA, Jul. 27-29, 1992, p. 144-152, Jul. 27, 1992.
Calvano et al. "A Network-Based Analysis of Systemic Inflammation in Humans", Nature, 437: 1032-1037, Oct. 13, 2005.
Carrot et al. "The Diagnostic and Prognostic Accuracy of Five Markers of Serious Bacterial Infection in Malawian Children With Sign of Severe Infection", PLoS ONE, 4(8): e6621-1-e6621-8, Aug. 2009.
Chagan-Yasutan et al. "Persistent Elevation of Plasma Osteopontin Levels in HIV Patients Despite Highly Active Antiretroviral Therapy", The Tohoku Journal of Experimental Medicine, 218(4): 285-292, Aug. 2009.
Chaussabel et al. "Analysis of Significance Patterns Identifies Ubiquitous and Disease-Specific Gene-Expression Signatures in Patient Peripheral Blood Leukocytes", Annals of the New York Academy of Sciences, 1062: 146-154, 2005.
Chen et al. "Discordant Protein and mRNA Expression in Lung Adenocarcinomas", Molecular & Cellular Proteomics: MCP, 1(4): 304-313, Apr. 2002.
Chieux et al. "MxA Protein in Capillary Blood of Children With Viral Infections", Journal of Medical Virology, 59: 547-551, 1999.
Chieux et al. "The MxA Protein Levels in Whole Blood Lysates of Patients With Various Viral Infections", Journal of Virological Methods, 70: 183-191, 1998.
Corada et al. "Monoclonal Antibodies Directed to Different Regions of Vascular Endothelial Cadherin Extracellular Dornain Affect Adhesion and Clustering of the Protein and Modulate Endothelial Permeability", Blood, 97(6): 1679-1684, Mar. 15, 2001.
Cowland et al. "Molerular Charaderization and Pattern of Tissue Expression of the Gene for Neutrophil Gelatinase-Associated Upocalin from Humans", Genomics, 45:17-23,1997.
Cristianini et al. "An Introduction to Support Vector Machines and Other Kernel-Based Learning Methods: Contents", Cambridge University Press, 4 P., 2000.
Crowe et al. "Quantitative lmmunocytofluorographic Analysis of CD4 Surface Antigen Expression and HIV Infection of Human Peripheral Blood Monocyte/Macrophages", Aids Research and Human Retroviruses, 3(2): 135-145, 1987.
Cummins et al. "The TRAIL to Viral Pathogenesis: The Good, the Bad and the Ugly". Current Molecular Medicine, XP055056835, 9(4): 495-505, May 1, 2009.
Duda et al. "Contents", Pattern Classification, 2nd Ed., 11 P., 2001.
Eberl et al. "A Rapid Crosstalk of Human ?? T Cells and Monocytes Drives the Acute Inflammation in Bacterial Infections", PLOS Pathogens 5(2): 1-16, 2009.

(56) References Cited

OTHER PUBLICATIONS

Falschlehner et al. "Following TRAIL's Path in the Immune System", Immunology, XP055056763, 127(2): 145-154, Jun. 1, 2009. Chapter 'Trail in Viral and Bacterial Infections'.
Feezor et al. "Molecular Characterization of the Acute Inflammatory Response to Infections With Gram-Negaitve Versus Gram-Positive Bacteria", Infection and Immunity, 71(10): 5803-5813, Oct. 2003.
Furey et al. "Support Vector Machine Classification and Validation of Cancer Tissue Samples Using Microarray Expression Data", Bioinformatics, 16(10): 906-914, Oct. 2000.
Halminen et al. "Expression of MxA Protein in Blood Lymphocytes Discriminates Between Viral and Bacterial Infections in Febrile Children", Pediatric Research, 41(5): 647-650, May 1997.
Hanley et al. "A Method of Comparing the Areas Under Receiver Operating Characteristics Curves Derived From the Same Cases", Radiology, 148(3): 839-843, Sep. 1983.
Hastie et al. "The Elements of Statistical Learning: Data Mining, Inference, and Prediction", Springer Series in Statistics, 2nd Ed., p. 1-745, 2001.
Hinson et al. "Viperin Is Highly Induced in Neutrophils and Macrophages during Acute and Chronic Lymphocytic Choriomeningitis Virus Infection", The Journal of Immunology, 184:5723-5731, 2010.
Hoffmann et al. "TRAIL Limits Excessive Host Immune Responses in Bacterial Meningitis", JCI The Journal of Clinical Investigation, 11(7): 2004-2013, Jul. 2, 2007.
Holland et al. "STAT3 Mutations in the Hyper-IgE Syndrome", The New England Journal of Medicine, 357(16): 1608-1619, Oct. 18, 2007.
Janols et al. "Lymphocyte and Monocyte Flow Cytometry Immunophenotyping as a Diagnostic Tool in Uncharacteristic Inflammatory Disorders", BMC Infectious Diseases, XP002663504, 10(205): 1-9, 2010. Abstract.
Jenner et al. "Insights Into Host Responses Against Pathogens From Transcriptional Profiling", Nature Review Microbiology, 3: 281-294, Apr. 2005.
Kaizer et al. "Gene Expression in Peripheral Blood Mononuclear Cells From Children With Diabetes", The Journal of Clinical Endocrinology & Metabolism, 92(9): 3705-3711, 2007.
Kawada et al. "Analysis of Gene-Expression Profiles by Oligonucleotide Microarray in Children With Influenza", Journal of General Virology, 87: 1677-1683, 2006.
Kohavi et al. "Wrappers for Feature Subset Selection", Artifical Intelligence, 97: 273-324, 1997.
Kotelkin et al. "Respiratory Syncytial Virus Infections Sensitizes Cells to Apoptosis Mediated by Tumor Necrosis Factor-Related Apoptosis-Inducing Ligand", Journal of Virology, XP055056816, 77(17): 9156-9172, Aug. 12, 2003. Fig.5B.
Lampe et al. "Expression of the Interferon-Induced MxA Protein in Viral Encephalitis", Neuropathology and Applied Neurobiology, 29(3): 273-279, May 27, 2003.
Le Roux "Les Examens a Visee Etiologique Dans les Pneumopathies Communautaires de l'Enfant (Hors Imagerie) [Laboratory Investigations in Acute Lower Respiratory Tract Infections in Children]", Archives de Pediatrie, XP002663501, 5(Suppl.1): 28S-32S, 1998. Abstract.
Leibovici et al. "The Benefit of Appropriate Empirical Antibiotic Treatment in Patients with Bloodstream Infection", Journal of Internal Medicine, 244(5): 379-386, Nov. 1, 1998.
Liabeuf et al. "The Circulating Soluble TRAIL Is a Negative Marker for Inflammation Inversely Associated With the Mortality Risk in Chronic Kidney Disease Patients", Nephrology Dialysis Transplantation, 25(8): 2596-2602, Advance Access Publication Feb. 26, 2010. Abstract, P.2597, Right Col., 2nd Para, Figs.2, 3.
Liu et al. "Early Days: Genomics and Human Responses to Infection", Current Opinion in Microbiology, 9: 312-319, Available Online May 6, 2006.

Malcolm et al. "Microarrays Analysis of Lipopolysaccharide-Treated Human Neutrophils", American Journal of Physiology, Lung Cellular & Molecular Physiology, 284(4): L663-L670, First Published Dec. 20, 2002.
Mount "Bioinformatics: Sequence and Genome Analysis", Chaps. 1-10: 1-564, 2001.
Nakabayashi et al. "MxA-Based Recognition of Viral Illness in Febrile Children by a Whole Blood Assay", Pediatric Research, 60(6): 770-774, 2006.
Neu et al. "Expression of Tumor Necrosis Factor-?-Related Apoptosis-Inducing Ligand and Its Proapoptotic Receptors Is Down-Regulated during Gastric Infection with Virulent cagA+/NacAs1+ Helicobacter pylori Strains", The Journal of Infectious Diseases 191(4): 571-578, Feb. 15, 2005.
Niederman "Biological Markers to Determine Eligibility in Trials for Community-Acquired Pneumonia: A Focus on Procalcitonin", Clinical Infectious Diseases, XP002670357, 47(Suppl.3): S127-S132, Dec. 2008.
Niessner et al. "Prognostic Value of Apoptosis Markers in Advanced Heart Failure Patients", European Heart Journal, 30(7): 789-796, Published Online Feb. 4, 2009. Abstract, Table 2, Fig.2.
Oda et al. "A Comprehensive Map of the Toll-Like Receptor Signaling Network", Molecular Systems Biology, 2(2006.0015): 1-20, Apr. 18, 2006.
Oved et al. "A Novel Host-Proteome Signature for Distinguishing Between Acute Bacterial and Viral Infections", PLOS ONE, 10(3): e0120012-1-e120012-18, Mar. 18, 2015. Figs.3C, 4.
Padlan "X-Ray Crystallography of Antibodies", Advances in Protein Chemistry, 49: 57-133; 1996.
Paul et al. "Systematic Review and Meta-Analysis of the Efficacy of Appropriate Empiric Antibiotic Therapy for Sepsis", Antimicrobial Agents and Chemotherapy, 54(11): 4851-4863, Nov. 2010.
Radom-Aizik et al. "Effects of 30 Min. of Aerobic Exercise on Gene Expression in Human Neutrophils", Journal of Applied Physiology, 104: 236-243, 2008.
Ramilo et al. "Gene Expression Patterns in Blood Leukocytes Discriminate Patients With Acute Infections", Blood, 109(5): 2066-2077, Mar. 1, 2007.
RayBiotech "Mouse L308 Array, Membrane [AAM-BLM-1]1-Series-308-Label-Based-Mouse-Cytok", RayBiotech, XP055473187, Retrieved From the Internet, 7 P., May 7, 2018.
Rosseau et al. "Comparative Transcriptional Profiling of the Lung Reveals Shared and Distinct Features of Streptococcus pneumoniae and Influenza A Virus Infection", Immunology, 120: 380-391, 2006.
Secchiero et al. "Potential Prognostic Significance of Decreased Serum Levels of TRAIL After Acute Myocardial Infarction", PLoS ONE, XP055056988, 4(2): e4442-1-e4442-6, Feb. 16, 2009. Fig.1.
Shimetani et al. "Levels of Three Inflammation Markers, C-Reactive Protein, Serum Amyloid a Protein and Procalcitonin, in the Serum and Cerebrospinal Fluid of Patients With Meningitis", Scandinavian Journal of Clinical and Laboratory Investigation, XP008113027, 61(7): 567-574, 2001. Abstract.
Singer et al. "The Third International Consensus Definitions for Sepsis and Septic Shock (Sepsis-3)", Journal of the American Medical Association, JAMA, 315(8): 801-810, Feb. 23, 2016. Box 3, Fig.
Smith et al. "Quantitative Assessment of Human Whole Blood RNA as a Potential Biomarker for Infectious Disease", Analyst, 132: 1200-1209, First Published Oct. 31, 2007.
Sukumaran et al. "Early Transcriptional Response of Human Neutrophils to Anaplasma Phagocytophilum Infection", Infection and Immunity, 73(12): 8089- 8099, Dec. 1, 2005.
Sullivan Pepe et al. "Combining Diagnostic Test Results to Increase Accuracy", Biostatistics, XP055033234, 1(2): 123-140, Jun. 1, 2000. Abstract, Section 2.4.
Tang et al. "Gene-Expression Profiling of Gram-Positive and Gram-Negative Sepsis in Critically Ill Patients", Critical Care Medicine, 36(4): 1125-1128, 2008.
Tang et al. "Hypoxic Preconditioning Enhances the Benefit of Cardiac Progenitor Cell Therapy for Treatment of Myocardial Infarction by Inducing CXCR4 Expression", Circulation Research, XP055473182, 10400(1): 1209-1216, May 22, 2009. Online Table 1.

(56) References Cited

OTHER PUBLICATIONS

Tang et al. "The Use of Gene-Expression Profiling to Identify Candidate Genes in Human Sepsis", American Journal of Respiratory and Critical Care Medicine, 176: 676-684, Originally Published Jun. 15, 2007.
Thivierge et al. "Eukaryotic Elongation Factor 1A Interacts With Turnip Mosaic Virus RNA-Dependent RNA Polymerase and VPg-Pro in Virus-Induced Vesicles", Virology, XP002663503, 377(1): 216-225, Jul. 2008. Abstract, P.220, r-h Col., Para 3-P.222, r-h Col., Para 1.
Tian et al. "Soluble Tumor Necrosis Factor Related Apoptosis Inducing Ligand Level as a Predictor of Severity of Sepsis and the Risk of Mortality in Septic Patients", PLOS One, 8(12): e82204-1-e82204-5, Dec. 12, 2013. 'Study Design' Para, 'Inclusion Criteria' Para, Table 1, Figs.1, 3, Abstract, Table 1.
Tisato et al. "Low Circulating TRAIL Levels Are Associated with Increase of Resistin and Lipocalin-2/ngal Adipokines in Postmenopausal Women", Mediators of Inflammation, Article ID 5356020, 8 pages, 2017.
Torkkola "Feature Extraction by Non-Parametric Mutual Information Maximization", Journal of Machine Learning Research, 3: 1415-1438, Mar. 2003.
Tsuji "TRAILing Gastrointestinal Pathogenesis", Journal of Gastroenterology and Hepatology, 18(7): 753-755, Published Online Jun. 10, 2003.
Tworoger et al. "Collection, Processing, and Storage of Biological Samples in Epidemiologic Studies: Sex Hormones, Carotenoids, Inflammatory Markers, and Proteomics as Examples", Cancer Epidemiol Biomarkers and Prevention,15(9): 1578-1581, Sep. 2006.
Vapnik "Statistical Learning Theory", Adaptive and Learning Systems for Signal Processing, Communications, and Control, p. 1-732, 1998.—Part I.
Vapnik "Statistical Learning Theory", Adaptive and Learning Systems for Signal Processing, Communications, and Control, p. 1-732, 1998.—Part II.
Vapnik "Statistical Learning Theory", Adaptive and Learning Systems for Signal Processing, Communications, and Control, p. 1-732, 1998.—Part III.
Vapnik "Statistical Learning Theory", Adaptive and Learning Systems for Signal Processing, Communications, and Control, p. 1-732, 1998.—Part IV.
Vogel et al. "Sequence Signatures and mRNA Concentration Can Explain Two-Thirds of Protein Abundance Variation in a Human Cell Line", Molecular Systems Biology, 6(Art.400): 1-9, Published Online Aug. 24, 2010.
Wang et al. "Rotavirus Infection Alters Peripheral T-Cell Homeostasis in Children With Acute Diarrhea", Journal of Virology, 81(8): 3904-3912, Apr. 2007.
Whiteside et al. "Role of Human Natural Killer Cells in Health and Disease", Clinical and Diagnostic Laboratory Immunology, 1(2): 125-133, Mar. 31, 1994.
Xu et al. "Lipocalins as Biochemical Markers of Disease", Biochimica et Biophysica Acta, XP002376345, 1482(1): 298-307, Oct. 18, 2000. Abstract, Sections 3, 5, P.303, Co1.2 - P.304, Co1.1, Bridging Para, P.304, Cols.1-2, Bidging Para, Fig.1, Table 1.
Yamaji et al. "Significance of Eukaryotic Translation Elongation Factor 1A in Tobacco Mosaic Virus Infection", Archives of Virology, XP002663502, 155(2): 263-268, Feb. 2010. Abstract.
Yeung et al. "Serum Cytokines in Differentiating Between Viral and Bacterial Enterocolitis", Annals of Tropical Paediatrics, 24(4): 337-343, Published Online Jul. 18, 2013.
Zaas et al. "A Host-Based RT-PCR Gene Expression Signature to Identify Acute Respiratory Viral Infection", Science Translational Medicine, 5(203): 203ra126-1-203m126-19, Sep. 18, 2013.
Zaas et al. "Gene Expression Signatures Diagnose Influenza and Other Symptomatic Respiratory Viral Infections in Humans", Cell Host & Microbe, XP002670360, 6(3): 207-217, Sep. 17, 2009. Abstract, P.212, 1-h Col., P.213, 1-h Col., Fig.4.
Zhu et al. "Use of Differential Display Analysis to Assess the Effect of Human Cytomegalovirus Infection on the Accumulation of Cellular RNAs: Induction of Interferon-Responsive RNAs", Proc. Natl. Acad. Sci. USA, XP002088235, 94(25): 13985-13990, Dec. 9, 1997. Abstract, Fig.2.
Zillox et al. "Gene Expression Changes in Peripheral Blood Mononuclear Cells During Measles Virus Infection", Clinical and Vaccine Immunology, 14(7):918-923, Jul. 2007.
Communication Pursuant to Article 94(3) EPC dated Jul. 31, 2019 From the European Patent Office Re. Application No. 18162713.4. (4 pages).
Ludwig et al. "Tumor Necrosis Factor related Apoptosis Inducing Ligand: A Novell Antitumor Activity" Cancer Research 64: 3386-3390,May 15, 2004.
Notice of Reason for Rejection dated Aug. 20, 2019 From the Japan Patent Office Re. Application No. 2017-507867 and Its Translation Into English. (5 Pages).
Translation dated Mar. 20, 2019 of Notification of Office Action dated Feb. 19, 2019 From the State Intellectual Property Office of the People's Republic of China Re. Application No. 201580075265.0. (5 Pages).
Communication Pursuant to Article 94(3) EPC dated Mar. 25, 2020 From the European Patent Office Re. Application No. 18162713.4. (5 Pages).
Communication Pursuant to Article 94(3) EPC dated Mar. 27, 2020 From the European Patent Office Re. Application No. 15868614.7. (6 Pages).
Official Action dated Mar. 26, 2020 from the US Patent and Trademark Office Re. U.S. Appl. No. 16/687,726. (47 pages).
Official Action dated Mar. 31, 2020 from the US Patent and Trademark Office Rc. U.S. Appl. No. 15/531,747. (21 pages).
Restriction Official Action dated Apr. 2, 2020 from the US Patent and Trademark Office Re. U.S. Appl. No. 16/081,069. (7 pages).
Greenspan et al. "Defining Epitopes: It's Not As Easy As It Seems", Nature Biotechnology, 17: 936-937, Oct. 1999.
Lloyd et al. "Modelling the Human Immune Response: Performance of a 1011, Human Antibody Repertoire Against a Broad Panel of Therapeutically Revelant Antigens", Protein Engineering, Design & Selection 22(3): 159-168, Oct. 29, 2008.
Rudikoff et al. "Single Amino Acid Substitution Altering Antigen-Binding Specificity", PNAS, 79(6): 1979-1983, Mar. 1982.
Notification of Lack of Unity and Search Report dated Jan. 21, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (12 Pages).
Office Action dated Feb. 18, 2019 From the Israel Patent Office Re. Application No. 250585 and Its Translation Into English. (6 Pages).
Requisition by the Examiner dated Feb. 21, 2019 From the Innovation, Science and Economic Development Canada, Canadian Intellectual Property Office Re. Application No. 2,863,819. (8 Pages).
International Preliminary Report on Patentability dated Jan. 24, 2019 From the International Bureau of WIPO Re. Application No. PCT/IL2017/050780. (9 Pages).
International Preliminary Report on Patentability dated Jan. 24, 2019 From the International Bureau of WIPO Re. Application No. PCT/IL2017/050781. (7 Pages).
Translation of Notification dated Jan. 30, 2019 From OA of Jan. 11, 2019 From the State Intellectual Property Office of the People's Republic of China Re. Application No. 201580055946.0.(1 Page).
International Preliminary Report on Patentability dated Apr. 11, 2019 From the International Bureau of WIPO Re. Application No. PCT/IL2017/051088. (6 Pages).
International Preliminary Report on Patentability dated Apr. 11, 2019 From the International Bureau of WIPO Re. Application No. PCT/IL2017/051089. (7 Pages).
Notice of Reasons for Rejection dated Apr. 2, 2019 From the Japan Patent Office Re. Application No. 2017-126712 and Its Translation Into English. (8 Pages).
Official Action dated Apr. 15, 2019 From the US Patent and Trademark Office Re. U.S. Appl. No. 15/237,728. (16 Pages).
Official Action dated Mar. 5, 2020 From the US Patent and Trademark Office Re. U.S. Appl. No. 15/713,722. (24 pages).

(56) References Cited

OTHER PUBLICATIONS

Notification of Office Action and Search Report dated Jul. 28, 2020 From the State Intellectual Property Office of the People's Republic of China Re. Application No. 201810781584.9 and Its Translation of Office Action Into English.
Bai et al. "A New Early Diagnostic Marker for Inflammatory Diseases—sTREM-1", International Journal of Pathology and Clinical Medicine, 27(1): 73-76, Feb. 2007.
Cai et al. "The Study on the Relationship Between PCT and CRP in Infective Diseases", Journal al of Qiqihar University of Medicine, 32(5): 696-697, 2011.
Final Official Action dated Sep. 8, 2020 from the US Patent and Trademark Office Re. U.S. Appl. No. 16/687,726. (28 pages).
Restriction Official Action dated Sep. 10, 2020 from the US Patent and Trademark Office Re. U.S. Appl. No. 16/316,631. (6 pages).
Communication Pursuant to Article 94(3) EPC dated May 25, 2020 From the European Patent Office Re. Application No. 11748712.4. (7 Pages).
Official Action dated May 7, 2020 from the US Patent and Trademark Office Re. U.S. Appl. No. 16/157,193. (23 pages).
Supplementary European Search Report and the European Search Opinion dated May 4, 2020 From the European Patent Office Re. Application No. 17855163.6. (9 Pages).
Forde et al. "The Beneficial Pleiotropic Effects of Tumour Necrosis Factor-Related Apoptosis-Inducing Ligand (TRAIL) Within the Vasculature: A Review of the Evidence", Atherosclerosis, XP029468976, 247: 87-96, Available Online Feb. 9, 2016.
Sasaki et al. "Differentiating Between Bacterial and Viral Infection by Measuring Both C-Reactive Protein and 2'-5'-Oligoadenylate Synthetase as Inflammatory Markers", Journal of Infection and Chemotherapy, XP055696216, 8(1): 76-80, Mar. 2002.
Communication Pursuant to Article 94(3) EPC dated Aug. 18, 2020 From the European Patent Office Re. Application No. 11748712.4. (3 Pages).
Communication Pursuant to Article 94(3) EPC dated Sep. 25, 2020 From the European Patent Office Re. Application No. 17827122.7. (5 Pages).
European Search Report and the European Search Opinion dated Sep. 28, 2020 From the European Patent Office Re. Application No. 20164056.2. (10 Pages).
Interview Summary dated Oct. 14, 2020 from the US Patent and Trademark Office Re. Application No. 16/081,906. (3 pages).
Office Action dated Jul. 30, 2020 From the Israel Patent Office Re. Application No. 261529 and Its Translation Into English. (5 Pages).
Office Action dated Jul. 30, 2020 From the Israel Patent Office Re. Application No. 261530 and Its Translation Into English. (5 Pages).
Restriction Official Action dated Jul. 30, 2020 from the US Patent and Trademark Office Re. U.S. Appl. No. 16/081,906. (7 pages).
Partial European Search Report and Provisional Opinion dated Jun. 25, 2020 From the European Search Report Re. Application No. 20164056.2. (11 Pages).
Pepe et al. "Combining Diagnostic Test Results to Increase Accuracy", Biostatistics, XP055033234, 1(2): 123-140, Jun. 2000.
Communication Pursuant to Article 94(3) EPC dated Jun. 4, 2020 From the European Patent Office Re. Application No. 17759388.6. (3 Pages).
Supplementary European Search Report and the European Search Opinion dated May 18, 2020 From the European Patent Office Re. Application No. 17855164.4 (13 Pages).
Shommu et al. "Metabolomic and Inflammatory Mediator Based Biomarker Profiling as a Potential Novel Method to Aid Pediatric Appendicitis Identification", PLOS ONE, XP055692841, 13(3): e0193563-1-e0193563-13, Mar. 12, 2018.
Interview Summary dated Feb. 1, 2021 From the US Patent and Trademark Office Re. U.S. Appl. No. 16/687,726. (2 Pages).
Patent Examination Report dated Feb. 8, 2021 From the Australian Government, IP Australia Re. Application No. 2015302870. (4 Pages).
Official Action dated Mar. 9, 2021 From the US Patent and Trademark Office Re. U.S. Appl. No. 16/316,631. (121 Pages).

Communication Pursuant to Article 94(3) EPC dated Mar. 17, 2021 From the European Patent Office Re. Application No. 15868614.7. (5 Pages).
Notification of Office Action dated Mar. 5, 2021 From the State Intellectual Property Office of the People's Republic of China Re. Application No. 201810781584.9 and Its Translation of Office Action Into English. (13 Pages).
Official Action dated Mar. 10, 2021 From the US Patent and Trademark Office Re. U.S. Appl. No. 16/081,906. (127 Pages).
Shair et al. "Epstein-Barr Virus Latent Membrane Protein-1 Effects on Junctional Plakoglobin and Induction of a Cadherin Switch", Cancer Research, Cell, Tumor, and Stem Cell Biology, 69(14): 5734-5742, Jul. 15, 2009.
Communication Pursuant to Article 94(3) EPC dated Nov. 12, 2020 From the European Patent Office Re. Application No. 17759389.4. (6 Page).
Official Action dated Oct. 20, 2020 From the US Patent and Trademark Office Re. U.S. Appl. No. 16/081,069. (112 Pages).
Official Action dated Nov. 23, 2020 From the US Patent and Trademark Office Re. U.S. Appl. No. 16/355,984. (9 pages).
Official Action dated Dec. 30, 2020 from the US Patent and Trademark Office Re. U.S. Appl. No. 16/334,033. (112 pages).
Requisition by the Examiner dated Dec. 7, 2020 From the Innovation, Science and Economic Development Canada, Canadian Intellectual Property Office Re. Application No. 2,863,819. (4 Pages).
Restriction Official Action dated Dec. 9, 2020 from the US Patent and Trademark Office Re. U.S. Appl. No. 16/336,528. (7 pages).
Bone et al. "Definitions for Sepsis and Organ Failure and Guidelines for the Use of Innovative Therapies in Sepsis", Chest, 101(6): 1644-1655, 1992.
Ju et al. "Research Progress of Some Inflammatory Markers in Infectious Diseases", Chinese Journal of Practical Internal Medicine, 30(Suppl.1): 80-81, Jun. 2010. With an English Translation.
Kang et al. "Low serum TNF-Related Apoptosis-Inducing Ligand (TRAIL) Levels Are Associated with Acute Ischemic Stroke Severity", Atherosclerosis, 240: 228-233, 2015.
Michowitz et al. "The Involvement of Tumor Necrosis Factor-Related Apoptosis- Inducing Ligand(TRAIL) in Atherosclerosis.", Journal of the American College of Cardiology, 45(7): 1018-1024, 2005.
Osmancik et al. "Prognostic Value of TNF-Related Apoptosis Inducing Ligand (TRAIL) in Acute Coronary Syndrome Patients", PLoS One, 8(2): e53860, 2013.
ThermoFisher Scientific "Interferon Alpha Inducible Protein 27: IF127", ThermoFisher Scientific, Product Details, 2 P., 2020.
ThermoFisher Scientific "Interferon Induced Protein 44 Like: IF144L", ThermoFisher Scientific, Product Details, 2 P., 2020.
ThermoFisher Scientific "TaqMan Gene Expression Assay Solutions: Proven 5' Nuclease-Based Real-Time PCR Chemistry", Thermo Fisher Scientific, Applied Biosystems, 11 P., 2015.
Volpato et al. "Association of Tumor Necrosis Factor-Related Apoptosis-Inducing Ligand with Total and Cardiovascular Mortality in Older Adults", Atherosclerosis, 215: 452-458, 2011.
Zaas et al. Supplementary Materials for "A Host-Based RT-PCR Gene Expression Signature to Identify Acute Respiratory Viral Infection", Science Translational Medicine, 5(203): 203ra126-1-203ra126-21, Sep. 18, 2013.
European Search Report and the European Search Opinion dated Jul. 14, 2020 From the European Patent Office Re. Application No. 21170448.1. (6 Pages).
Notice of Allowance Dated and Interview Summary dated Jul. 19, 2021 from US Patent and Trademark Office Re. U.S. Appl. No. 16/687,726. (24 pages).
Translation dated Jul. 22, 2021 of Notification of Office Action dated Jul. 13, 2021 From the State Intellectual Property Office of the People's Republic of China Re. Application No. 20180781584.9. (2 Pages).
Translation dated Jul. 27, 2021 of Notification of Office Action dated Jul. 2, 2021 From the State Intellectual Property Office of the People's Republic of China Re. Application No. 201780055014.5. (12 Pages).

\* cited by examiner

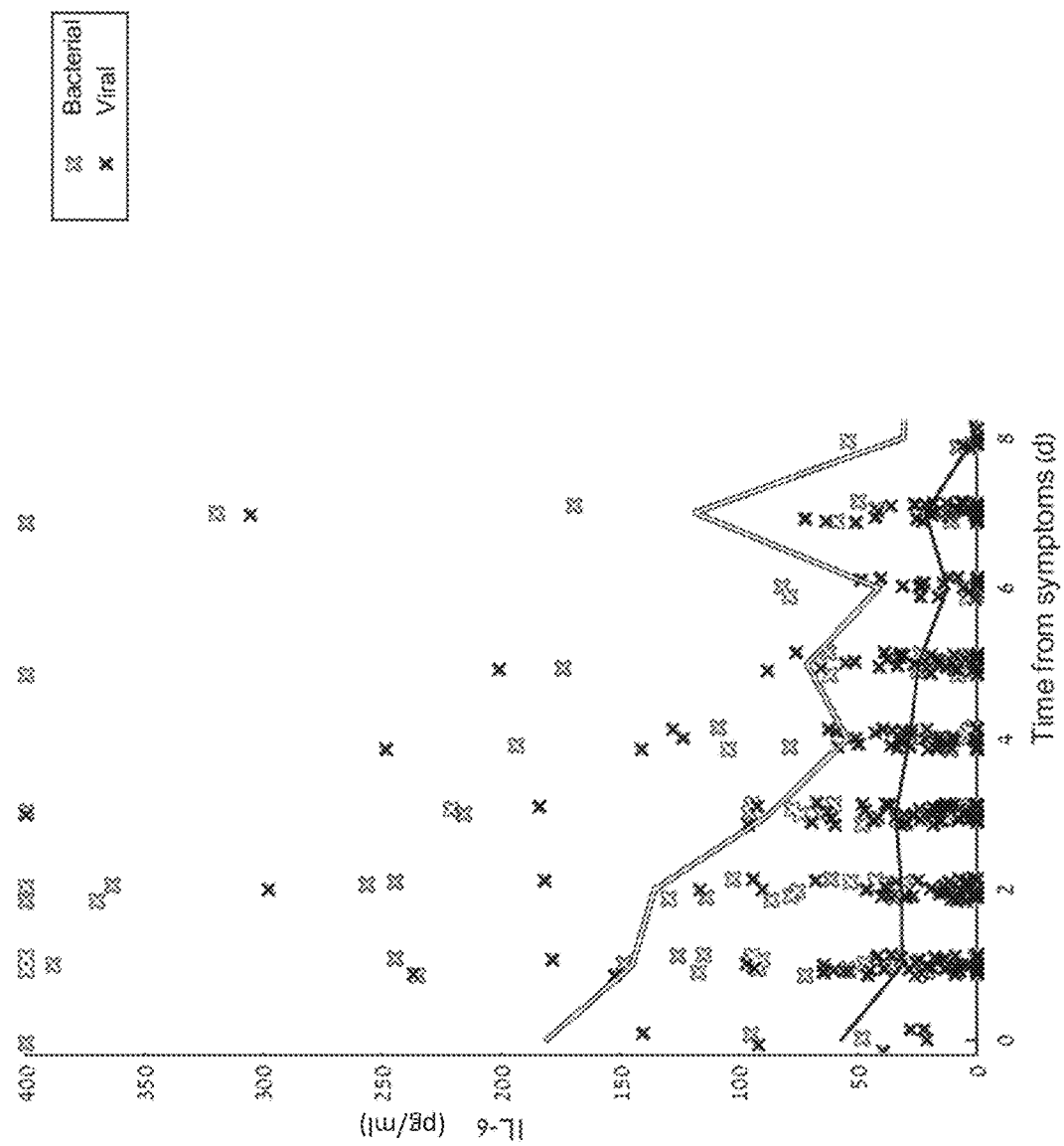

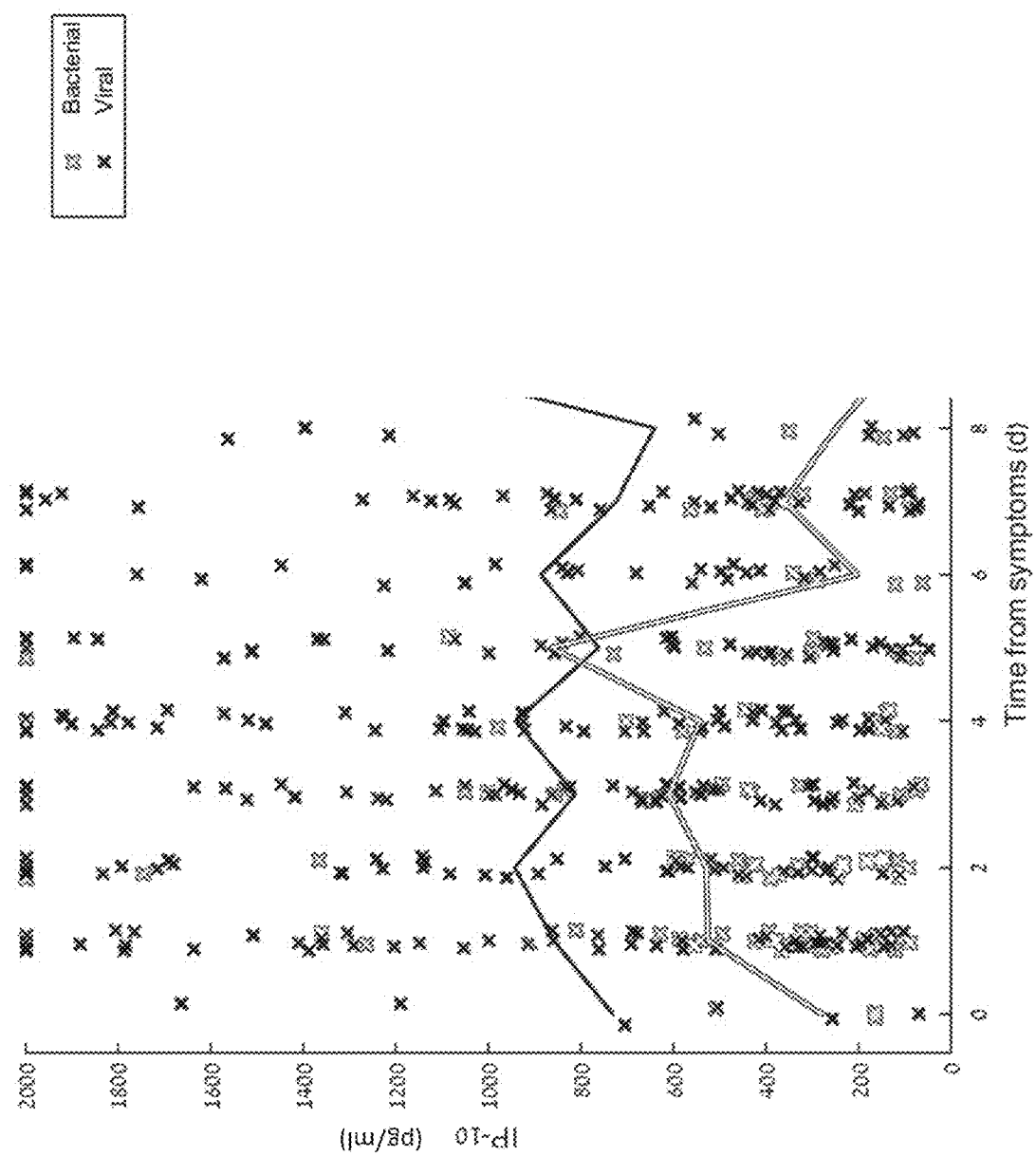

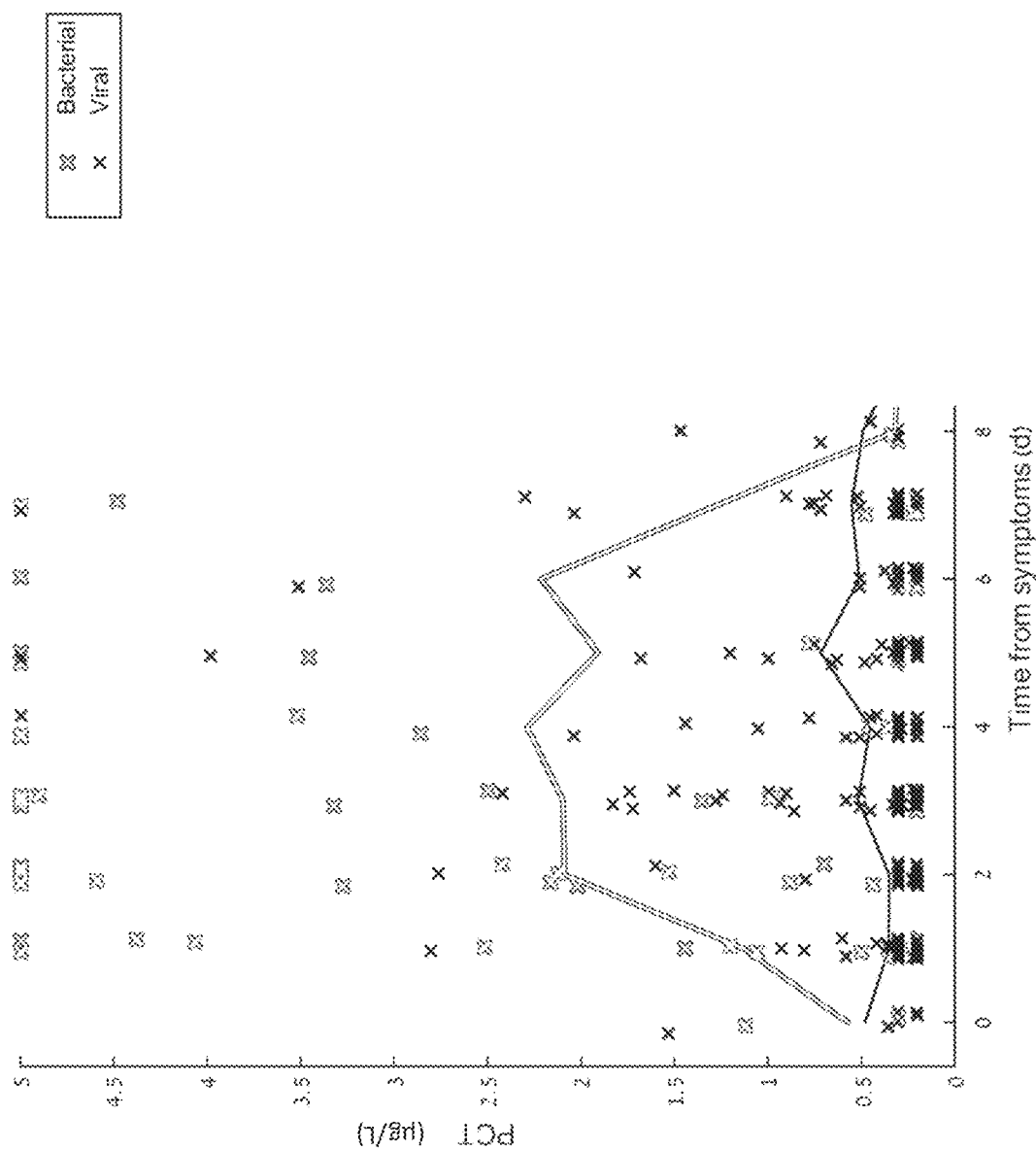

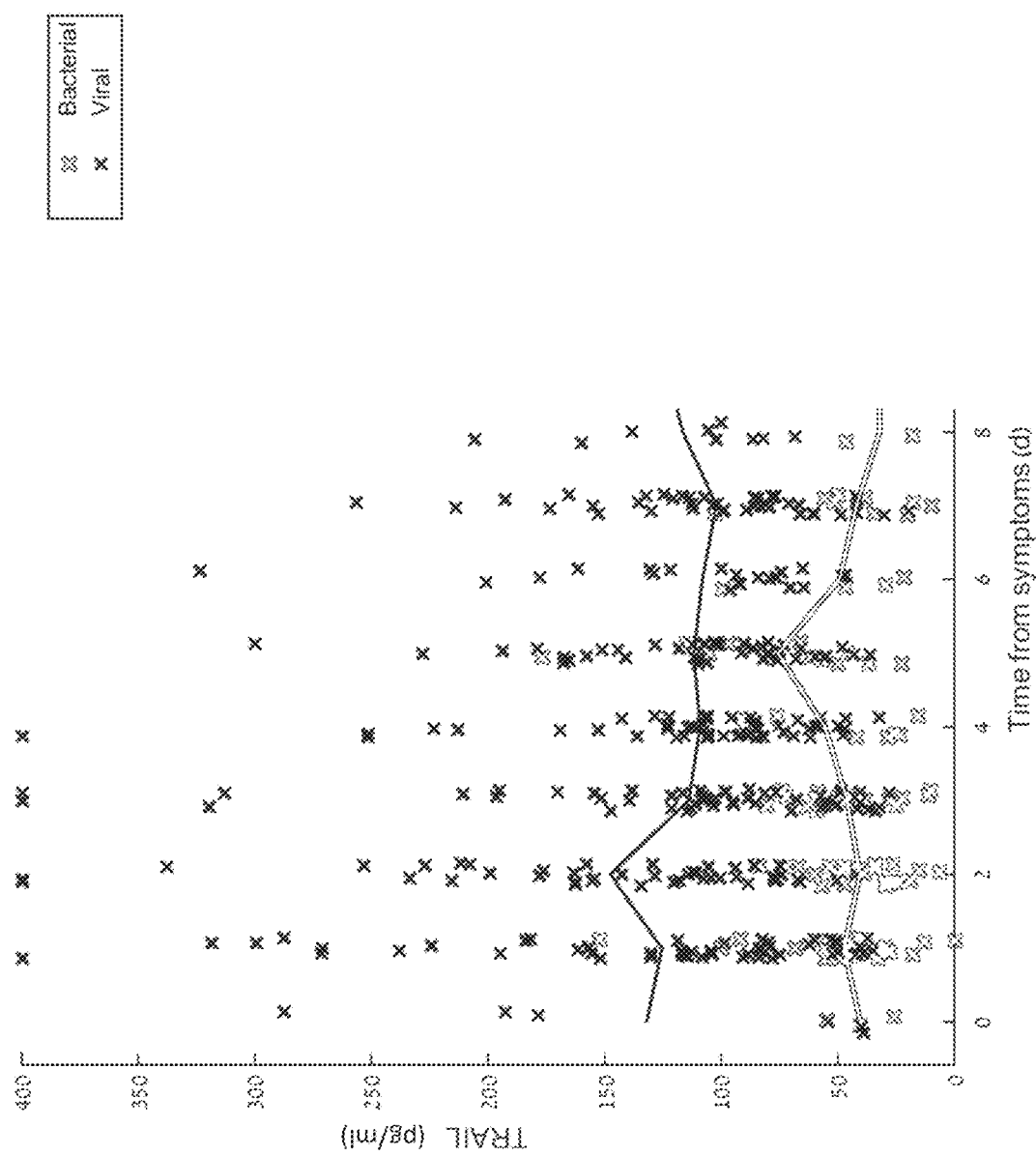

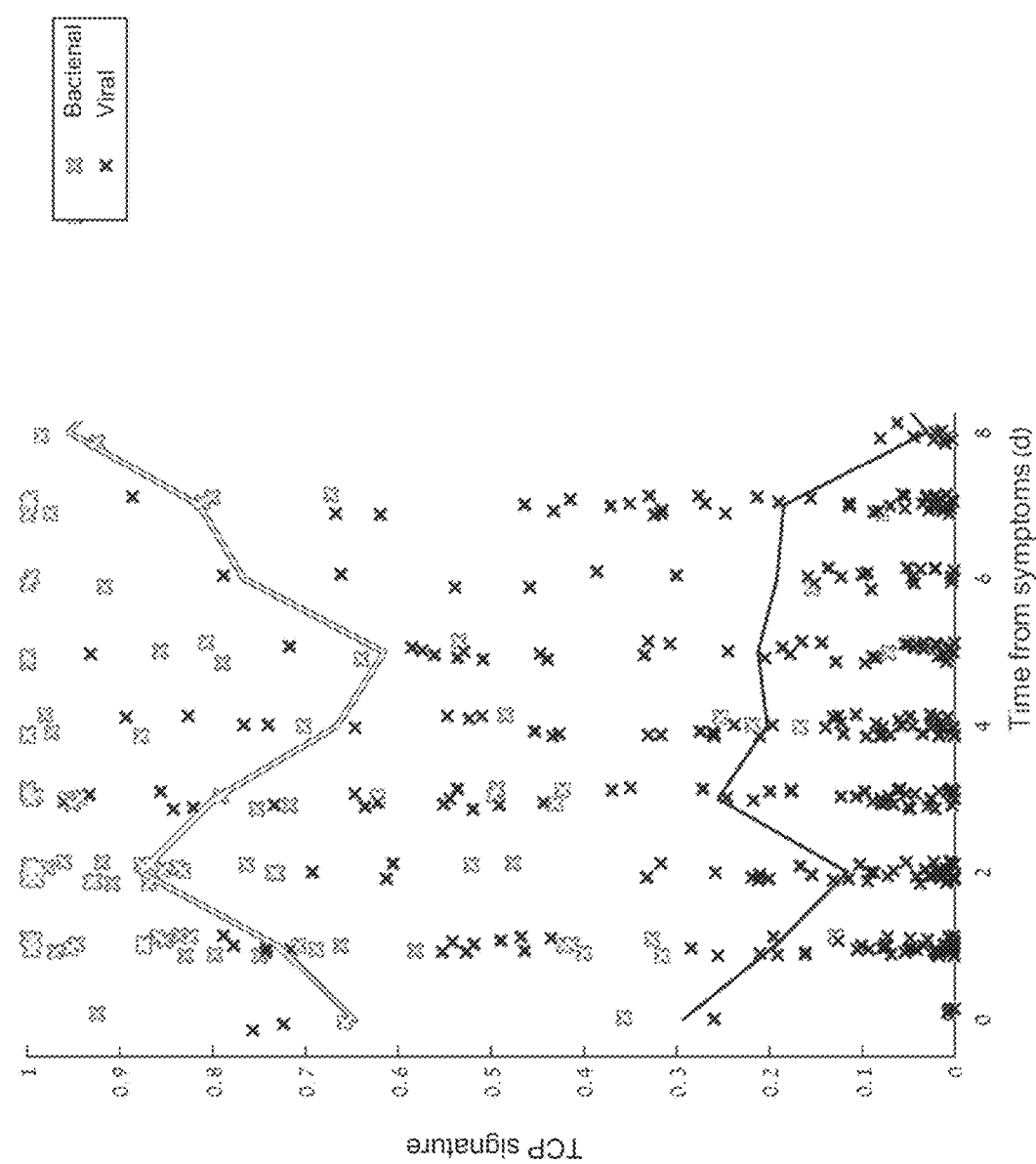

Time course of different proteins in bacterial patients

FIG. 10A

| cutoff | 250 |
|---|---|
| hill | 10 |

| TCP | IL-6 | | | | | | | | | | | | | | | | | | | | |
|---|---|---|---|---|---|---|---|---|---|---|---|---|---|---|---|---|---|---|---|---|---|
| | 1 | 20 | 40 | 60 | 80 | 100 | 120 | 140 | 160 | 180 | 200 | 220 | 240 | 260 | 280 | 300 | 320 | 340 | 360 | 380 | 400 |
| 0.0% | 0.0% | 0.0% | 0.0% | 0.0% | 0.0% | 0.0% | 0.0% | 0.3% | 1.1% | 3.6% | 9.7% | 21.8% | 39.9% | 59.7% | 75.6% | 86.1% | 92.2% | 95.6% | 97.5% | 98.6% | 99.1% |
| 5.0% | 5.0% | 5.0% | 5.0% | 5.0% | 5.0% | 5.0% | 5.0% | 5.3% | 6.1% | 8.6% | 14.2% | 25.7% | 42.9% | 61.7% | 76.9% | 86.8% | 92.6% | 96.0% | 97.6% | 98.6% | 99.1% |
| 10.0% | 10.0% | 10.0% | 10.0% | 10.0% | 10.0% | 10.0% | 10.0% | 10.3% | 11.0% | 13.2% | 18.7% | 29.6% | 45.9% | 63.7% | 78.1% | 87.5% | 93.0% | 96.0% | 97.7% | 98.6% | 99.1% |
| 15.0% | 15.0% | 15.0% | 15.0% | 15.0% | 15.0% | 15.0% | 15.0% | 15.3% | 16.0% | 18.0% | 23.1% | 33.5% | 48.9% | 65.7% | 79.3% | 88.2% | 93.4% | 96.2% | 97.8% | 98.7% | 99.2% |
| 20.0% | 20.0% | 20.0% | 20.0% | 20.0% | 20.0% | 20.0% | 20.0% | 20.2% | 20.9% | 22.9% | 27.8% | 37.4% | 51.9% | 67.7% | 80.5% | 88.9% | 93.8% | 96.3% | 97.8% | 98.7% | 99.2% |
| 25.0% | 25.0% | 25.0% | 25.0% | 25.0% | 25.0% | 25.0% | 25.0% | 25.2% | 25.9% | 27.7% | 32.3% | 41.3% | 55.0% | 69.8% | 81.7% | 89.6% | 94.1% | 96.7% | 98.0% | 98.8% | 99.2% |
| 30.0% | 30.0% | 30.0% | 30.0% | 30.0% | 30.0% | 30.0% | 30.0% | 30.2% | 30.8% | 32.5% | 36.9% | 45.2% | 58.0% | 71.8% | 83.0% | 90.3% | 94.5% | 96.9% | 98.1% | 98.8% | 99.3% |
| 35.0% | 35.0% | 35.0% | 35.0% | 35.0% | 35.0% | 35.0% | 35.0% | 35.2% | 35.7% | 37.3% | 41.3% | 49.2% | 61.0% | 73.8% | 84.2% | 91.0% | 94.9% | 97.1% | 98.2% | 98.9% | 99.3% |
| 40.0% | 40.0% | 40.0% | 40.0% | 40.0% | 40.0% | 40.0% | 40.0% | 40.2% | 40.7% | 42.2% | 45.8% | 53.1% | 64.0% | 75.8% | 85.4% | 91.7% | 95.3% | 97.4% | 98.3% | 98.9% | 99.3% |
| 45.0% | 45.0% | 45.0% | 45.0% | 45.0% | 45.0% | 45.0% | 45.0% | 45.2% | 45.6% | 47.0% | 50.3% | 57.0% | 67.0% | 77.8% | 86.6% | 92.4% | 95.7% | 97.5% | 98.4% | 99.0% | 99.3% |
| 50.0% | 50.0% | 50.0% | 50.0% | 50.0% | 50.0% | 50.0% | 50.0% | 50.2% | 50.6% | 51.8% | 54.8% | 60.9% | 70.0% | 79.8% | 87.8% | 93.0% | 96.1% | 97.7% | 98.5% | 99.0% | 99.4% |
| 55.0% | 55.0% | 55.0% | 55.0% | 55.0% | 55.0% | 55.0% | 55.0% | 55.1% | 55.5% | 56.6% | 59.4% | 64.8% | 73.0% | 81.9% | 89.0% | 93.7% | 96.4% | 97.9% | 98.6% | 99.1% | 99.4% |
| 60.0% | 60.0% | 60.0% | 60.0% | 60.0% | 60.0% | 60.0% | 60.0% | 60.1% | 60.5% | 61.4% | 63.9% | 68.7% | 76.0% | 83.9% | 90.2% | 94.4% | 96.8% | 98.1% | 98.7% | 99.1% | 99.4% |
| 65.0% | 65.0% | 65.0% | 65.0% | 65.0% | 65.0% | 65.0% | 65.0% | 65.1% | 65.4% | 66.3% | 68.4% | 72.6% | 79.0% | 85.9% | 91.3% | 95.1% | 97.2% | 98.3% | 98.8% | 99.1% | 99.4% |
| 70.0% | 70.0% | 70.0% | 70.0% | 70.0% | 70.0% | 70.0% | 70.0% | 70.1% | 70.3% | 71.1% | 72.9% | 76.5% | 82.0% | 87.9% | 92.5% | 95.8% | 97.5% | 98.4% | 98.9% | 99.2% | 99.5% |
| 75.0% | 75.0% | 75.0% | 75.0% | 75.0% | 75.0% | 75.0% | 75.0% | 75.1% | 75.3% | 75.9% | 77.4% | 80.4% | 85.0% | 89.9% | 93.6% | 96.5% | 97.9% | 98.6% | 99.0% | 99.2% | 99.5% |
| 80.0% | 80.0% | 80.0% | 80.0% | 80.0% | 80.0% | 80.0% | 80.0% | 80.1% | 80.2% | 80.7% | 81.9% | 84.4% | 88.0% | 91.9% | 94.8% | 97.1% | 98.3% | 98.8% | 99.1% | 99.3% | 99.5% |
| 85.0% | 85.0% | 85.0% | 85.0% | 85.0% | 85.0% | 85.0% | 85.0% | 85.0% | 85.2% | 85.5% | 86.5% | 88.3% | 91.0% | 94.0% | 96.0% | 97.8% | 98.7% | 99.0% | 99.2% | 99.4% | 99.6% |
| 90.0% | 90.0% | 90.0% | 90.0% | 90.0% | 90.0% | 90.0% | 90.0% | 90.0% | 90.1% | 90.4% | 91.0% | 92.2% | 94.0% | 96.0% | 97.1% | 98.4% | 99.0% | 99.2% | 99.4% | 99.5% | 99.6% |
| 95.0% | 95.0% | 95.0% | 95.0% | 95.0% | 95.0% | 95.0% | 95.0% | 95.0% | 95.1% | 95.2% | 95.5% | 96.1% | 97.0% | 98.0% | 98.5% | 99.1% | 99.4% | 99.4% | 99.5% | 99.6% | 99.7% |
| 100.0% | 100.0% | 100.0% | 100.0% | 100.0% | 100.0% | 100.0% | 100.0% | 100.0% | 100.0% | 100.0% | 100.0% | 100.0% | 100.0% | 100.0% | 100.0% | 100.0% | 100.0% | 100.0% | 100.0% | 100.0% | 100.0% |

TCP signature Fuzzy OR IL-6 smooth

FIG. 10B

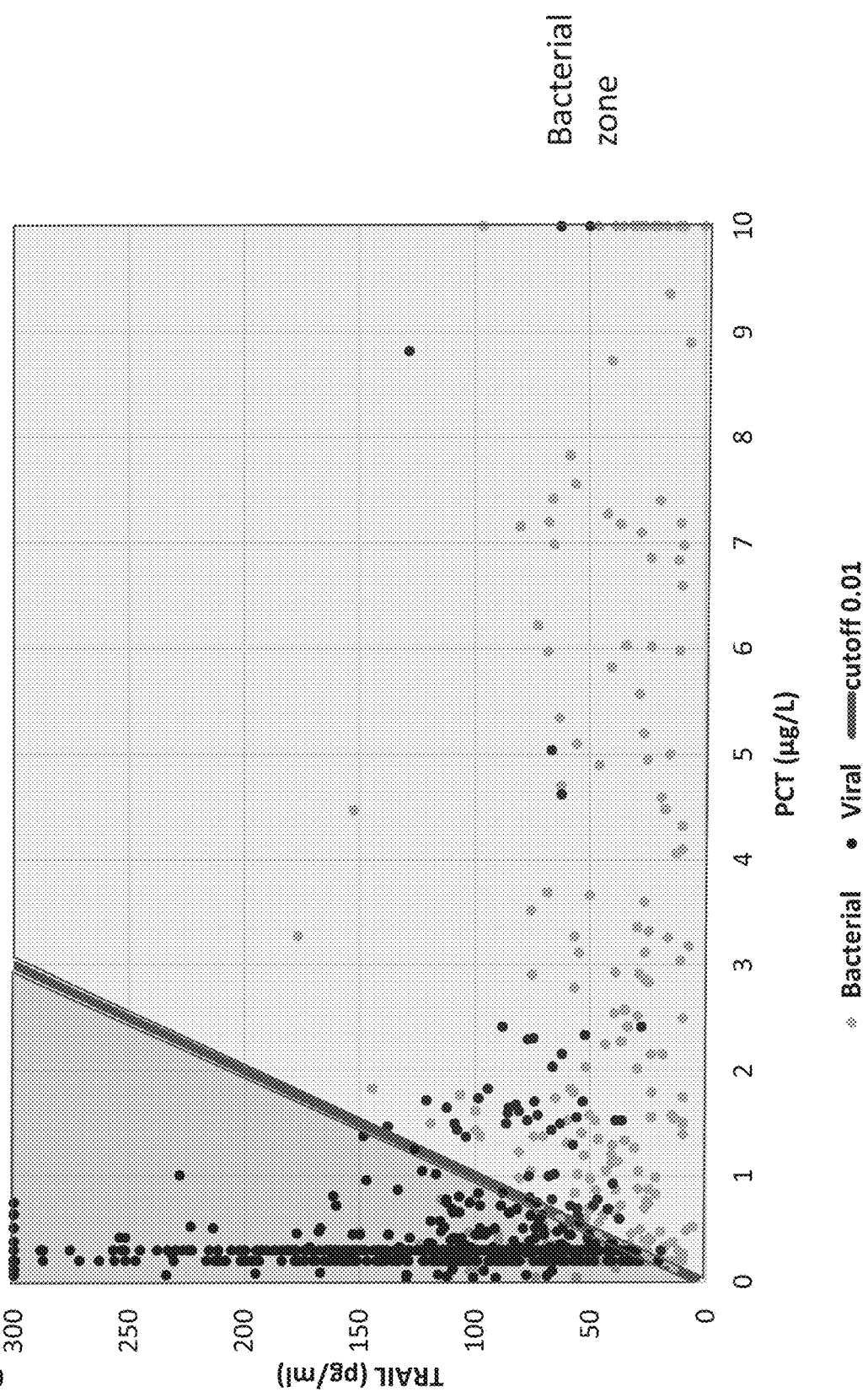

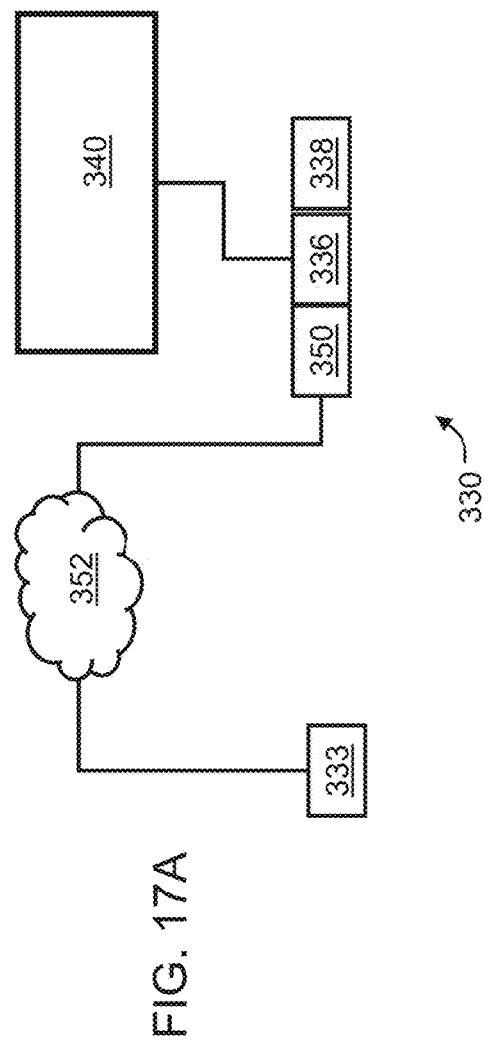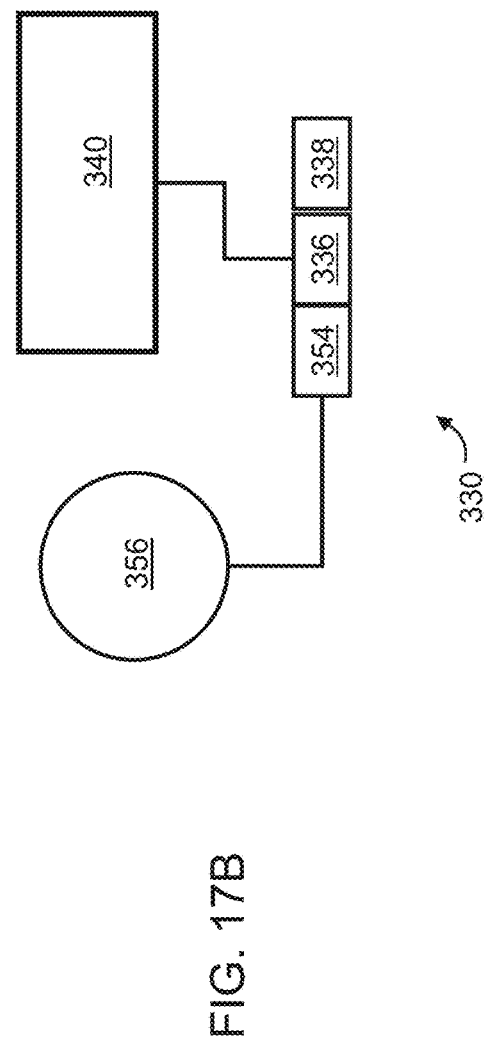

PROTEIN SIGNATURES FOR DISTINGUISHING BETWEEN BACTERIAL AND VIRAL INFECTIONS

RELATED APPLICATIONS

This application is a Continuation of PCT Patent Application No. PCT/IL2017/050780 having International filing date of Jul. 10, 2017, which claims the benefit of priority under 35 USC § 119(e) of U.S. Provisional Patent Application No. 62/360,418 filed on Jul. 10, 2016. The contents of the above applications are all incorporated by reference as if fully set forth herein in their entirety.

SEQUENCE LISTING STATEMENT

The ASCII file, entitled 75463SequenceListing.txt, created on Jan. 3, 2019, comprising 58,567 bytes, submitted concurrently with the filing of this application is incorporated herein by reference.

FIELD AND BACKGROUND OF THE INVENTION

The present invention, in some embodiments thereof, relates to the identification of signatures and determinants associated with bacterial and viral infections. More specifically it was discovered that certain protein determinants are differentially expressed in a statistically significant manner in subjects with bacterial and viral infections.

Antibiotics are the world's most prescribed class of drugs with a 25-30 billion $US global market. Antibiotics are also the world's most misused drug with a significant fraction of all drugs (40-70%) being wrongly prescribed.

One type of antibiotics misuse is when the drug is administered in case of a non-bacterial disease, such as a viral infection, for which antibiotics is ineffective. For example, according to the USA center for disease control and prevention CDC, over 60 Million wrong antibiotics prescriptions are given annually to treat flu in the US. The health-care and economic consequences of the antibiotics over-prescription include: (i) the cost of antibiotics that are unnecessarily prescribed globally, estimated at >$10 billion annually; (ii) side effects resulting from unnecessary antibiotics treatment are reducing quality of healthcare, causing complications and prolonged hospitalization (e.g. allergic reactions, Antibiotics-associated diarrhea, intestinal yeast etc.) and (iii) the emergence of resistant strains of bacteria as a result of the overuse.

Resistance of microbial pathogens to antibiotics is increasing world-wide at an accelerating rate ("CDC—Get Smart: Fast Facts About Antibiotic Resistance" 2013; "European Surveillance of Antimicrobial Consumption Network (ESAC-Net)" 2014; "CDC—About Antimicrobial Resistance" 2013; "Threat Report 2013|Antimicrobial Resistance|CDC" 2013), with a concomitant increase in morbidity and mortality associated with infections caused by antibiotic resistant pathogens ("Threat Report 2013|Antimicrobial Resistance|CDC" 2013). At least 2 million people are infected with antibiotic resistant bacteria each year in the US alone, and at least 23,000 people die as a direct result of these infections ("Threat Report 2013|Antimicrobial Resistance|CDC" 2013). In the European Union, an estimated 400,000 patients present with resistant bacterial strains each year, of which 25,000 patients die ("WHO Europe—Data and Statistics" 2014). Consequently, the World Health Organization has warned that therapeutic coverage will be insufficient within 10 years, putting the world at risk of entering a "post-antibiotic era", in which antibiotics will no longer be effective against infectious diseases ("WHO|Antimicrobial Resistance" 2013). The CDC considers this phenomenon "one of the world's most pressing health problems in the 21$^{st}$ century" ("CDC—About Antimicrobial Resistance" 2013).

Antibiotics under-prescription is not uncommon either. For example up to 15% of adult bacterial pneumonia hospitalized patients in the US receive delayed or no Abx treatment, even though in these instances early treatment can save lives and reduce complications.

Technologies for infectious disease diagnostics have the potential to reduce the associated health and financial burden associated with antibiotics misuse. Ideally, such a technology should: (i) accurately differentiate between a bacterial and viral infections; (ii) be rapid (within minutes); (iii) be able to differentiate between pathogenic and non-pathogenic bacteria that are part of the body's natural flora; (iv) differentiate between mixed co-infections and pure viral infections and (v) be applicable in cases where the pathogen is inaccessible (e.g. sinusitis, pneumonia, otitis-media, bronchitis, etc).

Circulating host-proteins are routinely used to support diagnosis of infection (for example IL-6, PCT and CRP). However, these markers are sensitive to inter-patient variability, including time from symptom onset, clinical syndrome, and pathogen species [1-6]. For example, multiple studies found that procalcitonin is valuable for guiding antimicrobial therapy duration and for predicting disease severity [7-9], however its diagnostic accuracy for detecting bacterial etiology in cases such as sepsis and pneumonia has been challenged [1,10-13]. Elevated CRP levels are suggestive of a bacterial infection [14], but similar levels may be observed in patients with some viral strains (e.g., adenovirus and influenza) [15], and inflammatory diseases. Combinations of these proteins resulted in limited-to-moderate diagnostic improvement over individual proteins, presumably since they share biological pathways, and are thus inherently sensitive to the same factors.

To overcome this the present inventors have previously developed a multi-protein signature for distinguishing between bacterial and viral infections [16]. The signature includes both viral- and bacterial-induced proteins (TRAIL [TNF-related apoptosis-inducing ligand], CRP [C-reactive protein], IP-10 [Interferon gamma-induced protein-10]— TCP signature). When tested in a heterogeneous group of patients, in a clinical study that included 1002 subjects presenting with various acute infection conditions, the TCP signature demonstrated sensitivity of 92%±4 and specificity of 89%±3 [16].

Correct identification of bacterial patients is of high importance as these patients require antibiotic treatment and in some cases more aggressive management (hospitalization, additional diagnostic tests etc). Misclassification of bacterial patients increases the chance of morbidity and mortality. Therefore, increasing the sensitivity of a diagnostic test that distinguishes between bacterial and viral infections is desired, even at a cost of reduced specificity.

Additional background art includes US Patent Application No. 20080171323, WO2011/132086 and WO2013/117746.

SUMMARY OF THE INVENTION

According to an aspect of some embodiments of the present invention there is provided a method of distinguishing between an infective exacerbation state and a non-infective exacerbation state of chronic obstructive pulmonary disease (COPD) in a subject, the method comprising measuring the amount of at least two polypeptides selected from the group consisting of TNF-related apoptosis-inducing ligand (TRAIL), C-reactive protein (CRP), Interferon gamma-induced protein 10 (IP10), Interleukin 6 (IL-6) and Procalcitonin (PCT) in a sample derived from the subject, wherein the amount is indicative of the exacerbation state of COPD.

According to an aspect of some embodiments of the present invention there is provided a method of distinguishing between sepsis and non-infective systemic inflammatory response syndrome (SIRS) comprising measuring the amount of at least two polypeptides selected from the group consisting of TNF-related apoptosis-inducing ligand (TRAIL), C-reactive protein (CRP), Interferon gamma-induced protein 10 (IP10), Interleukin 6 (IL-6) and Procalcitonin (PCT) in a sample derived from the subject, wherein the amount is indicative of sepsis or non-infective SIRS.

According to an aspect of some embodiments of the present invention there is provided a method of ruling in sepsis in a subject suspected of having in infection comprising:

(a) measuring the amount of at least two polypeptides selected from the group consisting of TNF-related apoptosis-inducing ligand (TRAIL), C-reactive protein (CRP), Interferon gamma-induced protein 10 (IP10), Interleukin 6 (IL-6) and Procalcitonin (PCT) in a sample derived from the subject;

(b) measuring the respiratory rate of the subject;

(c) analyzing the mental state of the subject; and (d) measuring the blood pressure of the subject;

wherein when each of steps provide a result which is indicative of sepsis, sepsis is ruled in.

According to an aspect of some embodiments of the present invention there is provided a method of analyzing biological data, the method comprising:

obtaining biological data containing at least expression levels of TNF-related apoptosis-inducing ligand (TRAIL), C-reactive protein (CRP), Interferon gamma-induced protein-10 (IP-10) and Interleukin 6 (IL-6) in the blood of a subject;

applying a non-linear multinomial logistic regression to expression levels of the TRAIL, the CRP, the IP-10 to provide a calculated score;

calculating a distance between a segment of a curved line and an axis defined by a direction, the distance being calculated at a point over the curved line defined by a coordinate $\delta$ along the direction; and correlating the distance to the presence of, absence of, or likelihood that the subject has, a bacterial infection;

wherein at least 90% of the segment is between a lower bound line $f(\delta)-\varepsilon_0$ and an upper bound line $f(\delta)+\varepsilon_1$, wherein the $f(\delta)$ equals $1/(1+\exp(-\delta))$, wherein the coordinate $\delta$, once calculated, equals $a_0+a_1 X+a_2 Y$, wherein the X is a value of the calculated score, and the Y is a value of the IL-6 in pg/ml, wherein each of the $\varepsilon_0$ and the $\varepsilon_1$ is less than 0.5, and wherein $a_0$ is from about 2.75 to about 3.40, $a_1$ is from about 4.5 to about 5.5, and $a_2$ is from about 0.0044 to about 0.0055.

According to an aspect of some embodiments of the present invention there is provided a method of analyzing biological data, the method comprising:

obtaining biological data containing at least expression levels of TNF-related apoptosis-inducing ligand (TRAIL), C-reactive protein (CRP), Interferon gamma-induced protein-10 (IP-10) and Procalcitonin (PCT) in the blood of a subject;

applying a non-linear multinomial logistic regression to expression levels of the TRAIL, the CRP, the IP-10 to provide a calculated score;

calculating a distance between a segment of a curved line and an axis defined by a direction, the distance being calculated at a point over the curved line defined by a coordinate $\delta$ along the direction; and correlating the distance to the presence of, absence of, or likelihood that the subject has, a bacterial infection;

wherein at least 90% of the segment is between a lower bound line $f(\delta)-\varepsilon_0$ and an upper bound line $f(\delta)+\varepsilon_1$, wherein the $f(\delta)$ equals $1/(1+\exp(-\delta))$, wherein the coordinate $\delta$, once calculated, equals $a_0+a_1 X+a_2 Y$, wherein the X is a value of the calculated score, and the Y is a value of the PCT in μg/L, wherein each of the $\varepsilon_0$ and the $\varepsilon_1$ is less than 0.5, and wherein $a_0$ is from about 2.70 to about 3.30, $a_1$ is from about 4.55 to about 5.60, and $a_2$ is from about 0.176 to about 0.215.

According to an aspect of some embodiments of the present invention there is provided a method of analyzing biological data, the method comprising:

obtaining biological data containing expression levels of C-reactive protein (CRP), Interleukin 6 (IL-6), and TNF-related apoptosis-inducing ligand (TRAIL) in the blood of a subject;

calculating a distance between a segment of a curved line and an axis defined by a direction, the distance being calculated at a point over the curved line defined by a coordinate $\delta$ along the direction; and correlating the distance to the presence of, absence of, or likelihood that the subject has, a bacterial infection;

wherein at least 90% of the segment is between a lower bound line $f(\delta)-\varepsilon_0$ and an upper bound line $f(\delta)+\varepsilon_1$, wherein the $f(\delta)$ equals $1/(1+\exp(-\delta))$, wherein the coordinate $\delta$, once calculated, equals $a_0+a_1 X+a_2 Y+a_3 Z$, wherein the X is a value of the CRP in μg/ml, the Y is a value of the IL-6 in pg/ml and the Z is a value of the TRAIL in pg/ml, wherein each of the $\varepsilon_0$ and the $\varepsilon_1$ is less than 0.5, and wherein $a_0$ is from about −1.05 to about −0.85, $a_1$ is from about 0.025 to about 0.032, $a_2$ is from about 0.004 to about 0.006, and $a_3$ is from about −0.022 to about −0.017.

According to an aspect of some embodiments of the present invention there is provided a method of analyzing biological data, the method comprising:

obtaining biological data containing expression levels of C-reactive protein (CRP), Procalcitonin (PCT), and TNF-related apoptosis-inducing ligand (TRAIL) in the blood of a subject;

calculating a distance between a segment of a curved line and an axis defined by a direction, the distance being calculated at a point over the curved line defined by a coordinate $\delta$ along the direction; and correlating the distance to the presence of, absence of, or likelihood that the subject has, a bacterial infection;

wherein at least 90% of the segment is between a lower bound line $f(\delta)-\varepsilon_0$ and an upper bound line $f(\delta)+\varepsilon_1$, wherein the $f(\delta)$ equals $1/(1+\exp(-\delta))$, wherein the coordinate $\delta$, once calculated, equals $a_0+a_1 X+a_2 Y+a_3 Z$, wherein the X is a value of the CRP in μg/ml, the Y is a value of the PCT in μg/L and the Z is a value of the TRAIL in pg/ml, wherein each of the $\varepsilon_0$ and the $\varepsilon_1$ is less than 0.5, and wherein $a_0$ is from about −0.60 to about −0.48, $a_1$ is from about 0.024 to about 0.31, $a_2$ is from about 0.13 to about 0.16, and $a_3$ is from about −0.025 to about −0.019.

According to an aspect of some embodiments of the present invention there is provided a method of analyzing biological data, the method comprising:

obtaining biological data containing expression levels of Interferon gamma-induced protein 10 (IP-10), Procalcitonin (PCT), and TNF-related apoptosis-inducing ligand (TRAIL) in the blood of a subject;

calculating a distance between a segment of a curved line and an axis defined by a direction, the distance being calculated at a point over the curved line defined by a coordinate $\delta$ along the direction; and correlating the distance to the presence of, absence of, or likelihood that the subject has, a bacterial infection;

wherein at least 90% of the segment is between a lower bound line $f(\delta)-\varepsilon_0$ and an upper bound line $f(\delta)+\varepsilon_0$ wherein the $f(\delta)$ equals $1/(1+\exp(-\delta))$, wherein the coordinate $\delta$, once calculated, equals $a_0+a_1X+a_2Y+a_3Z$, wherein the X is a value of the IP-10 in µg/ml, the Y is a value of the PCT in µg/L and the Z is a value of the TRAIL in pg/ml, wherein each of the $\varepsilon_0$ and the $\varepsilon_1$ is less than 0.5, and wherein $a_0$ is from about 1.42 to about 1.75, $a_1$ is from about 0.00024 to about 0.00031, $a_2$ is from about 0.23 to about 0.29, and $a_3$ is from about −0.038 to about −0.030.

According to an aspect of some embodiments of the present invention there is provided a method of analyzing biological data, the method comprising:

obtaining biological data containing at least expression levels of TNF-related apoptosis-inducing ligand (TRAIL), C-reactive protein (CRP), Interferon gamma-induced protein-10 (IP-10), Interleukin 6 (IL-6) and Procalcitonin (PCT) in the blood of a subject;

applying a non-linear multinomial logistic regression to expression levels of the TRAIL, the CRP, the IP-10 to provide a calculated score;

calculating a distance between a segment of a curved line and an axis defined by a direction, the distance being calculated at a point over the curved line defined by a coordinate $\delta$ along the direction; and correlating the distance to the presence of, absence of, or likelihood that the subject has, a bacterial infection;

wherein at least 90% of the segment is between a lower bound line $f(\delta)-\varepsilon_0$ and an upper bound line $f(\delta)+\varepsilon_0$ wherein the $f(\delta)$ equals $1/(1+\exp(-\delta))$, wherein the coordinate $\delta$, once calculated, equals $a_0+a_1X+a_2Y+a_3Z$, wherein the X is a value of the calculated score, the Y is a value of the IL-6 in pg/L and the Z is a value of the PCT in µg/ml, wherein each of the $\varepsilon_0$ and the $\varepsilon_1$ is less than 0.5, and wherein $a_0$ is from about −3.48 to about −2.84, $a_1$ is from about 4.40 to about 5.39, $a_2$ is from about 0.0041 to about 0.0051, and $a_3$ is from about 0.14 to about 0.18.

According to an aspect of some embodiments of the present invention there is provided a method of analyzing biological data, the method comprising:

obtaining biological data containing expression levels of C-reactive protein (CRP), Interleukin 6 (IL-6), Procalcitonin (PCT), and TNF-related apoptosis-inducing ligand (TRAIL) in the blood of a subject;

calculating a distance between a segment of a curved line and an axis defined by a direction, the distance being calculated at a point over the curved line defined by a coordinate $\delta$ along the direction; and correlating the distance to the presence of, absence of, or likelihood that the subject has, a bacterial infection;

wherein at least 90% of the segment is between a lower bound line $f(\delta)-\varepsilon_0$ and an upper bound line $f(\delta)+\varepsilon_0$ wherein the $f(\delta)$ equals $1/(1+\exp(-\delta))$, wherein the coordinate $\delta$, once calculated, equals $a_0+a_1X+a_2Y+a_3Z+a_4T$, wherein the X is a value of the CRP in µg/ml, the Y is a value of the IL-6 in pg/ml, the Z is a value of the PCT in µg/L and the T is a value of the TRAIL in pg/ml, wherein each of the $\varepsilon_0$ and the $\varepsilon_1$ is less than 0.5, and wherein $a_0$ is from about −1.13 to about −0.92, $a_1$ is from about 0.025 to about 0.031, $a_2$ is from about 0.0045 to about 0.0055, $a_3$ is from about 0.098 to about 0.13 and $a_4$ is from about −0.021 to about −0.016.

According to an aspect of some embodiments of the present invention there is provided a method of analyzing biological data, the method comprising:

obtaining biological data containing expression levels of Interleukin 6 (IL-6), Interferon gamma-induced protein-10 (IP-10), Procalcitonin (PCT), and TNF-related apoptosis-inducing ligand (TRAIL) in the blood of a subject;

calculating a distance between a segment of a curved line and an axis defined by a direction, the distance being calculated at a point over the curved line defined by a coordinate $\delta$ along the direction; and correlating the distance to the presence of, absence of, or likelihood that the subject has, a bacterial infection;

wherein at least 90% of the segment is between a lower bound line $f(\delta)-\varepsilon_0$ and an upper bound line $f(\delta)+\varepsilon_0$ wherein the $f(\delta)$ equals $1/(1+\exp(-\delta))$, wherein the coordinate $\delta$, once calculated, equals $a_0+a_1X+a_2Y+a_3Z+a_4T$, wherein the X is a value of the IL-6 in pg/ml, the Y is a value of the IP-10 in pg/ml, the Z is a value of the PCT in µg/L and the T is a value of the TRAIL in pg/ml, wherein each of the $\varepsilon_0$ and the $\varepsilon_1$ is less than 0.5, and wherein $a_0$ is from about 1.029 to about 1.258, $a_1$ is from about 0.0049 to about 0.0060, $a_2$ is from about 0.00013 to about 0.00017, $a_3$ is from about 0.19 to about 0.24 and $a_4$ is from about −0.033 to about −0.027.

According to an aspect of some embodiments of the present invention there is provided a method of analyzing biological data, the method comprising:

obtaining biological data containing expression levels of C-reactive protein (CRP), Interleukin 6 (IL-6), Interferon gamma-induced protein-10 (IP-10), Procalcitonin (PCT), and TNF-related apoptosis-inducing ligand (TRAIL) in the blood of a subject;

calculating a distance between a segment of a curved line and an axis defined by a direction, the distance being calculated at a point over the curved line defined by a coordinate $\delta$ along the direction; and correlating the distance to the presence of, absence of, or likelihood that the subject has, a bacterial infection;

wherein at least 90% of the segment is between a lower bound line $f(\delta)-\varepsilon_0$ and an upper bound line $f(\delta)+\varepsilon_1$, wherein the $f(\delta)$ equals $1/(1+\exp(-\delta))$, wherein the coordinate $\delta$, once calculated, equals $a_0+a_1X+a_2Y+a_3Z+a_4T+a_5W$, wherein the X is a value of the CRP in µg/ml, wherein the Y is a value of the IL-6 in pg/ml, the Z is a value of the IP-10 in pg/ml, the T is a value of the PCT in µg/L and the W is a value of the TRAIL in pg/ml, wherein each of the $\varepsilon_0$ and the $\varepsilon_1$ is less than 0.5, and wherein $a_0$ is from about −3.08 to about −2.52, $a_1$ is from about 0.10 to about 0.13, $a_2$ is from about 0.038 to about 0.047, $a_3$ is from about 0.008 to about 0.010, $a_4$ is from about −0.17 to about −0.13 and as is from about 0.0044 to about 0.0054.

According to an aspect of some embodiments of the present invention there is provided a method of diagnosing an infection type in a subject comprising measuring the amount of at least two polypeptides selected from the group consisting of TRAIL, CRP, IP10, IL-6 and PCT in a sample derived from the subject, wherein the sample is derived from the subject no more than two days following symptom onset, wherein the amount is indicative of the infection type.

According to an aspect of some embodiments of the present invention there is provided a method of diagnosing an infection in a subject comprising measuring the amount of each of the polypeptides TRAIL, CRP, IP10 and at least one additional polypeptide selected from the group consisting of IL-6 and PCT in a sample derived from the subject, wherein the amount is indicative of the infection.

According to an aspect of some embodiments of the present invention there is provided a method of diagnosing an infection in a subject comprising measuring the amount of each of the polypeptides TRAIL, CRP and IL-6 in a sample derived from the subject, wherein the amount is indicative of the infection.

According to an aspect of some embodiments of the present invention there is provided a kit for diagnosing an infection comprising:

(i) an antibody which specifically detects TRAIL;
(ii) an antibody which specifically detects IP10:
(iii) an antibody which specifically detects CRP; and
(iv) at least one additional antibody which specifically detects IL-6 or PCT.

According to an aspect of some embodiments of the present invention there is provided a kit for diagnosing an infection comprising:

(i) an antibody which specifically detects TRAIL;
(ii) an antibody which specifically detects IL-6:
(iii) an antibody which specifically detects CRP; and
(iv) at least one additional antibody which specifically detects IP10 or PCT.

According to some embodiments of the invention, step (a) is effected prior to steps (b), (c) and (d).

According to some embodiments of the invention, step (a) is effected following steps (b), (c) and (d).

According to some embodiments of the invention, the at least two polypeptides comprises each of TNF-related apoptosis-inducing ligand (TRAIL), C-reactive protein (CRP) and Interferon gamma-induced protein 10 (IP10).

According to some embodiments of the invention, the at least two polypeptides comprises each of TNF-related apoptosis-inducing ligand (TRAIL), C-reactive protein (CRP), Interferon gamma-induced protein 10 (IP10), Interleukin 6 (IL-6) and Procalcitonin (PCT).

According to some embodiments of the invention, when the amount of TRAIL is below a predetermined level, the amount of CRP is above a predetermined level, the amount of IP-10 is below a predetermined level and the amount of PCT is above a predetermined level and the amount of IL-6 is above a predetermined level, the subject is diagnosed as having sepsis.

According to some embodiments of the invention, the at least two polypeptides comprises each of TNF-related apoptosis-inducing ligand (TRAIL), C-reactive protein (CRP) and Interferon gamma-induced protein 10 (IP10).

According to some embodiments of the invention, the at least two polypeptides comprises each of TNF-related apoptosis-inducing ligand (TRAIL), C-reactive protein (CRP), Interferon gamma-induced protein 10 (IP10), Interleukin 6 (IL-6) and Procalcitonin (PCT).

According to some embodiments of the invention, the sample is derived from the subject no more than one day following symptom onset.

According to some embodiments of the invention, the at least two polypeptides comprises each of TNF-related apoptosis-inducing ligand (TRAIL), C-reactive protein (CRP) and Interferon gamma-induced protein 10 (IP10).

According to some embodiments of the invention, the at least two polypeptides comprises each of TNF-related apoptosis-inducing ligand (TRAIL), C-reactive protein (CRP) and Procalcitonin (PCT).

According to some embodiments of the invention, the at least two polypeptides comprises each of TNF-related apoptosis-inducing ligand (TRAIL), C-reactive protein (CRP), Interferon gamma-induced protein 10 (IP10), Interleukin 6 (IL-6) and Procalcitonin (PCT).

According to some embodiments of the invention, the level of the IL-6 and the PCT are taken into account when their concentration passes a threshold level, and are not taken into account otherwise.

According to some embodiments of the invention, the diagnosing is effected using an algorithm in which the weight of the IL-6 and the PCT increase as their concentration increases.

According to some embodiments of the invention, the method comprises measuring the amount of each of the polypeptides TRAIL, CRP, IP10, IL-6 and PCT in the sample.

According to some embodiments of the invention, when the amount of TRAIL is below a predetermined level, the amount of CRP is above a predetermined level, the amount of IP-10 is below a predetermined level and the amount of IL-6 is above a predetermined level, the infection is a bacterial infection or when the amount of TRAIL is below a predetermined level, the amount of CRP is above a predetermined level, the amount of IP-10 is below a predetermined level and the amount of PCT is above a predetermined level, the infection is a bacterial infection.

According to some embodiments of the invention, the amount of TRAIL is below a predetermined level, the amount of CRP is above a predetermined level, the amount of IP-10 is below a predetermined level, the amount of PCT is above a predetermined level and the amount of IL-6 is above a predetermined level, the infection is a bacterial infection.

According to some embodiments of the invention, the sample is derived from the subject no more than two days following symptom onset.

According to some embodiments of the invention, when the amount of TRAIL is below a predetermined level, the amount of CRP is above a predetermined level and the amount of IL-6 is above a predetermined level, the infection is a bacterial infection.

According to some embodiments of the invention, when the amount of TRAIL is above a predetermined level, the amount of CRP is below a predetermined level and the amount of IL-6 is below a predetermined level, the infection is a viral infection.

According to some embodiments of the invention, the method further comprises measuring the amount of IP10 or PCT.

According to some embodiments of the invention, the method further comprises measuring the amount of IP10 and PCT.

According to some embodiments of the invention, the method further comprises measuring the amount of at least one polypeptide set forth in Table 2.

According to some embodiments of the invention, the infection is a viral infection, a bacterial infection or a mixed infection.

According to some embodiments of the invention, the infection is sepsis.

According to some embodiments of the invention, no more than 20 polypeptides are measured.

According to some embodiments of the invention, the no more than 5 polypeptides which are differentially expressed in a statistically significant manner in subjects with a bacterial infection compared to subjects with a viral infection are measured.

According to some embodiments of the invention, the sample is whole blood or a fraction thereof.

According to some embodiments of the invention, the blood fraction sample comprises cells selected from the group consisting of lymphocytes, monocytes and granulocytes.

According to some embodiments of the invention, the blood fraction sample comprises serum or plasma.

According to some embodiments of the invention, the kit comprises antibodies which specifically detect the TRAIL, the IP10, the CRP, the IL-6 and the PCT.

According to some embodiments of the invention, the antibodies are attached to a detectable moiety.

According to some embodiments of the invention, the antibodies are attached to a solid support.

According to some embodiments of the invention, the kit comprises antibodies that specifically detect no more than 10 polypeptides.

According to some embodiments of the invention, the kit comprises antibodies that specifically detect no more than 5 polypeptides.

According to some embodiments of the invention, each of the additional antibodies comprise a detectable label selected from the group consisting of a radioactive label, a fluorescent label, a chemiluminescent label, a colorimetric label and an enzyme.

According to some embodiments of the invention, the enzyme is horseradish peroxidase or alkaline phosphatase.

According to some embodiments of the invention, the each of the antibodies are monoclonal antibodies.

According to some embodiments of the invention, the applying the non-linear multinomial logistic regression comprises calculating a value of probabilistic classification function which, once calculated, equals about $\exp(\xi)/(1+\exp(\xi+\exp(\eta))$, wherein $\xi=b_0+b_1P+b_2P^{0.5}+b_3P^2+b_4Q+b_5R+b_6R^{0.5}$ and $\eta=c_0+c_1P+c_2P^{0.5}+c_3P^2+c_4Q+c_5R+c_6R^{0.5}$, wherein the P is a value of the CRP, the Q is a value of the IP-10, and the R is a value of the TRAIL, and wherein $b_0$ is from about 4.96 to about 6.1, $b_1$ is from about $-0.07$ to about $-0.05$, $b_2$ is from about 1.33 to about 1.64, $b_3$ is from about 0.000031 to about 0.000039, $b_4$ is from about 0.007 to about 0.010, $b_5$ is from about 0.055 to about 0.071, $b_6$ is from about 1.62 to about 1.98, $c_0$ is from about $-0.93$ to about $-0.75$, $c_1$ is from about $-0.054$ to about $-0.044$, $c_2$ is from about 1.02 to about 1.25, $c_3$ is from about $-0.000057$ to about $-0.000046$, $c_4$ is from about 0.0080 to about 0.0098, $c_5$ is from about 0.036 to about 0.045 and $c_6$ is from about 0.054 to about 0.066.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 10A-B. Fuzzy OR models surface plot. The output of the Fuzzy OR model is a likelihood of a bacterial infection as a function of TCP signature (y-axis) and IL-6 concentrations in pg/ml. A. This example depicts the formula "Fuzzy OR formula #5" presented in section "Using Fuzzy OR model to generate improved signatures for distinguishing between bacterial and viral patients" below, using IL-6 cutoff of 250 pg/ml and hill coefficient of 10. B. The surface plot depicted in the figure corresponds to the following formula using different IL-6 cutoffs as indicated:

Figure 1:
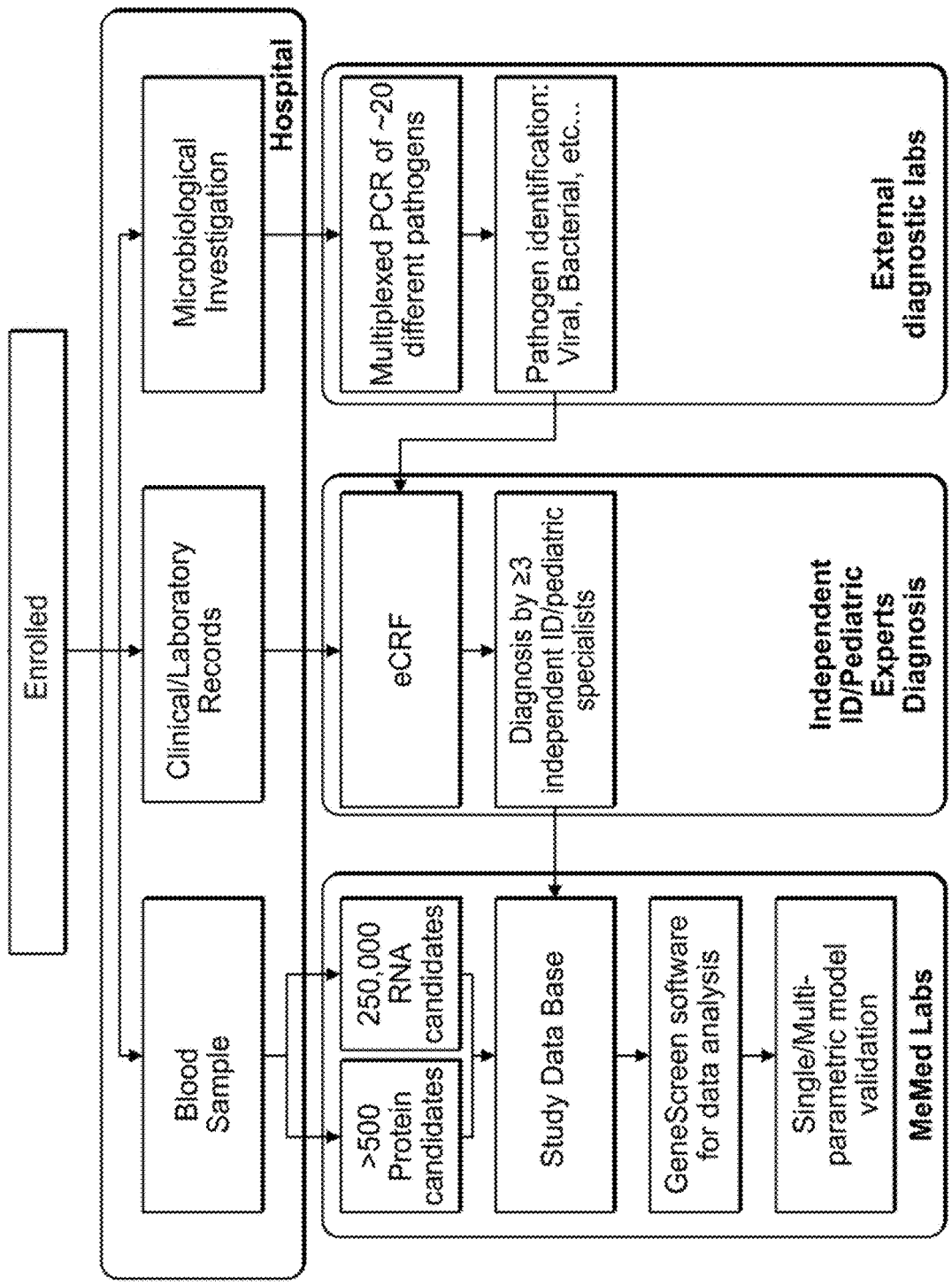
FIG. 1: Clinical study workflow.
Figure 2:
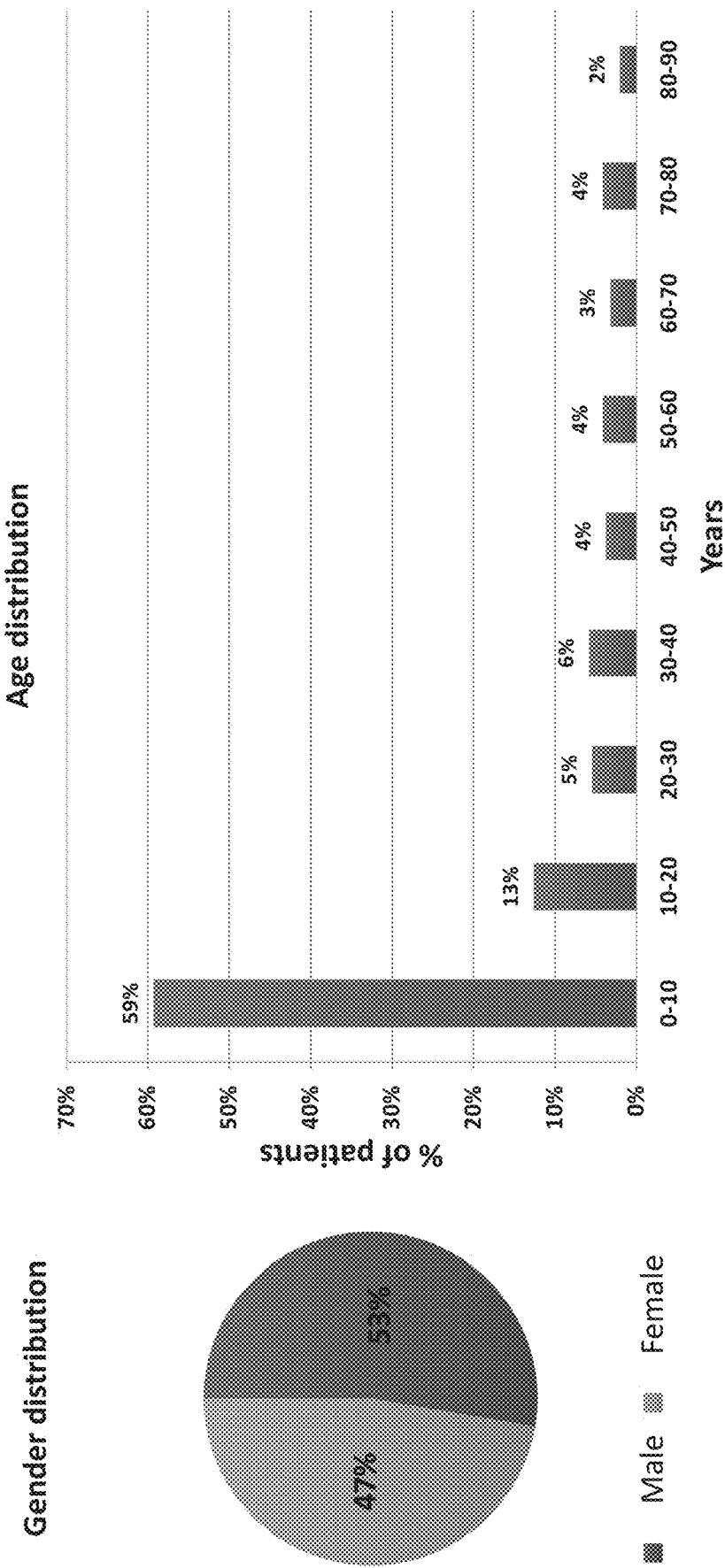
FIG. 2: Distribution of age and gender of the infectious disease patients enrolled in the clinical study (N=948).
Figure 3:
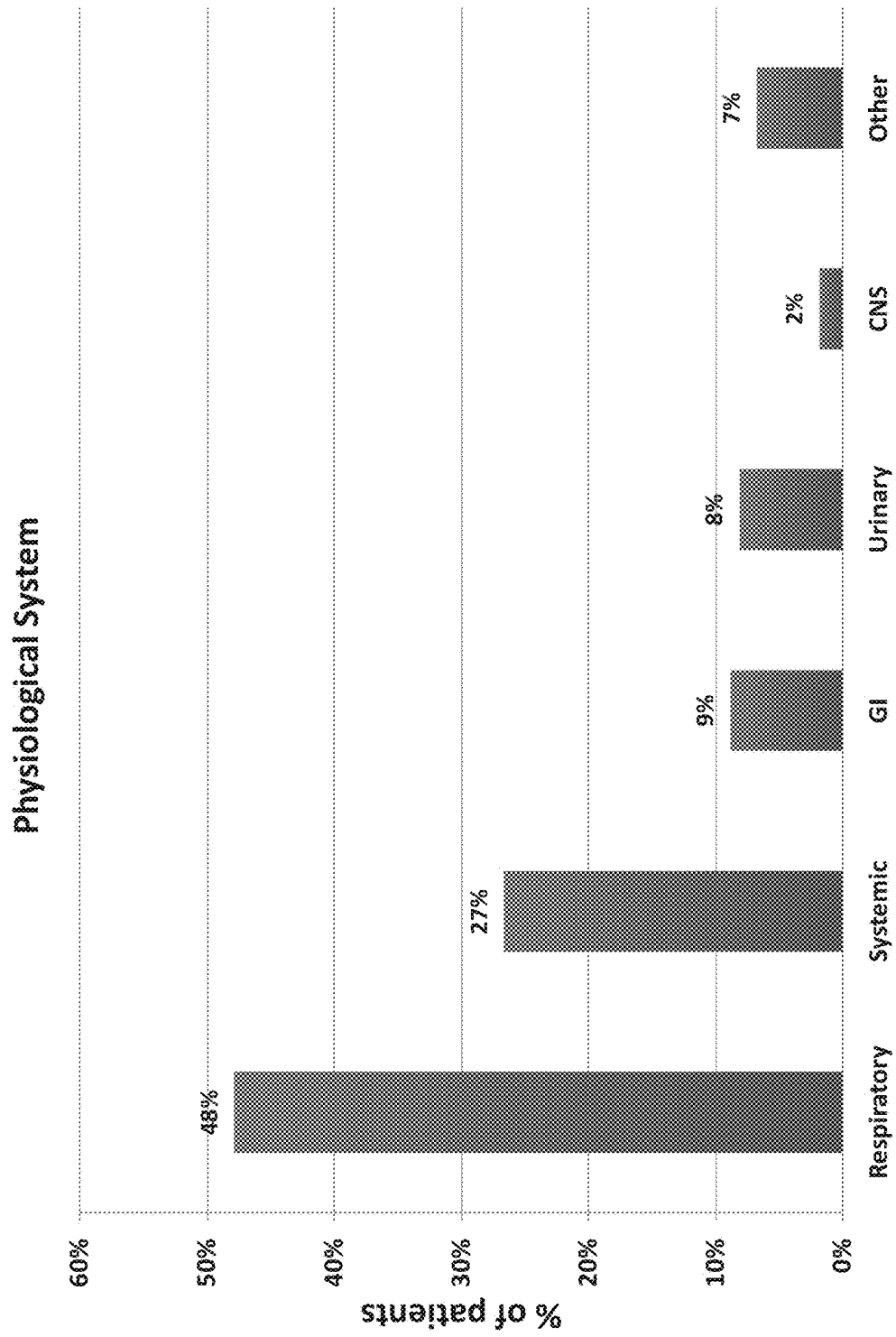
FIG. 3: Distribution of physiological systems of the infectious disease patients enrolled in the clinical study.
Figure 4:
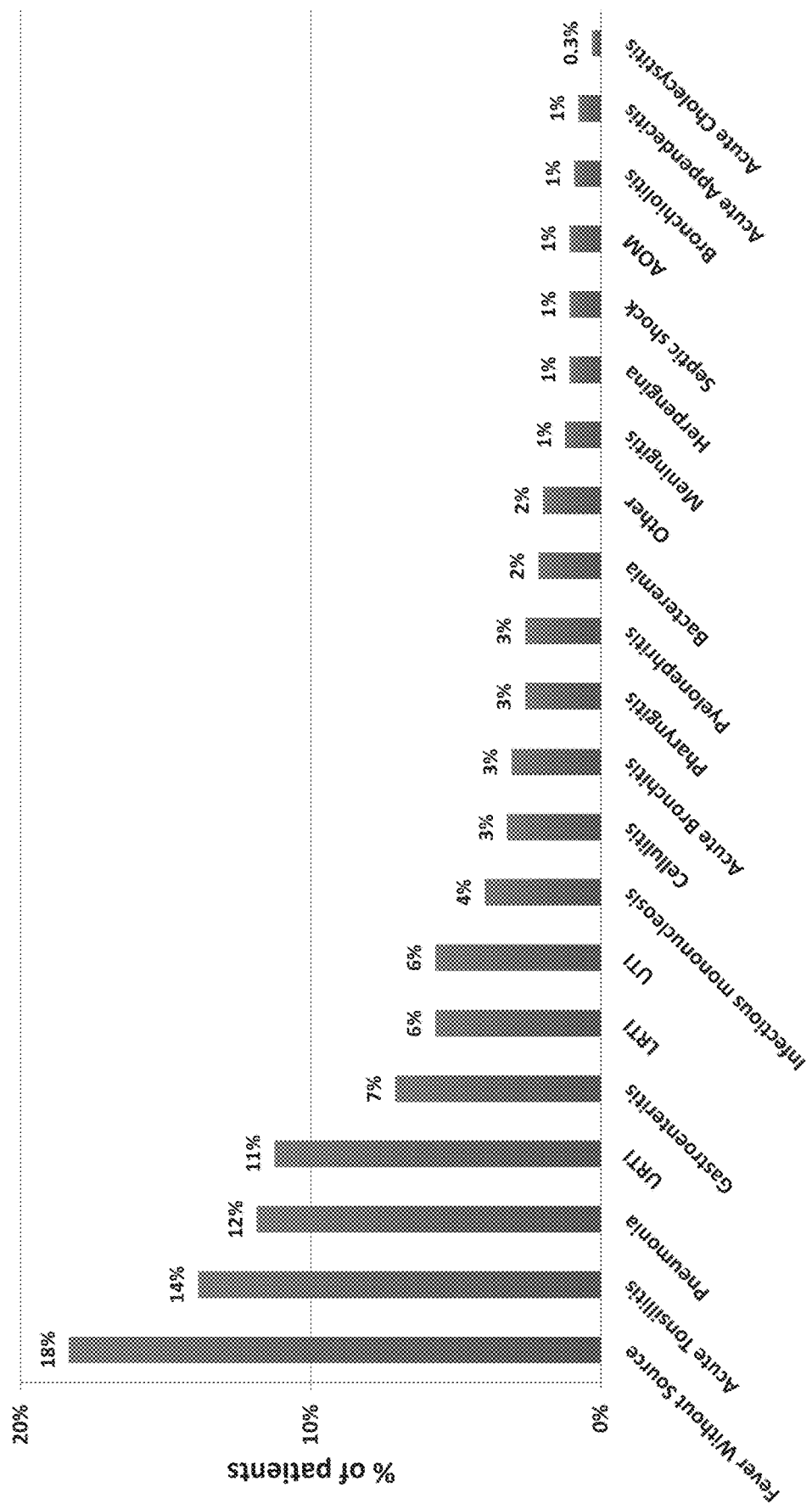
FIG. 4: Distribution of major clinical syndromes of the infectious disease patients enrolled in the clinical study.
Figure 5:
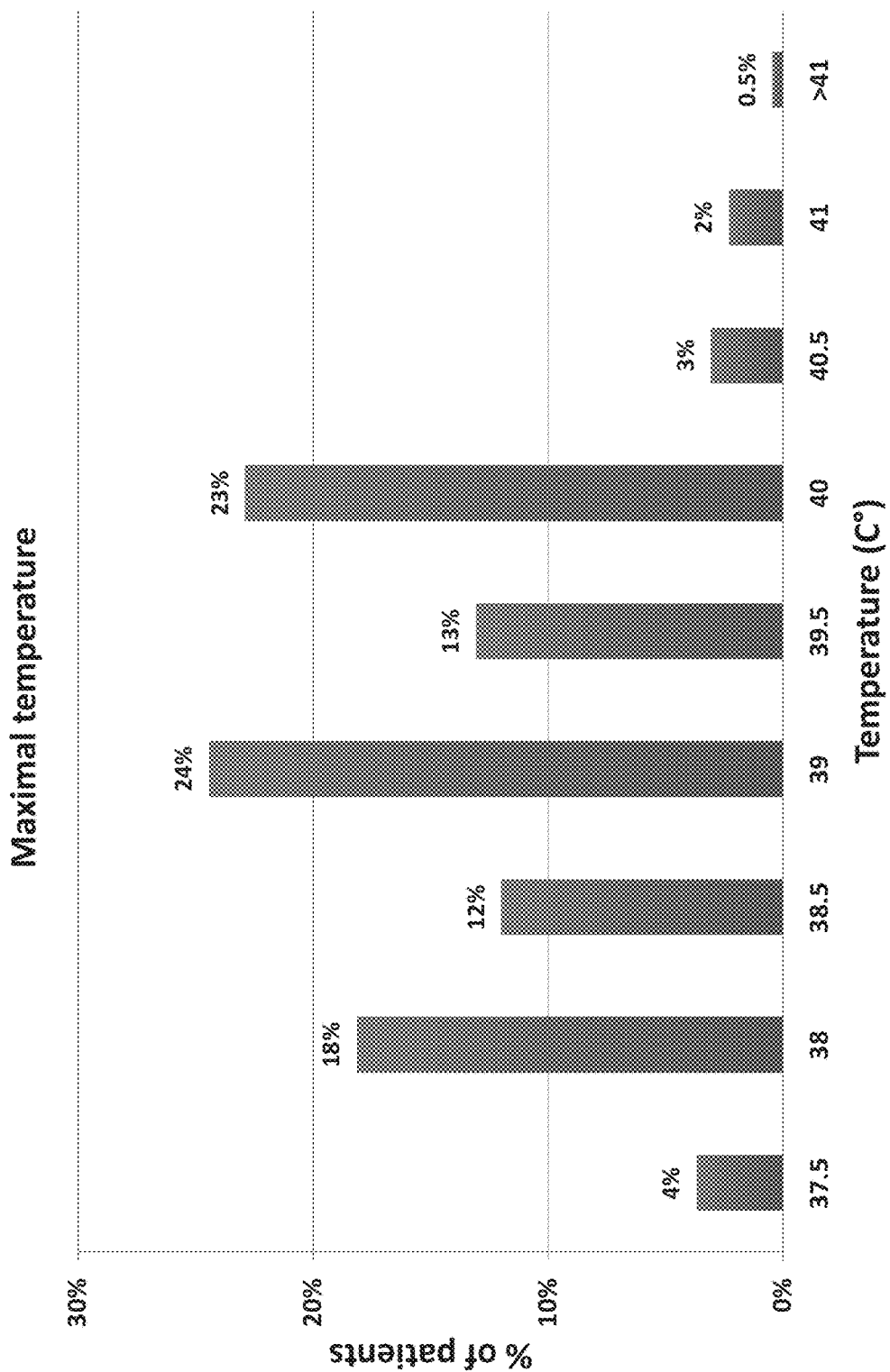
FIG. 5: Distribution of maximal body temperatures of the infectious disease patients enrolled in the clinical study.
Figure 6:
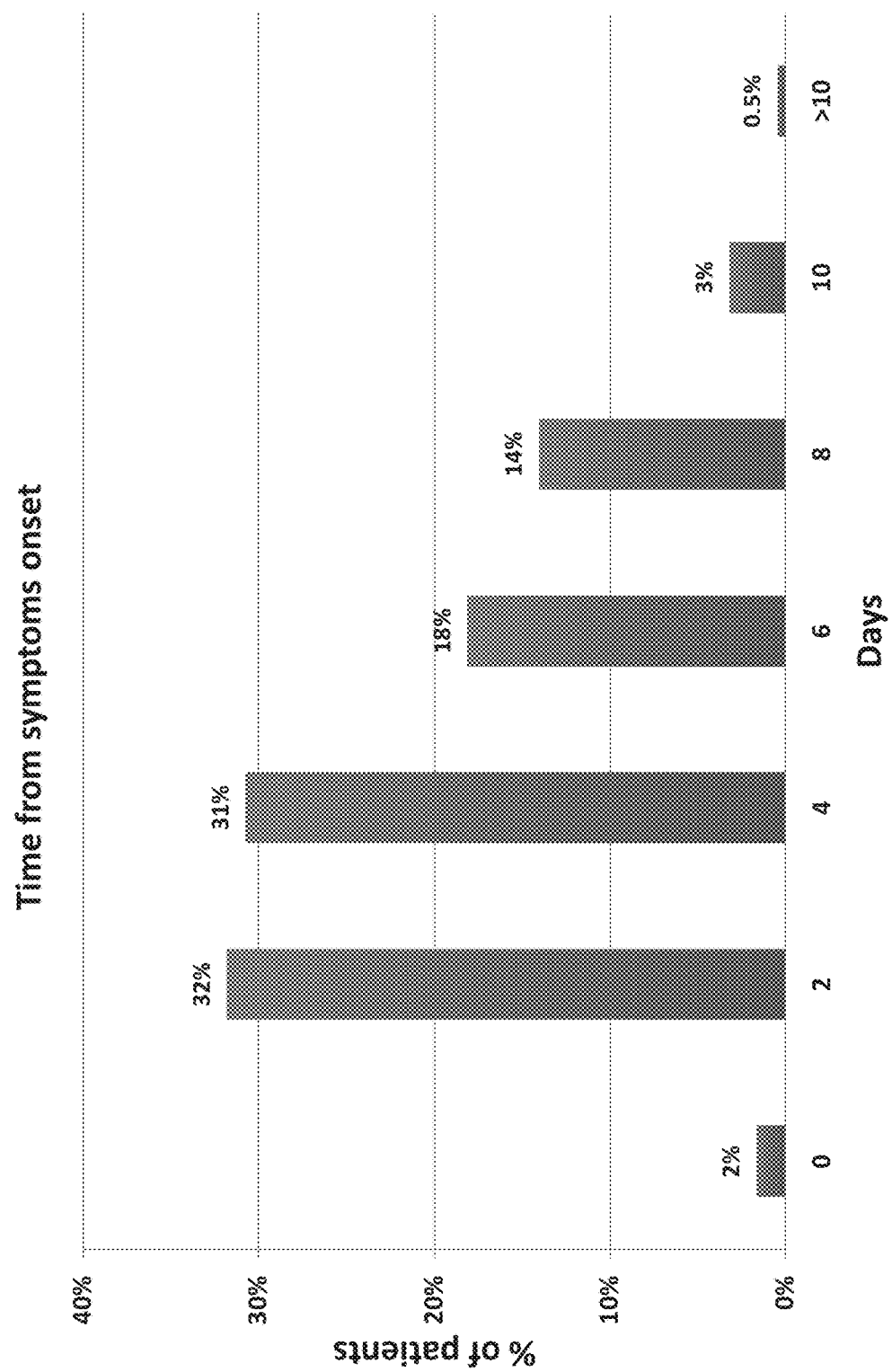
FIG. 6: Distribution of time from initiation of symptoms of the infectious disease patients enrolled in the clinical study.
Figure 7:
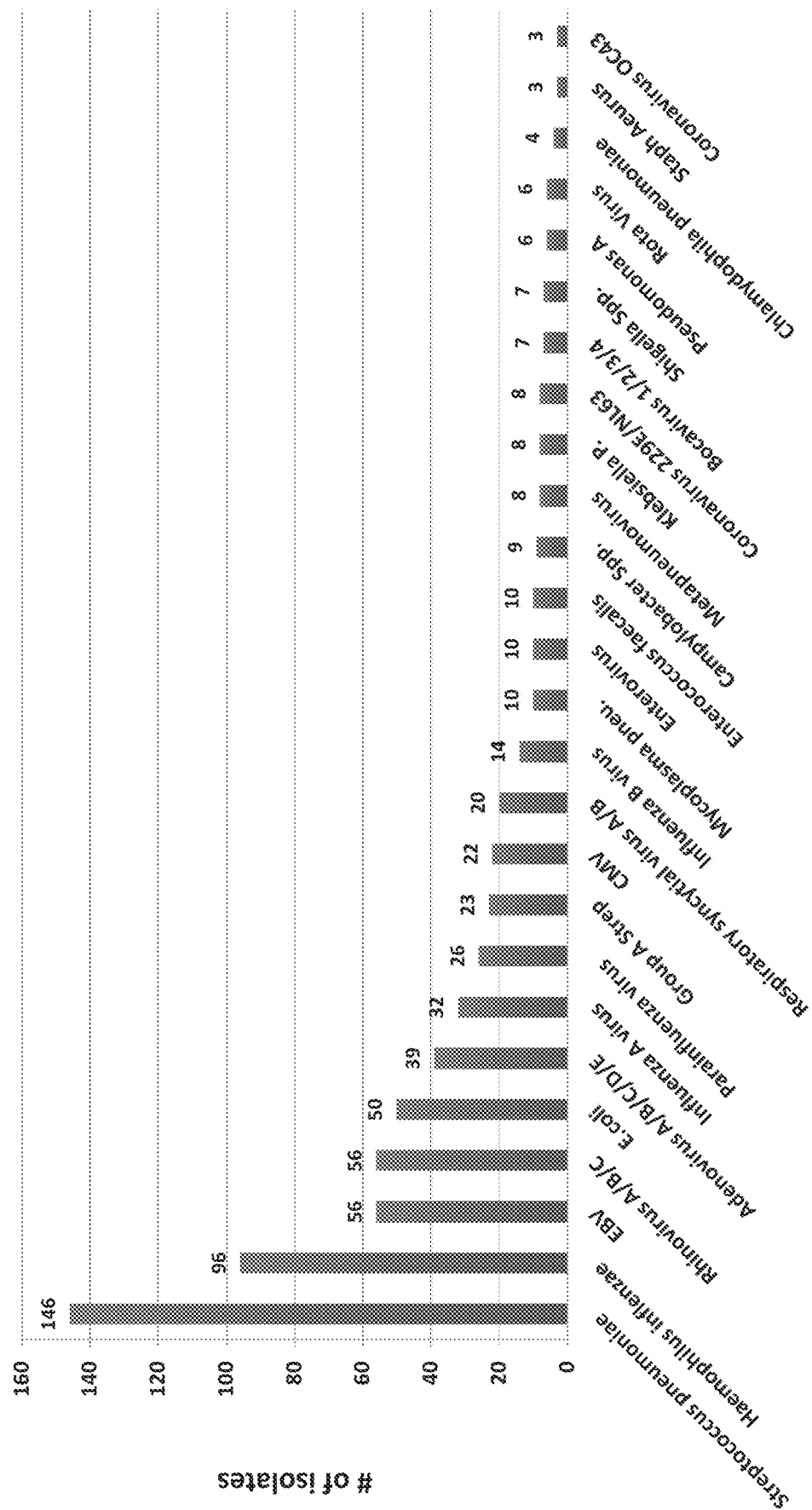
FIG. 7: Pathogen isolated from infectious disease patients enrolled in the clinical study FIGS. 8A-F. Protein temporal dynamics-Protein serum levels measured in patients at different times after symptom onset are depicted in black 'x' (viral), and white 'x' (bacterial). Average serum levels are depicted by solid lines. The dynamics of the following proteins are shown: (A) CRP; (B) IL-6; (C) IP-10; (D) PCT; (E) TRAIL; (F) TCP signature.

$$MaxProb = \max\left(IX_{Prob}, \frac{1}{1+\left(\frac{IL6}{c_{IL6}}\right)^{-h_{IL6}}}\right)$$

FIGS. 11A-D. Fuzzy OR model results—combined score of the TCP signature and IL-6 using the hill-function, when applying different IL-6 cutoffs and hill coefficients as indicated (respectively): (A) 250 pg/ml and 6; (B) 250 pg/ml and 10; (C) 350 pg/ml and 6; (D) 350 pg/ml and 10. The X axis represents the TCP signature score (ranging from 0 to 1, equivalent to 0-100%), and the Y axis represents the IL-6 concentration in pg/ml. The color represents the combined score (likelihood of bacterial infection), wherein white represents a score of 1 and black represents a score of 0 (equivalent to 100% and 0% respectively). The surface lines represent round scores (e.g., 0.95, 0.9, 0.85). Overlaid on the plot are actual values of 378 bacterial (white) and 570 viral (black) patients.

FIGS. 12A-G: Cutoff dependent models. (A) Illustration of a quadrary separation pattern that can separate between bacterial, viral and mixed (bacterial-viral co-infection), generated by applying a single TRAIL and PCT cutoffs as indicated. (B) TRAIL and PCT levels of 378 bacterial (grey)

and 570 viral (black) patients. Dashed lines represent an example of TRAIL cutoff of 75 pg/ml, and an example of PCT cutoff of 0.5 µg/L. Diagnostic labels were determined by panel of experts as described in the Examples section. (C) Illustration of the different diagnostic labels (viral, bacterial, mixed and healthy), generated by applying TRAIL and PCT cutoffs. TRAIL cutoff 1 (low levels) is used to rule in bacterial infections and TRAIL cutoff 2 (high levels) is used to rule in viral infections. Integration of TRAIL and PCT cutoffs generates different diagnostic results: (i) a pure bacterial infection is indicated in cases wherein PCT is lower than PCT cutoff 1 AND TRAIL is lower than TRAIL cutoff 1; OR in cases wherein PCT is higher than PCT cutoff 1 AND TRAIL is lower than TRAIL cutoff 2; (ii) a pure viral infection is indicated in cases wherein PCT is lower than PCT cutoff 1 AND TRAIL is higher than TRAIL cutoff 2; (iii) mixed bacterial-viral co-infection is indicated in cases wherein PCT is higher than PCT cutoff 1 AND TRAIL is higher than TRAIL cutoff 2; (iv) healthy (or non-infectious) condition is indicated in cases wherein PCT is lower than PCT cutoff 1 AND TRAIL is higher than TRAIL cutoff 1 but is lower than TRAIL cutoff 2. (D) TRAIL and PCT levels of 378 bacterial (dark grey), 570 viral (black), and 109 non-infectious (control; black) patients. Dashed lines represent an example of TRAIL cutoff 1 of 50 pg/ml, TRAIL cutoff 2 of 100 pg/ml, and an example of PCT cutoff of 0.5 µg/L. Diagnostic labels were determined by panel of experts as described in the Examples section. (E) A classifier for distinguishing between bacterial and viral patients based on the PCT/TRAIL ratio.

TRAIL and PCT levels of 378 bacterial (grey), 570 viral (black) patients are presented. Diagnostic labels were determined by panel of experts as described in the Examples section. The cutoff for separating between bacterial and viral patients is represented by the bold line that equals PCT/TRAIL=0.05. This classifier will label a patient as bacterial in case PCT/TRAIL>0.05 and as viral in case PCT/TRAIL<0.05. (F) A classifier for distinguishing between bacterial and viral patients based on the PCT/TRAIL ratio. TRAIL and PCT levels of 378 bacterial (grey), 570 viral (black) patients are presented. Diagnostic labels were determined by panel of experts as described in the Examples section. The cutoff for separating between bacterial and viral patients is represented by the bold line that equals PCT/TRAIL=0.02. This classifier will label a patient as bacterial in case PCT/TRAIL>0.02 and as viral in case PCT/TRAIL<0.02. (G) A classifier for distinguishing between bacterial and viral patients based on the PCT/TRAIL ratio. TRAIL and PCT levels of 378 bacterial (grey), 570 viral (black) patients are presented. Diagnostic labels were determined by panel of experts as described in the Examples section. The cutoff for separating between bacterial and viral patients is represented by the bold line that equals PCT/TRAIL=0.01. This classifier will label a patient as bacterial in case PCT/TRAIL>0.01 and as viral in case PCT/TRAIL<0.01.

Figure 13:
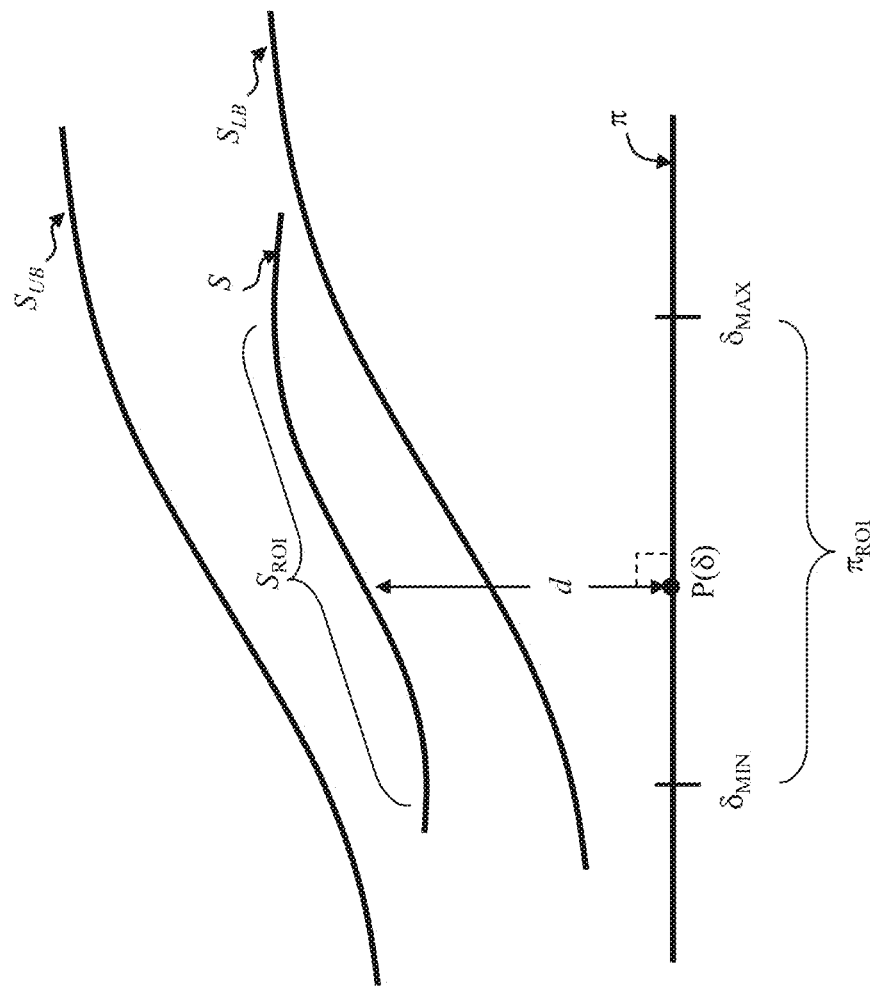
Figure 14:
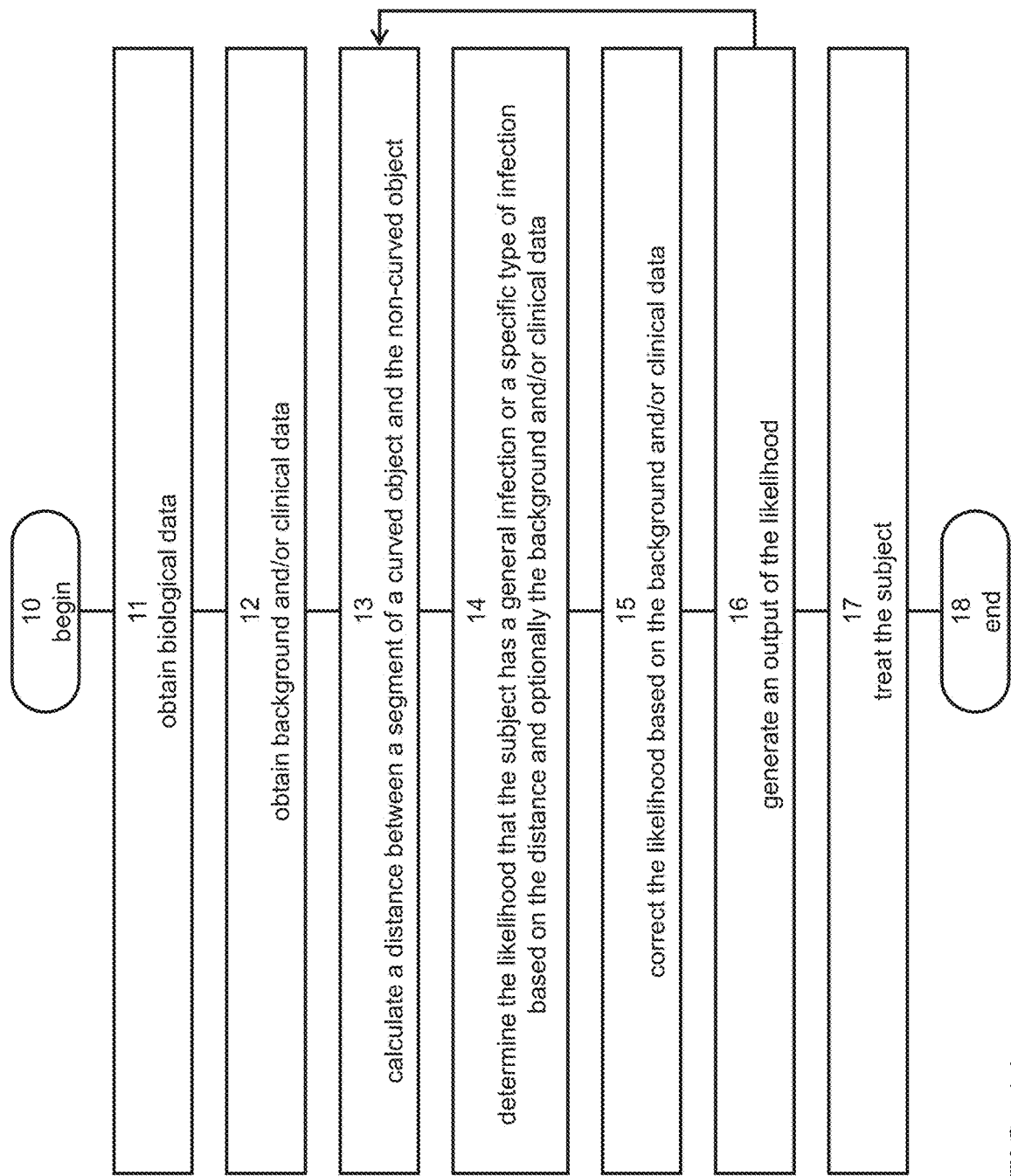
Figure 16:
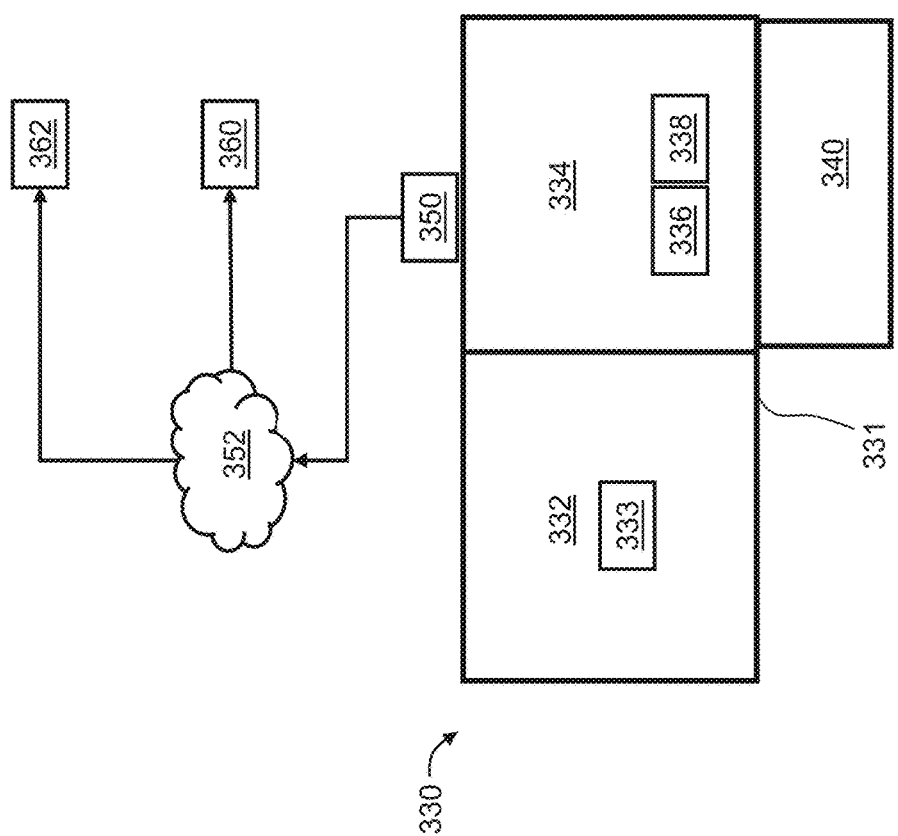

FIG. 13 is a schematic illustration of geometrical objects that can be used for determining a likelihood, according to some embodiments of the present invention;

FIG. 14 is a flowchart diagram of a method suitable for analyzing biological data obtained from a subject, according to some embodiments of the present invention;

FIGS. 15A-D a schematic illustrations of a procedure for obtaining a smooth version of a segment of a curved object, according to some embodiments of the present invention;

FIG. 16 is a schematic illustration of a block diagram of a system for analyzing biological data, according to some embodiments of the present invention; and FIGS. 17A and 17B are schematic illustrations of a block diagram of a system for analyzing biological data, in embodiments of the invention in which the system comprises a network interface (FIG. 17A) and a user interface (FIG. 17B).

DESCRIPTION OF SPECIFIC EMBODIMENTS OF THE INVENTION

The present invention, in some embodiments thereof, relates to the identification of signatures and determinants associated with infections. The signatures may be used to distinguish between bacterial and viral infections and also to distinguish between sepsis and non-infectious systemic inflammatory response syndrome (SIRS) and to distinguish between an infective exacerbation state and a non-infective exacerbation state in patients with chronic obstructive pulmonary disease (COPD).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Methods of distinguishing between bacterial and viral infections by analyzing protein determinants have been disclosed in International Patent Application WO2013/117746, to the present inventors. Seeking to expand the number and type of determinants that can aid in accurate diagnosis, the present inventors have now carried out additional experiments and have identified other determinants that can be used for this aim.

Correct identification of bacterial patients is of high importance as these patients require antibiotic treatment and in some cases more aggressive management (hospitalization, additional diagnostic tests etc). Misclassification of bacterial patients increases the chance of morbidity and mortality. Therefore, increasing the sensitivity of a biomarker or diagnostic test that distinguishes between bacterial and viral infections may be desired, even though specificity may be reduced.

Whilst reducing the present invention to practice, the present inventors noted that the markers PCT and IL-6 increase the sensitivity of a previously disclosed signature—TRAIL, CRP and IP-10 (referred to herein as the TCP signature). More specifically, the present inventors have shown that PCT and IL-6 provide a temporal dynamic pattern that complements the TCP signature which is particularly useful in diagnosing infections at a very early stage.

In some embodiments, the TCP signature is calculated as one or more probabilistic classification functions which receive the values of the expression of the TRAIL, CRP and IP-10, and output a score. Based on the type of the respective probabilistic classification function, the score can represent the likelihood that the subject has, a viral infection, a bacterial infection or has no infection. A probabilistic classification function that returns a score that represents the likelihood that the subject has a viral infection can be calculated as $\exp(\eta)/(1+\exp(\xi)+\exp(\eta))$, a probabilistic classification function that returns a score that represents the likelihood that the subject has a bacterial infection can be calculated as $\exp(\xi)/(1+\exp(\xi)+\exp(\eta))$, and a probabilistic classification function that returns a score that represents the likelihood that the subject has no infection can be calculated as $1/(1+\exp(\xi+\exp(\eta)))$, where $\xi=b_0+b_1P+b_2P^{0.5}+b_3P^2+b_4Q+b_5R+b_6R^{0.5}$ and $1=c_0+c_1P+c_2P^{0.5}+c_3P^2+c_4Q+c_5R+c_6R^{0.5}$, where P is a value of CRP, Q is a value of IP-10, and R is a value of TRAIL, and where $b_0$ is from about 4.96 to about 6.1, $b_1$ is from about −0.07 to about −0.05, $b_2$ is from about 1.33 to about 1.64, $b_3$ is from about 0.000031 to about 0.000039, $b_4$ is from about 0.007 to about 0.010, $b_5$ is from about 0.055 to about 0.071, $b_6$ is from about 1.62 to about 1.98, $c_0$ is from about −0.93 to about −0.75, $c_1$ is from about −0.054 to about −0.044, $c_2$ is from about 1.02 to about 1.25, $c_3$ is from about −0.000057 to about −0.000046, $c_4$ is from about 0.0080 to about 0.0098, $c_5$ is from about 0.036 to about 0.045 and $c_6$ is from about 0.054 to about 0.066. More preferred values for the parameters $b_0, \ldots, b_6$ and $c_0, \ldots, c_6$ are provided in Table 3, below.

Furthermore, the present inventors predict that the TCP signature together with PCT and/or IL-6 is useful for distinguishing between additional diseases states such as between a non-infective exacerbation state and an infective exacerbation state in chronic obstructive pulmonary disease (COPD) patients and between sepsis and non-infective systemic inflammatory response syndrome (SIRS).

Thus, according to a first aspect of the present invention there is provided a method of diagnosing an infection in a subject comprising measuring the amount of each of the polypeptides TRAIL, CRP, IP10 and at least one additional polypeptide selected from the group consisting of IL-6 and PCT in a sample derived from the subject, wherein the amount is indicative of the infection type.

According to another aspect of the present invention there is provided a method of diagnosing an infection in a subject comprising measuring the amount of each of the polypeptides TRAIL, CRP and IL-6 in a sample derived from the subject, wherein the amount is indicative of the infection.

The methods disclosed herein are used to identify subjects with an infection or a specific infection type. By type of infection it is meant to include bacterial infections, viral infections, mixed infections, no infection (i.e., non-infectious). More specifically, some methods of the invention are used to distinguish subjects having a bacterial infection, a viral infection, a mixed infection (i.e., bacterial and viral co-infection), patients with a non-infectious disease and healthy individuals. Some methods of the present invention can also be used to monitor or select a treatment regimen for a subject who has a an infection, and to screen subjects who have not been previously diagnosed as having an infection, such as subjects who exhibit risk factors developing an infection. Some methods of the present invention are used to identify and/or diagnose subjects who are asymptomatic for an infection. "Asymptomatic" means not exhibiting the traditional signs and symptoms.

Thus, the infection type may be a bacterial infection, a viral infection or a mixed infection.

In various aspects the method distinguishes a virally infected subject from either a subject with non-infectious disease or a healthy subject; a bacterially infected subject, from either a subject with non-infectious disease or a healthy subject; a subject with an infectious disease from either a subject with an non-infectious disease or a healthy subject; a bacterially infected subject from a virally infected subject; a mixed infected subject from a virally infected subject; a mixed infected subject from a bacterially infected subject and a bacterially or mixed infected and subject from a virally infected subject.

A mixed infected subject refers to a subject having a bacterial and viral co-infection.

The infection may be an acute or chronic infection.

A chronic infection is an infection that develops slowly and lasts a long time. Viruses that may cause a chronic infection include Hepatitis C and HIV. One difference between acute and chronic infection is that during acute infection the immune system often produces IgM+ antibodies against the infectious agent, whereas the chronic phase of the infection is usually characteristic of IgM−/IgG+ antibodies. In addition, acute infections cause immune mediated necrotic processes while chronic infections often cause inflammatory mediated fibrotic processes and scaring (e.g. Hepatitis C in the liver). Thus, acute and chronic infections may elicit different underlying immunological mechanisms.

As used herein, the term "infection" refers to a state caused by an infectious agent of viral or bacterial origin. The bacterial infection may be the result of gram-positive, gram-negative bacteria or atypical bacteria.

The term "Gram-positive bacteria" are bacteria that are stained dark blue by Gram staining. Gram-positive organisms are able to retain the crystal violet stain because of the high amount of peptidoglycan in the cell wall.

The term "Gram-negative bacteria" are bacteria that do not retain the crystal violet dye in the Gram staining protocol.

The term "Atypical bacteria" are bacteria that do not fall into one of the classical "Gram" groups. They are usually, though not always, intracellular bacterial pathogens. They include, without limitations, Mycoplasmas spp., *Legionella* spp. Rickettsiae spp., and Chlamydiae spp.

In one embodiment, the level of the determinant may be used to rule in an infection type. In another embodiment, the level of the determinant may be used to rule out an infection type.

By "ruling in" an infection it is meant that the subject has that type of infection.

By "ruling out" an infection it is meant that the subject does not have that type of infection.

The subjects of this aspect of the present invention may present with a variety of pathogens including, but not limited to Adenovirus, Coronavirus, Parainfluenza virus, Influenza A virus, Influenza B virus, Respiratory syncytial virus A/B, *Chlamydophila* pneumoniae, *Mycoplasma pneumoniae*, *Legionella pneumophila*, Rota Virus, *Staphylococcus aureus, Streptococcus pneumoniae*, Astrovirus, Enteric Adenovirus, Norovirus G I and G II, Bocavirus 1/2/3/4, Enterovirus, CMV virus, EBV virus, Group A Strep, or *Escherichia coli*.

In one embodiment, the method is used to distinguish between non-infective Systemic inflammatory response syndrome (SIRS) and sepsis.

SIRS is a serious condition related to systemic inflammation, organ dysfunction, and organ failure. It is defined as 2 or more of the following variables: fever of more than 38° C. (100.4° F.) or less than 36° C. (96.8° F.); heart rate of more than 90 beats per minute; respiratory rate of more than 20 breaths per minute or arterial carbon dioxide tension ($PaCO_2$) of less than 32 mm Hg; abnormal white blood cell count (>12,000/µL or <4,000/µL or >10% immature [band] forms). SIRS is nonspecific and can be caused by ischemia, inflammation, trauma, infection, or several insults combined. Thus, SIRS is not always related to infection.

Sepsis is a life-threatening condition that is caused by inflammatory response to an infection. The early diagnosis of sepsis is essential for clinical intervention before the disease rapidly progresses beyond initial stages to the more severe stages, such as severe sepsis or septic shock, which are associated with high mortality. Current diagnostics are limited in their ability to distinguish between non-infective SIRS and sepsis. Therefore, there is a need for new biomarkers or combinations of biomarkers that can provide added value in the accurate and timely diagnosis of sepsis.

According to this embodiment, sepsis may be diagnosed as the presence of SIRS criteria in the presence of a known infection.

Thus, according to one aspect, there is provided a method of distinguishing between sepsis and non-infective systemic inflammatory response syndrome (SIRS) comprising measuring the amount of at least two polypeptides selected from the group consisting of TNF-related apoptosis-inducing ligand (TRAIL), C-reactive protein (CRP), Interferon gamma-induced protein 10 (IP10), Interleukin 6 (IL-6) and Procalcitonin (PCT) in a sample derived from the subject, wherein said amount is indicative of sepsis or non-infective SIRS.

Particular combinations of polypeptides are described herein below.

According to this aspect the subject that is tested has been diagnosed with SIRS. The method that is carried out is used to determine if the SIRS is infective (i.e. sepsis) or non-infective.

In another embodiment, sepsis is diagnosed in a subject suspected of having an infection and which fulfils each of the three criteria:

Respiratory rate greater or equal to_22/min

Altered mentation (e.g. a Glasgow coma score of less than 15)

Systolic blood pressure lower than or equal to_100 mmHg.

Further criteria for diagnosing sepsis are disclosed in Singer et al. 2016, 315(8):801-810 JAMA.

Thus, according to another aspect of the present invention there is provided a method of ruling in sepsis in a subject suspected of having in infection comprising:

(a) measuring the amount of at least two polypeptides selected from the group consisting of TNF-related apoptosis-inducing ligand (TRAIL), C-reactive protein (CRP), Interferon gamma-induced protein 10 (IP10), Interleukin 6 (IL-6) and Procalcitonin (PCT) in a sample derived from the subject;

(b) measuring the respiratory rate of the subject;

(c) analyzing the mental state of the subject; and (d) measuring the blood pressure of the subject;

wherein when each of steps are indicative of sepsis, sepsis is ruled in.

Particular combinations of polypeptides are described herein below.

It will be appreciated that steps (b), (c) and (d) may be carried out as part of determining the SOFA score (originally the Sepsis-related Organ Failure Assessment; Vincent J. L et al Intensive Care Med. 1996; 22(7):707-710) of a subject.

In one embodiment, step (a) is carried out in order to confirm the subject has an infection. Only when subjects have a confirmed infection are steps (b), (c) and (d) carried out to confirm sepsis.

In another embodiment, the subject has a suspected infection, steps (b), (c) ad (d) are carried out to rule in sepsis; and step (a) is carried out to corroborate the diagnosis.

The present inventors contemplate analyzing the amount of at least two polypeptides selected from the group consisting of TNF-related apoptosis-inducing ligand (TRAIL), C-reactive protein (CRP), Interferon gamma-induced protein 10 (IP10), Interleukin 6 (IL-6) and Procalcitonin (PCT) in a sample derived from the subject in order to confirm that the subject has an infection.

In another aspect, sepsis is ruled in a subject suspected of having an infection when his SOFA score is above 2.

In one embodiment, analyzing the amount of at least two polypeptides selected from the group consisting of TNF-related apoptosis-inducing ligand (TRAIL), C-reactive protein (CRP), Interferon gamma-induced protein 10 (IP10), Interleukin 6 (IL-6) and Procalcitonin (PCT) in a sample derived from the subject is carried out in order to confirm the subject has an infection. Only when subjects have a confirmed infection is the SOFA analysis carried out to diagnose sepsis (when the subject has a SOFA score of more than or equal to 2, the subject is diagnosed with sepsis).

Alternatively, a SOFA analysis is carried out to diagnose sepsis. Analyzing the amount of at least two polypeptides selected from the group consisting of TNF-related apoptosis-inducing ligand (TRAIL), C-reactive protein (CRP), Interferon gamma-induced protein 10 (IP10), Interleukin 6 (IL-6) and Procalcitonin (PCT) in a sample derived from the subject is carried out in order to confirm the subject has the sepsis.

In another embodiment, the method is used to discriminate between bacterial and viral etiologies in patients with chronic obstructive pulmonary disease (COPD) exacerbation.

In still another embodiment, the method is used to distinguish between an infective exacerbation state and a non-infective exacerbation state of chronic obstructive pulmonary disease (COPD) in a subject.

Chronic obstructive pulmonary disease (COPD) is an obstructive, inflammatory lung disease characterized by long-term poor airflow. The main symptoms include shortness of breath and cough with sputum production. COPD is a progressive disease, worsening over time.

An exacerbation of COPD may be defined as an event in the natural course of the disease characterized by a change in the patient's baseline dyspnea, cough, and/or sputum that is beyond normal day-to-day variations. The exacerbation is typically acute. It may present with signs of increased work of breathing such as fast breathing, a fast heart rate, sweating, active use of muscles in the neck, a bluish tinge to the skin, and confusion or combative behavior in very severe exacerbations. Crackles may also be heard over the lungs on examination with a stethoscope.

Particular combinations of polypeptides are described herein below.

The subjects (e.g. children) may present with a particular clinical syndrome—for example, low respiratory tract infection (LRTI) infection, upper respiratory tract infection (URTI) or a serious bacterial infection (SBI) such as UTI (urinary tract infections), septic shock, bacteremia, pneumonia or meningitis.

"Measuring" or "measurement," or alternatively "detecting" or "detection," means assessing the presence, absence, quantity or amount (which can be an effective amount) of the determinant within a clinical or subject-derived sample, including the derivation of qualitative or quantitative concentration levels of such determinants.

A "sample" in the context of the present invention is a biological sample isolated from a subject and can include, by way of example and not limitation, whole blood, serum, plasma, saliva, mucus, breath, urine, CSF, sputum, sweat, stool, hair, seminal fluid, biopsy, rhinorrhea, tissue biopsy, cytological sample, platelets, reticulocytes, leukocytes, epithelial cells, or whole blood cells.

In a particular embodiment, the sample is a blood sample—e.g. serum or a sample comprising blood cells. In a particular embodiment, the sample is depleted of red blood cells.

In one embodiment, the sample is derived from the subject no more ten days following symptom onset, no more than five days following symptom onset, no more than four days following symptom onset, no more than three days following symptom onset, no more than two days following symptom onset or preferably no more than one day following symptom onset.

The sample may be fresh or frozen.

Other contemplated combinations are provided herein below:

TRAIL, CRP, IP-10 and PCT;
TRAIL, IP-10 and PCT;
TRAIL, CRP, IP-10 and IL-6;
TRAIL, CRP, IP-10, PCT and IL-6;
TRAIL, CRP and PCT;
TRAIL, CRP and IL-6;
TRAIL, CRP, PCT and IL-6

Information regarding the above mentioned polypeptides is provided in Table 1, herein below.

TABLE 1

| Protein symbol | Full Gene Name | RefSeq DNA sequence | RefSeq proteins |
|---|---|---|---|
| CRP | C-reactive protein, pentraxin-related | NC_000001.11 NT_004487.20 NC_018912.2 | NP_000558.2 |
| TRAIL | Tumor necrosis factor superfamily member 10 | NC_000003.12 NC_018914.2 NT_005612.17 | NP_001177871.1 NP_001177872.1 NP_003801.1 |
| IP-10 | Chemokine (C—X—C motif) ligand 10 | NC_000004.12 NC_018915.2 NT_016354.20 | NP_001556.2 |
| Procalcitonin (PCT) | Calcitonin-related polypeptide alpha | NC_000011.10 NC_018922.2 NT_009237.19 | NP_001029124.1 NP_001029125.1 NP_001732.1 |
| IL-6 | Interleukin 6 | NC_000007.14 NT_007819.18 NC_018918.2 | NP_000591.1 |

A "subject" in the context of the present invention may be a mammal (e.g. a human, dog, cat, horse, cow, sheep, pig or goat). According to another embodiment, the subject is a bird (e.g. chicken, turkey, duck or goose). According to a particular embodiment, the subject is a human. The subject can be male or female. The subject may be an adult (e.g. older than 18, 21, or 22 years or a child (e.g. younger than 18, 21 or 22 years). In another embodiment, the subject is an adolescent (between 12 and 21 years), an infant (29 days to less than 2 years of age) or a neonate (birth through the first 28 days of life).

The subject can be one who has been previously diagnosed or identified as having an infection, and optionally has already undergone, or is undergoing, a therapeutic intervention for the infection. Alternatively, a subject can also be one who has not been previously diagnosed as having an infection. For example, a subject can be one who exhibits one or more risk factors for having an infection.

According to a particular embodiment, the subject does not show signs of having had a heart attack (e.g. has a normal level of creatine kinase, troponin or serum myoglobin, and/or has a normal ECG or EKG).

In one embodiment, the subject is one which has undergone a trauma (e.g. car accident or combat related trauma) and/or has undergone a surgical procedure.

As mentioned, in order to determine the type of infection, the amount of each of the following polypeptides are determined: TRAIL, CRP, IP10, together with either IL-6 and/or PCT.

Alternatively, in order to determine the type of infection, the amount of TRAIL, CRP and IL-6 are measured in a sample derived from the subject, wherein the amount is indicative of the infection type.

Exemplary ranges of the mentioned polypeptides in bacterial and viral patients include without limitation:

CRP—CRP levels of 0-40 µg/ml are usually indicative of a viral infection, while 40-400 µg/ml are usually indicative of a bacterial infection. Bacterial infection can usually be ruled in if CRP levels are higher than 50, 60, 70 or more preferably 80 µg/ml, and ruled out if CRP levels are lower than 30 and more preferably 20 µg/ml.

TRAIL—TRAIL levels of 100-1000 pg/ml are usually indicative of a viral infection, while 0-85 pg/ml are usually indicative of a bacterial infection. Bacterial infection can usually be ruled in if TRAIL levels are lower than 85 pg/ml, 70 pg/ml, 60 pg/ml or more preferably 50 pg/ml, and ruled out if TRAIL levels are higher than 100 pg/ml.

IP-10—IP-10 levels of 300-2000 pg/ml are usually indicative of a viral infection, while 160-860 pg/ml are usually indicative of a bacterial infection. Viral infection can usually be ruled in if IP10 levels are higher than 800 pg/ml, and ruled out if IP10 levels are lower than 300 pg/ml.

PCT—PCT levels higher than 0.5 µg/L are usually indicative of a bacterial infection.

IL-6—IL-6 levels higher than 100 pg/ml are usually indicative of a bacterial infection.

CRP:

C-reactive protein; additional aliases of CRP include without limitation RP11-419N10.4 and PTX1.

An exemplary amino acid sequence of human CRP is set forth below in SEQ ID NO: 1.

The level of CRP typically increases in infections (as compared to non-infectious diseases), with the level of CRP being higher in bacterial infections as opposed to viral infections.

Thus, when the level of CRP is above a predetermined level, it is indicative that the infection is a bacterial infection and a bacterial infection may be ruled in (or a viral infection may be ruled out).

When the level of CRP is below a predetermined level, it is indicative that the infection is a viral infection and a viral infection may be ruled in (or a bacterial infection may be ruled out).

TRAIL:

The protein encoded by this gene is a cytokine that belongs to the tumor necrosis factor (TNF) ligand family. The present invention contemplates measuring either the soluble and/or the membrane form of this protein. In one embodiment, only the soluble form of this protein is measured. Additional names of the gene include without limitations APO2L, TNF-related apoptosis-inducing ligand, TNFSF10 and CD253. This protein binds to several members of the TNF receptor superfamily such as TNFRSF10A/TRAILR1, TNFRSF10B/TRAILR2, TNFRSF10C/TRAILR3, TNFRSF10D/TRAILR4, and possibly also to TNFRSF11B/OPG Exemplary amino acid sequences of TRAIL are set forth in SEQ ID NOs: 4-8.

In a particular embodiment, TRAIL is the protein that is recognized by the antibody of the kit R&D systems, Human TRAIL/TNFSF10 Quantikine ELISA Kit catalog #DTRL00.

The level of TRAIL increases in viral infections (as compared to non-infectious diseases), and decreases in bacterial infections (as compared to non-infectious diseases).

Thus, when the level of TRAIL is above a predetermined level, it is indicative that the infection is a viral infection and a viral infection may be ruled in (or a bacterial infection may be ruled out).

When the level of TRAIL is below a predetermined level, it is indicative that the infection is a bacterial infection and a bacterial infection may be ruled in (or a viral infection may be ruled out).

For example, a bacterial infection may be ruled out if the polypeptide concentration of TRAIL determined is higher than a pre-determined first threshold value. Optionally, the method further includes determining if a subject has a viral infection (i.e., ruling in a viral infection). A viral infection is ruled in if the polypeptide concentration of TRAIL is higher than a pre-determined second threshold value.

In another specific embodiment the invention includes determining if a subject does not have a viral infection (i.e. ruling out a viral infection). A viral infection is ruled out if the polypeptide concentration of TRAIL determined is lower than a pre-determined first threshold value. Optionally, the method further includes determining if a subject has a bacterial infection (i.e., ruling in a bacterial infection). A bacterial infection is ruled in if the polypeptide concentration of TRAIL is lower than a pre-determined second threshold value.

IP10:

This gene encodes a chemokine of the CXC subfamily and ligand for the receptor CXCR3. Additional names of the gene include without limitations: CXCL10, Gamma-IP10, INP10 and chemokine (C-X-C motif) ligand 10.

An exemplary amino acid sequence of human IP10 is set forth in SEQ ID NO: 16.

In a particular embodiment, IP10 is the protein that is recognized by the antibody of the kit (R&D systems, Human CXCL10/IP-10 Quantikine ELISA Kit catalog #DIP100).

The level of IP10 increases in infections (as compared to non-infectious diseases), with the level of IP10 being higher in viral infections as opposed to bacterial infections.

Thus, when the level of IP10 is above a predetermined level, it is indicative that the infection is a viral infection and a viral infection may be ruled in (or a bacterial infection may be ruled out).

When the level of IP10 is below a predetermined level, it is indicative that the infection is a bacterial infection and a bacterial infection may be ruled in (or a viral infection may be ruled out).

IL-6:

This gene encodes a cytokine that functions in inflammation and the maturation of B cells. In addition, the encoded protein has been shown to be an endogenous pyrogen capable of inducing fever in people with autoimmune diseases or infections. The protein is primarily produced at sites of acute and chronic inflammation, where it is secreted into the serum and induces a transcriptional inflammatory response through interleukin 6 receptor, alpha. The functioning of this gene is implicated in a wide variety of inflammation-associated disease states, including susceptibility to diabetes mellitus and systemic juvenile rheumatoid arthritis.

Exemplary amino acid sequences of human IL-6 is set forth in SEQ ID NOs: 23 and 24.

The data presented herein shows that the level of IL-6 increases in infections (as compared to non-infectious diseases), with the level of IL-6 being higher in bacterial infections as opposed to viral infections.

Thus, when the level of IL-6 is above a predetermined level, it is indicative that the infection is a bacterial infection and a bacterial infection may be ruled in (or a viral infection may be ruled out).

When the level of IL-6 is below a predetermined level, it is indicative that the infection is a viral infection and a viral infection may be ruled in (or a bacterial infection may be ruled out).

PCT:

Procalcitonin (PCT) is a peptide precursor of the hormone calcitonin, the latter being involved with calcium homeostasis.

Exemplary amino acid sequences of human PCT are set forth in SEQ ID NOs: 19-22.

The level of PCT typically increases in infections (as compared to non-infectious diseases), with the level of PCT being higher in bacterial infections as opposed to viral infections.

Thus, when the level of PCT is above a predetermined level, it is indicative that the infection is a bacterial infection and a bacterial infection may be ruled in (or a viral infection may be ruled out).

When the level of PCT is below a predetermined level, it is indicative that the infection is a viral infection and a viral infection may be ruled in (or a bacterial infection may be ruled out).

The concentrations of each of the above identified polypeptides may be combined (e.g. by way of a pre-determined mathematical function) to compute a score and the score may be compared to a predetermined reference value as further described herein below.

Further information on generating pre-determined mathematical functions in general and for CRP, IP10 and TRAIL in particular are provided in International Patent Application IL2015/050823, the contents of which are incorporated herein by reference.

Statistical classification algorithms which may be used to calculate the score include, but are not limited to Support Vector Machine (SVM), Logistic Regression (Log Reg), Neural Network, Bayesian Network, and a Hidden Markov Model. Alternatively, the integration of the different proteins into a single predictive score could be achieved by applying "Fuzzy OR model" analysis, as shown in the Examples section herein below.

In one embodiment, the level of PCT and/or IL-6 is taken into account in the statistical classification together with the TRAIL, CRP, IP-10 signature (TCP signature) only when concentrations reaches a threshold level. Thus, for example only when the level of PCT is above 1, 1.5, 2, 2.5, 5, or 7.5 µg/L, is PCT included in the algorithm together with the TCP signature. Similarly, only when the level of IL-6 is above 100, 200, 240, 250, 280, 320, or 350 pg/nil is IL-6 included in the algorithm together with the TCP signature. It will be appreciated that the weight of PCT and IL-6 in the algorithm may vary according to its concentration. For example, if the level of PCT is above 5 µg/L, then its relative weight may be higher with respect to the TCP signature that if the level of PCT is below 5 µg/L.

A reference value can be relative to a number or value derived from population studies, including without limitation, such subjects having the same infection, subject having the same or similar age range, subjects in the same or similar ethnic group, or relative to the starting sample of a subject undergoing treatment for an infection. Such reference values can be derived from statistical analyses and/or risk prediction data of populations obtained from mathematical algorithms and computed indices of infection. Reference determinant indices can also be constructed and used using algorithms and other methods of statistical and structural classification.

In one embodiment of the present invention, the reference value is the amount (i.e. level) of determinants in a control sample derived from one or more subjects who do not have an infection (i.e., healthy, and or non-infectious individuals). In a further embodiment, such subjects are monitored and/or periodically retested for a diagnostically relevant period of time ("longitudinal studies") following such test to verify continued absence of infection. Such period of time may be one day, two days, two to five days, five days, five to ten days, ten days, or ten or more days from the initial testing date for determination of the reference value. Furthermore, retrospective measurement of determinants in properly banked historical subject samples may be used in establishing these reference values, thus shortening the study time required.

A reference value can also comprise the amounts of determinants derived from subjects who show an improvement as a result of treatments and/or therapies for the infection. A reference value can also comprise the amounts of determinants derived from subjects who have confirmed infection by known techniques.

An example of a bacterially infected reference value index value is the mean or median concentrations of that determinant in a statistically significant number of subjects having been diagnosed as having a bacterial infection.

An example of a virally infected reference value is the mean or median concentrations of that determinant in a statistically significant number of subjects having been diagnosed as having a viral infection.

In another embodiment, the reference value is an index value or a baseline value. An index value or baseline value is a composite sample of an effective amount of determinants from one or more subjects who do not have an infection. A baseline value can also comprise the amounts of determinants in a sample derived from a subject who has shown an improvement in treatments or therapies for the infection. In this embodiment, to make comparisons to the subject-derived sample, the amounts of determinants are similarly calculated and compared to the index value. Optionally, subjects identified as having an infection, are chosen to receive a therapeutic regimen to slow the progression or eliminate the infection.

Additionally, the amount of the determinant can be measured in a test sample and compared to the "normal control level," utilizing techniques such as reference limits, discrimination limits, or risk defining thresholds to define cutoff points and abnormal values. The "normal control level" means the level of one or more determinants or combined determinant indices typically found in a subject not suffering from an infection. Such normal control level and cutoff points may vary based on whether a determinant is used alone or in a formula combining with other determinants into an index. Alternatively, the normal control level can be a database of determinant patterns from previously tested subjects.

The effectiveness of a treatment regimen can be monitored by detecting a determinant in an effective amount (which may be one or more) of samples obtained from a subject over time and comparing the amount of determinants detected. For example, a first sample can be obtained prior to the subject receiving treatment and one or more subsequent samples are taken after or during treatment of the subject.

For example, the methods of the invention can be used to discriminate between bacterial, viral and mixed infections (i.e. bacterial and viral co-infections.) This will allow patients to be stratified and treated accordingly.

In a specific embodiment of the invention a treatment recommendation (i.e., selecting a treatment regimen) for a subject is provided by identifying the type infection (i.e., bacterial, viral, mixed infection or no infection) in the subject according to the method of any of the disclosed methods and recommending that the subject receive an antibiotic treatment if the subject is identified as having bacterial infection or a mixed infection; or an anti-viral treatment is if the subject is identified as having a viral infection.

In another embodiment, the methods of the invention can be used to prompt additional targeted diagnosis such as pathogen specific PCRs, chest-X-ray, cultures etc. For example, a diagnosis that indicates a viral infection according to embodiments of this invention, may prompt the usage of additional viral specific multiplex-PCRs, whereas a diagnosis that indicates a bacterial infection according to embodiments of this invention may prompt the usage of a bacterial specific multiplex-PCR. Thus, one can reduce the costs of unwarranted expensive diagnostics.

In a specific embodiment, a diagnostic test recommendation for a subject is provided by identifying the infection type (i.e., bacterial, viral, mixed infection or no infection) in the subject according to any of the disclosed methods and recommending a test to determine the source of the bacterial infection if the subject is identified as having a bacterial infection or a mixed infection; or a test to determine the source of the viral infection if the subject is identified as having a viral infection.

As well as measuring the polypeptide determinants mentioned herein above, the present inventors contemplate measuring at least one, two, three, four, five, six, seven, eight, nine, ten or more additional (non-identical) determinants (polypeptide, RNA or other), wherein the at least one additional determinant is set forth in US Patent Application No. 20080171323, WO2011/132086 and WO2013/117746 and PCT Application IL 2015/051024 and PCT Application IL 2015/051201 and Provisional Application No. 62/302,849 the contents of each are incorporated herein by reference. Other polypeptide determinants contemplated by the present inventors are the polypeptide counterparts of the RNA determinants described therein.

In one embodiment, at least of the additional determinants is set forth in Table 2 herein below.

TABLE 2

| Protein symbol | Full Gene Name | RefSeq DNA sequence | RefSeq proteins |
|---|---|---|---|
| IL1R/ IL1R1/ IL1RA | Interleukin 1 receptor, type I | NC_000002.12 NT_005403.18 NC_018913.2 | NP_000868.1 NP_001275635.1 |
| SAA/ SAA1 | Serum amyloid A1 | NC_000011.10 NC_018922.2 NT_009237.19 | NP_000322.2 NP_001171477.1 NP_954630.1 |
| TREM1 | Triggering receptor expressed on myeloid cells 1 | NC_000006.12 NT_007592.16 NC_018917.2 | NP_001229518.1 NP_001229519.1 NP_061113.1 |
| TREM2 | Triggering receptor expressed on myeloid cells 2 | NC_000006.12 NT_007592.16 NC_018917.2 | NP_001258750.1 NP_061838.1 |
| RSAD2 | Radical S-adenosyl methionine domain containing 2 | NC_000002.12 NT_005334.17 NC_018913.2 | NP_542388.2 |
| NGAL | Lipocalin 2 | NC_000009.12 NC_018920.2 NT_008470.20 | NP_005555.2 |
|  | Matrix metallopeptidase 8 | NC_000011.10 NT_033899.9 NC_018922.2 | NP_001291370.1 NP_001291371.1 NP_002415.1 |
| MX1 | MX Dynamin-Like GTPase 1 | NC_000021.9 NT_011512.12 NC_018932.2 | NP_001138397.1 NP_001171517.1 NP_001269849.1 NP_002453.2 |
| Neopterin | 2-amino-6-(1,2,3-trihydroxypropyl)-1H-pteridin-4-one IUPAC name | N/A | N/A |

According to this aspect of the present invention, in order to distinguish between the different infection types, no more than 30 determinants (e.g. proteins that are differentially expressed in a statistically significant manner in subjects with a bacterial infection compared to subjects with a viral infection) are measured, no more than 25 determinants are measured, no more than 20 determinants are measured, no more than 15 determinants are measured, no more than 10 determinants are measured, no more than 9 determinants are measured, no more than 8 determinants are measured, no more than 7 determinants are measured, no more than 6 determinants are measured, no more than 5 determinants are measured or even no more than 4 determinants are measured.

Other determinants that may be measured according to aspects of the present invention include pathogen (bacterial or viral) specific RNA or polypeptide determinants. This may be carried out in order to aid in identification of a specific pathogen. The measurements may be effected simultaneously with the above described measurements or consecutively.

Methods of measuring the levels of polypeptides are well known in the art and include, e.g., immunoassays based on antibodies to proteins, aptamers or molecular imprints.

The polypeptide determinants can be detected in any suitable manner, but are typically detected by contacting a sample from the subject with an antibody, which binds the determinant and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological sample as described above, and may be the same sample of biological sample used to conduct the method described above.

In one embodiment, the antibody which specifically binds the determinant is attached (either directly or indirectly) to a signal producing label, including but not limited to a radioactive label, an enzymatic label, a hapten, a reporter dye or a fluorescent label.

Immunoassays carried out in accordance with some embodiments of the present invention may be homogeneous assays or heterogeneous assays. In a homogeneous assay the immunological reaction usually involves the specific antibody (e.g., anti-determinant antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels, which may be employed, include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample.

Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al., titled "Methods for Modulating Ligand-Receptor Interactions and their Application," U.S. Pat. No. 4,659,678 to Forrest et al., titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogeneous Specific Binding Assay Employing a Coenzyme as Label." The determinant can also be detected with antibodies using flow cytometry. Those skilled in the art will be familiar with flow cytometric techniques which may be useful in carrying out the methods disclosed herein (Shapiro 2005). These include, without limitation, Cytokine Bead Array (Becton Dickinson) and Luminex technology.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}$S, $^{125}$I, $^{131}$I), enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of determinant proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth U. and Muller D. 2002).

For determinant-proteins, polypeptides, mutations, and polymorphisms known to have enzymatic activity, the activities can be determined in vitro using enzyme assays known in the art. Such assays include, without limitation, kinase assays, phosphatase assays, reductase assays, among many others. Modulation of the kinetics of enzyme activities can be determined by measuring the rate constant $K_M$ using known algorithms, such as the Hill plot, Michaelis-Menten equation, linear regression plots such as Lineweaver-Burk analysis, and Scatchard plot.

In particular embodiments, the antibodies of the present invention are monoclonal antibodies.

Suitable sources for antibodies for the detection of determinants include commercially available sources such as, for example, Abazyme, Abnova, AssayPro, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, against any of the polypeptide determinants described herein.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Those skilled in the art will be familiar with numerous suitable detectors that widely available from a variety of commercial sources and may be useful for carrying out the method disclosed herein. Commonly, an optical image of a substrate comprising bound labeling moieties is digitized for subsequent computer analysis. See generally The Immunoassay Handbook [The Immunoassay Handbook. Third Edition. 2005].

Traditional laboratory risk factors and additional clinical parameters may also be measured together with the above described polypeptides to further increase the accuracy of the signatures.

"Traditional laboratory risk factors" encompass biomarkers isolated or derived from subject samples and which are currently evaluated in the clinical laboratory and used in traditional global risk assessment algorithms, such as absolute neutrophil count (abbreviated ANC), absolute lymphocyte count (abbreviated ALC), white blood count (abbreviated WBC), neutrophil % (defined as the fraction of white blood cells that are neutrophils and abbreviated Neu (%)), lymphocyte % (defined as the fraction of white blood cells that are lymphocytes and abbreviated Lym (%)), monocyte % (defined as the fraction of white blood cells that are monocytes and abbreviated Mon (%)), Sodium (abbreviated Na), Potassium (abbreviated K), Bilirubin (abbreviated Bili).

"Clinical parameters" encompass all non-sample or non-analyte biomarkers of subject health status or other characteristics, such as, without limitation, age (Age), ethnicity (RACE), gender (Sex), core body temperature (abbreviated "temperature"), maximal core body temperature since initial appearance of symptoms (abbreviated "maximal temperature"), time from initial appearance of symptoms (abbreviated "time from symptoms") or family history (abbreviated FamHX).

The patient medical background conditions such as chronic lung diseases and diabetes may affect its immune response to infection that is reflected by changes in diagnostic accuracy of immune-based diagnostics (see Example 1, herein below). Thus, information regarding the patient background clinical conditions could potentially be integrated with protein biomarker classifiers predicted outcome in order to improve patient diagnosis.

As mentioned, the signature polypeptides described herein are particularly useful at classifying early infections.

Thus, according to another aspect of the present invention there is provided a method of diagnosing an infection in a subject comprising measuring the amount of at least two polypeptides selected from the group consisting of TRAIL, CRP, IP10, IL-6 and PCT in a sample derived from the subject, wherein the sample is derived from the subject no more than two days following symptom onset, wherein the amount is indicative of the infection.

In one embodiment, the sample is derived from the subject no more than one day following symptom onset.

Exemplary symptoms include but are not limited to fever, nausea, headache, rash and/or muscle soreness.

Exemplary pairs of polypeptides that may be analyzed for any of the aspects described herein include:
TRAIL and CRP;
TRAIL and IP10;
TRAIL and IL-6;
TRAIL and PCT;
CRP and IP10;
CRP and IL-6;
CRP and PCT;
IP10 and IL-6;
IP10 and PCT;
IL-6 and PCT;
MX1 and PCT or
MX1 and IL-6.

Exemplary triplets of polypeptides that may be analyzed include:
TRAIL, CRP and IP10;
TRAIL, CRP and IL6;
TRAIL, IP10 and PCT; or
TRAIL, CRP and PCT.

Exemplary quadruplets of polypeptides that may be analyzed include:
TRAIL, CRP, IP-10, PCT;
TRAIL, CRP, IP-10, IL-6; or
TRAIL, CRP, PCT, IL-6.

In another embodiment, each of the polypeptides are measured: TRAIL, CRP,
IP-10, PCT and IL-6.

For particular embodiments, when the amount of TRAIL is below a predetermined level, the amount of CRP is above a predetermined level, the amount of IP-10 is below a predetermined level and the amount of IL-6 is above a predetermined level, the subject is diagnosed as having sepsis. Alternatively, when the amount of TRAIL is below a predetermined level, the amount of CRP is above a predetermined level, the amount of IP-10 is below a predetermined level and the amount of PCT is above a predetermined level, the subject is diagnosed as having sepsis. Alternatively, when the amount of TRAIL is below a predetermined level, the amount of CRP is above a predetermined level, the amount of IP-10 is below a predetermined level, the amount of PCT is above a predetermined level and the amount of IL-6 is above a predetermined level, the subject is diagnosed as having sepsis.

In other embodiments, when the amount of TRAIL is below a predetermined level, the amount of CRP is above a predetermined level, and the amount of IL-6 is above a predetermined level, the subject is diagnosed as having sepsis. Alternatively, when the amount of TRAIL is below a predetermined level, the amount of CRP is above a predetermined level, and the amount of PCT is above a predetermined level, the subject is diagnosed as having sepsis. Alternatively, when the amount of TRAIL is below a predetermined level, the amount of CRP is above a predetermined level, the amount of PCT is above a predetermined level and the amount of IL-6 is above a predetermined level, the subject is diagnosed as having sepsis.

As mentioned, the markers and combinations thereof may be measured to distinguish between a non-infectious exacerbation state and an infectious exacerbation state of chronic obstructive pulmonary disease (COPD) in a subject. The method comprises measuring the amount of at least two polypeptides selected from the group consisting of TNF-related apoptosis-inducing ligand (TRAIL), C-reactive protein (CRP), Interferon gamma-induced protein 10 (IP10), Interleukin 6 (IL-6) and Procalcitonin (PCT) in a sample derived from the subject, wherein the amount is indicative of the exacerbation state of COPD.

It will be appreciated that if the exacerbation is due to an infection, the levels of the markers will change according to the infection type (viral/bacterial) as described herein above. If the exacerbation is not due to an infection type, the levels of the markers will be similar to a non-infectious subject.

According to a further aspect of the present invention there is provided a method of determining an infection type in subjects with trauma-induced or combat-related wounds comprising measuring the amount of each of the polypeptides TNF-related apoptosis-inducing ligand (TRAIL), C-reactive protein (CRP), Interferon gamma-induced protein 10 (IP10) and at least one additional polypeptide selected from the group consisting of Interleukin 6 (IL-6) and Procalcitonin (PCT) in a sample derived from the subject, wherein the amount is indicative of the infection type. In yet another embodiment, these signatures are specifically used to monitor post-surgery patients.

Kits

Some aspects of the invention also include a determinant-detection reagent such as antibodies packaged together in the form of a kit. The kit may contain in separate containers antibodies (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. The detectable label may be attached to a secondary antibody which binds to the Fc portion of the antibody which recognizes the determinant. Instructions (e.g., written, tape, VCR, CD-ROM, etc.) for carrying out the assay may be included in the kit.

The kits of this aspect of the present invention may comprise additional components that aid in the detection of the determinants such as enzymes, salts, buffers etc. necessary to carry out the detection reactions.

Thus, according to another aspect of the present invention, there is provided a kit for diagnosing an infection type comprising:
(i) an antibody which specifically detects TRAIL;
(ii) an antibody which specifically detects IP10:
(iii) an antibody which specifically detects CRP; and
(iv) at least one additional antibody which specifically detects IL-6 or PCT.

According to still another aspect of the present invention there is provided a kit for diagnosing an infection type comprising:
(i) an antibody which specifically detects TRAIL;
(ii) an antibody which specifically detects IL-6:
(iii) an antibody which specifically detects CRP; and
(iv) at least one additional antibody which specifically detects IP10 or PCT.

For example, determinant detection reagents (e.g. antibodies) can be immobilized on a solid matrix such as a porous strip or an array to form at least one determinant detection site. The measurement or detection region of the porous strip may include a plurality of sites. A test strip may also contain sites for negative and/or positive controls. Alternatively, control sites can be located on a separate strip from the test strip. Optionally, the different detection sites may contain different amounts of immobilized detection reagents, e.g., a higher amount in the first detection site and lesser amounts in subsequent sites. Upon the addition of test sample, the number of sites displaying a detectable signal provides a quantitative indication of the amount of determinants present in the sample. The detection sites may be configured in any suitably detectable shape and are typically in the shape of a bar or dot spanning the width of a test strip.

Examples of "Monoclonal antibodies for measuring TRAIL", include without limitation: Mouse, Monoclonal (55B709-3) IgG; Mouse, Monoclonal (2E5) IgG1; Mouse, Monoclonal (2E05) IgG1; Mouse, Monoclonal (M912292) IgG1 kappa; Mouse, Monoclonal (IIIF6) IgG2b; Mouse, Monoclonal (2E1-1B9) IgG1; Mouse, Monoclonal (RIK-2) IgG1, kappa; Mouse, Monoclonal M181 IgG1; Mouse, Monoclonal VI10E IgG2b; Mouse, Monoclonal MAB375 IgG1; Mouse, Monoclonal MAB687 IgG1; Mouse, Monoclonal HS501 IgG1; Mouse, Monoclonal clone 75411.11 Mouse IgG1; Mouse, Monoclonal T8175-50 IgG; Mouse, Monoclonal 2B2.108 IgG1; Mouse, Monoclonal B-T24 IgG1; Mouse, Monoclonal 55B709.3 IgG1; Mouse, Monoclonal D3 IgG1; Goat, Monoclonal C19 IgG; Rabbit, Monoclonal H257 IgG; Mouse, Monoclonal 500-M49 IgG; Mouse, Monoclonal 05-607 IgG; Mouse, Monoclonal B-T24 IgG1; Rat, Monoclonal (N2B2), IgG2a, kappa; Mouse, Monoclonal (1A7-2B7), IgG1; Mouse, Monoclonal (55B709.3), IgG and Mouse, Monoclonal B-S23*IgG1.

Soluble TRAIL and membrane TRAIL can be distinguished by using different measuring techniques and samples. For example, Soluble TRAL can be measured without limitation in cell free samples such as serum or plasma, using without limitation lateral flow immunoassay (LFIA), as further described herein below. Membrane TRAIL can be measured in samples that contain cells using cell based assays including without limitation flow cytometry, ELISA, and other immunoassays.

Lateral Flow Immunoassays (LFIA):

This is a technology which allows rapid measurement of analytes at the point of care (POC) and its underlying principles are described below. According to one embodiment, LFIA is used in the context of a hand-held device.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex.

After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the wick, that simply acts as a waste container. Lateral Flow Tests can operate as either competitive or sandwich assays.

Different formats may be adopted in LFIA. Strips used for LFIA contain four main components. A brief description of each is given before describing format types.

Sample Application Pad:

It is made of cellulose and/or glass fiber and sample is applied on this pad to start assay. Its function is to transport the sample to other components of lateral flow test strip (LFTS). Sample pad should be capable of transportation of the sample in a smooth, continuous and homogenous manner. Sample application pads are sometimes designed to pretreat the sample before its transportation. This pretreatment may include separation of sample components, removal of interferences, adjustment of pH, etc.

Conjugate Pad:

It is the place where labeled biorecognition molecules are dispensed. Material of conjugate pad should immediately release labeled conjugate upon contact with moving liquid sample. Labeled conjugate should stay stable over entire life span of lateral flow strip. Any variations in dispensing, drying or release of conjugate can change results of assay significantly. Poor preparation of labeled conjugate can adversely affect sensitivity of assay. Glass fiber, cellulose, polyesters and some other materials are used to make conjugate pad for LFIA. Nature of conjugate pad material has an effect on release of labeled conjugate and sensitivity of assay.

Nitrocellulose Membrane:

It is highly critical in determining sensitivity of LFIA. Nitrocellulose membranes are available in different grades. Test and control lines are drawn over this piece of membrane. So an ideal membrane should provide support and good binding to capture probes (antibodies, aptamers etc.). Nonspecific adsorption over test and control lines may affect results of assay significantly, thus a good membrane will be characterized by lesser non-specific adsorption in the regions of test and control lines. Wicking rate of nitrocellulose membrane can influence assay sensitivity. These membranes are easy to use, inexpensive, and offer high affinity for proteins and other biomolecules. Proper dispensing of bioreagents, drying and blocking play a role in improving sensitivity of assay.

Adsorbent Pad:

It works as sink at the end of the strip. It also helps in maintaining flow rate of the liquid over the membrane and stops back flow of the sample. Adsorbent capacity to hold liquid can play an important role in results of assay.

All these components are fixed or mounted over a backing card. Materials for backing card are highly flexible because they have nothing to do with LFIA except providing a platform for proper assembling of all the components. Thus backing card serves as a support and it makes easy to handle the strip.

Major steps in LFIA are (i) preparation of antibody against target analyte (ii) preparation of label (iii) labeling of biorecognition molecules (iv) assembling of all components onto a backing card after dispensing of reagents at their proper pads (v) application of sample and obtaining results.

Sandwich Format:

In a typical format, label (Enzymes or nanoparticles or fluorescence dyes) coated antibody or aptamer is immobilized at conjugate pad. This is a temporary adsorption which can be flushed away by flow of any buffer solution. A primary antibody or aptamer against target analyte is immobilized over test line. A secondary antibody or probe against labeled conjugate antibody/aptamer is immobilized at control zone.

Sample containing the analyte is applied to the sample application pad and it subsequently migrates to the other parts of strip. At conjugate pad, target analyte is captured by the immobilized labeled antibody or aptamer conjugate and results in the formation of labeled antibody conjugate/analyte complex. This complex now reaches at nitrocellulose membrane and moves under capillary action. At test line, label antibody conjugate/analyte complex is captured by another antibody which is primary to the analyte. Analyte becomes sandwiched between labeled and primary antibodies forming labeled antibody conjugate/analyte/primary antibody complex. Excess labeled antibody conjugate will be captured at control zone by secondary antibody. Buffer or excess solution goes to absorption pad. Intensity of color at test line corresponds to the amount of target analyte and is measured with an optical strip reader or visually inspected. Appearance of color at control line ensures that a strip is functioning properly.

Competitive Format:

Such a format suits best for low molecular weight compounds which cannot bind two antibodies simultaneously. Absence of color at test line is an indication for the presence of analyte while appearance of color both at test and control lines indicates a negative result. Competitive format has two layouts. In the first layout, solution containing target analyte is applied onto the sample application pad and prefixed labeled biomolecule (antibody/aptamer) conjugate gets hydrated and starts flowing with moving liquid. Test line contains pre-immobilized antigen (same analyte to be detected) which binds specifically to label conjugate. Control line contains pre-immobilized secondary antibody which has the ability to bind with labeled antibody conjugate. When liquid sample reaches at the test line, pre-immobilized antigen will bind to the labeled conjugate in case target analyte in sample solution is absent or present in such a low quantity that some sites of labeled antibody conjugate were vacant. Antigen in the sample solution and the one which is immobilized at test line of strip compete to bind with labeled conjugate. In another layout, labeled analyte conjugate is dispensed at conjugate pad while a primary antibody to analyte is dispensed at test line. After application of analyte solution a competition takes place between analyte and labeled analyte to bind with primary antibody at test line.

Multiplex Detection Format:

Multiplex detection format is used for detection of more than one target species and assay is performed over the strip containing test lines equal to number of target species to be analyzed. It is highly desirable to analyze multiple analytes simultaneously under same set of conditions. Multiplex detection format is very useful in clinical diagnosis where multiple analytes which are inter-dependent in deciding about the stage of a disease are to be detected. Lateral flow strips for this purpose can be built in various ways i.e. by increasing length and test lines on conventional strip, making other structures like stars or T-shapes. Shape of strip for LFIA will be dictated by number of target analytes. Miniaturized versions of LFIA based on microarrays for multiplex detection of DNA sequences have been reported to have several advantages such as less consumption of test reagents, requirement of lesser sample volume and better sensitivity.

Labels:

Any material that is used as a label should be detectable at very low concentrations and it should retain its properties upon conjugation with biorecognition molecules. This conjugation is also expected not to change features of biorecognition probes. Ease in conjugation with biomolecules and stability over longer period of time are desirable features for a good label. Concentrations of labels down to $10^{-9}$ M are optically detectable. After the completion of assay, some labels generate direct signal (as color from gold colloidal) while others require additional steps to produce analytical signal (as enzymes produce detectable product upon reaction with suitable substrate). Hence the labels which give direct signal are preferable in LFA because of less time consumption and reduced procedure.

Gold Nanoparticles:

Colloidal gold nanoparticles are the most commonly used labels in LFA. Colloidal gold is inert and gives very perfect spherical particles. These particles have very high affinity toward biomolecules and can be easily functionalized. Optical properties of gold nanoparticles are dependent on size and shape. Size of particles can be tuned by use of suitable chemical additives. Their unique features include environment friendly preparation, high affinity toward proteins and biomolecules, enhanced stability, exceptionally higher values for charge transfer and good optical signaling. Optical signal of gold nanoparticles in colorimetric LFA can be amplified by deposition of silver, gold nanoparticles and enzymes.

Magnetic Particles and Aggregates:

Colored magnetic particles produce color at the test line which is measured by an optical strip reader but magnetic signals coming from magnetic particles can also be used as detection signals and recorded by a magnetic assay reader. Magnetic signals are stable for longer time compared to optical signals and they enhance sensitivity of LFA by 10 to 1000 folds.

Fluorescent and Luminescent Materials:

Fluorescent molecules are widely used in LFA as labels and the amount of fluorescence is used to quantitate the concentration of analyte in the sample. Detection of proteins is accomplished by using organic fluorophores such as rhodamine as labels in LFA.

Current developments in nanomaterial have headed to manufacture of quantum dots which display very unique electrical and optical properties. These semiconducting particles are not only water soluble but can also be easily combined with biomolecules because of closeness in dimensions. Owing to their unique optical properties, quantum dots have come up as a substitute to organic fluorescent dyes. Like gold nanoparticles QDs show size dependent optical properties and a broad spectrum of wavelengths can be monitored. Single light source is sufficient to excite quantum dots of all different sizes. QDs have high photo stability and absorption coefficients.

Upconverting phosphors (UCP) are characterized by their excitation in infra-red region and emission in high energy visible region. Compared to other fluorescent materials, they have a unique advantage of not showing any auto fluorescence. Because of their excitation in IR regions, they do not photo degrade biomolecules. A major advantage lies in their production from easily available bulk materials. Although difference in batch to batch preparation of UCP reporters can affect sensitivity of analysis in LFA, it was observed that they can enhance sensitivity of analytical signal by 10 to 100 folds compared to gold nanoparticles or colored latex beads, when analysis is carried out under same set of biological conditions.

Enzymes:

Enzymes are also employed as labels in LFA. But they increase one step in LFA which is application of suitable substrate after complete assay. This substrate will produce color at test and control lines as a result of enzymatic reaction. In case of enzymes, selection of suitable enzyme substrate combination is one necessary requirement in order to get a colored product for strip reader or electroactive product for electrochemical detection. In other words, sensitivity of detection is dependent on enzyme substrate combination.

Colloidal Carbon:

Colloidal carbon is comparatively inexpensive label and its production can be easily scaled up. Because of their black color, carbon NPs can be easily detected with high sensitivity. Colloidal carbon can be functionalized with a large variety of biomolecules for detection of low and high molecular weight analytes.

Detection Systems:

In case of gold nanoparticles or other color producing labels, qualitative or semi-quantitative analysis can be done by visual inspection of colors at test and control lines. The major advantage of visual inspection is rapid qualitative answer in "Yes" or "NO". Such quick replies about presence of an analyte in clinical analysis have very high importance. Such tests help doctors to make an immediate decision near the patients in hospitals in situations where test results from central labs cannot be waited for because of huge time consumption. But for quantification, optical strip readers are employed for measurement of the intensity of colors produced at test and control lines of strip. This is achieved by inserting the strips into a strip reader and intensities are recorded simultaneously by imaging softwares.

Optical images of the strips can also be recorded with a camera and then processed by using a suitable software. Procedure includes proper placement of strip under the camera and a controlled amount of light is thrown on the areas to be observed. Such systems use monochromatic light and wavelength of light can be adjusted to get a good contrast among test and control lines and background. In order to provide good quantitative and reproducible results, detection system should be sensitive to different intensities of colors. Optical standards can be used to calibrate an optical reader device. Automated systems have advantages over manual imaging and processing in terms of time consumption, interpretation of results and adjustment of variables.

In case of fluorescent labels, a fluorescence strip reader is used to record fluorescence intensity of test and control lines. Fluorescence brightness of test line increased with an increase in nitrated seruloplasmin concentration in human serum when it was detected with a fluorescence strip reader. A photoelectric sensor was also used for detection in LFIA where colloidal gold is exposed to light emitting diode and resulting photoelectrons are recorded. Chemiluminescence which results from reaction of enzyme and substrate is measured as a response to amount of target analyte. Magnetic strip readers and electrochemical detectors are also reported as detection systems in LFTS but they are not very common. Selection of detector is mainly determined by the label employed in analysis.

Examples of "Monoclonal antibodies for measuring CRP", include without limitation: Mouse, Monoclonal (108-2A2); Mouse, Monoclonal (108-7G41D2); Mouse, Monoclonal (12D-2C-36), IgG1; Mouse, Monoclonal (1G1), IgG1; Mouse, Monoclonal (5A9), IgG2a kappa; Mouse, Monoclonal (63F4), IgG1; Mouse, Monoclonal (67A1), IgG1; Mouse, Monoclonal (8B-5E), IgG1; Mouse, Monoclonal (B893M), IgG2b, lambda; Mouse, Monoclonal (C1), IgG2b; Mouse, Monoclonal (C11F2), IgG; Mouse, Monoclonal (C2), IgG1; Mouse, Monoclonal (C3), IgG1; Mouse, Monoclonal (C4), IgG1; Mouse, Monoclonal (C5), IgG2a; Mouse, Monoclonal (C6), IgG2a; Mouse, Monoclonal (C7), IgG1; Mouse, Monoclonal (CRP103), IgG2b; Mouse, Monoclonal (CRP11), IgG1; Mouse, Monoclonal (CRP135), IgG1; Mouse, Monoclonal (CRP169), IgG2a; Mouse, Monoclonal (CRP30), IgG1; Mouse, Monoclonal (CRP36), IgG2a; Rabbit, Monoclonal (EPR283Y), IgG; Mouse, Monoclonal (KT39), IgG2b; Mouse, Monoclonal (N-a), IgG1; Mouse, Monoclonal (N1G1), IgG1; Monoclonal (P5A9AT); Mouse, Monoclonal (S5G1), IgG1; Mouse, Monoclonal (SB78c), IgG1; Mouse, Monoclonal (SB78d), IgG1 and Rabbit, Monoclonal (Y284), IgG.

Polyclonal antibodies for measuring determinants include without limitation antibodies that were produced from sera by active immunization of one or more of the following: Rabbit, Goat, Sheep, Chicken, Duck, Guinea Pig, Mouse, Donkey, Camel, Rat and Horse.

Examples of detection agents, include without limitation: scFv, dsFv, Fab, sVH, F(ab')$_2$, Cyclic peptides, Haptamers, A single-domain antibody, Fab fragments, Single-chain variable fragments, Affibody molecules, Affilins, Nanofitins, Anticalins, Avimers, DARPins, Kunitz domains, Fynomers and Monobody.

In particular embodiments, the kit does not comprise a number of antibodies that specifically recognize more than 50, 20 15, 10, 9, 8, 7, 6, 5 or 4 polypeptides.

In other embodiments, the array of the present invention does not comprise a number of antibodies that specifically recognize more than 50, 20 15, 10, 9, 8, 7, 6, 5 or 4 polypeptides.

Some aspects of the present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like infection, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

A machine-readable storage medium can comprise a data storage material encoded with machine readable data or data arrays which, when using a machine programmed with instructions for using the data, is capable of use for a variety of purposes. Measurements of effective amounts of the biomarkers of the invention and/or the resulting evaluation of risk from those biomarkers can be implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system used in some aspects of the invention may also be considered to be implemented as a computer-readable storage medium, configured with a computer program, where the storage medium so configured causes a computer to operate in a specific and predefined manner to perform various functions described herein.

The polypeptide determinants of the present invention, in some embodiments thereof, can be used to generate a "reference determinant profile" of those subjects who do not have an infection. The determinants disclosed herein can also be used to generate a "subject determinant profile" taken from subjects who have an infection. The subject determinant profiles can be compared to a reference determinant profile to diagnose or identify subjects with an infection. The subject determinant profile of different infection types can be compared to diagnose or identify the type of infection. The reference and subject determinant profiles of the present invention, in some embodiments thereof, can be contained in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other disease-risk algorithms and computed indices such as those described herein.

The effectiveness of a treatment regimen can be monitored by detecting a determinant in an effective amount (which may be one or more) of samples obtained from a subject over time and comparing the amount of determinants detected. For example, a first sample can be obtained prior to the subject receiving treatment and one or more subsequent samples are taken after or during treatment of the subject.

For example, the methods of the invention can be used to discriminate between bacterial, viral and mixed infections (i.e. bacterial and viral co-infections). This will allow patients to be stratified and treated accordingly.

In a specific embodiment of the invention a treatment recommendation (i.e., selecting a treatment regimen) for a subject is provided by identifying the type infection (i.e., bacterial, viral, mixed infection or no infection) in the subject according to the method of any of the disclosed methods and recommending that the subject receive an antibiotic treatment if the subject is identified as having bacterial infection or a mixed infection; or an anti-viral treatment is if the subject is identified as having a viral infection.

Examples of antibiotic agents include, but are not limited to Daptomycin; Gemifloxacin; Telavancin; Ceftaroline; Fidaxomicin; Amoxicillin; Ampicillin; Bacampicillin; Carbenicillin; Cloxacillin; Dicloxacillin; Flucloxacillin; Mezlocillin; Nafcillin; Oxacillin; Penicillin G; Penicillin V; Piperacillin; Pivampicillin; Pivmecillinam; Ticarcillin; Aztreonam; Imipenem; Doripenem; Meropenem; Ertapenem; Clindamycin; Lincomycin; Pristinamycin; Quinupristin; Cefacetrile (cephacetrile); Cefadroxil (cefadroxyl); Cefalexin (cephalexin); Cefaloglycin (cephaloglycin); Cefalonium (cephalonium); Cefaloridine (cephaloridine); Cefalotin (cephalothin); Cefapirin (cephapirin); Cefatrizine; Cefazaflur; Cefazedone; Cefazolin (cephazolin); Cefradine (cephradine); Cefroxadine; Ceftezole; Cefaclor; Cefamandole; Cefmetazole; Cefonicid; Cefotetan; Cefoxitin; Cefprozil (cefproxil); Cefuroxime; Cefuzonam; Cefcapene; Cefdaloxime; Cefdinir; Cefditoren; Cefetamet; Cefixime; Cefmenoxime; Cefodizime; Cefotaxime; Cefpimizole; Cefpodoxime; Cefteram; Ceftibuten; Ceftiofur; Ceftiolene; Ceftizoxime; Ceftriaxone; Cefoperazone; Ceftazidime; Cefclidine; Cefepime; Cefluprenam; Cefoselis; Cefozopran; Cefpirome; Cefquinome; Fifth Generation; Ceftobiprole; Ceftaroline; Not Classified; Cefaclomezine; Cefaloram; Cefaparole; Cefcanel; Cefedrolor; Cefempidone; Cefetrizole; Cefivitril; Cefmatilen; Cefmepidium; Cefovecin; Cefoxazole; Cefrotil; Cefsumide; Cefuracetime; Ceftioxide; Azithromycin; Erythromycin; Clarithromycin; Dirithromycin; Roxithromycin; Telithromycin; Amikacin; Gentamicin; Kanamycin; Neomycin; Netilmicin; Paromomycin; Streptomycin; Tobramycin; Flumequine; Nalidixic acid; Oxolinic acid; Piromidic acid; Pipemidic acid; Rosoxacin; Ciprofloxacin; Enoxacin; Lomefloxacin; Nadifloxacin; Norfloxacin; Ofloxacin; Pefloxacin; Rufloxacin; Balofloxacin; Gatifloxacin; Grepafloxacin; Levofloxacin; Moxifloxacin; Pazufloxacin; Sparfloxacin; Temafloxacin; Tosufloxacin; Besifloxacin; Clinafloxacin; Gemifloxacin; Sitafloxacin; Trovafloxacin; Prulifloxacin; Sulfamethizole; Sulfamethoxazole; Sulfisoxazole; Trimethoprim-Sulfamethoxazole; Demeclocycline; Doxycycline; Minocycline; Oxytetracycline; Tetracycline; Tigecycline; Chloramphenicol; Metronidazole; Tinidazole; Nitrofurantoin; Vancomycin; Teicoplanin; Telavancin; Linezolid; Cycloserine 2; Rifampin; Rifabutin; Rifapentine; Bacitracin; Polymyxin B; Viomycin; Capreomycin.

If a viral infection is ruled in, the subject may be treated with an antiviral agent. Examples of antiviral agents include, but are not limited to Abacavir; Aciclovir; Acyclovir; Adefovir; Amantadine; Amprenavir; Ampligen; Arbidol; Atazanavir; Atripla; Balavir; Boceprevirertet; Cidofovir; Combivir; Dolutegravir; Darunavir; Delavirdine; Didanosine; Docosanol; Edoxudine; Efavirenz; Emtricitabine; Enfuvirtide; Entecavir; Ecoliever; Famciclovir; Fomivirsen; Fosamprenavir; Foscarnet; Fosfonet; Fusion inhibitor; Ganciclovir; Ibacitabine; Imunovir; Idoxuridine; Imiquimod; Indinavir; Inosine; Integrase inhibitor; Interferon type III; Interferon type II; Interferon type I; Interferon; Lamivudine; Lopinavir; Loviride; Maraviroc; Moroxydine; Methisazone; Nelfinavir; Nevirapine; Nexavir; Oseltamivir; Peginterferon alfa-2a; Penciclovir; Peramivir; Pleconaril; Podophyllotoxin; Raltegravir; Reverse transcriptase inhibitor; Ribavirin; Rimantadine; Ritonavir; Pyramidine; Saquinavir; Sofosbuvir; StavudineTelaprevir; Tenofovir; Tenofovir disoproxil; Tipranavir; Trifluridine; Trizivir; Tromantadine; Truvada; traporved; Valaciclovir; Valganciclovir; Vicriviroc; Vidarabine; Viramidine; Zalcitabine; Zanamivir; Zidovudine; RNAi antivirals; inhaled rhibovirons; monoclonal antibody respigams; neuriminidase blocking agents.

In another embodiment, the methods of the invention can be used to prompt additional targeted diagnosis such as pathogen specific PCRs, chest-X-ray, cultures etc. For example, a diagnosis that indicates a viral infection according to embodiments of this invention, may prompt the usage of additional viral specific multiplex-PCRs, whereas a diagnosis that indicates a bacterial infection according to embodiments of this invention may prompt the usage of a bacterial specific multiplex-PCR. Thus, one can reduce the costs of unwarranted expensive diagnostics.

In a specific embodiment, a diagnostic test recommendation for a subject is provided by identifying the infection type (i.e., bacterial, viral, mixed infection or no infection) in the subject according to any of the disclosed methods and recommending a test to determine the source of the bacterial infection if the subject is identified as having a bacterial infection or a mixed infection; or a test to determine the source of the viral infection if the subject is identified as having a viral infection.

Performance and Accuracy Measures of the Invention.

The performance and thus absolute and relative clinical usefulness of the invention may be assessed in multiple ways as noted above. Amongst the various assessments of performance, some aspects of the invention are intended to provide accuracy in clinical diagnosis and prognosis. The accuracy of a diagnostic or prognostic test, assay, or method concerns the ability of the test, assay, or method to distinguish between subjects having an infection is based on whether the subjects have, a "significant alteration" (e.g., clinically significant and diagnostically significant) in the levels of a determinant. By "effective amount" it is meant that the measurement of an appropriate number of determinants (which may be one or more) to produce a "significant alteration" (e.g. level of expression or activity of a determinant) that is different than the predetermined cut-off point (or threshold value) for that determinant (s) and therefore indicates that the subject has an infection for which the determinant (s) is an indication. The difference in the level of determinant is preferably statistically significant. As noted below, and without any limitation of the invention, achieving statistical significance, and thus the preferred analytical, diagnostic, and clinical accuracy, may require that combinations of several determinants be used together in panels and combined with mathematical algorithms in order to achieve a statistically significant determinant index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. One way to achieve this is by using the Matthews correlation coefficient (MCC) metric, which depends upon both sensitivity and specificity. Use of statistics such as area under the ROC curve (AUC), encompassing all potential cut point values, is preferred for most categorical risk measures when using some aspects of the invention, while for continuous risk measures, statistics of goodness-of-fit and calibration to observed results or other gold standards, are preferred.

By predetermined level of predictability it is meant that the method provides an acceptable level of clinical or diagnostic accuracy. Using such statistics, an "acceptable degree of diagnostic accuracy", is herein defined as a test or assay (such as the test used in some aspects of the invention for determining the clinically significant presence of determinants, which thereby indicates the presence an infection type) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence or absence of an infection or response to therapy with at least 75% total accuracy, more preferably 80%, 85%, 90%, 95%, 97%, 98%, 99% or greater total accuracy.

Alternatively, the methods predict the presence of a bacterial infection or response to therapy with at least 75% sensitivity, more preferably 80%, 85%, 90%, 95%, 97%, 98%, 99% or greater sensitivity.

Alternatively, the methods predict the presence of a viral infection or response to viral therapy with at least 75% specificity, more preferably 80%, 85%, 90%, 95%, 97%, 98%, 99% or greater specificity.

Alternatively, the methods rule out the presence of a bacterial infection or rule in a viral infection with at least 75% NPV, more preferably 80%, 85%, 90%, 95%, 97%, 98%, 99% or greater NPV. Alternatively, the methods rule in the presence of a bacterial infection or rule out a viral infection with at least 75% PPV, more preferably 80%, 85%, 90%, 95%, 97%, 98%, 99% or greater PPV.

Alternatively, the methods predict the presence of a viral infection or response to therapy with at least 75% specificity, more preferably 80%, 85%, 90%, 95%, 97%, 98%, 99% or greater specificity. Alternatively, the methods predict the presence or absence of an infection or response to therapy with an MCC larger than 0.2, 0.3, 0.4, 0.5, 0.6, 0.7, 0.8, 0.9 or 1.0.

In general, alternative methods of determining diagnostic accuracy are commonly used for continuous measures, when a disease category has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

In general, by defining the degree of diagnostic accuracy, i.e., cut points on a ROC curve, defining an acceptable AUC value, and determining the acceptable ranges in relative concentration of what constitutes an effective amount of the determinants of the invention allows for one of skill in the art to use the determinants to identify, diagnose, or prognose subjects with a pre-determined level of predictability and performance.

Furthermore, other unlisted biomarkers will be very highly correlated with the determinants (for the purpose of this application, any two variables will be considered to be "very highly correlated" when they have a Coefficient of Determination ($R^2$) of 0.5 or greater). Some aspects of the present invention encompass such functional and statistical equivalents to the aforementioned determinants. Furthermore, the statistical utility of such additional determinants is substantially dependent on the cross-correlation between multiple biomarkers and any new biomarkers will often be required to operate within a panel in order to elaborate the meaning of the underlying biology.

One or more of the listed determinants can be detected in the practice of the present invention, in some embodiments thereof. For example, two (2), three (3), four (4), five (5), ten (10), fifteen (15), twenty (20), forty (40), or more determinants can be detected.

In some aspects, all determinants listed herein can be detected. Preferred ranges from which the number of determinants can be detected include ranges bounded by any minimum selected from between one and, particularly two, three, four, five, six, seven, eight, nine ten, twenty, or forty. Particularly preferred ranges include two to five (2-5), two to ten (2-10), two to twenty (2-20), or two to forty (2-40).

Construction of Determinant Panels

Groupings of determinants can be included in "panels", also called "determinant-signatures", "determinant signatures", or "multi-determinant signatures." A "panel" within the context of the present invention means a group of biomarkers (whether they are determinants, clinical parameters, or traditional laboratory risk factors) that includes one or more determinants. A panel can also comprise additional biomarkers, e.g., clinical parameters, traditional laboratory risk factors, known to be present or associated with infection, in combination with a selected group of the determinants listed herein.

As noted above, many of the individual determinants, clinical parameters, and traditional laboratory risk factors listed, when used alone and not as a member of a multi-biomarker panel of determinants, have little or no clinical use in reliably distinguishing individual normal subjects, subjects at risk for having an infection (e.g., bacterial, viral or co-infection), and thus cannot reliably be used alone in classifying any subject between those three states. Even where there are statistically significant differences in their mean measurements in each of these populations, as commonly occurs in studies which are sufficiently powered, such biomarkers may remain limited in their applicability to an individual subject, and contribute little to diagnostic or prognostic predictions for that subject. A common measure of statistical significance is the p-value, which indicates the probability that an observation has arisen by chance alone; preferably, such p-values are 0.05 or less, representing a 5% or less chance that the observation of interest arose by chance. Such p-values depend significantly on the power of the study performed.

Despite this individual determinant performance, and the general performance of formulas combining only the traditional clinical parameters and few traditional laboratory risk factors, the present inventors have noted that certain specific combinations of two or more determinants can also be used as multi-biomarker panels comprising combinations of determinants that are known to be involved in one or more physiological or biological pathways, and that such information can be combined and made clinically useful through the use of various formulae, including statistical classification algorithms and others, combining and in many cases extending the performance characteristics of the combination beyond that of the individual determinants. These specific combinations show an acceptable level of diagnostic accuracy, and, when sufficient information from multiple determinants is combined in a trained formula, they often reliably achieve a high level of diagnostic accuracy transportable from one population to another.

The general concept of how two less specific or lower performing determinants are combined into novel and more useful combinations for the intended indications, is a key aspect of some embodiments of the invention. Multiple biomarkers can yield significant improvement in performance compared to the individual components when proper mathematical and clinical algorithms are used; this is often evident in both sensitivity and specificity, and results in a greater AUC or MCC. Significant improvement in performance could mean an increase of 1%, 2%, 3%, 4%, 5%, 8%, 10% or higher than 10% in different measures of accuracy such as total accuracy, AUC, MCC, sensitivity, specificity, PPV or NPV. Secondly, there is often novel unperceived information in the existing biomarkers, as such was necessary in order to achieve through the new formula an improved level of sensitivity or specificity. This hidden information may hold true even for biomarkers which are generally regarded to have suboptimal clinical performance on their own. In fact, the suboptimal performance in terms of high false positive rates on a single biomarker measured alone may very well be an indicator that some important additional information is contained within the biomarker results—information which would not be elucidated absent the combination with a second biomarker and a mathematical formula.

On the other hand, it is often useful to restrict the number of measured diagnostic determinants (e.g., protein biomarkers), as this allows significant cost reduction and reduces required sample volume and assay complexity. Accordingly, even when two signatures have similar diagnostic performance (e.g., similar AUC or sensitivity), one which incorporates fewer proteins could have significant utility and ability to reduce to practice. For example, a signature that includes 5 proteins compared to 10 proteins and performs similarly has many advantages in real world clinical setting and thus is desirable. Therefore, there is value and invention in being able to reduce the number of genes incorporated in a signature while retaining similar levels of accuracy. In this context similar levels of accuracy could mean plus or minus 1%, 2%, 3%, 4%, 5%, 8%, or 10% in different measures of accuracy such as total accuracy, AUC, MCC, sensitivity, specificity, PPV or NPV; a significant reduction in the number of genes of a signature includes reducing the number of genes by 2, 3, 4, 5, 6, 7, 8, 9, 10 or more than 10 genes.

Several statistical and modeling algorithms known in the art can be used to both assist in determinant selection choices and optimize the algorithms combining these choices. Statistical tools such as factor and cross-biomarker correlation/covariance analyses allow more rationale approaches to panel construction. Mathematical clustering and classification tree showing the Euclidean standardized distance between the determinants can be advantageously used. Pathway informed seeding of such statistical classification techniques also may be employed, as may rational approaches based on the selection of individual determinants based on their participation across in particular pathways or physiological functions.

Ultimately, formula such as statistical classification algorithms can be directly used to both select determinants and to generate and train the optimal formula necessary to combine the results from multiple determinants into a single index. Often, techniques such as forward (from zero potential explanatory parameters) and backwards selection (from all available potential explanatory parameters) are used, and information criteria, such as AIC or BIC, are used to quantify the tradeoff between the performance and diagnostic accuracy of the panel and the number of determinants used. The position of the individual determinant on a forward or backwards selected panel can be closely related to its provision of incremental information content for the algorithm, so the order of contribution is highly dependent on the other constituent determinants in the panel.

Construction of Clinical Algorithms

Any formula may be used to combine determinant results into indices useful in the practice of the invention. As indicated above, and without limitation, such indices may indicate, among the various other indications, the probability, likelihood, absolute or relative risk, time to or rate of conversion from one to another disease states, or make predictions of future biomarker measurements of infection. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from determinant results in the relevant training population. Amongst other uses, such formula may be intended to map the feature space derived from one or more determinant inputs to a set of subject classes (e.g. useful in predicting class membership of subjects as normal, having an infection), to derive an estimation of a probability function of risk using a Bayesian approach, or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual determinant measurements into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on clinical-determinants such as time from symptoms, gender, race, or sex, where specific formula are used solely on subjects within a class or continuously combining a clinical-determinants as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al., (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al., 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula.

There are various ways (and formulations) to combine two biomarkers into one predictive score. For example, using dual cutoffs—one for each biomarker, generates a quadrary separation pattern that can separate between bacterial, viral and mixed (bacterial-viral co-infection) patients. For some biomarkers, adding another cutoff also enables the identification of healthy patients by generating a separation pattern composed of six units. Alternatively, the separation between bacterial and viral patients could be based on the ratio between the two biomarkers. Using a defined cutoff for the ratio between the two biomarkers generates a line that separates between bacterial and viral zones.

Another way to combine two biomarkers is using statistical classification algorithms that can generate various unique separation hyperplanes that distinguish between two groups of patients with high levels of accuracy in a cutoff independent manner. Importantly, cutoff independent models (generated for example using statistical classification algorithms) can provide a likelihood score (e.g., 90% chance for bacterial infection) compared to a binary result (bacterial or viral result only) obtained using defined cutoffs and a quadrary/six units separation patterns. Thus, it can provide additional clinical information that can guide correct patient management. Examples for statistical classification algorithms include Artificial Neural Networks (ANN), Support Vector Machines (SVM), Bayesian Networks (BN), K-Nearest Neighbor (KNN) and Logistic Regression.

Thus, certain embodiments of this invention include combining two polypeptides out of the list of polypeptides that includes for example CRP, TRAIL, PCT, IL-6, IP-10, MX1, for distinguishing between bacterial and viral patients.

In one embodiment, the separation is based on applying dual cutoffs (one for each biomarker) and generating a quadrary separation pattern.

In another embodiment, the separation is based on applying dual cutoffs for one biomarker and a single cutoff for the second biomarker and generating a six unit separation pattern.

In another embodiment, the separation is based on the ratio between the two biomarkers using a defined cutoff.

In yet another embodiment, the combination of the two biomarkers is performed in a cutoff independent manner using statistical classification algorithms.

Some determinants may exhibit trends that depends on the patient age (e.g. the population baseline may rise or fall as a function of age). One can use an 'Age dependent normalization or stratification' scheme to adjust for age related differences. Performing age dependent normalization, stratification or distinct mathematical formulas can be used to improve the accuracy of determinants for differentiating between different types of infections. For example, one skilled in the art can generate a function that fits the population mean levels of each determinant as function of age and use it to normalize the determinant of individual subjects levels across different ages. Another example is to stratify subjects according to their age and determine age specific thresholds or index values for each age group independently.

In the context of the present invention the following statistical terms may be used:

"TP" is true positive, means positive test result that accurately reflects the tested-for activity. For example in the context of the present invention a TP, is for example but not limited to, truly classifying a bacterial infection as such.

"TN" is true negative, means negative test result that accurately reflects the tested-for activity. For example in the context of the present invention a TN, is for example but not limited to, truly classifying a viral infection as such.

"FN" is false negative, means a result that appears negative but fails to reveal a situation. For example in the context of the present invention a FN, is for example but not limited to, falsely classifying a bacterial infection as a viral infection.

"FP" is false positive, means test result that is erroneously classified in a positive category. For example in the context of the present invention a FP, is for example but not limited to, falsely classifying a viral infection as a bacterial infection.

"Sensitivity" is calculated by TP/(TP+FN) or the true positive fraction of disease subjects.

"Specificity" is calculated by TN/(TN+FP) or the true negative fraction of non-disease or normal subjects.

"Total accuracy" is calculated by (TN+TP)/(TN+FP+TP+FN).

"Positive predictive value" or "PPV" is calculated by TP/(TP+FP) or the true positive fraction of all positive test results. It is inherently impacted by the prevalence of the disease and pre-test probability of the population intended to be tested.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

"MCC" (Matthews Correlation coefficient) is calculated as follows: MCC=(TP*TN−FP*FN)/{(TP+FN)*(TP+FP)*(TN+FP)*(TN+FN)}^0.5 where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a single metric (Baldi, Brunak et al. 2000). It is also useful for measuring and optimizing classification accuracy in cases of unbalanced class sizes (Baldi, Brunak et al. 2000).

Often, for binary disease state classification approaches using a continuous diagnostic test measurement, the sensitivity and specificity is summarized by a Receiver Operating Characteristics (ROC) curve according to Pepe et al., "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4$^{th}$ edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Matthews correlation coefficient (MCC), or as a likelihood, odds ratio, Receiver Operating Characteristic (ROC) curve, Area Under the Curve (AUC) among other measures.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value". Non-limiting examples of "formulas" include sums, ratios, and regression operators, such as coefficients or exponents, biomarker value transformations and normalizations (including, without limitation, those normalization schemes based on clinical-determinants, such as gender, age, or ethnicity), rules and guidelines, statistical classification models, and neural networks trained on historical populations. Of particular use in combining determinants are linear and non-linear equations and statistical classification analyses to determine the relationship between levels of determinants detected in a subject sample and the subject's probability of having an infection or a certain type of infection.

In panel and combination construction, of particular interest are structural and syntactic statistical classification algorithms, and methods of index construction, utilizing pattern recognition features, including established techniques such as cross-correlation, Principal Components Analysis (PCA), factor rotation, Logistic Regression (Log Reg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, and Hidden Markov Models, among others. Other techniques may be used in survival and time to event hazard analysis, including Cox, Weibull, Kaplan-Meier and Greenwood models well known to those of skill in the art. Many of these techniques are useful either combined with a determinant selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome.

The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Analytical accuracy" refers to the reproducibility and predictability of the measurement process itself, and may be summarized in such measurements as coefficients of variation (CV), Pearson correlation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC and MCC, time to result, shelf life, etc. as relevant.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

In the context of the present invention the following abbreviations may be used: Antibiotics (Abx), Adverse Event (AE), Arbitrary Units (A.U.), Complete Blood Count (CBC), Case Report Form (CRF), Chest X-Ray (CXR), Electronic Case Report Form (eCRF), Food and Drug Administration (FDA), Good Clinical Practice (GCP), Gastrointestinal (GI), Gastroenteritis (GE), International Conference on Harmonization (ICH), Infectious Disease (ID), In vitro diagnostics (IVD), Lower Respiratory Tract Infection (LRTI), Myocardial infarction (MI), Polymerase chain reaction (PCR), Per-oss (P.O), Per-rectum (P.R), Standard of Care (SoC), Standard Operating Procedure (SOP), Urinary Tract Infection (UTI), Upper Respiratory Tract Infection (URTI).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed.

(1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Methods
Patient Recruitment:

A total of 1057 patients were recruited to the study of whom 948 had a suspected infectious disease and 109 had a non-infectious disease (control group). Informed consent was obtained from each participant or legal guardian, as applicable. Inclusion criteria for the infectious disease cohort included: clinical suspicion of an acute infectious disease, peak fever >37.5° C. since symptoms onset, and duration of symptoms ≤12 days. Inclusion criteria for the control group included: clinical impression of a non-infectious disease (e.g., trauma, stroke and myocardial infarction), or healthy subjects. Exclusion criteria included: evidence of any episode of acute infectious disease in the two weeks preceding enrollment; diagnosed congenital immune deficiency; current treatment with immunosuppressive or immunomodulatory therapy; active malignancy, proven or suspected human immunodeficiency virus (HIV)-1, hepatitis B virus (HBV), or hepatitis C virus (HCV) infection. Importantly, in order to enable broad generalization, antibiotic treatment at enrollment did not cause exclusion from the study. An overview of study workflow is depicted in FIG. 1.

Enrollment Process and Data Collection:

For each patient, the following baseline variables were recorded: demographics, physical examination, medical history (e.g. main complaints, underlying diseases, chronically-administered medications, comorbidities, time of symptom onset, and peak temperature), complete blood count (CBC) obtained at enrollment, and chemistry panel (e.g. creatinine, urea, electrolytes, and liver enzymes). A nasal swab was obtained from each patient for further microbiological investigation, and a blood sample was obtained for protein screening and validation. Additional samples were obtained as deemed appropriate by the physician (e.g. urine and stool samples in cases of suspected urinary tract infection [UTI], and gastroenteritis [GI] respectively). Radiological tests were obtained at the discretion of the physician (e.g. chest X-ray for suspected lower respiratory tract infection [LRTI]). All information was recorded in a custom electronic case report form (eCRF).

Establishing the Reference Standard:

Currently, no single reference standard exists for determining bacterial and viral infections in a wide range of clinical syndromes. Therefore, a rigorous reference standard was created following recommendations of the Standards for Reporting of Diagnostic Accuracy (STARD) [21]. First, a thorough clinical and microbiological investigation was performed for each patient as described above. Then, all the data collected throughout the disease course was reviewed by a panel of up to three physicians that assigned one of the following diagnostic labels to each patient: (i) bacterial; (ii) viral; (iii) no apparent infectious disease or healthy (controls); and (iv) indeterminate. Importantly, the panel members were blinded to the labeling of their peers to prevent group pressure or influential personality bias as recommended by NHS-HTA [22], and to the results of the host-proteins measurements.

Samples, Procedures and Sample Processing:

Venous blood samples were stored at 4° C. for up to 5 hours, subsequently fractionated into plasma, serum and total leukocytes, and stored at −80° C. Nasal swabs and stool samples were stored at 4° C. for up to 72 hours and subsequently transported to a certified service laboratory for multiplex PCRs. C-reactive protein (CRP) was measured from serum using either Cobas-6000, Cobas-Integra-400/800, or Modular-Analytics-P800 (Roche). Procalcitonin (PCT) was measured using either Elecsys BRAHMS PCT Kit or LIAISON BRAHMS PCT Kit. Other host-determinants were measured using enzyme-linked immunosorbent-assay (ELISA).

Statistical Analysis

Primary Analysis was Based on Area Under the Receiver operating curve (AUC), Matthews correlation coefficient (MCC), sensitivity, specificity, total accuracy. positive predictive value (PPV), and negative predictive value (NPV). These measures are defined as follows:

$$\text{Sensitivity} = \frac{TP}{TP+FN}$$

$$\text{Specificity} = \frac{TN}{TN+FP}$$

$$\text{total accuracy} = \frac{TP+TN}{TP+FN+TN+FP}$$

$$PPV = \frac{TP}{TP+FP} = \frac{\text{sensitivity} \cdot \text{prevalence}}{\text{sensitivity} \cdot \text{prevalence} + (1-\text{specificity}) \cdot (1-\text{prevalence})}$$

$$NPV = \frac{TN}{TN+FN} = \frac{\text{specificity} \cdot (1-\text{prevalence})}{\text{specificity} \cdot (1-\text{prevalence}) + (1-\text{sensitivity}) \cdot (\text{prevalence})}$$

$$MCC = \frac{TP \times TN - FP \times FN}{\sqrt{(TP+FP)(TP+FN)(TN+FP)(TN+FN)}}$$

P, N, TP, FP, TN, FN are positives, negatives, true-positives, false-positives, true-negatives, and false-negatives, respectively. Unless mentioned otherwise, positives and negatives refer to patients with bacterial and viral infections, respectively.

Results
Patients Characteristics:

The Studied Group of Acute Infection Patients Included 47% females and 53% males aged 1 month to 88 years. The patients presented with a variety of clinical syndromes affecting different physiological systems (e.g., respiratory, urinal, central nervous system, systemic). Detailed characterization of studied patients is depicted in FIGS. 2-7.

Importantly, as improved identification of bacterial patients was the primary end goal of the inventors, the evaluated cohort was deliberately enriched with hard to diagnose patients, previously classified by individual proteins or the TCP signature as false negative or false positives. Therefore the performance measures of the TCP in the following sections are significantly lower than what would be expected in the general population.

Generating New Host-Protein Signatures with Improved Ability to Identify Bacterial Infected Patients and Distinguish them from Viral Patients:

The TCP signature predictive score is calculated using a non-linear Multinomial Logistic Regression model (MLR; Table 3). The model provides a viral or other (including non-infectious) labels when the predictive score is between 0-35; a bacterial label when the predictive score is between 65-100; and an equivocal result when the predictive score is between 35-65. Its measures of accuracy on the studied cohort are summarized in Table 4.

TABLE 3

Non-linear Multinomial Logistic Regression coefficients of the TCP signature

|  | Class (viral) | Class (bacterial) |
|---|---|---|
| Constant | $c_0 = -0.8388$ | $b_0 = 5.5123$ |
| CRP | $c_1 = -0.0487$ | $b_1 = -0.0636$ |
| CRP^0.5 | $c_2 = 1.1367$ | $b_2 = 1.4877$ |
| CRP^2 | $c_3 = -5.14E-05$ | $b_3 = 3.50E-05$ |
| IP-10 | $c_4 = 0.0089$ | $b_4 = 0.0085$ |
| TRAIL | $c_5 = 0.0408$ | $b_5 = 0.0646$ |
| TRAIL^0.5 | $c_6 = -0.6064$ | $b_6 = -1.8039$ |

TABLE 4

Measures of accuracy of the TCP (TRAIL-CRP-IP-10) signature in distinguishing between bacterial (n = 378) and viral (n = 570) patients.

|  | AUC | Total accuracy | Sensitivity | Specificity | PPV | NPV |
|---|---|---|---|---|---|---|
| TCP signature | 0.9 | 0.82 | 0.79 | 0.84 | 0.77 | 0.86 |

In trying to improve the sensitivity of the TCP signature we evaluated different ways to combine it with additional proteins such as IL-6 and PCT. We initially evaluated the performance of PCT and IL-6 as individual classifiers in cutoff independent (using logistic regression models; Table 5), and dependent manner (Table 6). The logistic regression model used for calculating IL-6 or PCT measures of accuracy in a cutoff independent manner is:

$$P(B) = \frac{1}{1 + e^{-\lambda}}$$
$$\lambda = a_0 + a_1 * X$$

TABLE 5

Measures of accuracy of IL-6 and PCT in distinguishing between bacterial (n = 378) and viral (n = 570) patients, calculated for a logistic regression model that optimized each biomarker performances in a cutoff independent manner.

|  | Total | | | | | | Logistic regression coefficients | |
|---|---|---|---|---|---|---|---|---|
|  | AUC | MCC | accuracy | Sensitivity | Specificity | PPV | NPV | Constant | protein |
| IL-6 | 0.72 | 0.34 | 0.67 | 0.68 | 0.66 | 0.57 | 0.75 | -1.12 | 0.011 |
| PCT | 0.59 | 0.28 | 0.62 | 0.47 | 0.73 | 0.53 | 0.67 | -0.977 | 0.488 |

TABLE 6

Measures of accuracy of IL-6 and PCT in distinguishing between bacterial (n = 378) and viral (n = 570) patients, calculated for different protein cutoffs as indicated.

|  | Sensitivity | Specificity | PPV | NPV |
|---|---|---|---|---|
| IL-6 (25 pg/ml) | 0.62 | 0.74 | 0.57 | 0.78 |
| (50 pg/ml) | 0.47 | 0.87 | 0.67 | 0.75 |
| (100 pg/ml) | 0.31 | 0.95 | 0.78 | 0.71 |
| (200 pg/ml) | 0.16 | 0.98 | 0.81 | 0.68 |
| (300 pg/ml) | 0.13 | 0.99 | 0.92 | 0.67 |
| PCT (0.5 μg/L) | 0.39 | 0.86 | 0.61 | 0.72 |
| PCT (1 μg/L) | 0.32 | 0.94 | 0.74 | 0.71 |
| PCT (1.5 μg/L) | 0.26 | 0.96 | 0.78 | 0.70 |
| PCT (2 μg/L) | 0.22 | 0.98 | 0.87 | 0.69 |
| PCT (2.5 μg/L) | 0.20 | 0.99 | 0.93 | 0.69 |

Statistical Classification Algorithms

Both PCT and IL-6 were poor-medium classifiers in the studied cohort with a maximal sensitivity of 0.68 (IL-6) and 0.47 (PCT). To test whether they are able to improve the sensitivity of the TCP signature requires: i) to mathematically combine them with the TCP model; and ii) to test the new combination on hundreds of real world clinical samples. To combine the TCP signature with IL-6 and PCT, several statistical approaches were applied in order to generate different unique separation hyperplanes that distinguish between bacterial and viral patients with higher levels of accuracy. The inventors first examined multiple statistical classification algorithms and computational models including Artificial Neural Networks (ANN), Support Vector Machines (SVM), Bayesian Networks (BN), K-Nearest Neighbor (KNN) and Logistic Regression. Results using Logistic Regression are provided herein below. The performance (accuracy levels) of the developed models using real world infectious disease clinical samples described above was evaluated (Tables 7-9). A set of quantitative parameters (model coefficients) that specifically define the hyperplane separating between two patient groups are provided in Tables 7-9. As clinically demonstrated, both IL-6 and PCT (and IL-6+PCT) were able to improve the sensitivity of the TCP signature and comprising proteins (Tables 7-9).

TABLE 7

Logistic regression models combining the TCP signature with either PCT or IL-6 and their measures of accuracy in distinguishing between bacterial (n = 378) and viral (n = 570) patients.

| Added protein | AUC | MCC | Total accuracy | Sensitivity | Specificity | PPV | NPV | Logistic regression coefficients | | |
|---|---|---|---|---|---|---|---|---|---|---|
| | | | | | | | | Constant | TCP Signature | Added protein |
| IL-6 (pg/ml) | 0.90 | 0.64 | 0.83 | 0.82 | 0.84 | 0.77 | 0.87 | −3.0954 | 5.0059 | 0.004961 |
| PCT (µg/L) | 0.90 | 0.62 | 0.82 | 0.80 | 0.83 | 0.76 | 0.86 | −3.0017 | 5.0839 | 0.19589 |

TABLE 8

Logistic regression models of protein/determinant triplets and their measures of accuracy in distinguishing between bacterial (n = 378) and viral (n = 570) patients.

| Determinant 1 | Determinant 2 | Determinant 3 | AUC | MCC | Total accuracy | Sensitivity | Specificity | PPV | NPV | Logistic regression coefficients | | | |
|---|---|---|---|---|---|---|---|---|---|---|---|---|---|
| | | | | | | | | | | Constant | Determinant 1 | Determinant 2 | Determinant 3 |
| CRP (µg/ml) | IL-6 (pg/ml) | TRAIL (pg/ml) | 0.91 | 0.66 | 0.84 | 0.83 | 0.85 | 0.79 | 0.88 | −0.95196 | 0.028267 | 0.0052342 | −0.01929 |
| CRP (µg/ml) | PCT (µg/L) | TRAIL (pg/ml) | 0.90 | 0.65 | 0.83 | 0.84 | 0.82 | 0.76 | 0.88 | −0.53429 | 0.027591 | 0.14651 | −0.02187 |
| IP-10 (pg/ml) | PCT (µg/L) | TRAIL (pg/ml) | 0.86 | 0.54 | 0.78 | 0.77 | 0.79 | 0.71 | 0.84 | 1.5867 | 0.000277 | 0.26332 | −0.034124 |
| TCP signature | IL-6 (pg/ml) | PCT (µg/L) | 0.91 | 0.64 | 0.83 | 0.81 | 0.85 | 0.78 | 0.87 | −3.1573 | 4.8972 | 0.0046277 | 0.16037 |

TABLE 9

Logistic regression models of protein/determinant quads and their measures of accuracy in distinguishing between bacterial (n = 378) and viral (n = 570) patients.

| Protein 1 | Protein 2 | Protein 3 | Protein 4 | AUC | MCC | Total accuracy | Sensitivity | Specificity | PPV | NPV | Logistic regression coefficients | | | | |
|---|---|---|---|---|---|---|---|---|---|---|---|---|---|---|---|
| | | | | | | | | | | | Constant | Protein 1 | Protein 2 | Protein 3 | Protein 4 |
| CRP (µg/ml) | IL-6 (pg/ml) | PCT (µg/L) | TRAIL (pg/ml) | 0.91 | 0.66 | 0.84 | 0.84 | 0.84 | 0.77 | 0.89 | −1.0278 | 0.027874 | 0.004972 | 0.10982 | −0.01896 |
| IL-6 (pg/ml) | IP-10 (pg/ml) | PCT (µg/L) | TRAIL (pg/ml) | 0.87 | 0.54 | 0.79 | 0.79 | 0.79 | 0.71 | 0.85 | 1.1437 | 0.0055258 | 0.000155 | 0.21664 | −0.03034 |

Using Fuzzy OR Model to Generate Improved Signatures for Distinguishing Between Bacterial and Viral Patients The inventors developed the models which incorporates the measurements of PCT and or IL-6 with the results of the TCP model in a manner that allows a significant improvement in model specificity. These models are referred to as "Fuzzy Or models."

Figure 10B:
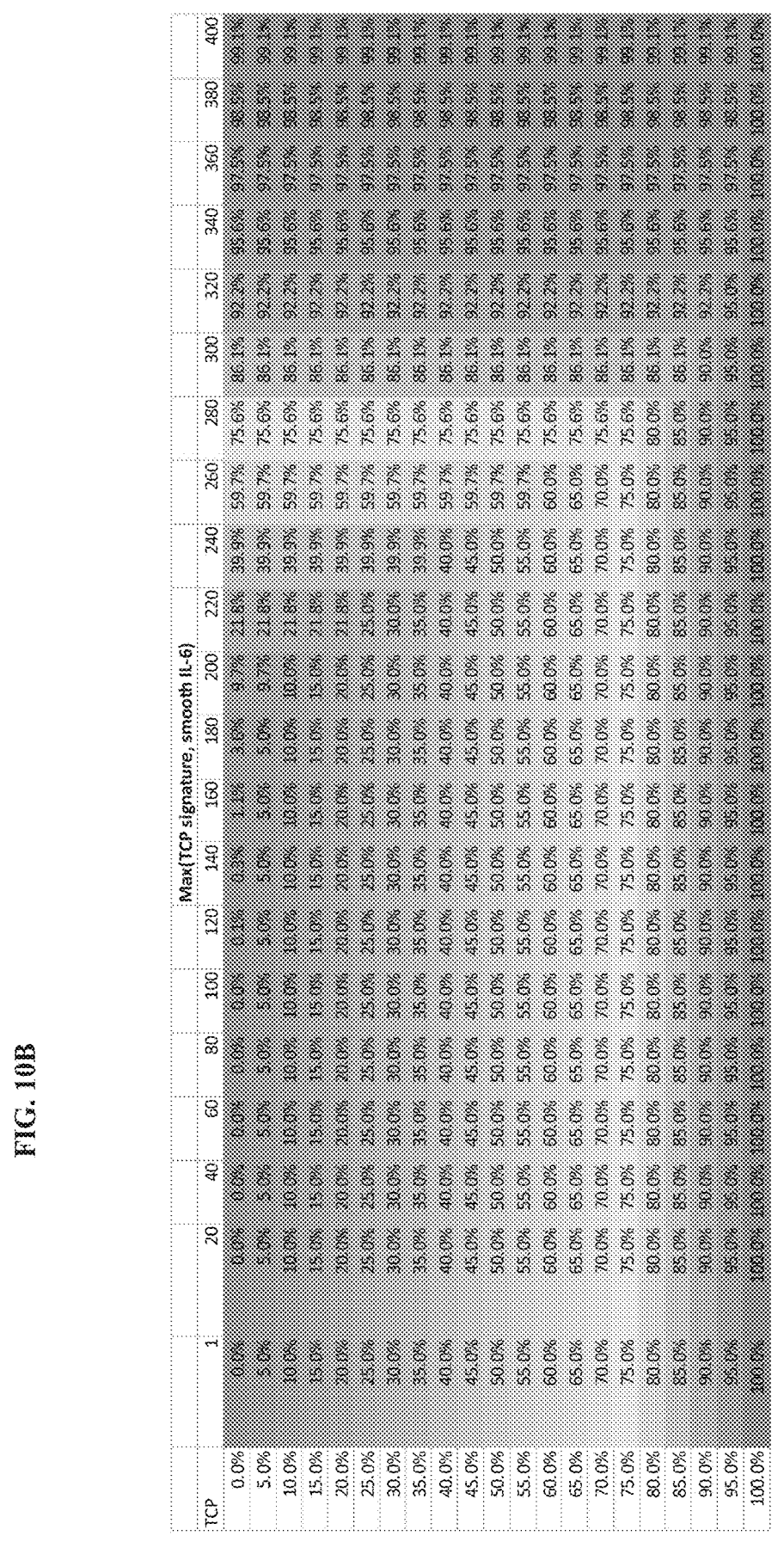

The rationale behind the construction of the Fuzzy or Model is as follows: in the data the inventors found that both and PCT have relatively very low sensitivity but reasonable specificity, for distinguishing between bacterial and viral etiologies. This is particularly true for relatively high cutoffs (e.g., IL-6 cutoff of 100 pg/ml gives sensitivity of 31% and specificity of 95%; PCT cutoff of 2 µg/L gives sensitivity of 22%, specificity of 98%; Tables 10-12). Accordingly, the inventors devised a novel model that incorporates the TCP signature with levels of IL-6, PCT or both. In particular the new Fuzzy OR model gives low weight to low or medium levels of IL-6 and PCT, because the inventors found that such low levels add limited information beyond the TCP signature. Accordingly, the Fuzzy OR model was devised such that the signature is by and large dominated by the likelihood of the TCP signature (FIGS. 10A-B).

However, as IL-6 and PCT levels become higher (for example without limitation 100, 200, 240, 250, 280, 320, and 350 pg/ml for IL-6 and 1, 1.5, 2, 2.5, 5, and 7.5 µg/L for PCT), they start to increase the likelihood of bacterial infection. The hill coefficient, is applied to control over the slope of the transition between TCP signature prediction to IL-6 or PCT. The result of the combined model is a single likelihood score for prediction of bacterial infections that has improved sensitivity compared to the TCP model (FIGS. 11A-D and Table 6).

Examples of such models are described in Fuzzy OR formulas #1-6, below:

Fuzzy OR formula #1

$$FuzzyOrProb = TCP_{Prob} * \frac{1}{1+\left(\frac{PCT}{c_{PCT}}\right)^{h_{PCT}}} + \frac{1}{1+\left(\frac{PCT}{c_{PCT}}\right)^{-h_{PCT}}}$$

were
$TCP_{prob}$=TCP signature score/100 (scale of 0-1)
$h_{PCT}$=PCT model hill coefficient
$c_{PCT}$=PCT model cutoff Fuzzy OR formula #2

$$FuzzyOrProb = TCP_{Prob} * \frac{1}{1+\left(\frac{IL6}{c_{IL6}}\right)^{h_{IL6}}} + \frac{1}{1+\left(\frac{IL6}{c_{IL6}}\right)^{-h_{IL6}}}$$

$TCP_{prob}$=TCP signature score/100 (scale of 0-1)
$H_{IL6}$=IL-6 model hill coefficient
$C_{IL6}$=IL-6 model cutoff Fuzzy OR formula #3

$$FuzzyOrProb = \left(TCP_{Prob} * \frac{1}{1+\left(\frac{IL6}{c_{IL6}}\right)^{h_{IL6}}} + \frac{1}{1+\left(\frac{IL6}{c_{IL6}}\right)^{-h_{IL6}}}\right) * \frac{1}{1+\left(\frac{PCT}{c_{PCT}}\right)^{h_{PCT}}} + \frac{1}{1+\left(\frac{PCT}{c_{PCT}}\right)^{-h_{PCT}}}$$

Fuzzy OR formula #4
In one preferred embodiment a very small constant ($\varepsilon$) is added to the protein concentrations to prevent numeric instability:

$$FuzzyOrProb = TCP_{Prob} * \frac{1}{1+\left(\frac{PCT+\varepsilon}{c_{PCT}}\right)^{h_{PCT}}} + \frac{1}{1+\left(\frac{PCT+\varepsilon}{c_{PCT}}\right)^{-h_{PCT}}}$$

$TCP_{prob}$=TCP signature score/100 (scale of 0-1)
$h_{PCT}$=PCT model hill coefficient
$c_{PCT}$=PCT model cutoff Fuzzy OR formula #5

$$FuzzyOrProb = TCP_{Prob} * \frac{1}{1+\left(\frac{IL6+\varepsilon}{c_{IL6}}\right)^{h_{IL6}}} + \frac{1}{1+\left(\frac{IL6+\varepsilon}{c_{IL6}}\right)^{-h_{IL6}}}$$

$TCP_{prob}$=TCP signature score/100 (scale of 0-1)
$H_{IL6}$=IL-6 model hill coefficient
$C_{IL6}$=IL-6 model cutoff Fuzzy OR formula #6

$$FuzzyOrProb = \left(TCP_{Prob} * \frac{1}{1+\left(\frac{IL6+\varepsilon}{c_{IL6}}\right)^{h_{IL6}}} + \frac{1}{1+\left(\frac{IL6+\varepsilon}{c_{IL6}}\right)^{-h_{IL6}}}\right) * \frac{1}{1+\left(\frac{PCT+\varepsilon}{c_{PCT}}\right)^{h_{PCT}}} + \frac{1}{1+\left(\frac{PCT+\varepsilon}{c_{PCT}}\right)^{-h_{PCT}}}$$

The inventors further evaluated the performance (accuracy levels) of the developed model in distinguishing between bacterial and viral patients (Tables 10-12), and between bacterial and non-bacterial (viral plus non-infectious) patients (Tables 13-15). The Fuzzy OR models significantly improved the TCP signature sensitivity. For example, combining IL-6 and the TCP signature resulted in sensitivity levels of 0.834-0.888 depending on the cutoff applied (Table 10). Combining PCT and the TCP signature resulted in sensitivity levels of 0.82-0.99 depending on the cutoff applied (Table 11). Combining both PCT and IL-6 with the TCP signature resulted in sensitivity levels of 0.855-0.995 depending on the cutoffs applied (Table 12). Similar improvements were observed for distinguishing between bacterial and non-bacterial (viral plus non-infectious) patients (Tables 13-15). The optimal cutoff of either IL-6, PCT or both depends on the balance between optimal sensitivity and specificity and may vary according to the desired use and/or clinical setting.

TABLE 10

Measures of accuracy in distinguishing between bacterial (n = 378) and viral (n = 570) patients of different combinations of the TCP signature and IL-6 generated using Fuzzy OR analysis in different IL-6 model cutoffs as indicated.

| IL-6 cutoff (pg/ml) | Sensitivity | Specificity | % Equivocal | PPV | NPV |
|---|---|---|---|---|---|
| 50 | 0.888 | 0.767 | 10.7% | 0.72 | 0.91 |
| 100 | 0.859 | 0.845 | 12.3% | 0.79 | 0.90 |
| 150 | 0.849 | 0.865 | 12.6% | 0.81 | 0.90 |
| 200 | 0.846 | 0.875 | 12.7% | 0.82 | 0.89 |
| 250 | 0.845 | 0.886 | 13.7% | 0.83 | 0.89 |
| 300 | 0.844 | 0.898 | 13.9% | 0.85 | 0.90 |
| 350 | 0.841 | 0.900 | 13.6% | 0.85 | 0.89 |
| 400 | 0.840 | 0.900 | 13.8% | 0.85 | 0.89 |
| 450 | 0.837 | 0.900 | 13.8% | 0.85 | 0.89 |
| 500 | 0.834 | 0.904 | 14.0% | 0.85 | 0.89 |

TABLE 11

Measures of accuracy in distinguishing between bacterial (n = 378) and viral (n = 570) patients of different combinations of the TCP signature and PCT generated using Fuzzy OR analysis in different PCT cutoffs as indicated.

| PCT cutoff (μg/L) | Sensitivity | Specificity | % Equivocal | PPV | NPV |
|---|---|---|---|---|---|
| 0.1 | 0.992 | 0.023 | 0.1% | 0.40 | 0.81 |
| 0.25 | 0.964 | 0.214 | 3.4% | 0.44 | 0.90 |
| 0.5 | 0.881 | 0.757 | 11.6% | 0.71 | 0.90 |
| 1 | 0.865 | 0.837 | 12.2% | 0.78 | 0.90 |
| 1.5 | 0.859 | 0.860 | 13.5% | 0.80 | 0.90 |
| 2 | 0.841 | 0.888 | 13.6% | 0.83 | 0.89 |
| 2.5 | 0.841 | 0.896 | 13.9% | 0.84 | 0.89 |
| 5 | 0.828 | 0.898 | 13.9% | 0.84 | 0.89 |
| 7.5 | 0.827 | 0.900 | 14.1% | 0.84 | 0.89 |
| 10 | 0.820 | 0.902 | 14.2% | 0.85 | 0.88 |

TABLE 12

Measures of accuracy in distinguishing between bacterial (n = 378) and viral (n = 570) patients of different combinations of the TCP signature and PCT and IL-6 generated using Fuzzy OR analysis in different PCT/IL-6 cutoffs as indicated.

| IL-6 cutoff (pg/ml) | PCT cutoff (μg/L) | Sensitivity | Specificity | % Equivocal | PPV | NPV |
|---|---|---|---|---|---|---|
| 50 | 0.1 | 0.995 | 0.021 | 0.1% | 0.40 | 0.86 |
| 50 | 0.25 | 0.967 | 0.191 | 3.1% | 0.44 | 0.90 |
| 50 | 0.5 | 0.922 | 0.657 | 8.6% | 0.64 | 0.93 |
| 50 | 1.5 | 0.907 | 0.731 | 9.6% | 0.69 | 0.92 |
| 50 | 2.5 | 0.901 | 0.762 | 10.5% | 0.72 | 0.92 |
| 150 | 0.1 | 0.992 | 0.023 | 0.1% | 0.40 | 0.81 |
| 150 | 0.25 | 0.964 | 0.211 | 3.2% | 0.44 | 0.90 |
| 150 | 0.5 | 0.899 | 0.738 | 11.2% | 0.70 | 0.92 |
| 150 | 1.5 | 0.880 | 0.826 | 12.1% | 0.77 | 0.91 |
| 150 | 2.5 | 0.863 | 0.860 | 12.6% | 0.81 | 0.90 |
| 250 | 0.1 | 0.992 | 0.023 | 0.1% | 0.40 | 0.81 |
| 250 | 0.25 | 0.964 | 0.213 | 3.2% | 0.44 | 0.90 |
| 250 | 0.5 | 0.897 | 0.750 | 11.5% | 0.71 | 0.91 |
| 250 | 1.5 | 0.877 | 0.842 | 12.8% | 0.79 | 0.91 |
| 250 | 2.5 | 0.859 | 0.877 | 13.4% | 0.83 | 0.90 |
| 300 | 0.1 | 0.992 | 0.023 | 0.1% | 0.40 | 0.81 |
| 300 | 0.25 | 0.964 | 0.214 | 3.1% | 0.44 | 0.90 |
| 300 | 0.5 | 0.897 | 0.756 | 11.4% | 0.71 | 0.92 |
| 300 | 1.5 | 0.877 | 0.854 | 13.0% | 0.80 | 0.91 |
| 300 | 2.5 | 0.858 | 0.889 | 13.6% | 0.84 | 0.90 |
| 500 | 0.1 | 0.992 | 0.023 | 0.1% | 0.40 | 0.81 |
| 500 | 0.25 | 0.964 | 0.214 | 3.1% | 0.44 | 0.90 |
| 500 | 0.5 | 0.893 | 0.757 | 11.3% | 0.71 | 0.91 |
| 500 | 1.5 | 0.873 | 0.858 | 13.0% | 0.81 | 0.91 |
| 500 | 2.5 | 0.855 | 0.894 | 13.5% | 0.84 | 0.90 |

TABLE 13

Measures of accuracy in distinguishing between bacterial (n = 378) and non-bacterial (viral + non-infectious; n = 679) patients of different combinations of the TCP signature and IL-6 generated using Fuzzy OR analysis in different IL-6 cutoffs as indicated.

| IL-6 cutoff (pg/ml) | Sensitivity | Specificity | % Equivocal | PPV | NPV |
|---|---|---|---|---|---|
| 50 | 0.888 | 0.802 | 10.4% | 0.72 | 0.93 |
| 100 | 0.859 | 0.870 | 11.9% | 0.79 | 0.92 |
| 150 | 0.849 | 0.886 | 12.1% | 0.81 | 0.91 |
| 200 | 0.846 | 0.894 | 12.2% | 0.82 | 0.91 |
| 250 | 0.845 | 0.903 | 13.2% | 0.83 | 0.91 |
| 300 | 0.844 | 0.913 | 13.3% | 0.84 | 0.91 |
| 350 | 0.841 | 0.915 | 13.1% | 0.85 | 0.91 |
| 400 | 0.840 | 0.916 | 13.2% | 0.85 | 0.91 |
| 450 | 0.837 | 0.916 | 13.2% | 0.84 | 0.91 |
| 500 | 0.834 | 0.919 | 13.4% | 0.85 | 0.91 |

TABLE 14

Measures of accuracy in distinguishing between bacterial (n = 378) and non-bacterial (viral + non-infectious; n = 679) patients of different combinations of the TCP signature and PCT generated using Fuzzy OR analysis in different PCT cutoffs as indicated.

| PCT cutoff (μg/L) | Sensitivity | Specificity | % Equivocal | PPV | NPV |
|---|---|---|---|---|---|
| 0.1 | 0.992 | 0.024 | 0.1% | 0.36 | 0.84 |
| 0.25 | 0.964 | 0.236 | 3.3% | 0.41 | 0.92 |
| 0.5 | 0.881 | 0.793 | 11.3% | 0.70 | 0.92 |
| 1 | 0.865 | 0.861 | 11.8% | 0.78 | 0.92 |
| 1.5 | 0.859 | 0.880 | 13.0% | 0.80 | 0.92 |
| 2 | 0.841 | 0.904 | 13.1% | 0.83 | 0.91 |
| 2.5 | 0.841 | 0.910 | 13.3% | 0.84 | 0.91 |
| 5 | 0.828 | 0.912 | 13.3% | 0.84 | 0.91 |
| 7.5 | 0.827 | 0.914 | 13.5% | 0.84 | 0.91 |
| 10 | 0.820 | 0.917 | 13.6% | 0.84 | 0.90 |

TABLE 15

Measures of accuracy in distinguishing between bacterial (n = 378) and non-bacterial (viral + non-infectious; n = 679) patients of different combinations of the TCP signature and PCT and IL-6 generated using Fuzzy OR analysis in different PCT/IL-6 cutoffs as indicated.

| IL-6 cutoff (pg/ml) | PCT cutoff (μg/L) | Sensitivity | Specificity | % Equivocal | PPV | NPV |
|---|---|---|---|---|---|---|
| 50 | 0.1 | 0.995 | 0.022 | 0.1% | 0.36 | 0.88 |
| 50 | 0.25 | 0.967 | 0.215 | 3.0% | 0.41 | 0.92 |
| 50 | 0.5 | 0.922 | 0.706 | 8.6% | 0.64 | 0.94 |
| 50 | 1.5 | 0.907 | 0.770 | 9.5% | 0.69 | 0.94 |
| 50 | 2.5 | 0.901 | 0.797 | 10.3% | 0.72 | 0.93 |
| 150 | 0.1 | 0.992 | 0.024 | 0.1% | 0.36 | 0.84 |
| 150 | 0.25 | 0.964 | 0.233 | 3.1% | 0.41 | 0.92 |
| 150 | 0.5 | 0.899 | 0.776 | 10.9% | 0.69 | 0.93 |
| 150 | 1.5 | 0.880 | 0.852 | 11.7% | 0.77 | 0.93 |
| 150 | 2.5 | 0.863 | 0.880 | 12.1% | 0.80 | 0.92 |
| 250 | 0.1 | 0.992 | 0.024 | 0.1% | 0.36 | 0.84 |
| 250 | 0.25 | 0.964 | 0.234 | 3.1% | 0.41 | 0.92 |
| 250 | 0.5 | 0.897 | 0.787 | 11.2% | 0.70 | 0.93 |
| 250 | 1.5 | 0.877 | 0.865 | 12.3% | 0.78 | 0.93 |
| 250 | 2.5 | 0.859 | 0.895 | 12.9% | 0.82 | 0.92 |
| 300 | 0.1 | 0.992 | 0.024 | 0.1% | 0.36 | 0.84 |
| 300 | 0.25 | 0.964 | 0.236 | 3.0% | 0.41 | 0.92 |
| 300 | 0.5 | 0.897 | 0.792 | 11.1% | 0.71 | 0.93 |
| 300 | 1.5 | 0.877 | 0.875 | 12.5% | 0.80 | 0.93 |
| 300 | 2.5 | 0.858 | 0.905 | 13.1% | 0.84 | 0.92 |
| 500 | 0.1 | 0.992 | 0.024 | 0.1% | 0.36 | 0.84 |
| 500 | 0.25 | 0.964 | 0.236 | 3.0% | 0.41 | 0.92 |
| 500 | 0.5 | 0.893 | 0.793 | 11.0% | 0.71 | 0.93 |
| 500 | 1.5 | 0.873 | 0.879 | 12.5% | 0.80 | 0.93 |
| 500 | 2.5 | 0.855 | 0.908 | 13.0% | 0.84 | 0.92 |

Figure 8A:
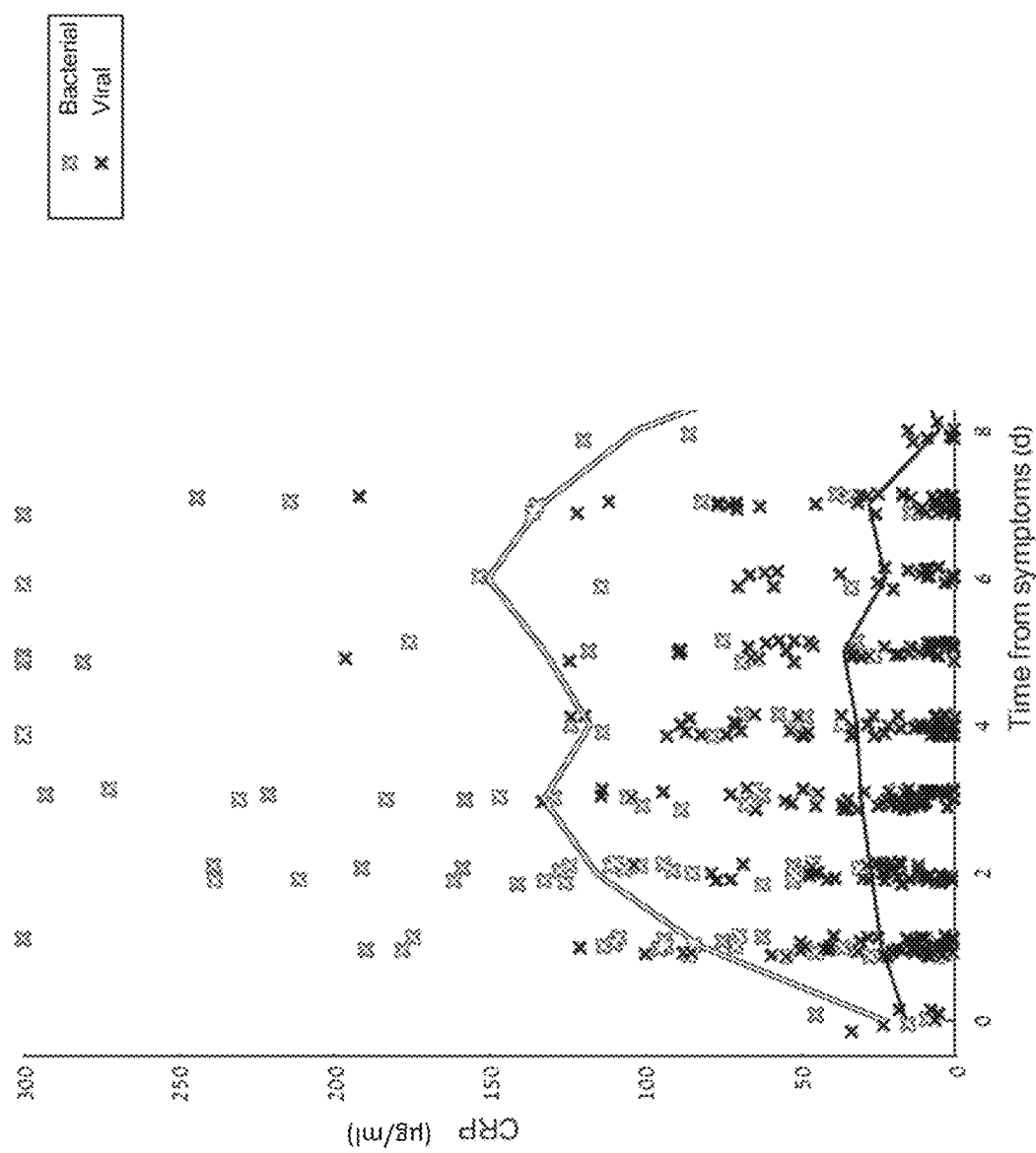
Figure 9:
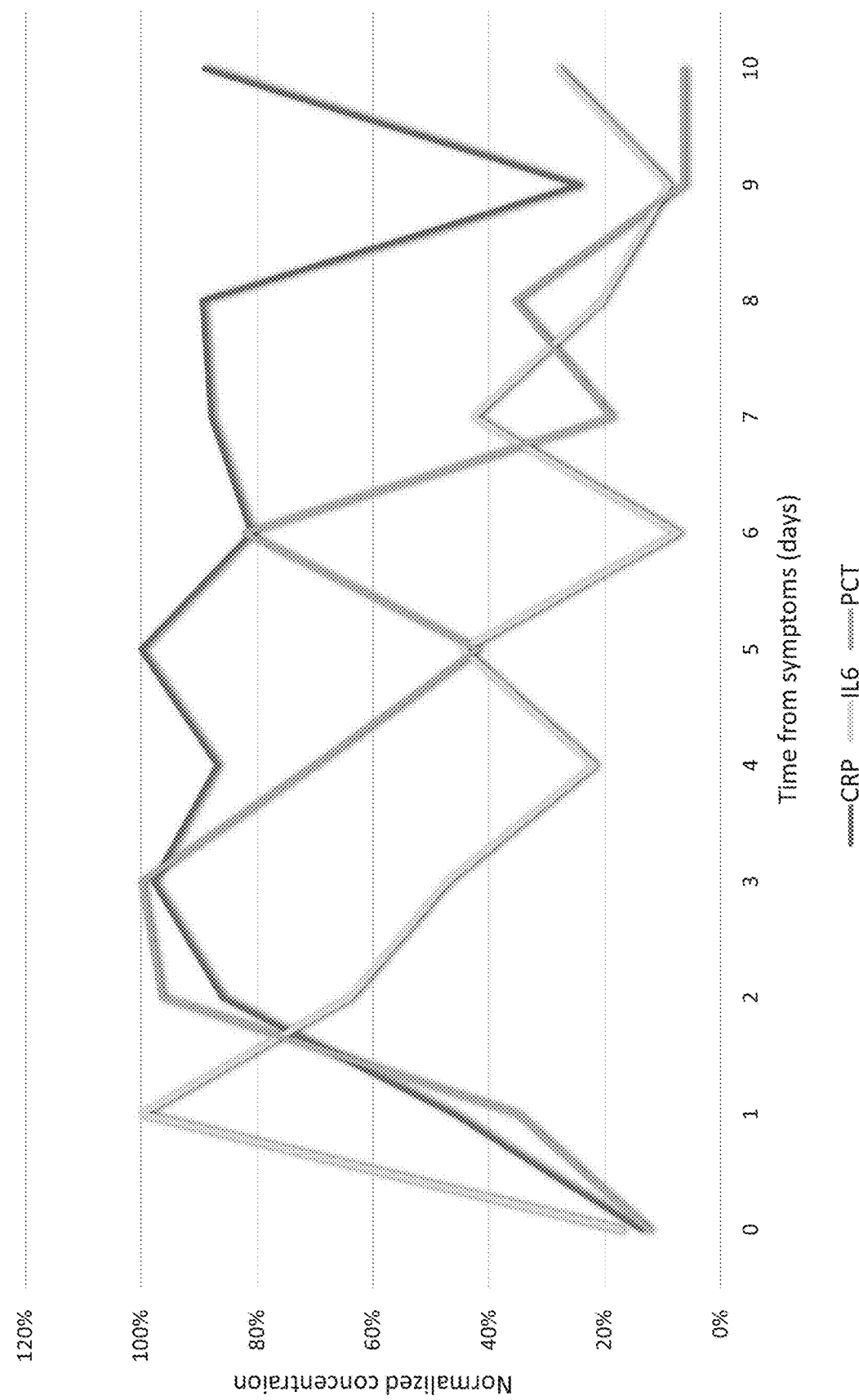
FIG. 9. Temporal dynamics of bacterially induced biomarkers. Average levels of IL-6, PCT, and CRP measured at different times after symptom onset from serum samples of bacterially infected patients.
Figure 11A:
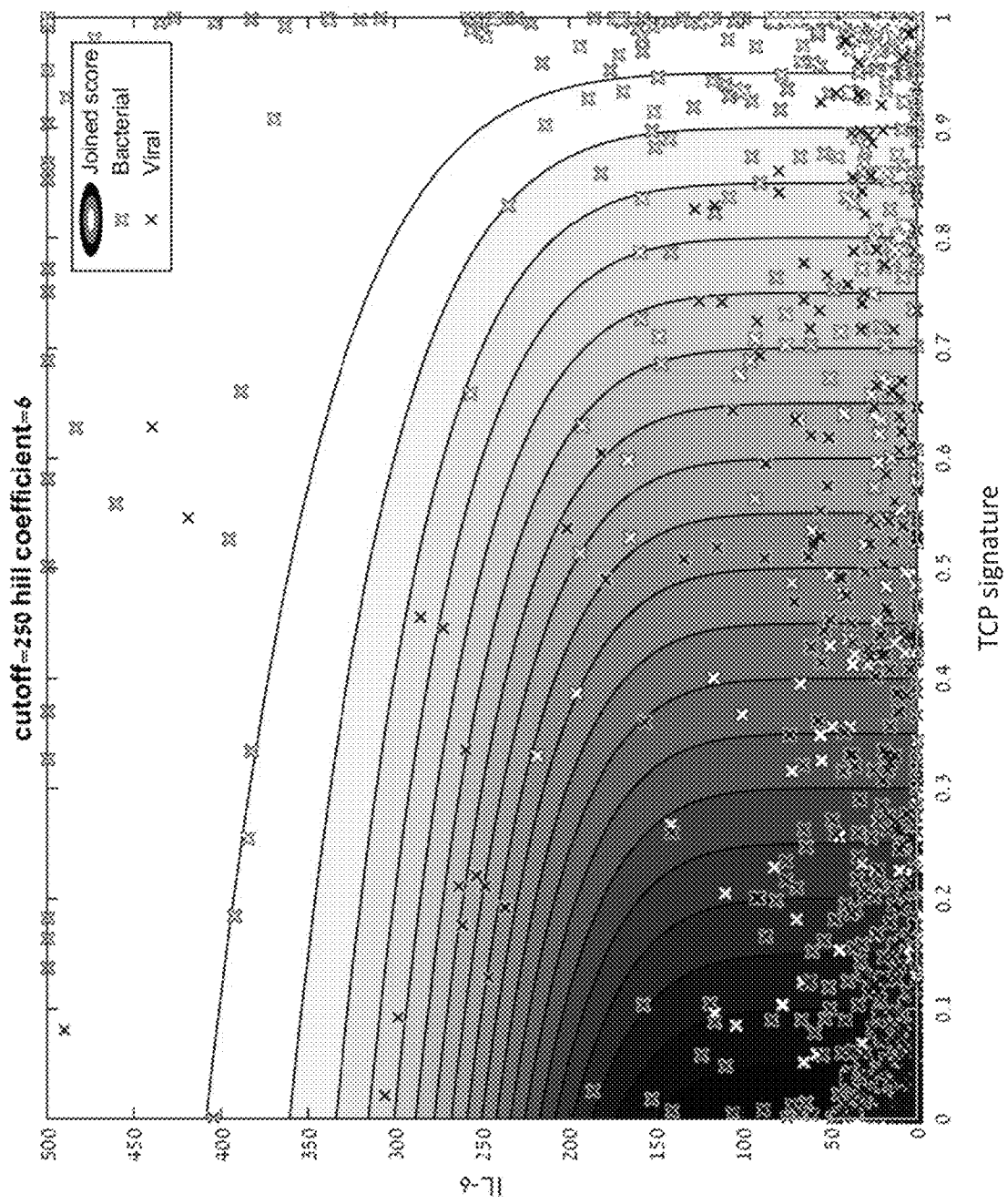
Figure 11B:
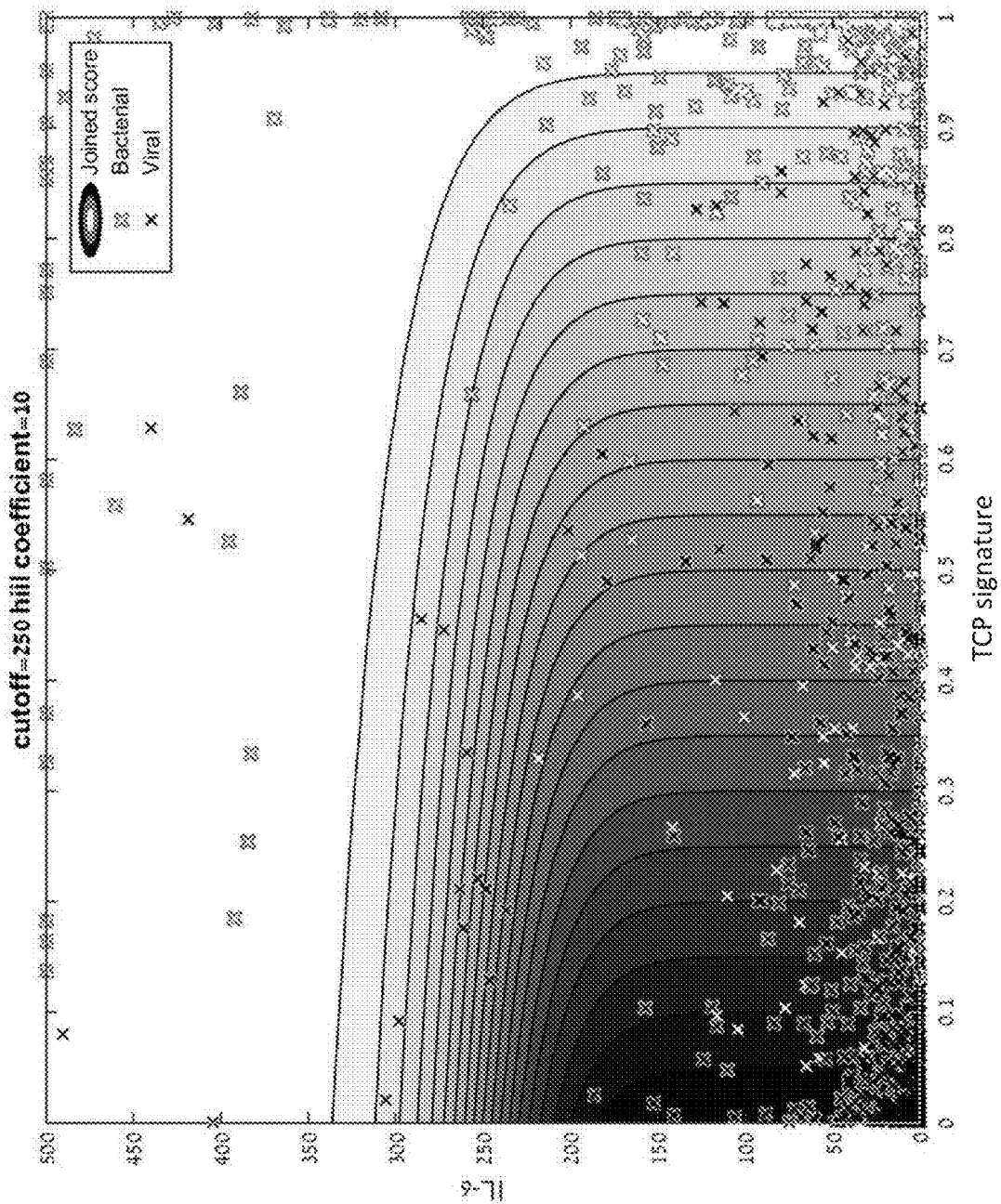
Figure 11C:
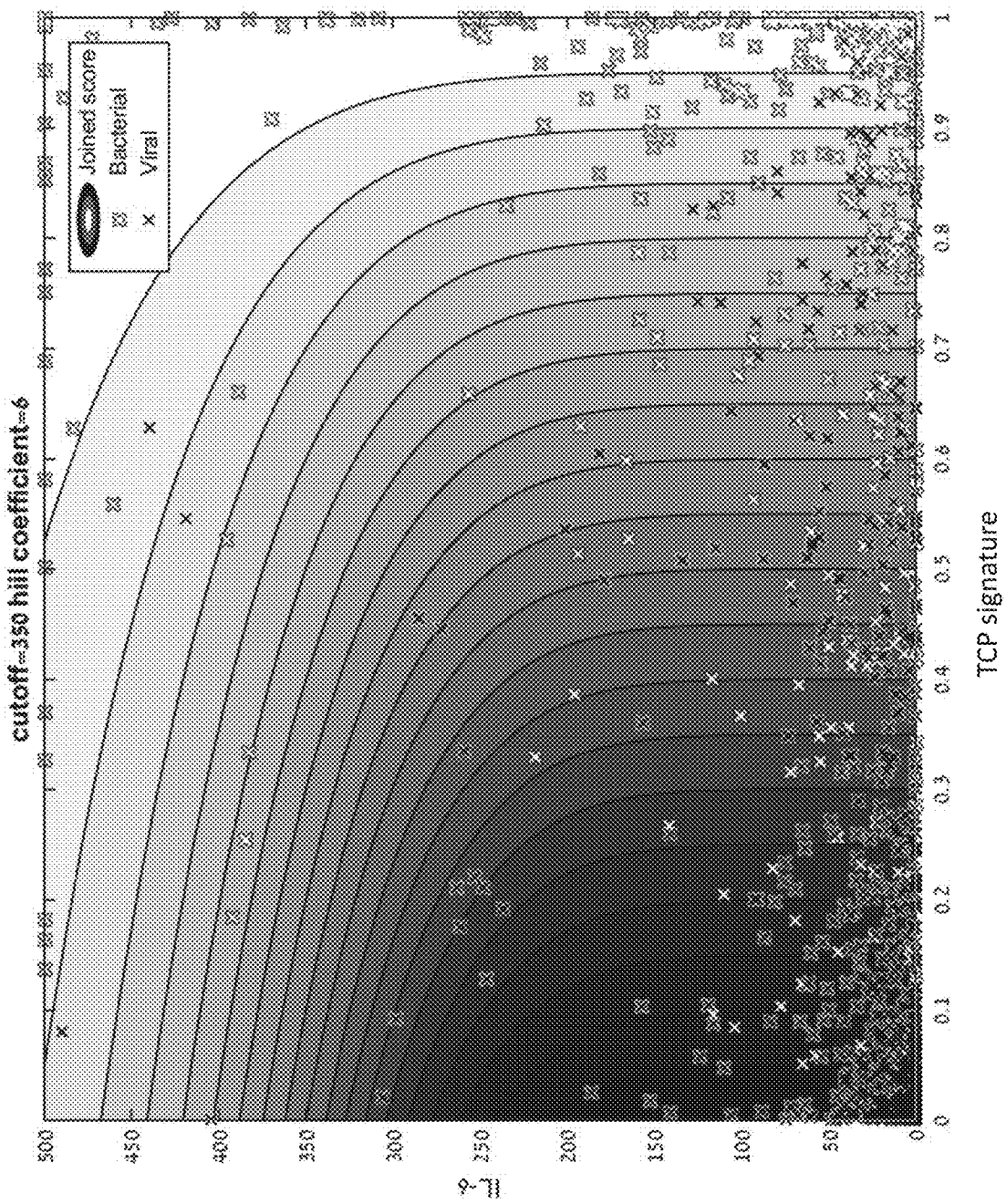
Figure 11D:
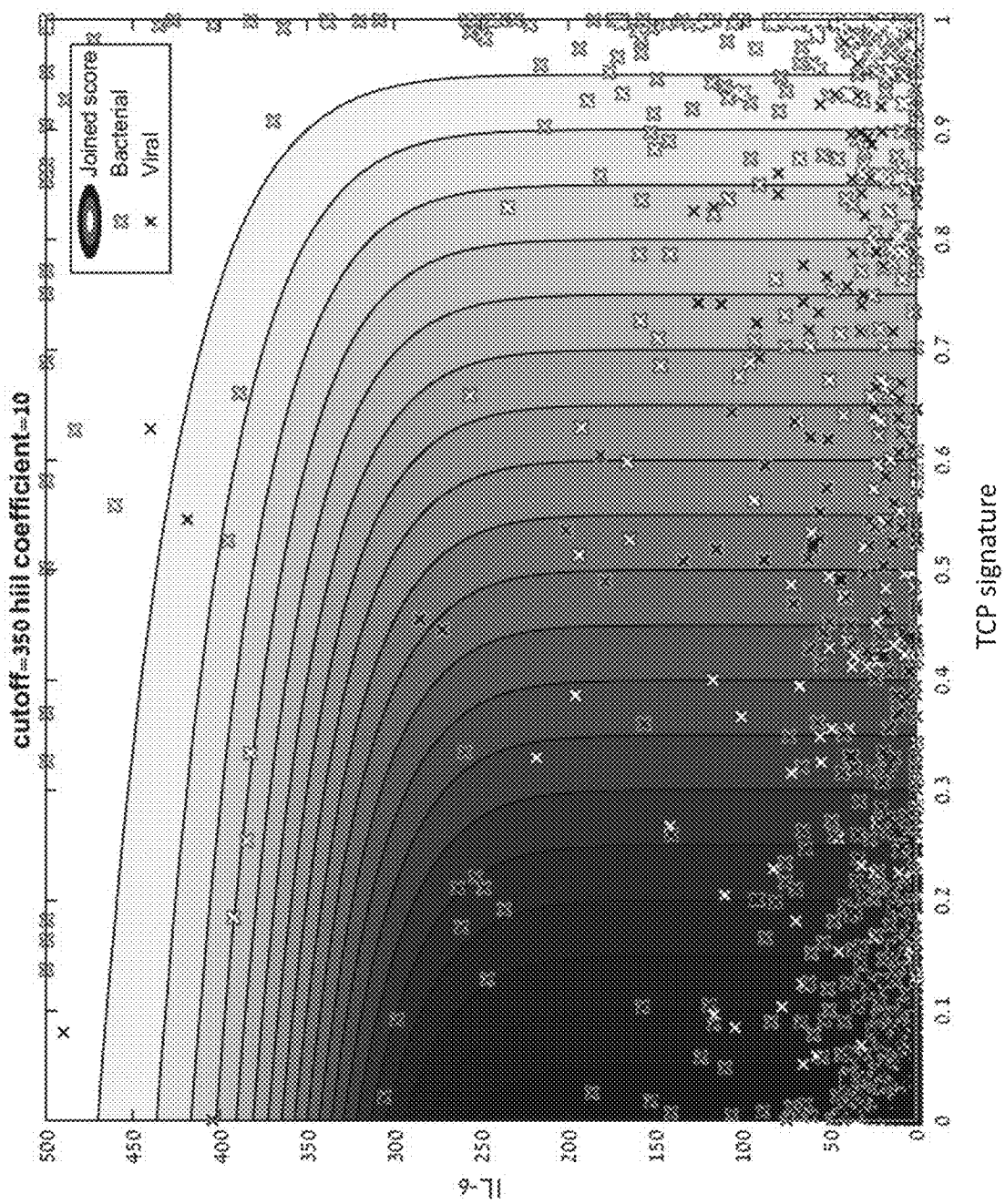

Combining TCP Signature with IL-6 and PCT Improves the Ability to Diagnose Early Infections Interestingly, we find that one class of examples in which the contribution of IL-6 or PCT to the TCP signature, is particularly pronounced, is during early bacterial infections. Indeed, the rise in IL-6 levels in response to bacterial infections can be detected as early as the first day of symptoms onset and precedes the rise in other bacterially induced proteins (FIGS. 8A-9). Consequently, adding IL-6, PCT or both to the TCP signature significantly improved sensitivity (0.891, 0.886 and 0.913 respectively compared to 0.837; Table 16) without compromising specificity when applied on 107 patients 0-1 days from symptoms onset. Importantly, adding PCT or IL-6 (or both) to the TCP signature did not only improve sensitivity but also reduced the portion of patients with equivocal results, meaning that a higher number of patients will receive definitive diagnostic result (bacterial or viral) when using these biomarkers in combination using the Fuzzy OR models.

TABLE 16

Measures of accuracy in distinguishing between bacterial and viral patients of different combinations of the TCP signature and PCT and IL-6 generated using Fuzzy OR analysis 0-1 days after symptoms onset (n = 107). PCT cutoff = 2.5 µg/L; IL-6 cutoff = 250 pg/ml; Hill coefficient = 10.
Days 0-1

| n = 107 | Sensitivity | Specificity | % Equivocal | PPV | NPV |
|---|---|---|---|---|---|
| TCP | 0.837 | 0.878 | 0.140 | 0.9 | 0.86 |
| TCP + IL-6 | 0.891 | 0.875 | 0.121 | 0.9 | 0.89 |

TABLE 16-continued

Measures of accuracy in distinguishing between bacterial and viral patients of different combinations of the TCP signature and PCT and IL-6 generated using Fuzzy OR analysis 0-1 days after symptoms onset (n = 107). PCT cutoff = 2.5 µg/L; IL-6 cutoff = 250 pg/ml; Hill coefficient = 10.
Days 0-1

| n = 107 | Sensitivity | Specificity | % Equivocal | PPV | NPV |
|---|---|---|---|---|---|
| TCP + PCT | 0.886 | 0.878 | 0.131 | 0.9 | 0.9 |
| TCP + PCT + IL-6 | 0.913 | 0.875 | 0.121 | 0.9 | 0.91 |

Sub-Group Analysis

The present inventors further evaluated the ability of IL-6 and PCT to improve the sensitivity and accuracy levels of the TCP signature in various patient sub-groups using the Fuzzy OR model. Patients were stratified according to several categories (i.e., clinical syndrome; specific pathogen; and age), and measures of accuracy were calculated for different combinations of IL-6, PCT and the TCP signature generated using the Fuzzy OR model (PCT cutoff=2.5 µg/L; IL-6 cutoff=250 pg/ml; Hill coefficient=10; Tables 17-19). Adding PCT and IL-6 was able to improve the TCP signature performance in various patient sub-groups (Tables 17-19). For example, the combined model improved the sensitivity of the TCP signature in identifying patients with serious bacterial infections (SBI), which are at high risk for adverse outcomes (0.92 vs 0.9; Table 19). This combination was also superior in various clinical syndromes, specific pathogens and age groups (Table 19).

TABLE 17

Measures of accuracy in distinguishing between bacterial and viral patients of a combination of the TCP signature and PCT generated using Fuzzy OR analysis in various patient sub-groups. PCT cutoff = 2.5 µg/L; Hill coefficient = 10.

| | TCP signature | | | | | TCP signature + PCT (2.5 µg/L) | | | | |
|---|---|---|---|---|---|---|---|---|---|---|
| | Sensitivity | Specificity | % Equivocal | PPV | NPV | Sensitivity | Specificity | % Equivocal | PPV | NPV |
| Syndrome | | | | | | | | | | |
| LRTI | 0.89 | 0.95 | 0.13 | 0.97 | 0.82 | 0.89 | 0.95 | 0.11 | 0.97 | 0.82 |
| SBI | 0.90 | 1.00 | 0.12 | 1.00 | 0.63 | 0.91 | 1.00 | 0.10 | 1.00 | 0.66 |
| Pathogen | | | | | | | | | | |
| Adenovirus | 0.87 | 0.92 | 0.12 | 0.99 | 0.47 | 0.88 | 0.92 | 0.11 | 0.99 | 0.49 |
| Parainfluenza virus | 0.87 | 1.00 | 0.10 | 1.00 | 0.36 | 0.88 | 1.00 | 0.09 | 1.00 | 0.38 |
| Influenza A/B | 0.87 | 0.97 | 0.09 | 0.99 | 0.60 | 0.88 | 0.97 | 0.08 | 0.99 | 0.62 |
| RSV A/B | 0.87 | 0.94 | 0.10 | 0.99 | 0.55 | 0.88 | 0.94 | 0.09 | 0.99 | 0.57 |
| Enterovirus | 0.87 | 1.00 | 0.10 | 1.00 | 0.29 | 0.88 | 1.00 | 0.08 | 1.00 | 0.30 |
| CMV/EBV | 0.87 | 0.91 | 0.09 | 0.96 | 0.71 | 0.88 | 0.91 | 0.09 | 0.97 | 0.72 |
| Age | | | | | | | | | | |
| Infants (<3) | 0.71 | 0.95 | 0.12 | 0.74 | 0.94 | 0.73 | 0.94 | 0.11 | 0.74 | 0.94 |
| Children (<18) | 0.82 | 0.93 | 0.13 | 0.79 | 0.94 | 0.84 | 0.93 | 0.12 | 0.80 | 0.95 |
| Adults (>18) | 0.90 | 0.86 | 0.08 | 0.95 | 0.74 | 0.90 | 0.86 | 0.08 | 0.95 | 0.74 |

TABLE 18

Measures of accuracy in distinguishing between bacterial and viral patients of a combination of the TCP signature and IL-6 generated using Fuzzy OR analysis in various patient sub-groups. IL-6 cutoff = 250 pg/ml; Hill coefficient = 10.

| | TCP signature | | | | | TCP signature + IL-6 (250 pg/ml) | | | | |
|---|---|---|---|---|---|---|---|---|---|---|
| | Sensitivity | Specificity | % Equivocal | PPV | NPV | Sensitivity | Specificity | % Equivocal | PPV | NPV |
| Syndrome | | | | | | | | | | |
| LRTI | 0.89 | 0.95 | 0.13 | 0.97 | 0.82 | 0.90 | 0.95 | 0.13 | 0.97 | 0.84 |
| SBI | 0.90 | 1.00 | 0.12 | 1.00 | 0.63 | 0.91 | 1.00 | 0.12 | 1.00 | 0.64 |
| Pathogen | | | | | | | | | | |
| Adenovirus | 0.87 | 0.92 | 0.12 | 0.99 | 0.47 | 0.88 | 0.92 | 0.11 | 0.99 | 0.49 |
| Parainfluenza virus | 0.87 | 1.00 | 0.10 | 1.00 | 0.36 | 0.88 | 1.00 | 0.09 | 1.00 | 0.38 |
| Influenza A/B | 0.87 | 0.97 | 0.09 | 0.99 | 0.60 | 0.88 | 0.97 | 0.08 | 0.99 | 0.62 |
| RSV A/B | 0.87 | 0.94 | 0.10 | 0.99 | 0.55 | 0.88 | 0.94 | 0.10 | 0.99 | 0.57 |
| Enterovirus | 0.87 | 1.00 | 0.10 | 1.00 | 0.29 | 0.88 | 1.00 | 0.09 | 1.00 | 0.30 |
| CMV/EBV | 0.87 | 0.91 | 0.09 | 0.96 | 0.71 | 0.89 | 0.91 | 0.09 | 0.97 | 0.73 |
| Age | | | | | | | | | | |
| Infants (<3) | 0.71 | 0.95 | 0.12 | 0.74 | 0.94 | 0.74 | 0.94 | 0.12 | 0.72 | 0.94 |
| Children (<18) | 0.82 | 0.93 | 0.13 | 0.79 | 0.94 | 0.83 | 0.92 | 0.13 | 0.78 | 0.94 |
| Adults (>18) | 0.90 | 0.86 | 0.08 | 0.95 | 0.74 | 0.91 | 0.86 | 0.07 | 0.95 | 0.75 |

TABLE 19

Measures of accuracy in distinguishing between bacterial and viral patients of a combination of the TCP signature and IL-6 and PCT generated using Fuzzy OR analysis in various patient sub-groups. PCT cutoff = 2.5 μg/L; IL-6 cutoff = 250 pg/ml; Hill coefficient = 10.

| | TCP signature | | | | | TCP signature + PCT (2.5 μg/L) + IL-6 (250 pg/ml) | | | | |
|---|---|---|---|---|---|---|---|---|---|---|
| | Sensitivity | Specificity | % Equivocal | PPV | NPV | Sensitivity | Specificity | % Equivocal | PPV | NPV |
| Syndrome | | | | | | | | | | |
| LRTI | 0.89 | 0.95 | 0.13 | 0.97 | 0.82 | 0.90 | 0.95 | 0.11 | 0.97 | 0.84 |
| SBI | 0.90 | 1.00 | 0.12 | 1.00 | 0.63 | 0.92 | 1.00 | 0.10 | 1.00 | 0.67 |
| Pathogen | | | | | | | | | | |
| Adenovirus | 0.87 | 0.92 | 0.12 | 0.99 | 0.47 | 0.89 | 0.92 | 0.11 | 0.99 | 0.51 |
| Parainfluenza virus | 0.87 | 1.00 | 0.10 | 1.00 | 0.36 | 0.89 | 1.00 | 0.08 | 1.00 | 0.40 |
| Influenza A/B | 0.87 | 0.97 | 0.09 | 0.99 | 0.60 | 0.89 | 0.97 | 0.08 | 0.99 | 0.64 |
| RSV A/B | 0.87 | 0.94 | 0.10 | 0.99 | 0.55 | 0.89 | 0.94 | 0.09 | 0.99 | 0.59 |
| Enterovirus | 0.87 | 1.00 | 0.10 | 1.00 | 0.29 | 0.89 | 1.00 | 0.08 | 1.00 | 0.32 |
| CMV/EBV | 0.87 | 0.91 | 0.09 | 0.96 | 0.71 | 0.90 | 0.91 | 0.08 | 0.97 | 0.75 |
| Age | | | | | | | | | | |
| Infants (<3) | 0.71 | 0.95 | 0.12 | 0.74 | 0.94 | 0.75 | 0.93 | 0.11 | 0.72 | 0.94 |
| Children (<18) | 0.82 | 0.93 | 0.13 | 0.79 | 0.94 | 0.85 | 0.92 | 0.12 | 0.78 | 0.95 |
| Adults (>18) | 0.90 | 0.86 | 0.08 | 0.95 | 0.74 | 0.91 | 0.86 | 0.07 | 0.95 | 0.75 |

Combining Two Biomarkers to Distinguish Between Bacterial and Viral Infections

Figure 12A:
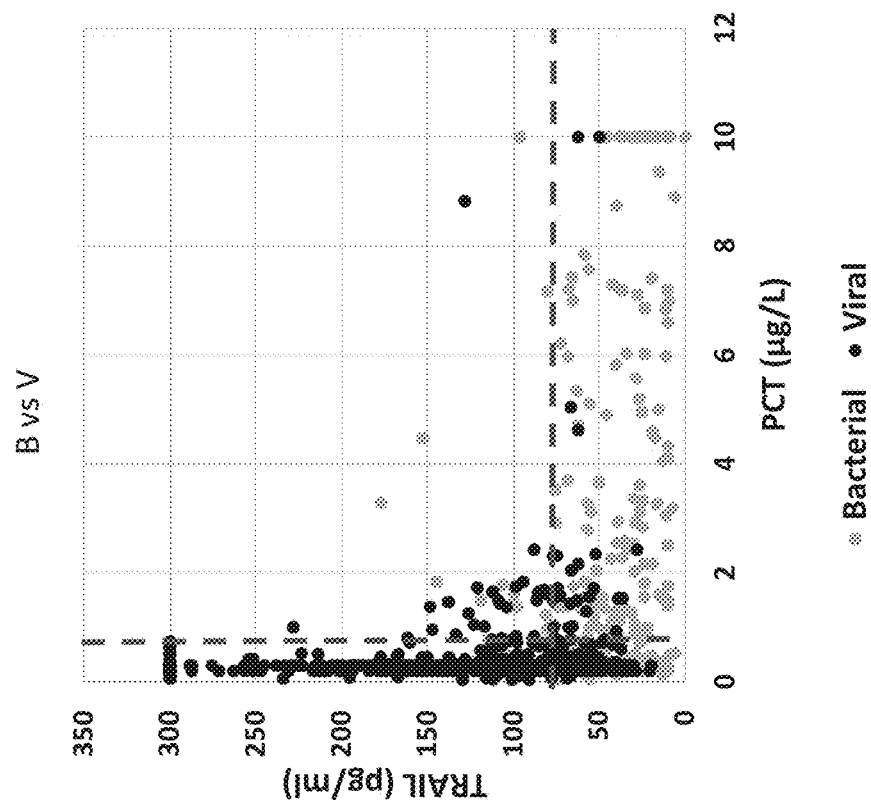
Figure 12B:
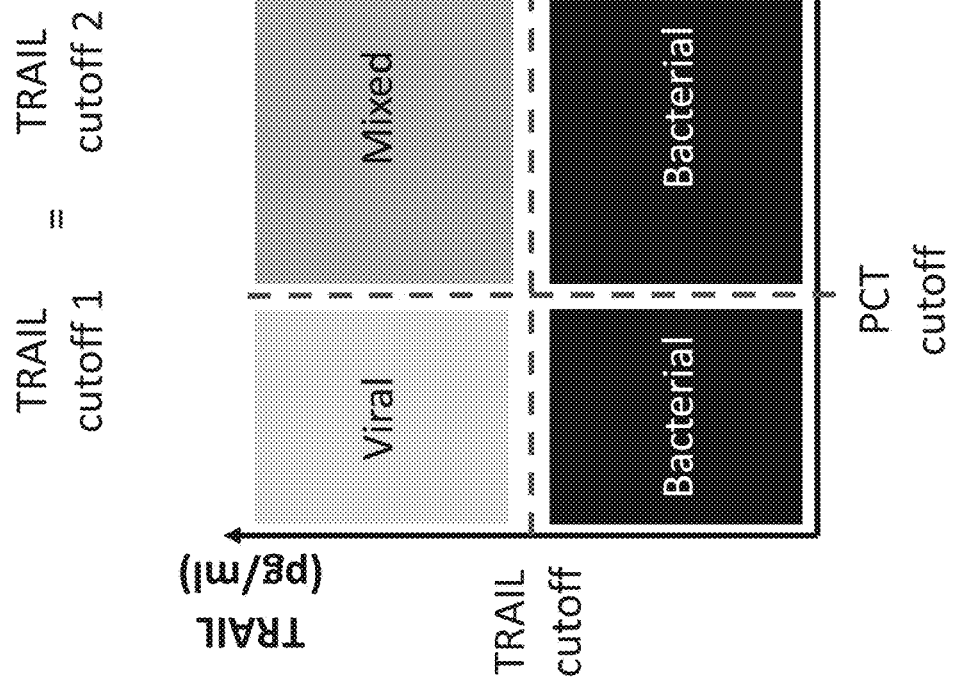
Figure 12D:
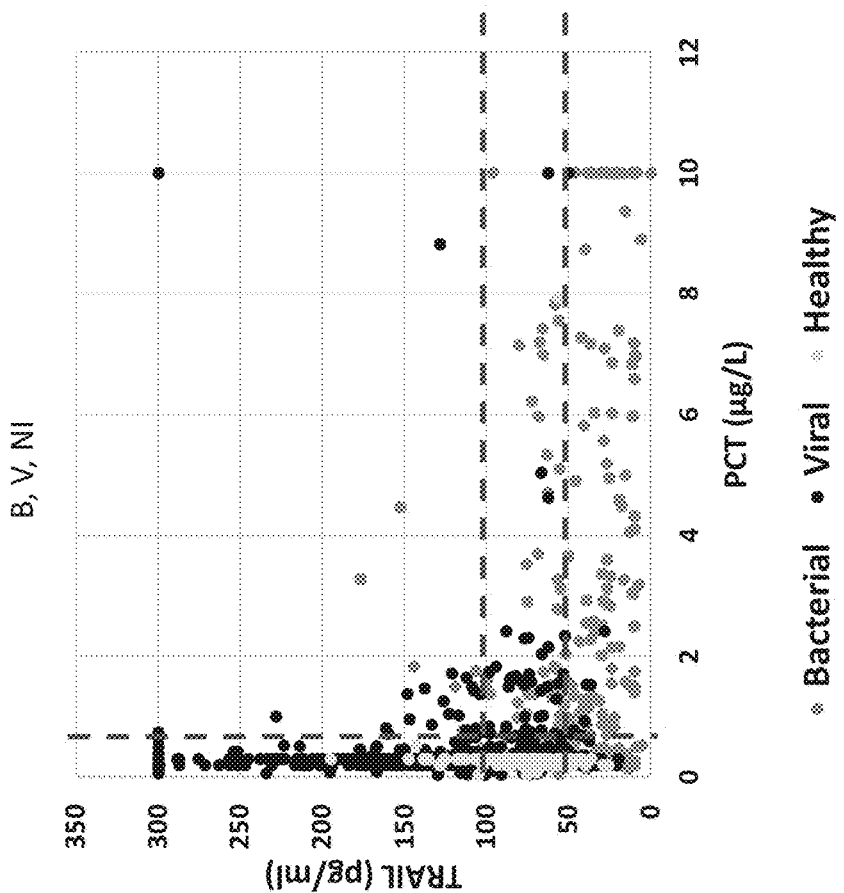
Figure 12C:
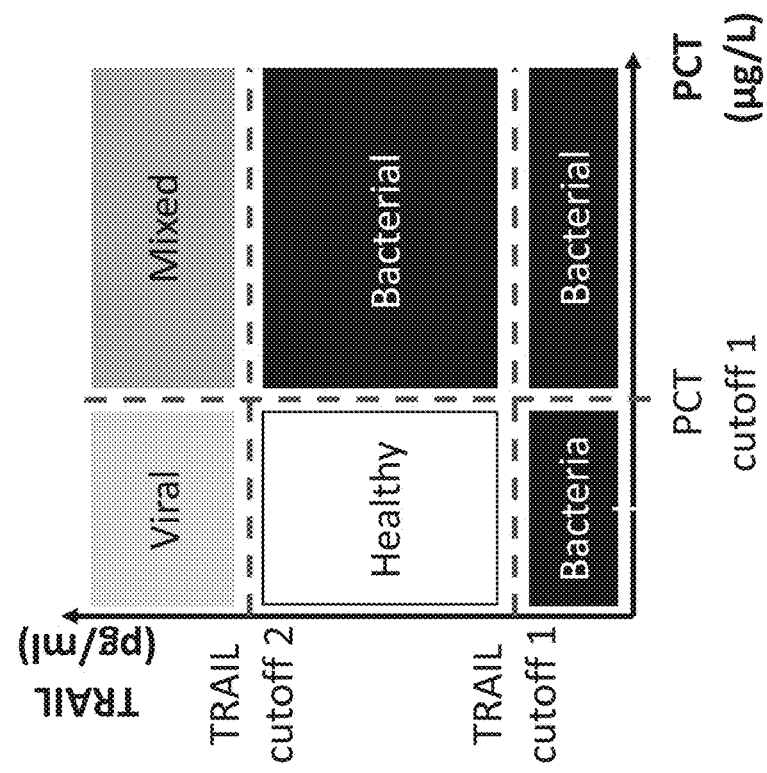

In certain clinical settings, for example at the point-of-care or in resource limited settings, it might be beneficial to use a smaller set of biomarkers. There are various ways (and formulations) to combine two biomarkers into one predictive score. For example, using dual cutoffs—one for each biomarker (e.g., one for TRAIL and one for PCT), generates a quadrary separation pattern that can separate between bacterial, viral and mixed (bacterial-viral co-infection) patients (FIG. 12A). Choosing the two suitable biomarkers as well as correct cutoffs is challenging and will affect the model ability to accurately separate between closely related data sets. For example, when the inventors combined TRAIL and PCT in this manner (TRAIL cutoff=75 pg/ml, PCT cutoff=0.5 μg/L), the model presented good sensitivity (87%) but poor specificity (64%; $n_{bacterial}$=378, $n_{viral}$=570, FIG. 12B). For some biomarkers (e.g., TRAIL), adding another cutoff also enables the identification of healthy patients by generating a separation pattern composed of six units (FIGS. 12C-D). In the examined data set this model resulted in sensitivity of 61% and specificity of 52% in distinguishing between bacterial and viral patients $n_{bacterial}$=378, $n_{viral}$=570, FIG. 12D).

Figure 12E:
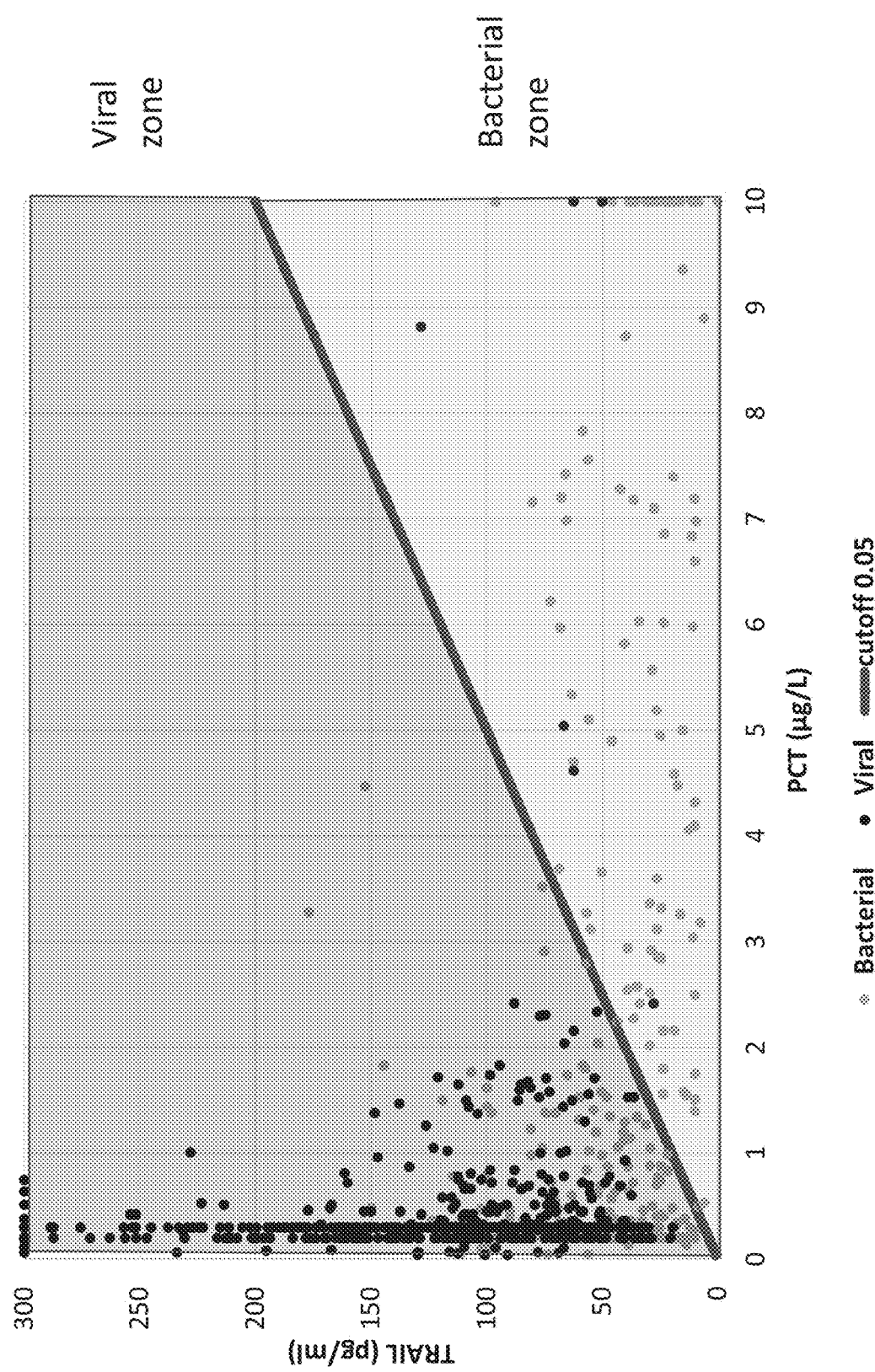
Figure 12F:
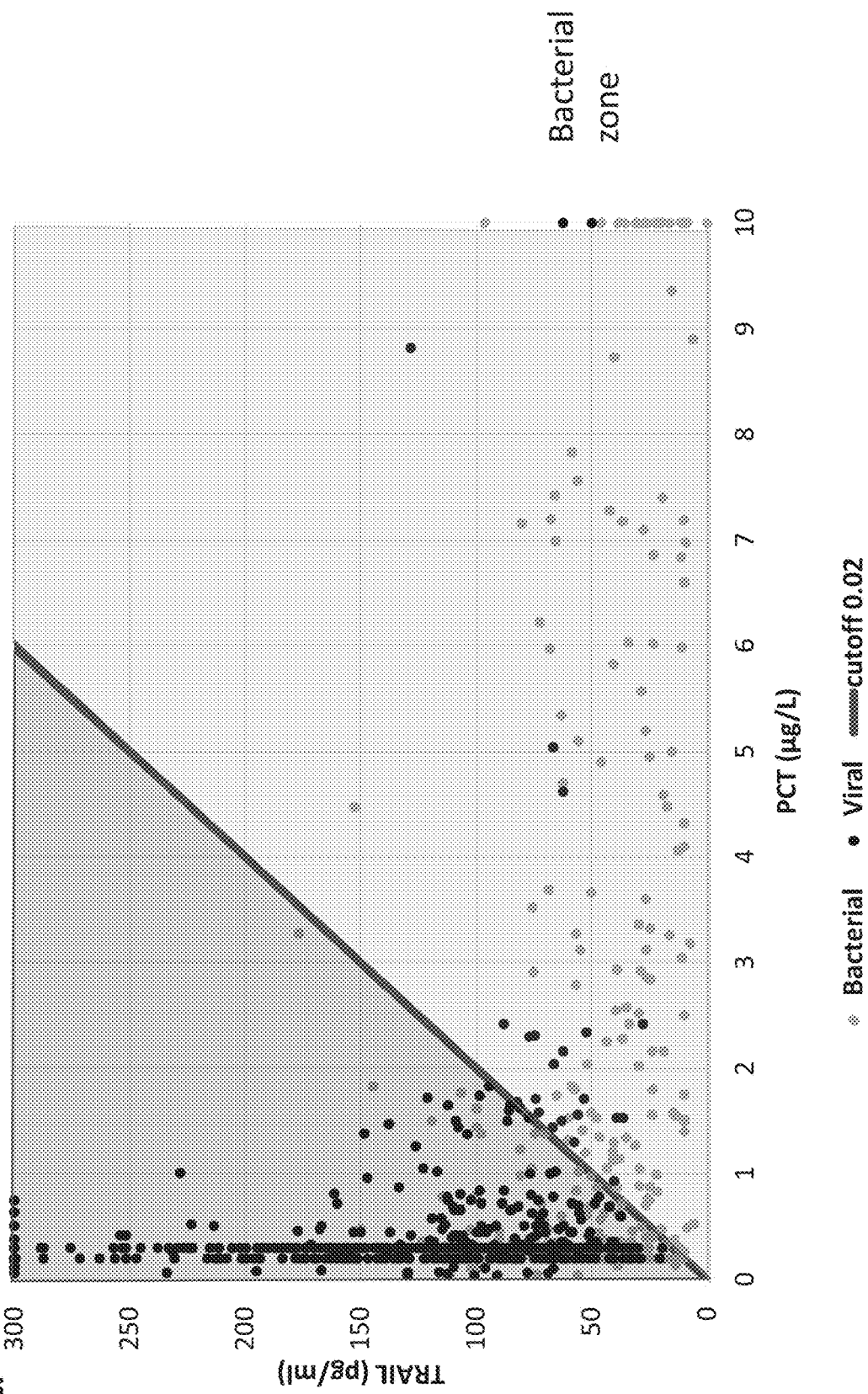

Alternatively, the separation between bacterial and viral patients could be based on the ratio between the two biomarkers. Using a defined cutoff for the ratio between the two biomarkers generates a line that separates between bacterial (below the line) and viral (above the line) zones (FIGS. 12E-G). The chosen cutoff will affect the classifier accuracy. For example, a classifier that used a PCT/TRAIL cutoff of 0.05 resulted in sensitivity of 24% and specificity of 99% in distinguishing between bacterial and viral patients ($n_{bacterial}$=378, $n_{viral}$=570, FIG. 12E). A classifier that used a PCT/TRAIL cutoff of 0.02 resulted in sensitivity of 33% and specificity of 96% in distinguishing between bacterial and viral patients ($n_{bacterial}$=378, $n_{viral}$=570, FIG. 12F). A classifier that used a PCT/TRAIL cutoff of 0.01 resulted in sensitivity of 46% and specificity of 91% in distinguishing between bacterial and viral patients ($n_{bacterial}$=378, $n_{viral}$=570, FIG. 12G).

Distinguishing Between Infectious and Non-Infectious Patients

Distinguishing between infectious and non-infectious patients is a crucial step in many clinical scenarios, in order to guide correct patient management and treatment. Notable examples include: (i) distinguishing between SIRS and sepsis (which is SIRS of infective origin), and (ii) distinguishing between a non-infective exacerbation state and an infective exacerbation state in chronic obstructive pulmonary disease (COPD). In these two examples classifying the patient as infectious will require more aggressive management including antibiotic treatment, follow-up microbiological diagnostics, and even ICU admission.

Therefore, the inventors developed logistic regression models and evaluated the accuracy levels of single biomarker noted above (CRP, IL-6, IP-10, PCT, TRAIL), and their combinations, in distinguishing between infectious (including bacterial, viral and mixed bacterial-viral co infection patients, n=948) and non-infectious patients (n=109).

TABLE 20

Measures of accuracy of CRP, IL-6, IP-10, PCT, and TRAIL in distinguishing between infectious (n = 948) and non-infectious patients (n = 109), calculated for a logistic regression model that optimized each biomarker performances in a cutoff independent manner.

| | Total | | | | | | Logistic regression coefficients | |
| --- | --- | --- | --- | --- | --- | --- | --- | --- |
| | AUC | accuracy | Sensitivity | Specificity | PPV | NPV | Constant | protein |
| CRP | 0.92 | 0.85 | 0.84 | 0.90 | 0.99 | 0.40 | −0.06985 | 0.21716 |
| IL-6 | 0.86 | 0.78 | 0.77 | 0.92 | 0.99 | 0.31 | 1.0671 | 0.15485 |
| IP-10 | 0.91 | 0.83 | 0.82 | 0.88 | 0.98 | 0.36 | −0.71024 | 0.011946 |
| PCT | 0.62 | 0.58 | 0.57 | 0.64 | 0.93 | 0.15 | 1.7155 | 0.97969 |
| TRAIL | 0.50 | 0.62 | 0.62 | 0.65 | 0.94 | 0.16 | 1.8402 | 0.003669 |

TABLE 21

Logistic regression models of protein/determinant couples and their measures of accuracy in distinguishing between infectious (n = 948) and non-infectious patients (n = 109).

| | | Total | | | | | | Logistic regression coefficients | | |
| --- | --- | --- | --- | --- | --- | --- | --- | --- | --- | --- |
| Protein 1 | Protein 2 | AUC | accuracy | Sensitivity | Specificity | PPV | NPV | Constant | Protein 1 | Protein 2 |
| CRP | IL-6 | 0.94 | 0.87 | 0.86 | 0.92 | 0.99 | 0.44 | | | |
| CRP | IP-10 | 0.98 | 0.93 | 0.92 | 0.95 | 0.99 | 0.59 | −0.22258 | 0.17054 | 0.071545 |
| CRP | PCT | 0.92 | 0.84 | 0.83 | 0.92 | 0.99 | 0.38 | −2.283 | 0.14251 | 0.00977 |
| CRP | TRAIL | 0.94 | 0.86 | 0.86 | 0.92 | 0.99 | 0.42 | −0.08523 | 0.2163 | 0.053308 |
| IL-6 | IP-10 | 0.95 | 0.89 | 0.89 | 0.92 | 0.99 | 0.48 | −2.148 | 0.23166 | 0.020457 |
| IL-6 | PCT | 0.87 | 0.80 | 0.79 | 0.90 | 0.99 | 0.33 | −1.5109 | 0.12335 | 0.010683 |
| IL-6 | TRAIL | 0.89 | 0.85 | 0.86 | 0.80 | 0.97 | 0.39 | 0.89294 | 0.15143 | 0.45166 |
| IP-10 | PCT | 0.92 | 0.85 | 0.85 | 0.87 | 0.98 | 0.40 | −0.22998 | 0.16311 | 0.0134 |
| IP-10 | TRAIL | 0.93 | 0.87 | 0.87 | 0.87 | 0.98 | 0.44 | −0.90764 | 0.011591 | 0.53428 |
| PCT | TRAIL | 0.76 | 0.63 | 0.61 | 0.79 | 0.96 | 0.19 | 0.16116 | 0.014205 | −0.01665 |
| CRP | IL-6 | 0.94 | 0.87 | 0.86 | 0.92 | 0.99 | 0.44 | 1.1198 | 1.1092 | 0.006076 |

TABLE 22

Logistic regression models of protein/determinant triplets and their measures of accuracy in distinguishing between infectious (n = 948) and non-infectious patients (n = 109).

| | | | Total | | | | | | Logistic regression coefficients | | | |
| --- | --- | --- | --- | --- | --- | --- | --- | --- | --- | --- | --- | --- |
| Protein 1 | Protein 2 | Protein 3 | AUC | accuracy | Sensitivity | Specificity | PPV | NPV | Constant | Protein 1 | Protein 2 | Protein 3 |
| CRP | IL-6 | IP-10 | 0.98 | 0.94 | 0.93 | 0.95 | 0.99 | 0.62 | −2.4974 | 0.11436 | 0.041151 | 0.009752 |
| CRP | IL-6 | PCT | 0.94 | 0.87 | 0.86 | 0.92 | 0.99 | 0.43 | −0.22151 | 0.17059 | 0.07155 | −0.00363 |
| CRP | IL-6 | TRAIL | 0.95 | 0.87 | 0.86 | 0.94 | 0.99 | 0.44 | −2.5706 | 0.17875 | 0.060296 | 0.023434 |
| CRP | IP-10 | PCT | 0.98 | 0.92 | 0.92 | 0.95 | 0.99 | 0.58 | −2.302 | 0.14204 | 0.009768 | 0.058902 |
| CRP | IP-10 | TRAIL | 0.98 | 0.93 | 0.93 | 0.94 | 0.99 | 0.59 | −2.3599 | 0.14368 | 0.009639 | 0.001109 |
| CRP | PCT | TRAIL | 0.94 | 0.86 | 0.85 | 0.94 | 0.99 | 0.41 | −2.2225 | 0.2286 | 0.16562 | 0.020729 |
| IL-6 | IP-10 | PCT | 0.95 | 0.89 | 0.89 | 0.91 | 0.99 | 0.49 | −1.6064 | 0.11947 | 0.010603 | 0.27096 |
| IL-6 | IP-10 | TRAIL | 0.96 | 0.91 | 0.91 | 0.90 | 0.99 | 0.53 | −1.1742 | 0.11749 | 0.011416 | −0.00542 |
| IL-6 | PCT | TRAIL | 0.89 | 0.83 | 0.84 | 0.80 | 0.97 | 0.36 | −0.52984 | 0.15868 | 0.55959 | 0.014242 |
| IP-10 | PCT | TRAIL | 0.93 | 0.88 | 0.88 | 0.87 | 0.98 | 0.46 | −0.05898 | 0.013874 | 0.456 | −0.01578 |

TABLE 23

Logistic regression models of protein/determinant quads and their measures of accuracy
in distinguishing between infectious (n = 948) and non-infectious patients (n = 109).

| Protein 1 | Protein 2 | Protein 3 | Protein 4 | AUC | Total accuracy | Sensitivity | Specificity | PPV | NPV | Logistic regression coefficients | | | | |
|---|---|---|---|---|---|---|---|---|---|---|---|---|---|---|
| | | | | | | | | | | Constant | Protein 1 | Protein 2 | Protein 3 | Protein 4 |
| CRP | IL-6 | IP-10 | PCT | 0.98 | 0.94 | 0.94 | 0.95 | 0.99 | 0.64 | −2.4547 | 0.11547 | 0.041199 | 0.009758 | −0.1513 |
| CRP | IL-6 | IP-10 | TRAIL | 0.98 | 0.94 | 0.94 | 0.95 | 0.99 | 0.65 | −2.8515 | 0.11747 | 0.042224 | 0.009192 | 0.004988 |
| CRP | IL-6 | PCT | TRAIL | 0.95 | 0.87 | 0.86 | 0.94 | 0.99 | 0.44 | −2.6168 | 0.17768 | 0.060135 | 0.099076 | 0.023594 |
| CRP | IP-10 | PCT | TRAIL | 0.98 | 0.92 | 0.92 | 0.95 | 0.99 | 0.57 | −2.387 | 0.1433 | 0.009624 | 0.062724 | 0.001208 |
| IL-6 | IP-10 | PCT | TRAIL | 0.96 | 0.89 | 0.89 | 0.91 | 0.99 | 0.49 | −1.2757 | 0.11363 | 0.011347 | 0.27031 | −0.00536 |

TABLE 24

Measures of accuracy of a logistic regression model combining CRP, IL-6, IP-10, PCT, and TRAIL
in distinguishing between infectious (n = 948) and non-infectious patients (n = 109).

| AUC | Total accuracy | Sensitivity | Specificity | PPV | NPV | Logistic regression coefficients | | | | |
|---|---|---|---|---|---|---|---|---|---|---|
| | | | | | | Constant | CRP | IL-6 | IP-10 | PCT | TRAIL |
| 0.98 | 0.94 | 0.94 | 0.95 | 0.99 | 0.64 | −2.8044 | 0.11829 | 0.04227 | 0.009216 | −0.15115 | 0.00491 |

Example 2

Some embodiments of the present invention analyze the biological data by calculating a value of a likelihood function using the expression levels. When the value of a likelihood function, as calculated using the expression levels obtained from the subject, is between a lower bound $S_{LB}$ and an upper bound $S_{UB}$, wherein each of the lower and upper bounds is calculated using a combination δ (e.g., a linear combination) of the expression levels, the value of the likelihood function can be used to provide information pertaining an infection the subject is suffering from.

The lower bound $S_{LB}$ and upper bound $S_{UB}$ can be viewed geometrically as two curved objects, and the combination δ of the expression levels, can be can be viewed geometrically as a non-curved object, as illustrated schematically in FIG. 13. In this geometrical representation, the value of the likelihood function is represented by a distance d between the non-curved object 7C and a curved object S, where at least a segment $S_{ROI}$ of the curved object S is between the lower bound $S_{LB}$ and the upper bound $S_{UB}$.

Generally, each of the curved objects S, $S_{LB}$ and $S_{UB}$ is a manifold in n dimensions, where n is a positive integer, and the non-curved object π is a hyperplane in an n+1 dimensional space.

The concept of n-dimensional manifolds and hyperplanes in n+1 dimensions are well known to those skilled in the art of geometry. For example, when n=1 the first curved object is a curved line, and the non-curved object π is a hyperplane in 2 dimensions, namely a straight line defining an axis. When n=2, the first curved object is a curved surface, and the non-curved object π is a hyperplane in 3 dimensions, namely a flat plane, referred to below as "a plane".

In the simplest case each of S, $S_{LB}$ and $S_{UB}$ is a curved line and π is a straight axis defined by a direction.

Thus, the present embodiments provide information pertaining to the infection by calculating distances between curved and non-curved geometrical objects.

FIG. 14 is a flowchart diagram of a method suitable for analyzing biological data obtained from a subject, according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method begins at 10 and optionally and preferably continuous to 11 at which biological data containing, e.g., expression values of two or more determinants in the blood of a subject are obtained.

The method optionally and preferably continues to 12 at which background and/or clinical data that relate to the subject are obtained. In some embodiments of the present invention the background data includes the age of the subject, in some embodiments of the present invention the background data includes the ethnicity of the subject, in some embodiments of the present invention the background data includes the gender of the subject, in some embodiments of the present invention the clinical data includes a syndrome that the subject is experiencing, in some embodiments of the present invention the clinical data includes a pathogen suspected as being present in the subject.

The method proceeds to 13 at which the distance d between a segment of the curved object S (e.g., a curved line) and a non-curved object π (e.g., an axis defined by a direction) is calculated. The distance d is calculated at a point P(δ) over the curved line S defined by a coordinate δ along the direction. The direction is denoted herein using the same Greek letters as the coordinate, except that the direction is denoted by underlined Greek letters to indicate that these are vectors. Thus, when the coordinate is denoted δ, the direction is denoted δ̲.

The distance d is measured from S to the point P, perpendicularly to π. The segment $S_{ROI}$ of S is above a region-of-interest $\pi_{ROI}$ defined in the non-curved object $\pi$. For example, when $\pi$ is an axis, $\pi_{ROI}$ is a linear segment along the axis. Thus, $\pi_{ROI}$ is the projection of $S_{ROI}$ on $\pi$. For n=1, $S_{ROI}$ is preferably a curved segment of (the curve) S.

The coordinate $\delta$ is optionally and preferably defined by a combination of expression values of the determinants. For example, $\delta$ can be a combination of the determinants, according to the following equation:

$$\delta = a_0 + a_1 D_1 + a_2 D_2 + \ldots + \phi$$

where $a_0, a_1, \ldots$ are constant and predetermined coefficients, where each of the variables $D_1, D_2, \ldots$ is an expression levels of one of the determinants or some score pertaining to one or more of the determinants, and where $\phi$ is a function that is nonlinear with respect to at least one of the expression levels.

The function $\phi$ is optional and may, independently, be set to zero (or, equivalently, not included in the calculation of the respective coordinate). When $\phi=0$ the coordinate $\delta$ is a linear combination of the determinants.

The nonlinear function $\phi$ can optionally and preferably be expressed as a sum of powers of expression levels, for example, according to the following equations:

$$\phi = \Sigma_i q_i X_i^{\gamma i}$$

where i is a summation index, $q_i$ and $r_i$ are sets of coefficients, $X_i \in \{D_1, D_2, \ldots\}$, and $\gamma i$ is a numerical exponent. Note that the number of terms in the nonlinear function $\phi$ does not necessarily equals the number of the determinants, and that two or more terms in the sum may correspond to the same determinant, albeit with a different numerical exponent.

One or more of the predetermined coefficients ($a_i, q_i, r_i$) typically depends on the respective type of the determinant, but can also depend on the background and/or clinical data obtained at 12. Thus, the calculation of the distance d can optionally and preferably be based on the background and/or clinical data, because the location of the coordinate $\delta$ on $\pi$ can depend on such data. For example, the coefficient $a_i$ for a particular determinant $D_i$ can be different when the subject has a particular syndrome or pathogen, than when the subject does not have this particular syndrome or pathogen. In this case, the location of the point $P(\delta)$ on $\pi$ is different for subjects with the particular syndrome or pathogen, than for subjects without the particular syndrome or pathogen. Since the location is different, the distance d can also be different. Similarly, the coefficient $a_i$ (hence also the location of the point $P(\delta)$ on $\pi$) for a particular determinant $D_i$ can be different when the subject is of a particular age, gender and/or ethnicity, than when the subject is of a different age, gender and/or ethnicity.

The patient background and/or clinical data can be used for determining the coefficients, in more than one way. In some embodiments of the present invention, a lookup table is used. Such a lookup table can include a plurality of entries wherein each entry includes a determinant, information pertaining to the background and/or clinical data, and a coefficient that is specific to the determinant and the background and/or clinical data of the respective entry. Relevant clinical data includes but is not limited to absolute neutrophil count (abbreviated ANC), absolute lymphocyte count (abbreviated ALC), white blood count (abbreviated WBC), neutrophil % (defined as the fraction of white blood cells that are neutrophils and abbreviated Neu (%)), lymphocyte % (defined as the fraction of white blood cells that are lymphocytes and abbreviated Lym (%)), monocyte % (defined as the fraction of white blood cells that are monocytes and abbreviated Mon (%)), Sodium (abbreviated Na), Potassium (abbreviated K), Bilirubin (abbreviated Bili). Other clinical parameters are described herein below.

As used herein the term "patient background" refers to the history of diseases or conditions of the patient, or which the patient is prone to. For example, the patient medical background may include conditions such as chronic lung diseases and diabetes that affect its immune response to infection (see Example 1, herein below).

In some embodiments of the present invention, the coefficients are initially selected based on the particular determinants, (without taking into account the background and/or clinical data), and thereafter corrected, e.g., by normalization, based on the background and/or clinical data. For example, the coefficients can be normalized according to the age of the subject. In these embodiments, the subject is optionally and preferably stratified according to the subject's age, and the coefficient for the particular determinant is normalized by an age-dependent normalization procedure. In some embodiments, there are different coefficients, normalizations or stratification when the subject is an adult (e.g., older than 18, 21, or 22 years), than when the subject is a child (e.g., younger than 18, 21 or 22 years). In some embodiments, there are different coefficients, normalizations or stratifications when the subject is an adult (e.g., older than 18, 21, or 22 years), an adolescent (e.g., between 12 and 21 years), a child (e.g., between 2 and 12 years), an infant (e.g., 29 days to less than 2 years of age), and a neonates (e.g., birth through the first 28 days of life). In some embodiments, there are different coefficients, normalizations or stratification when the subject is older than 70, 65, 60, 55, 50, 40, 30, 22, 21, 18, 12, 2, 1 years than when the subject is older than 3, 2 and/or 1 month. In some embodiments, there are different coefficients, normalizations or stratification when the subject is younger than 70, 65, 60, 55, 50, 40, 30, 22, 21, 18, 12, 2, 1 year, than when the subject is older than 3, 2 and/or 1 month.

The boundaries of $\pi_{ROI}$ are denoted herein $\delta_{MIN}$ and $\delta_{MAX}$. These boundaries preferably correspond to the physiologically possible ranges of the expression values of the determinants. The range of the expression values can be set by the protocol used for obtaining the respective determinants. Alternatively, the expression values of one or more of the determinants that are used in the calculation of $\delta$ can be score values, for example, z-scored values, relative to a group of subjects previously diagnosed with a bacterial infection. These embodiments are particularly useful when the distance d is used for distinguishing between bacterial and viral infections. Still alternatively, the expression values of one or more of the determinants that are used in the calculation of $\delta$ can be score values, for example, z-scored values, relative to a group of subjects previously diagnosed with an infection. These embodiments are particularly useful when the distance d is used for distinguishing between infectious and non-infectious subjects. Still alternatively, the expression values of one or more of the determinants that are used in the calculation of $\delta$ can be score values, for example, z-scored values, relative to a group of subjects previously diagnosed with a mixed infection. These embodiments are particularly useful when the distance d is used for distinguishing between mixed infection and viral infection.

At least a major part of the segment $S_{ROI}$ of curved object S is between two curved objects referred to below as a lower bound curved object $S_{LB}$ and an upper bound curved object $S_{UB}$.

As used herein "major part of the segment $S_{ROI}$" refers to a part of a smoothed version $S_{ROI}$ whose length (when n=1), surface area (when n=2) or volume (when n≥3) is 60% or 70% or 80% or 90% or 95% or 99% of a smoothed version of the length, surface area or volume of $S_{ROI}$, respectively.

As used herein, "a smooth version of the segment $S_{ROI}$" refers to the segment $S_{ROI}$, excluding regions of $S_{ROI}$ at the vicinity of points at which the Gaussian curvature is above a curvature threshold, which is X times the median curvature of $S_{ROI}$, where X is 1.5 or 2 or 4 or 8.

The following procedure can be employed for the purpose of determining whether the major part of the segment $S_{ROI}$ is between $S_{LB}$ and $S_{UB}$. Firstly, a smoothed version of the segment $S_{ROI}$ is obtained. Secondly, the length (when n=1), surface area (when n=2) or volume (when n≥3) $A_1$ of the smoothed version of the segment $S_{ROI}$ is calculated. Thirdly, the length (when n=1) surface area (when n=2) or volume (when n≥3) $A_2$ of the part of the smoothed version of the segment $S_{ROI}$ that is between $S_{LB}$ and $S_{UB}$ is calculated. Fourthly, the percentage of $A_2$ relative to $A_1$ is calculated.

FIGS. 15A-D illustrates a procedure for obtaining the smooth version of $S_{ROI}$.

Figure 15A:
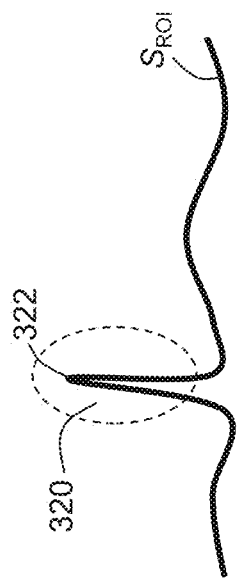
Figure 15B:
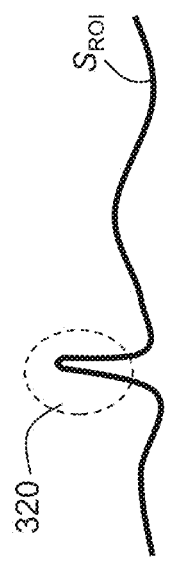
Figure 15C:
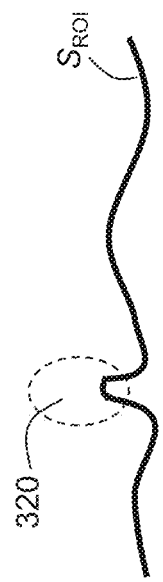
Figure 15D:

For clarity of presentation, $S_{ROI}$ is illustrated as a one dimensional segment, but the skilled person would understand that $S_{ROI}$ is generally an n-dimensional mathematical object. The Gaussian curvature is calculated for a sufficient number of sampled points on $S_{ROI}$. For example, when the manifold is represented as point cloud, the Gaussian curvature can be calculated for the points in the point cloud. The median of the Gaussian curvature is then obtained, and the curvature threshold is calculated by multiplying the obtained median by the factor X. FIG. 15A illustrates $S_{ROI}$ before the smoothing operation. Marked is a region 320 having one or more points 322 at which the Gaussian curvature is above the curvature threshold. The point or points at which with the Gaussian curvature is maximal within region 320 is removed and region 320 is smoothly interpolated, e.g., via polynomial interpolation, (FIG. 15B). The removal and interpolation is repeated iteratively (FIG. 15C) until the segment $S_{ROI}$ does not contain regions at which the Gaussian curvature is above the curvature threshold (FIG. 15D).

When n=1 (namely when S is a curved line), $S_{LB}$ is a lower bound curved line, and $S_{UB}$ an upper bound curved line. In these embodiments, $S_{LB}$ and $S_{UB}$ can be written in the form:

$$S_{LB}=f(\delta)-\varepsilon_0,$$

$$S_{UB}=f(\delta)+\varepsilon_1$$

where $f(\delta)$ is a probabilistic classification function of the coordinate $\delta$ (along the direction $\underline{\delta}$) which represents the likelihood that the test subject has an infection of a predetermined type (e.g., a bacterial infection, or a viral infection or a mixed infection). Also contemplated, are embodiments in which $f(\delta)$ is a probabilistic classification function which represents the likelihood that the test subject has an infection. In some embodiments of the invention $f(\delta)=1/(1+\exp(-\delta))$. In some embodiments of the invention both $S_{LB}$ and $S_{UB}$ are positive for any value of $\delta$ within $\pi_{ROI}$.

In any of the above embodiments each of the parameters $\varepsilon_0$ and $\varepsilon_1$ is less than 0.5 or less than 0.4 or less than 0.3 or less than 0.2 or less than 0.1 or less than 0.05.

The method preferably proceeds to 14 at which the calculated distance d is correlated to the presence of, absence of, or likelihood that the subject has, a disease or condition corresponding to the type of the probabilistic function f. For example, when the probabilistic function f represents the likelihood that the test subject has a bacterial infection, the calculated distance d is correlated to the presence of, absence of, or likelihood that the subject has, a bacterial infection, when the probabilistic function f represents the likelihood that the test subject has a viral infection, the calculated distance d is correlated to the presence of, absence of, or likelihood that the subject has, a viral infection, and when the probabilistic function f represents the likelihood that the test subject has a mixed infection, the calculated distance d is correlated to the presence of, absence of, or likelihood that the subject has, a mixed infection.

In various exemplary embodiments of the invention the correlation includes determining that the distance d is the likelihood that the subject has the respective infection (bacterial, viral, mixed). The likelihood is optionally and preferably compared to a predetermined threshold $\omega_B$, wherein the method can determine that it is likely that the subject has a bacterial infection when the likelihood is above $\omega_B$, and that it is unlikely that the subject has a bacterial infection otherwise. Typical values for $\omega_B$ include, without limitation, about 0.2, about 0.3, about 0.4, about 0.5, about 0.6 and about 0.7. Other likelihood thresholds are also contemplated.

In some embodiments of the present invention the method proceeds to 15 at which the likelihood is corrected based on the background and/or clinical data. Such a correction can be executed in more than one way. For example, the method can employ different predetermined thresholds $\omega_B$ for different ages, ethnicities, genders, syndromes, and/or suspected pathogens. The method can alternatively or additionally employ different values for one or both the parameters $\varepsilon_0$ and $\varepsilon_1$ for different ages, ethnicities, genders, syndromes, and/or suspected pathogens. The method can alternatively or additionally normalize the value of the probabilistic classification function $\delta$, based on the age, ethnicity, gender, syndrome, and/or suspected pathogen.

The method optionally and preferably continues to 16 at which an output of the likelihood(s) is generated. The output can be presented as text, and/or graphically and/or using a color index. The output can optionally include the results of the comparison to the threshold $\omega_B$. From 16 the method can optionally and preferably loops back to 13 for repeating the analysis using a different set of coefficients for the calculation of the coordinate $\delta$ and/or a different probabilistic classification function f. For example, the analysis can be initially executed using a set of coefficients and probabilistic classification function f that are selected for determining the presence of, absence of, or likelihood that the subject has, a bacterial infection or a mixed infection, and then, in a subsequent execution, the analysis can use a set of coefficients and probabilistic classification function f that are selected for determining the presence of, absence of, or likelihood that the subject has, a viral infection.

In some embodiments of the present invention, when the method determines that it is likely that the subject has a bacterial infection, the subject is treated (17) for the bacterial infection, as further detailed herein. In some embodiments of the present invention, when the method determines that it is likely that the subject has a viral infection, the subject is treated (17) for the viral infection, as further detailed herein.

The method ends at 18.

Following are representative examples of coefficients that can be used for defining the coordinate $\delta$ according to some embodiments of the present invention.

In some embodiments of the present invention the coordinate $\delta$ is calculated as $a_0+a_1X+a_2Y$, wherein X is a value of the score of the TCP signature as further detailed hereinabove, and Y is a value of the expression level of IL-6 in pg/ml, wherein $a_0$ is from about 2.75 to about 3.40, $a_1$ is from about 4.5 to about 5.5, and $a_2$ is from about 0.0044 to about 0.0055. In these embodiments the probabilistic classification function f represents the likelihood the subject has a bacterial infection. More preferred values for the parameters $a_0$, $a_1$ and $a_2$ in these embodiments are provided in Table 7.

In some embodiments of the present invention the coordinate δ is calculated as $a_0+a_1X+a_2Y$, wherein X is a value of the calculated score of the TCP signature as further detailed hereinabove, and the Y is a value of the expression level of PCT in μg/L, wherein $a_0$ is from about 2.70 to about 3.30, $a_1$ is from about 4.55 to about 5.60, and $a_2$ is from about 0.176 to about 0.215. In these embodiments the probabilistic classification function f represents the likelihood the subject has a bacterial infection. More preferred values for the parameters $a_0$, $a_1$ and $a_2$ in these embodiments are provided in Table 7.

In some embodiments of the present invention the coordinate δ is calculated as $a_0+a_1X+a_2Y+a_3Z$, wherein X is a value of the expression level of CRP in μg/ml, Y is a value of the expression level of IL-6 in pg/ml and Z is a value of the expression level of TRAIL in pg/ml, wherein $a_0$ is from about −1.05 to about −0.85, $a_1$ is from about 0.025 to about 0.032, $a_2$ is from about 0.004 to about 0.006, and $a_3$ is from about −0.022 to about −0.017. In these embodiments the probabilistic classification function f represents the likelihood the subject has a bacterial infection. More preferred values for the parameters $a_0$, $a_1$, $a_2$ and $a_3$ in these embodiments are provided in Table 8.

In some embodiments of the present invention the coordinate δ is calculated as $a_0+a_1X+a_2Y+a_3Z$, wherein X is a value of the expression level of CRP in μg/ml, Y is a value of the expression level of PCT in μg/L and Z is a value of the expression level of TRAIL in pg/ml, wherein $a_0$ is from about −0.60 to about −0.48, $a_1$ is from about 0.024 to about 0.31, $a_2$ is from about 0.13 to about 0.16, and $a_3$ is from about −0.025 to about −0.019. In these embodiments the probabilistic classification function f represents the likelihood the subject has a bacterial infection. More preferred values for the parameters $a_0$, $a_1$, $a_2$ and $a_3$ in these embodiments are provided in Table 8.

In some embodiments of the present invention the coordinate δ is calculated as $a_0+a_1X+a_2Y+a_3Z$, wherein X is a value of the expression level of IP-10 in μg/ml, Y is a value of the expression level of PCT in μg/L and Z is a value of the expression level of TRAIL in pg/ml, wherein $a_0$ is from about 1.42 to about 1.75, $a_1$ is from about 0.00024 to about 0.00031, $a_2$ is from about 0.23 to about 0.29, and $a_3$ is from about −0.038 to about −0.030. In these embodiments the probabilistic classification function f represents the likelihood the subject has a bacterial infection. More preferred values for the parameters $a_0$, $a_1$, $a_2$ and $a_3$ in these embodiments are provided in Table 8.

In some embodiments of the present invention the coordinate δ is calculated as $a_0+a_1X+a_2Y+a_3Z$, wherein X is a value of the calculated score of the TCP signature as further detailed hereinabove, Y is a value of the expression level of IL-6 in pg/L and the Z is a value of the expression level of PCT in μg/ml, wherein $a_0$ is from about −3.48 to about −2.84, $a_1$ is from about 4.40 to about 5.39, $a_2$ is from about 0.0041 to about 0.0051, and $a_3$ is from about 0.14 to about 0.18. In these embodiments the probabilistic classification function f represents the likelihood the subject has a bacterial infection. More preferred values for the parameters $a_0$, $a_1$, $a_2$ and $a_3$ in these embodiments are provided in Table 8.

In some embodiments of the present invention the coordinate δ is calculated as $a_0+a_1X+a_2Y+a_3Z+a_4T$, wherein X is a value of the expression level of CRP in μg/ml, Y is a value of the expression level of IL-6 in pg/ml, Z is a value of the expression level of PCT in μg/L and T is a value of the expression level of TRAIL in pg/ml, wherein $a_0$ is from about −1.13 to about −0.92, $a_1$ is from about 0.025 to about 0.031, $a_2$ is from about 0.0045 to about 0.0055, $a_3$ is from about 0.098 to about 0.13 and $a_4$ is from about −0.021 to about −0.016. In these embodiments the probabilistic classification function f represents the likelihood the subject has a bacterial infection. More preferred values for the parameters $a_0$, $a_1$, $a_2$, $a_3$ and $a_4$ in these embodiments are provided in Table 9.

In some embodiments of the present invention the coordinate δ is calculated as $a_0+a_1X+a_2Y+a_3Z+a_4T$, wherein X is a value of the expression level of IL-6 in pg/ml, Y is a value of the expression level of IP-10 in pg/ml, Z is a value of the expression level of PCT in μg/L and T is a value of the expression level of TRAIL in pg/ml, wherein $a_0$ is from about 1.029 to about 1.258, $a_1$ is from about 0.0049 to about 0.0060, $a_2$ is from about 0.00013 to about 0.00017, $a_3$ is from about 0.19 to about 0.24 and $a_4$ is from about −0.033 to about −0.027. In these embodiments the probabilistic classification function f represents the likelihood the subject has a bacterial infection. More preferred values for the parameters $a_0$, $a_1$, $a_2$, $a_3$ and $a_4$ in these embodiments are provided in Table 9.

In some embodiments of the present invention the coordinate δ is calculated as $a_0+a_1X+a_2Y+a_3Z+a_4T+a_5W$, wherein X is a value of the expression level of CRP in μg/ml, wherein Y is a value of the expression level of IL-6 in pg/ml, Z is a value of the expression level of IP-10 in pg/ml, T is a value of the expression level of PCT in μg/L and the W is a value of the expression level of TRAIL in pg/ml, wherein $a_0$ is from about −3.08 to about −2.52, $a_1$ is from about 0.10 to about 0.13, $a_2$ is from about 0.038 to about 0.047, $a_3$ is from about 0.008 to about 0.010, $a_4$ is from about −0.17 to about −0.13 and as is from about 0.0044 to about 0.0054. In these embodiments the probabilistic classification function f represents the likelihood the subject has an infection. More preferred values for the parameters $a_0$, $a_1$, $a_2$, $a_3$, $a_4$ and as in these embodiments are provided in Table 24.

In some embodiments, the method can be carried out using a system 330, which optionally and preferably, but not necessarily, comprises a hand-held device. The system can comprise two or more compartments, wherein the levels of determinants in the blood is measured in one of the compartments (e.g. using an immunohistochemical method), and wherein an analysis of the obtained levels is executed in the other compartment to provide an output relating to the diagnosis.

A block diagram of representative example of system 330 in embodiments in which system 330 comprises a hand-held device 331 is illustrated in FIG. 16. System 330 can comprise a first compartment 332 having a measuring system 333 configured to measure the expression value of the determinants in the blood of a subject. Measuring system 333 can perform at least one automated assay selected from the group consisting of an automated ELISA, an automated immunoassay, and an automated functional assay. System 330 can also comprise a second compartment 334 comprising a hardware processor 336 having a computer-readable medium 338 for storing computer program instructions for executing the operations described herein (e.g., computer program instructions for defining the first and/or second coordinates, computer program instructions for defining the curved line and/or plane, computer program instructions for calculating the first and/or distances, computer program instructions for correlating the calculated distance(s) to the presence of, absence of, or likelihood that the subject has, a bacterial and/or viral infection). Hardware processor 336 is configured to receive expression value measurements from first compartment 332 and execute the program instructions responsively to the measurements and output the processed data to a display device 340.

In some embodiments of the present invention system 330 communicates with a communication network, as schematically illustrated in the block diagram of FIG. 17A. In these embodiments, system 330 can comprise computer-readable medium 338, as further detailed hereinabove, and a hardware processor, such as, but not limited to, processor 336. Hardware processor 336 comprises a network interface 350 that communicates with a communication network 352. Via interface 350, hardware processor 336 receives expression value measurements from a measuring system, such as, but not limited to, measuring system 333, and executes the computer program instructions in computer-readable medium 338, responsively to the received measurements. Hardware processor 336 can then output the processed data to display device 340.

In some embodiments of the present invention system 330 communicates with a user, as schematically illustrated in the block diagram of FIG. 17B. In these embodiments, system 330 can comprise computer-readable medium 338, as further detailed hereinabove, and a hardware processor, such as, but not limited to, processor 336. Hardware processor 336 comprises a user interface 354 that communicates with a user 356. Via interface 350, hardware processor 336 receives expression value measurements from user 356. User 356 can obtain the expression value from an external source, or by executing at least one assay selected from the group consisting of an immunoassay and a functional assay, or by operating system 333 (not shown, see FIGS. 16 and 17A). Hardware processor 336 executes the computer program instructions in computer-readable medium 338, responsively to the received measurements. Hardware processor 336 can then output the processed data to display device 340.

Measuring the determinant levels is typically affected at the protein level as further described herein below.

Methods of Detecting Expression and/or Activity of Proteins

Expression and/or activity level of proteins expressed in the cells of the cultures of some embodiments of the invention can be determined using methods known in the arts and typically involve the use of antibodies. Such methods may be referred to an immunoassays. Immunoassays may be run in multiple steps with reagents being added and washed away or separated at different points in the assay. Multi-step assays are often called separation immunoassays or heterogeneous immunoassays. Some immunoassays can be carried out simply by mixing the reagents and sample and making a physical measurement. Such assays are called homogenous immunoassays or less frequently non-separation immunoassays. The use of a calibrator is often employed in immunoassays. Calibrators are solutions that are known to contain the analyte in question, and the concentration of that analyte is generally known. Comparison of an assay's response to a real sample against the assay's response produced by the calibrators makes it possible to interpret the signal strength in terms of the presence or concentration of analyte in the sample.

The antibody may be monoclonal, polyclonal, chimeric, or a fragment of the foregoing, and the step of detecting the reaction product may be carried out with any suitable immunoassay.

Suitable sources for antibodies for the detection of the polypeptides include commercially available sources such as, for example, Abazyme, Abnova, AssayPro, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, against any of the polypeptides described herein.

Polyclonal antibodies for measuring polypeptides include without limitation antibodies that were produced from sera by active immunization of one or more of the following: Rabbit, Goat, Sheep, Chicken, Duck, Guinea Pig, Mouse, Donkey, Camel, Rat and Horse.

Examples of additional detection agents, include without limitation: scFv, dsFv, Fab, sVH, $F(ab')_2$, Cyclic peptides, Haptamers, A single-domain antibody, Fab fragments, Single-chain variable fragments, Affibody molecules, Affilins, Nanofitins, Anticalins, Avimers, DARPins, Kunitz domains, Fynomers and Monobody.

The detection agents may be labeled with a label and detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Those skilled in the art will be familiar with numerous suitable detectors that widely available from a variety of commercial sources and may be useful for carrying out the method disclosed herein. Commonly, an optical image of a substrate comprising bound labeling moieties is digitized for subsequent computer analysis. See generally The Immunoassay Handbook (Wild 2005).

Enzyme Linked Immunosorbent Assay (ELISA):

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are a specifically bound. After the final wash step, the plate is developed by adding an enzymatic substrate to produce a visible signal, which indicates the quantity of antigen in the sample.

Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot:

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Fluorescence Activated Cell Sorting (FACS):

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Automated Immunoassay:

An automated analyzer applied to an immunoassay (often called "Automated Immunoassay") is a medical laboratory instrument designed to measure different chemicals and other characteristics in a number of biological samples quickly, with minimal human assistance. These measured properties of blood and other fluids may be useful in the diagnosis of disease. Many methods of introducing samples into the analyzer have been invented. This can involve placing test tubes of sample into racks, which can be moved along a track, or inserting tubes into circular carousels that rotate to make the sample available. Some analyzers require samples to be transferred to sample cups. However, the effort to protect the health and safety of laboratory staff has prompted many manufacturers to develop analyzers that feature closed tube sampling, preventing workers from direct exposure to samples. Samples can be processed singly, in batches, or continuously. Examples of automated immunoassay machines include, without limitation, ARCHITECT ci4100, ci8200 (2003), ci16200 (2007), ARCHITECT i1000SR, ARCHITECT i2000, i2000SR, i4000SR, AxSYM/AxSYM Plus, 1994 U.S., DS2, AIMS, AtheNA, DSX, ChemWell, UniCel DxI 860i Synchron Access Clinical System, UniCel DxC 680i Synchron Access Clinical System, Access/Access 2 Immunoassay System, UniCel DxI 600 Access Immunoassay System, UniCel DxC 600i Synchron Access Clinical System, UniCel DxI 800 Access Immunoassay System, UniCel DxC 880i Synchron Access Clinical System, UniCel DxI 660i Synchron Access Clinical System, SPA PLUS (Specialist Protein Analyzer), VIDAS Immunoassay Analyzer, BioPlex 2200, PhD System EVOLIS PR 3100TSC Photometer, MAGO 4S/2011 Mago Plus Automated EIA Processor, LIAISON XL/2010 LIAISON, ETI-MAX 3000 Agility, Triturus, HYTEC 288 PLUSDSX, VITROS ECi Immunodiagnostic System, VITROS 3600 Immunodiagnostic System, Phadia Laboratory System 100E, Phadia Laboratory System 250, Phadia Laboratory System 1000, Phadia Laboratory System 2500, Phadia Laboratory System 5000, cobas e 602/2010, cobas e411, cobas e601, MODULAR ANALYTICS E170, Elecsys 2010, Dimension EXL 200/2011, Dimension Xpand Plus Integrated Chemistry System, Dimension RxL Max/Max Suite Integrated Chemistry System; Dimension RxL Integrated Chemistry System, Dimension EXL with LM Integrated Chemistry System, Stratus CS Acute Care Diagnostic System, IMMULITE 2000 XPi Immunoassay System, ADVIA Centaur CP Immunoassay System, IMMULITE 2000, IMMULITE 1000, Dimension Vista 500 Intelligent Lab System, Dimension Vista 1500 Intelligent Lab System, ADVIA Centaur XP, AIA-900, AIA-360, AIA-2000, AIA-600 II, AIA-1800. Measurements of CRP, IP-10 and TRAIL can also be performed on a Luminex machine.

Lateral Flow Immunoassays (LFIA):

This is a technology which allows rapid measurement of analytes at the point of care (POC) and its underlying principles are described below. According to one embodiment, LFIA is used in the context of a hand-held device.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex.

After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the wick, that simply acts as a waste container. Lateral Flow Tests can operate as either competitive or sandwich assays.

Different formats may be adopted in LFIA. Strips used for LFIA contain four main components. A brief description of each is given before describing format types.

Sample Application Pad:

It is made of cellulose and/or glass fiber and sample is applied on this pad to start assay. Its function is to transport the sample to other components of lateral flow test strip (LFTS). Sample pad should be capable of transportation of the sample in a smooth, continuous and homogenous manner. Sample application pads are sometimes designed to pretreat the sample before its transportation. This pretreatment may include separation of sample components, removal of interferences, adjustment of pH, etc.

Conjugate Pad:

It is the place where labeled biorecognition molecules are dispensed. Material of conjugate pad should immediately release labeled conjugate upon contact with moving liquid sample. Labeled conjugate should stay stable over entire life span of lateral flow strip. Any variations in dispensing, drying or release of conjugate can change results of assay significantly. Poor preparation of labeled conjugate can adversely affect sensitivity of assay. Glass fiber, cellulose, polyesters and some other materials are used to make conjugate pad for LFIA. Nature of conjugate pad material has an effect on release of labeled conjugate and sensitivity of assay.

Nitrocellulose Membrane:

It is highly critical in determining sensitivity of LFIA. Nitrocellulose membranes are available in different grades. Test and control lines are drawn over this piece of membrane. So an ideal membrane should provide support and good binding to capture probes (antibodies, aptamers etc.). Nonspecific adsorption over test and control lines may affect results of assay significantly, thus a good membrane will be characterized by lesser non-specific adsorption in the regions of test and control lines. Wicking rate of nitrocellulose membrane can influence assay sensitivity. These membranes are easy to use, inexpensive, and offer high affinity for proteins and other biomolecules. Proper dispensing of bioreagents, drying and blocking play a role in improving sensitivity of assay.

Adsorbent Pad:

It works as sink at the end of the strip. It also helps in maintaining flow rate of the liquid over the membrane and stops back flow of the sample. Adsorbent capacity to hold liquid can play an important role in results of assay.

All these components are fixed or mounted over a backing card. Materials for backing card are highly flexible because they have nothing to do with LFIA except providing a platform for proper assembling of all the components. Thus backing card serves as a support and it makes easy to handle the strip.

Major steps in LFIA are (i) preparation of antibody against target analyte (ii) preparation of label (iii) labeling of biorecognition molecules (iv) assembling of all components onto a backing card after dispensing of reagents at their proper pads (v) application of sample and obtaining results.

Sandwich Format:

In a typical format, label (Enzymes or nanoparticles or fluorescence dyes) coated antibody or aptamer is immobilized at conjugate pad. This is a temporary adsorption which can be flushed away by flow of any buffer solution. A primary antibody or aptamer against target analyte is immobilized over test line. A secondary antibody or probe against labeled conjugate antibody/aptamer is immobilized at control zone.

Sample containing the analyte is applied to the sample application pad and it subsequently migrates to the other parts of strip. At conjugate pad, target analyte is captured by the immobilized labeled antibody or aptamer conjugate and results in the formation of labeled antibody conjugate/analyte complex. This complex now reaches at nitrocellulose membrane and moves under capillary action. At test line, label antibody conjugate/analyte complex is captured by another antibody which is primary to the analyte. Analyte becomes sandwiched between labeled and primary antibodies forming labeled antibody conjugate/analyte/primary antibody complex. Excess labeled antibody conjugate will be captured at control zone by secondary antibody. Buffer or excess solution goes to absorption pad. Intensity of color at test line corresponds to the amount of target analyte and is measured with an optical strip reader or visually inspected. Appearance of color at control line ensures that a strip is functioning properly.

Competitive Format:

Such a format suits best for low molecular weight compounds which cannot bind two antibodies simultaneously. Absence of color at test line is an indication for the presence of analyte while appearance of color both at test and control lines indicates a negative result. Competitive format has two layouts. In the first layout, solution containing target analyte is applied onto the sample application pad and prefixed labeled biomolecule (antibody/aptamer) conjugate gets hydrated and starts flowing with moving liquid. Test line contains pre-immobilized antigen (same analyte to be detected) which binds specifically to label conjugate. Control line contains pre-immobilized secondary antibody which has the ability to bind with labeled antibody conjugate. When liquid sample reaches at the test line, pre-immobilized antigen will bind to the labeled conjugate in case target analyte in sample solution is absent or present in such a low quantity that some sites of labeled antibody conjugate were vacant. Antigen in the sample solution and the one which is immobilized at test line of strip compete to bind with labeled conjugate. In another layout, labeled analyte conjugate is dispensed at conjugate pad while a primary antibody to analyte is dispensed at test line. After application of analyte solution a competition takes place between analyte and labeled analyte to bind with primary antibody at test line.

Multiplex Detection Format:

Multiplex detection format is used for detection of more than one target species and assay is performed over the strip containing test lines equal to number of target species to be analyzed. It is highly desirable to analyze multiple analytes simultaneously under same set of conditions. Multiplex detection format is very useful in clinical diagnosis where multiple analytes which are inter-dependent in deciding about the stage of a disease are to be detected. Lateral flow strips for this purpose can be built in various ways i.e. by increasing length and test lines on conventional strip, making other structures like stars or T-shapes. Shape of strip for LFIA will be dictated by number of target analytes. Miniaturized versions of LFIA based on microarrays for multiplex detection of DNA sequences have been reported to have several advantages such as less consumption of test reagents, requirement of lesser sample volume and better sensitivity.

Labels:

Any material that is used as a label should be detectable at very low concentrations and it should retain its properties upon conjugation with biorecognition molecules. This conjugation is also expected not to change features of biorecognition probes. Ease in conjugation with biomolecules and stability over longer period of time are desirable features for a good label. Concentrations of labels down to $10^{-9}$ M are optically detectable. After the completion of assay, some labels generate direct signal (as color from gold colloidal) while others require additional steps to produce analytical signal (as enzymes produce detectable product upon reaction with suitable substrate). Hence the labels which give direct signal are preferable in LFA because of less time consumption and reduced procedure.

Gold Nanoparticles:

Colloidal gold nanoparticles are the most commonly used labels in LFA. Colloidal gold is inert and gives very perfect spherical particles. These particles have very high affinity toward biomolecules and can be easily functionalized. Optical properties of gold nanoparticles are dependent on size and shape. Size of particles can be tuned by use of suitable chemical additives. Their unique features include environment friendly preparation, high affinity toward proteins and biomolecules, enhanced stability, exceptionally higher values for charge transfer and good optical signaling. Optical signal of gold nanoparticles in colorimetric LFA can be amplified by deposition of silver, gold nanoparticles and enzymes.

Magnetic Particles and Aggregates:

Colored magnetic particles produce color at the test line which is measured by an optical strip reader but magnetic signals coming from magnetic particles can also be used as detection signals and recorded by a magnetic assay reader. Magnetic signals are stable for longer time compared to optical signals and they enhance sensitivity of LFA by 10 to 1000 folds.

Fluorescent and Luminescent Materials:

Fluorescent molecules are widely used in LFA as labels and the amount of fluorescence is used to quantitate the concentration of analyte in the sample. Detection of proteins is accomplished by using organic fluorophores such as rhodamine as labels in LFA.

Current developments in nanomaterial have headed to manufacture of quantum dots which display very unique electrical and optical properties. These semiconducting particles are not only water soluble but can also be easily combined with biomolecules because of closeness in dimensions. Owing to their unique optical properties, quantum dots have come up as a substitute to organic fluorescent dyes. Like gold nanoparticles QDs show size dependent optical properties and a broad spectrum of wavelengths can be monitored. Single light source is sufficient to excite quantum dots of all different sizes. QDs have high photo stability and absorption coefficients.

Upconverting phosphors (UCP) are characterized by their excitation in infra-red region and emission in high energy visible region. Compared to other fluorescent materials, they have a unique advantage of not showing any auto fluorescence. Because of their excitation in IR regions, they do not photo degrade biomolecules. A major advantage lies in their production from easily available bulk materials. Although difference in batch to batch preparation of UCP reporters can affect sensitivity of analysis in LFA, it was observed that they can enhance sensitivity of analytical signal by 10 to 100 folds compared to gold nanoparticles or colored latex beads, when analysis is carried out under same set of biological conditions.

Enzymes:

Enzymes are also employed as labels in LFA. But they increase one step in LFA which is application of suitable substrate after complete assay. This substrate will produce color at test and control lines as a result of enzymatic reaction. In case of enzymes, selection of suitable enzyme substrate combination is one necessary requirement in order to get a colored product for strip reader or electroactive product for electrochemical detection. In other words, sensitivity of detection is dependent on enzyme substrate combination.

Colloidal Carbon:

Colloidal carbon is comparatively inexpensive label and its production can be easily scaled up. Because of their black color, carbon NPs can be easily detected with high sensitivity. Colloidal carbon can be functionalized with a large variety of biomolecules for detection of low and high molecular weight analytes.

Detection Systems:

In case of gold nanoparticles or other color producing labels, qualitative or semi-quantitative analysis can be done by visual inspection of colors at test and control lines. The major advantage of visual inspection is rapid qualitative answer in "Yes" or "NO". Such quick replies about presence of an analyte in clinical analysis have very high importance. Such tests help doctors to make an immediate decision near the patients in hospitals in situations where test results from central labs cannot be waited for because of huge time consumption. But for quantification, optical strip readers are employed for measurement of the intensity of colors produced at test and control lines of strip. This is achieved by inserting the strips into a strip reader and intensities are recorded simultaneously by imaging softwares. Optical images of the strips can also be recorded with a camera and then processed by using a suitable software. Procedure includes proper placement of strip under the camera and a controlled amount of light is thrown on the areas to be observed. Such systems use monochromatic light and wavelength of light can be adjusted to get a good contrast among test and control lines and background. In order to provide good quantitative and reproducible results, detection system should be sensitive to different intensities of colors. Optical standards can be used to calibrate an optical reader device. Automated systems have advantages over manual imaging and processing in terms of time consumption, interpretation of results and adjustment of variables.

In case of fluorescent labels, a fluorescence strip reader is used to record fluorescence intensity of test and control lines. Fluorescence brightness of test line increased with an increase in nitrated seruloplasmin concentration in human serum when it was detected with a fluorescence strip reader. A photoelectric sensor was also used for detection in LFIA where colloidal gold is exposed to light emitting diode and resulting photoelectrons are recorded. Chemiluminescence which results from reaction of enzyme and substrate is measured as a response to amount of target analyte. Magnetic strip readers and electrochemical detectors are also reported as detection systems in LFTS but they are not very common. Selection of detector is mainly determined by the label employed in analysis.

Immunohistochemical Analysis:

Immunoassays carried out in accordance with some embodiments of the present invention may be homogeneous assays or heterogeneous assays. In a homogeneous assay the immunological reaction usually involves the specific antibody (e.g., anti-MX1 and CRP antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels, which may be employed, include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase.

According to a particular embodiment, the antibody is immobilized to a porous strip to form a detection site. The measurement or detection region of the porous strip may include a plurality of sites, one for MX1 and one for CRP. A test strip may also contain sites for negative and/or positive controls.

Alternatively, control sites can be located on a separate strip from the test strip. Optionally, the different detection sites may contain different amounts of antibodies, e.g., a higher amount in the first detection site and lesser amounts in subsequent sites. Upon the addition of test sample, the number of sites displaying a detectable signal provides a quantitative indication of the amount of polypeptides present in the sample. The detection sites may be configured in any suitably detectable shape and are typically in the shape of a bar or dot spanning the width of a test strip.

The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}$S, $^{125}$I $^{131}$I), enzyme labels (e.g., horseradish peroxidase, alkaline phosphatase), and fluorescent labels (e.g., fluorescein, Alexa, green fluorescent protein, rhodamine) in accordance with known techniques.

Examples of monoclonal antibodies for measuring CRP include without limitation: Mouse, Monoclonal (108-2A2); Mouse, Monoclonal (108-7G41D2); Mouse, Monoclonal (12D-2C-36), IgG1; Mouse, Monoclonal (1G1), IgG1; Mouse, Monoclonal (5A9), IgG2a kappa; Mouse, Monoclonal (63F4), IgG1; Mouse, Monoclonal (67A1), IgG1; Mouse, Monoclonal (8B-5E), IgG1; Mouse, Monoclonal (B893M), IgG2b, lambda; Mouse, Monoclonal (C1), IgG2b; Mouse, Monoclonal (C11F2), IgG; Mouse, Monoclonal (C2), IgG1; Mouse, Monoclonal (C3), IgG1; Mouse, Monoclonal (C4), IgG1; Mouse, Monoclonal (C5), IgG2a; Mouse, Monoclonal (C6), IgG2a; Mouse, Monoclonal (C7), IgG1; Mouse, Monoclonal (CRP103), IgG2b; Mouse, Monoclonal (CRP11), IgG1; Mouse, Monoclonal (CRP135), IgG1; Mouse, Monoclonal (CRP169), IgG2a; Mouse, Monoclonal (CRP30), IgG1; Mouse, Monoclonal (CRP36), IgG2a; Rabbit, Monoclonal (EPR283Y), IgG; Mouse, Monoclonal (KT39), IgG2b; Mouse, Monoclonal (N-a), IgG1; Mouse, Monoclonal (N1G1), IgG1; Monoclonal (P5A9AT); Mouse, Monoclonal (S5G1), IgG1; Mouse, Monoclonal (SB78c), IgG1; Mouse, Monoclonal (SB78d), IgG1 and Rabbit, Monoclonal (Y284), IgG, Human C-Reactive Protein/CRP Biot MAb (Cl 232024), Mouse IgG2B, Human C-Reactive Protein/CRP MAb (Clone 232007), Mouse IgG2B, Human/Mouse/Porcine C-Reactive Protein/CRP MAb (Cl 232026), Mouse IgG2A.

Antibodies for measuring CRP include monoclonal antibodies for measuring CRP and polyclonal antibodies for measuring CRP.

Antibodies for measuring CRP also include antibodies that were developed to target epitopes from the list comprising of: Human plasma derived CRP, Human serum derived CRP, Mouse myeloma cell line NSO-derived recombinant human C-Reactive Protein/CRP (Phe17-Pro224 Accession #P02741).

As mentioned, the present invention also contemplates measuring determinants at the RNA level.

Methods of analyzing the amount of RNA are known in the art and are summarized infra:

Northern Blot Analysis:

This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radioisotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RT-PCR Analysis:

This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA In Situ Hybridization Stain:

In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the bound probe is detected using known methods. For example, if a radio-labeled probe is used, then the slide is subjected to a photographic emulsion which reveals signals generated using radio-labeled probes; if the probe was labeled with an enzyme then the enzyme-specific substrate is added for the formation of a colorimetric reaction; if the probe is labeled using a fluorescent label, then the bound probe is revealed using a fluorescent microscope; if the probe is labeled using a tag (e.g., digoxigenin, biotin, and the like) then the bound probe can be detected following interaction with a tag-specific antibody which can be detected using known methods.

In Situ RT-PCR Stain:

This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

DNA Microarrays/DNA Chips:

The expression of thousands of genes may be analyzed simultaneously using DNA microarrays, allowing analysis of the complete transcriptional program of an organism during specific developmental processes or physiological responses. DNA microarrays consist of thousands of individual gene sequences attached to closely packed areas on the surface of a support such as a glass microscope slide. Various methods have been developed for preparing DNA microarrays. In one method, an approximately 1 kilobase segment of the coding region of each gene for analysis is individually PCR amplified. A robotic apparatus is employed to apply each amplified DNA sample to closely spaced zones on the surface of a glass microscope slide, which is subsequently processed by thermal and chemical treatment to bind the DNA sequences to the surface of the support and denature them. Typically, such arrays are about 2×2 cm and contain about individual nucleic acids 6000 spots. In a variant of the technique, multiple DNA oligonucleotides, usually 20 nucleotides in length, are synthesized from an initial nucleotide that is covalently bound to the surface of a support, such that tens of thousands of identical oligonucleotides are synthesized in a small square zone on the surface of the support. Multiple oligonucleotide sequences from a single gene are synthesized in neighboring regions of the slide for analysis of expression of that gene. Hence, thousands of genes can be represented on one glass slide. Such arrays of synthetic oligonucleotides may be referred to in the art as "DNA chips", as opposed to "DNA microarrays", as described above [Lodish et al. (eds.). Chapter 7.8: DNA Microarrays: Analyzing Genome-Wide Expression. In: Molecular Cell Biology, 4th ed., W. H. Freeman, New York. (2000)].

Oligonucleotide Microarray—

In this method oligonucleotide probes capable of specifically hybridizing with the polynucleotides of some embodiments of the invention are attached to a solid surface (e.g., a glass wafer). Each oligonucleotide probe is of approximately 20-25 nucleic acids in length. To detect the expression pattern of the polynucleotides of some embodiments of the invention in a specific cell sample (e.g., blood cells), RNA is extracted from the cell sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Md., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix®, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

RNA Sequencing:

Methods for RNA sequence determination are generally known to the person skilled in the art. Preferred sequencing methods are next generation sequencing methods or parallel high throughput sequencing methods. An example of an envisaged sequence method is pyrosequencing, in particular 454 pyrosequencing, e.g. based on the Roche 454 Genome Sequencer. This method amplifies DNA inside water droplets in an oil solution with each droplet containing a single DNA template attached to a single primer-coated bead that then forms a clonal colony. Pyrosequencing uses luciferase to generate light for detection of the individual nucleotides added to the nascent DNA, and the combined data are used to generate sequence read-outs. Yet another envisaged example is Illumina or Solexa sequencing, e.g. by using the Illumina Genome Analyzer technology, which is based on reversible dye-terminators. DNA molecules are typically attached to primers on a slide and amplified so that local clonal colonies are formed. Subsequently one type of nucleotide at a time may be added, and non-incorporated nucleotides are washed away. Subsequently, images of the fluorescently labeled nucleotides may be taken and the dye is chemically removed from the DNA, allowing a next cycle. Yet another example is the use of Applied Biosystems' SOLiD technology, which employs sequencing by ligation. This method is based on the use of a pool of all possible oligonucleotides of a fixed length, which are labeled according to the sequenced position. Such oligonucleotides are annealed and ligated. Subsequently, the preferential ligation by DNA ligase for matching sequences typically results in a signal informative of the nucleotide at that position. Since the DNA is typically amplified by emulsion PCR, the resulting bead, each containing only copies of the same DNA molecule, can be deposited on a glass slide resulting in sequences of quantities and lengths comparable to Illumina sequencing. A further method is based on Helicos' Heliscope technology, wherein fragments are captured by polyT oligomers tethered to an array. At each sequencing cycle, polymerase and single fluorescently labeled nucleotides are added and the array is imaged. The fluorescent tag is subsequently removed and the cycle is repeated. Further examples of sequencing techniques encompassed within the methods of the present invention are sequencing by hybridization, sequencing by use of nanopores, microscopy-based sequencing techniques, microfluidic Sanger sequencing, or microchip-based sequencing methods. The present invention also envisages further developments of these techniques, e.g. further improvements of the accuracy of the sequence determination, or the time needed for the determination of the genomic sequence of an organism etc.

According to one embodiment, the sequencing method comprises deep sequencing.

As used herein, the term "deep sequencing" refers to a sequencing method wherein the target sequence is read multiple times in the single test. A single deep sequencing run is composed of a multitude of sequencing reactions run on the same target sequence and each, generating independent sequence readout.

It will be appreciated that the expression level of the determinants described herein can be an absolute expression level, a normalized expression and/or a relative expression level.

In general scientific context, normalization is a process by which a measurement raw data is converted into data that may be directly compared with other so normalized data. In the context of the present invention, measurements of expression levels are prone to errors caused by, for example, unequal degradation of measured samples, different loaded quantities per assay, and other various errors. More specifically, any assayed sample may contain more or less biological material than is intended, due to human error and equipment failures. Thus, the same error or deviation applies to both the polypeptide of the invention and to the control reference, whose expression is essentially constant. Thus, division of MX1 or CRP raw expression value by the control reference raw expression value yields a quotient which is essentially free from any technical failures or inaccuracies (except for major errors which destroy the sample for testing purposes) and constitutes a normalized expression value of the polypeptide. Since control reference expression values are equal in different samples, they constitute a common reference point that is valid for such normalization.

According to a particular embodiment, each of the polypeptide expression values are normalized using the same control reference.

Once the tests are carried out to determine the level of the determinants, a subject specific dataset is optionally generated which contains the results of the measurements.

The subject-specific dataset may be stored in a computer readable format on a non-volatile computer readable medium, and is optionally and preferably accessed by a hardware processor, such as a general purpose computer or dedicated circuitry.

As mentioned, the levels of the determinants (e.g. polypeptides) in the test subjects blood are compared to the levels of the identical polypeptides in a plurality of subjects' blood, when the subjects have already been verified as having a bacterial infection, viral infection or non-bacterial/non-viral disease on the basis of parameters other than the blood level of the polypeptides. The levels of the polypeptides of the plurality of subjects together with their verified diagnosis can be stored in a second dataset, also referred to herein as the "group dataset" or "prediagnosed dataset", as further described herein below.

The phrase "non-bacterial/non-viral disease" refers to disease that is not caused by a bacteria or virus. This includes diseases such as acute myocardial infarction, physical injury, epileptic attack, inflammatory disorders etc, fungal diseases, parasitic diseases etc.

The phrase "viral infection" as used herein refers to a disease that is caused by a virus and does not comprise a bacterial component.

Methods of analyzing a dataset, for example, for the purpose of calculating one or more probabilistic classification function representing the likelihood that a particular subject has a bacterial infection, or the likelihood that a particular subject has a viral infection or the likelihood that a particular subject has a non-bacterial non-viral disease, may be performed as described in the Examples section below.

For example, diagnosis may be supported using PCR diagnostic assays such as (i) Seeplex® RV15 for detection of parainfluenza virus 1, 2, 3, and 4, coronavirus 229E/NL63, adenovirus A/B/C/D/E, bocavirus 1/2/3/4, influenza virus A and B, metapneumovirus, coronavirus OC43, rhinovirus A/B/C, respiratory syncytial virus A and B, and Enterovirus, or (ii) Seeplex® PB6 for detection of *Streptococcus pneumoniae, Haemophilus influenzae, Chlamydophila pneumoniae, Legionella pneumophila, Bordetella pertussis*, and *Mycoplasma pneumoniae*.

Blood cultures, urine cultures and stool cultures may be analyzed for *Shigella* spp., *Campylobacter* spp. and *Salmonella* spp.; serological testing (IgM and/or IgG) for cytomegalovirus (CMV), Epstein-Barr virus (EBV), *Mycoplasma* Pneumonia, and *Coxiella burnetii* (Q-Fever).

Radiological tests (e.g. chest X-ray for suspected lower respiratory tract infection [LRTI]) may be used to confirm chest infections.

Alternatively, or additionally at least one trained physician may be used to establish the diagnosis.

Methods of determining the expression level of the polypeptides in the pre-diagnosed subjects have been described herein above.

Preferably, the same method which is used for determining the expression level of the polypeptides in the pre-diagnosed subjects is used for determining the level of the polypeptides in the test subject. Thus, for example if an immunoassay type method is used for determining the expression level of the polypeptides in the pre-diagnosed subjects, then an immunoassay type method should be used for determining the level of the polypeptides in the test subject.

It will be appreciated that, the type of blood sample need not be identical in the test subject and the pre-diagnosed subjects. Thus, for example, if a serum sample is used for determining the expression level of the polypeptides in the pre-diagnosed subjects, then a plasma sample may be used for determining the level of the polypeptides in the test subject.

The additional dimensions of the datasets provides additional information pertaining to the subject under analysis, to the other subjects and/or to levels of polypeptides other than CRP and MX1.

"Traditional laboratory risk factors" also referred to as "clinical data" encompass biomarkers isolated or derived from subject samples and which are currently evaluated in the clinical laboratory and used in traditional global risk assessment algorithms. Examples of same are provided herein above.

Preferably, at least one of the traditional laboratory risk factors of the subject under analysis is included in the subject specific dataset, and at least one of the traditional laboratory risk factors of one or more (more preferably all) of the other subjects is included in the group dataset. When the subject specific dataset includes at least one of the traditional laboratory risk factors, the risk factors can be included as a separate entry. When the group dataset includes the risk factors, the risk factors is optionally and preferably included per subject. Thus, for example, a group dataset entry can be described by the tuple (S, G, D, L {R}), where S, G, D and L have been introduced before and {R} is the at least one risk factor of subject S.

"Clinical parameters" encompass all non-sample or non-analyte biomarkers of subject health status or other characteristics, such as, without limitation, age (Age), ethnicity (RACE), gender (Sex), core body temperature (abbreviated "temperature"), maximal core body temperature since initial appearance of symptoms (abbreviated "maximal temperature"), time from initial appearance of symptoms (abbreviated "time from symptoms"), pregnancy, or family history (abbreviated FamHX).

Preferably, at least one of the clinical parameters of the subject under analysis is included in the subject specific dataset, and at least one of the clinical parameters of one or more (more preferably all) of the other subjects is included in the group dataset. When the subject specific dataset includes at least one of the clinical parameters, the clinical parameters can be included as a separate entry. When the group dataset includes the clinical parameters, the clinical parameters is optionally and preferably included per subject. Thus, for example, a group dataset entry can be described by the tuple (S, G, D, L {C}), where S, G, D and L have been introduced before and {C} is the clinical parameter of subject S.

As used herein "blood chemistry" refers to the concentration, or concentrations, of any and all substances dissolved in, or comprising, the blood. Representative examples of such substances, include, without limitation, albumin, amylase, alkaline phosphatase, bicarbonate, total bilirubin, BUN, C-reactive protein, calcium, chloride, LDL, HDL, total cholesterol, creatinine, CPK, γ-GT, glucose, LDH, inorganic phosphorus, lipase, potassium, total protein, AST, ALT, sodium, triglycerides, uric acid and VLDL.

Once the diagnosis has been made, it will be appreciated that a number of actions may be taken.

Thus, for example, if a bacterial infection is ruled in, then the subject may be treated with an antibiotic agent.

Examples of antibiotic agents include, but are not limited to Daptomycin; Gemifloxacin; Telavancin; Ceftaroline; Fidaxomicin; Amoxicillin; Ampicillin; Bacampicillin; Carbenicillin; Cloxacillin; Dicloxacillin; Flucloxacillin; Mezlocillin; Nafcillin; Oxacillin; Penicillin G; Penicillin V; Piperacillin; Pivampicillin; Pivmecillinam; Ticarcillin; Aztreonam; Imipenem; Doripenem; Meropenem; Ertapenem; Clindamycin; Lincomycin; Pristinamycin; Quinupristin; Cefacetrile (cephacetrile); Cefadroxil (cefadroxyl); Cefalexin (cephalexin); Cefaloglycin (cephaloglycin); Cefalonium (cephalonium); Cefaloridine (cephaloridine); Cefalotin (cephalothin); Cefapirin (cephapirin); Cefatrizine; Cefazaflur; Cefazedone; Cefazolin (cephazolin); Cefradine (cephradine); Cefroxadine; Ceftezole; Cefaclor; Cefamandole; Cefmetazole; Cefonicid; Cefotetan; Cefoxitin; Cefprozil (cefproxil); Cefuroxime; Cefuzonam; Cefcapene; Cefdaloxime; Cefdinir; Cefditoren; Cefetamet; Cefixime; Cefmenoxime; Cefodizime; Cefotaxime; Cefpimizole; Cefpodoxime; Cefteram; Ceftibuten; Ceftiofur; Ceftiolene; Ceftizoxime; Ceftriaxone; Cefoperazone; Ceftazidime; Cefclidine; Cefepime; Cefluprenam; Cefoselis; Cefozopran; Cefpirome; Cefquinome; Fifth Generation; Ceftobiprole; Ceftaroline; Not Classified; Cefaclomezine; Cefaloram; Cefaparole; Cefcanel; Cefedrolor; Cefempidone; Cefetrizole; Cefivitril; Cefmatilen; Cefmepidium; Cefovecin; Cefoxazole; Cefrotil; Cefsumide; Cefuracetime; Ceftioxide; Azithromycin; Erythromycin; Clarithromycin; Dirithromycin; Roxithromycin; Telithromycin; Amikacin; Gentamicin; Kanamycin; Neomycin; Netilmicin; Paromomycin; Streptomycin; Tobramycin; Flumequine; Nalidixic acid; Oxolinic acid; Piromidic acid; Pipemidic acid; Rosoxacin; Ciprofloxacin; Enoxacin; Lomefloxacin; Nadifloxacin; Norfloxacin; Ofloxacin; Pefloxacin; Rufloxacin; Balofloxacin; Gatifloxacin; Grepafloxacin; Levofloxacin; Moxifloxacin; Pazufloxacin; Sparfloxacin; Temafloxacin; Tosufloxacin; Besifloxacin; Clinafloxacin; Gemifloxacin; Sitafloxacin; Trovafloxacin; Prulifloxacin; Sulfamethizole; Sulfamethoxazole; Sulfisoxazole; Trimethoprim-Sulfamethoxazole; Demeclocycline; Doxycycline; Minocycline; Oxytetracycline; Tetracycline; Tigecycline; Chloramphenicol; Metronidazole; Tinidazole; Nitrofurantoin; Vancomycin; Teicoplanin; Telavancin; Linezolid; Cycloserine 2; Rifampin; Rifabutin; Rifapentine; Bacitracin; Polymyxin B; Viomycin; Capreomycin.

If a viral infection is ruled in, the subject may be treated with an antiviral agent. Examples of antiviral agents include, but are not limited to Abacavir; Aciclovir; Acyclovir; Adefovir; Amantadine; Amprenavir; Ampligen; Arbidol; Atazanavir; Atripla; Balavir; Boceprevirertet; Cidofovir; Combivir; Dolutegravir; Darunavir; Delavirdine; Didanosine; Docosanol; Edoxudine; Efavirenz; Emtricitabine; Enfuvirtide; Entecavir; Ecoliever; Famciclovir; Fomivirsen; Fosamprenavir; Foscarnet; Fosfonet; Fusion inhibitor; Ganciclovir; Ibacitabine; Imunovir; Idoxuridine; Imiquimod; Indinavir; Inosine; Integrase inhibitor; Interferon type III; Interferon type II; Interferon type I; Interferon; Lamivudine; Lopinavir; Loviride; Maraviroc; Moroxydine; Methisazone; Nelfinavir; Nevirapine; Nexavir; Oseltamivir; Peginterferon alfa-2a; Penciclovir; Peramivir; Pleconaril; Podophyllotoxin; Raltegravir; Reverse transcriptase inhibitor; Ribavirin; Rimantadine; Ritonavir; Pyramidine; Saquinavir; Sofosbuvir; StavudineTelaprevir; Tenofovir; Tenofovir disoproxil; Tipranavir; Trifluridine; Trizivir; Tromantadine; Truvada; traporved; Valaciclovir; Valganciclovir; Vicriviroc; Vidarabine; Viramidine; Zalcitabine; Zanamivir; Zidovudine;

RNAi antivirals; inhaled rhibovirons; monoclonal antibody respigams; neuriminidase blocking agents.

The information gleaned using the methods described herein may aid in additional patient management options. For example, the information may be used for determining whether a patient should or should not be admitted to hospital. It may also affect whether or not to prolong hospitalization duration. It may also affect the decision whether additional tests need to be performed or may save performing unnecessary tests such as CT and/or X-rays and/or MRI and/or culture and/or serology and/or PCR assay for specific bacteria and/or PCR assays for viruses and/or perform procedures such as lumbar puncture.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Tang B M, Eslick G D, Craig J C, McLean A S. Accuracy of procalcitonin for sepsis diagnosis in critically ill patients: systematic review and meta-analysis. Lancet Infect Dis. 2007; 7: 210-217. doi:10.1016/S1473-3099 (07)70052-X.
2. Limper M, de Kruif M D, Duits A J, Brandjes D P M, van Gorp ECM. The diagnostic role of Procalcitonin and other biomarkers in discriminating infectious from non-infectious fever. J Infect. 2010; 60: 409-416. doi:10.1016/j.jinf.2010.03.016.
3. Engel M F, Paling F P, Hoepelman A I M, van der Meer V, Oosterheert J J. Evaluating the evidence for the implementation of C-reactive protein measurement in adult patients with suspected lower respiratory tract infection in primary care: a systematic review. Fam Pract. 2012; 29: 383-393. doi:10.1093/fampra/cmr119.
4. Quenot J-P, Luyt C-E, Roche N, Chalumeau M, Charles P-E, Claessens Y-E, et al. Role of biomarkers in the management of antibiotic therapy: an expert panel review II: clinical use of biomarkers for initiation or discontinuation of antibiotic therapy. Ann Intensive Care. 2013; 3: 21. doi:10.1186/2110-5820-3-21.
5. van der Meer V, Neven A K, van den Broek P J, Assendelft W J J. Diagnostic value of C reactive protein in infections of the lower respiratory tract: systematic review. BMJ. 2005; 331: 26. doi:10.1136/bmj.38483.478183.EB.
6. Falk G, Fahey T. C-reactive protein and community-acquired pneumonia in ambulatory care: systematic review of diagnostic accuracy studies. Fam Pract. 2009; 26: 10-21. doi:10.1093/fampra/cmn095.
7. Henriquez-Camacho C, Losa J. Biomarkers for sepsis. BioMed Res Int. 2014; 2014: 547818. doi:10.1155/2014/547818
8. Schuetz P, Müller B, Christ-Crain M, Stolz D, Tamm M, Bouadma L, et al. Procalcitonin to initiate or discontinue antibiotics in acute respiratory tract infections. Cochrane Database Syst Rev. 2012; 9: CD007498. doi:10.1002/14651858.CD007498.pub2.
9. Reinhart K, Meisner M. Biomarkers in the critically ill patient: procalcitonin. Crit Care Clin. 2011; 27: 253-263. doi:10.1016/j.ccc.2011.01.002.
10. Pierrakos C, Vincent J-L. Sepsis biomarkers: a review. Crit Care Lond Engl. 2010; 14: R15. doi:10.1186/cc8872.
11. Musher D M, Roig I L, Cazares G, Stager C E, Logan N, Safar H. Can an etiologic agent be identified in adults who are hospitalized for community-acquired pneumonia: results of a one-year study. J Infect. 2013; 67: 11-18. doi:10.1016/j.jinf.2013.03.003.
12. Musher D M, Bebko S P, Roig I L. Serum procalcitonin level, viral polymerase chain reaction analysis, and lower respiratory tract infection. J Infect Dis. 2014; 209: 631-633. doi:10.1093/infdis/jit579.
13. Polzin A, Pletz M, Erbes R, Raffenberg M, Mauch H, Wagner S, et al. Procalcitonin as a diagnostic tool in lower respiratory tract infections and tuberculosis. Eur Respir J. 2003; 21: 939-943.
14. Woodhead M, Blasi F, Ewig S, Garau J, Huchon G, Ieven M, et al. Guidelines for the management of adult lower respiratory tract infections—Full version. Clin Microbiol Infect. 2011; 17: E1-E59. doi:10.1111/j.1469-0691.2011.03672.x.
15. Kunze W, Beier D, Groeger K. Adenovirus Respiratory Infections In Children. Do They Mimic Bacterial Infections? 2010; Available: http://www(dot)webmedcentral (dot)com/article view/1098.
16. Oved K, Cohen A, Boico O, Navon R, Friedman T, Etshtein L, et al. A Novel Host-Proteome Signature for Distinguishing between Acute Bacterial and Viral Infections. PLoS ONE. 2015; 10: e0120012. doi:10.1371/journal.pone.0120012.
17. Tilg H, Trehu E, Atkins M B, Dinarello C A, Mier J W. Interleukin-6 (IL-6) as an anti-inflammatory cytokine: induction of circulating IL-1 receptor antagonist and soluble tumor necrosis factor receptor p55. Blood. 1994; 83: 113-118.
18. Gabay C, Kushner I. Acute-Phase Proteins and Other Systemic Responses to Inflammation. N Engl J Med. 1999; 340: 448-454. doi:10.1056/NEJM199902113400607.
19. Kurt A N C, Aygun A D, Godekmerdan A, Kurt A, Dogan Y, Yilmaz E. Serum IL-1beta, IL-6, IL-8, and TNF-alpha levels in early diagnosis and management of neonatal sepsis. Mediators Inflamm. 2007; 2007: 31397. doi: 10.1155/2007/31397.
20. Reinhart K, Meisner M. Biomarkers in the Critically Ill Patient: Procalcitonin. Crit Care Clin. 2011; 27: 253-263. doi:10.1016/j.ccc.2011.01.002.
21. Bossuyt P M, Reitsma J B, Bruns D E, Gatsonis C A, Glasziou P P, Irwig L M, et al. The STARD Statement for Reporting Studies of Diagnostic Accuracy: Explanation and Elaboration. Ann Intern Med. 2003; 138: W1-W12.
22. Rutjes A W S, Reitsma J B, Coomarasamy A, Khan K S, Bossuyt P M M. Evaluation of diagnostic tests when there is no gold standard. A review of methods. Health Technol Assess Winch Engl. 2007; 11: iii, ix-51.
23. Zhang X, Liu D, Liu Y-N, Wang R, Xie L-X. The accuracy of presepsin (sCD14-ST) for the diagnosis of sepsis in adults: a meta-analysis. Crit Care. 2015; 19: 323. doi:10.1186/s13054-015-1032-4.

24. Salvi S. The silent epidemic of COPD in Africa. Lancet Glob Health. 2015; 3: e6-7. doi:10.1016/52214-109X(14)70359-6.
25. GOLD—the Global initiative for chronic Obstructive Lung Disease [Internet]. [cited 15 Apr. 2015]. Available: http://www(dot)goldcopd(dot)org/guidelines-global-strategy-for-diagnosis-management(dot)html.
26. WHO|The top 10 causes of death. In: WHO [Internet]. [cited 17 Mar. 2015]. Available: http://www(dot)who(dot)int/mediacentre/factsheets/fs310/en/.
27. Global Problems, Smart Solutions. In: Cambridge University Press [Internet]. [cited 15 Apr. 2015]. Available: http://www(dot)cambridge(dot)org/il/academic/subjects/economics/public-economics-and-public-policy/global-problems-smart-solutions-costs-and-benefits.
28. Hoogendoorn M. Economic impact of COPD: Empirical and model-based studies on the cost-effectiveness of treatment options. J Neurophysiol-J NEUROPHYSIOL. 2011.
29. Hurst J R, Vestbo J, Anzueto A, Locantore N, Müllerova H, Tal-Singer R, et al. Susceptibility to exacerbation in chronic obstructive pulmonary disease. N Engl J Med. 2010; 363: 1128-1138. doi:10.1056/NEJMoa0909883.
30. Kim V, Desai P, Newell J D, Make B J, Washko G R, Silverman E K, et al. Airway wall thickness is increased in COPD patients with bronchodilator responsiveness. Respir Res. 2014; 15: 84. doi:10.1186/s12931-014-0084-3.
31. Bhowmik A, Seemungal T A, Sapsford R J, Wedzicha J A. Relation of sputum inflammatory markers to symptoms and lung function changes in COPD exacerbations. Thorax. 2000; 55: 114-120.
32. Molyneaux P L, Mallia P, Cox M J, Footitt J, Willis-Owen S A G, Homola D, et al. Outgrowth of the bacterial airway microbiome after rhinovirus exacerbation of chronic obstructive pulmonary disease. Am J Respir Crit Care Med. 2013; 188: 1224-1231. doi:10.1164/rccm.201302-03410C.
33. Taylor A E, Finney-Hayward T K, Quint J K, Thomas C M R, Tudhope S J, Wedzicha J A, et al. Defective macrophage phagocytosis of bacteria in COPD. Eur Respir J. 2010; 35: 1039-1047. doi:10.1183/09031936.00036709.
34. Sethi S, Evans N, Grant B J B, Murphy T F. New strains of bacteria and exacerbations of chronic obstructive pulmonary disease. N Engl J Med. 2002; 347: 465-471. doi:10.1056/NEJMoa012561.
35. Lin C-L, Siu L-K, Lin J-C, Liu C-Y, Chian C-F, Lee C-N, et al. MAnnose-binding lectin gene polymorphism contributes to recurrence of infective exacerbation in patients with copd. Chest. 2011; 139: 43-51. doi:10.1378/chest.10-0375.
36. Schappert S M, Rechtsteiner E A. Ambulatory medical care utilization estimates for 2007. Vital Health Stat 13. 2011; 1-38.
37. De S, Williams G J, Hayen A, Macaskill P, McCaskill M, Isaacs D, et al. Value of white cell count in predicting serious bacterial infection in febrile children under 5 years of age. Arch Dis Child. 2014; 99: 493-499. doi:10.1136/archdischild-2013-304754.
38. Verbakel J Y, Van den Bruel A, Thompson M, Stevens R, Aertgeerts B, Oostenbrink R, et al. How well do clinical prediction rules perform in identifying serious infections in acutely ill children across an international network of ambulatory care datasets? BMC Med. 2013; 11: 10. doi:10.1186/1741-7015-11-10.
39. Launay E, Gras-Le Guen C, Martinot A, Assathiany R, Martin E, Blanchais T, et al. Why Children with Severe Bacterial Infection Die: A Population—Based Study of Determinants and Consequences of Suboptimal Care with a Special Emphasis on Methodological Issues. PLoS ONE. 2014; 9. doi:10.1371/journal.pone.0107286.
40. Teillant A, Gandra S, Barter D, Morgan D J, Laxminarayan R. Potential burden of antibiotic resistance on surgery and cancer chemotherapy antibiotic prophylaxis in the USA: a literature review and modelling study. Lancet Infect Dis. 2015; 15: 1429-1437. doi:10.1016/51473-3099(15)00270-4.
41. Shapiro H. Practical Flow Cytometry [Internet]. 2005. Available: http://onlinelibrary(dot)wiley(dot)com/doi/10.1002/0471722731(dot)fmatter/summary
42. Wirth U., Muller D. Post-translational modification detection using metastable ions in reflector matrix-assisted laser desorption/ionization-time of flight mass spectrometry. Proteomics. 2002; 2: 1445-1451.
43. Wild D. The Immunoassay Handbook. Third Edition. 2005.

What is claimed is:

1. A method of treating a subject suspected of having sepsis or a non-infective systemic inflammatory response syndrome (SIRS) comprising:
   (a) measuring the amount of TNF-related apoptosis-inducing ligand (TRAIL), C-reactive protein (CRP) and Interferon gamma-induced protein 10 (IP10) and at least one additional polypeptide selected from the group consisting of Interleukin 6 (IL-6) and Procalcitonin (PCT), wherein no more than 5 proteins are measured;
   (b) confirming that the subject has sepsis based on the expression level of said TRAIL, said CRP, said IP10 and said at least one additional polypeptides in a sample from the subject; and
   (c) treating the subject confirmed as having sepsis with an antibiotic, thereby treating the subject suspected of having sepsis or SIRS.

2. The method of claim 1, wherein said measuring comprises measuring each of TNF-related apoptosis-inducing ligand (TRAIL), C-reactive protein (CRP), Interferon gamma-induced protein 10 (IP10), Interleukin 6 (IL-6) and Procalcitonin (PCT).

3. The method of claim 1, wherein the sample is taken from the subject no more than one day following onset of symptoms.

* * * * *

SEQUENCE LISTING

```
<160> NUMBER OF SEQ ID NOS: 24

<210> SEQ ID NO 1
<211> LENGTH: 224
<212> TYPE: PRT
<213> ORGANISM: homo sapiens

<400> SEQUENCE: 1

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

Arg Gly Tyr Ser Ile Phe Ser Tyr Ala Thr Lys Arg Gln Asp Asn Glu
65                  70                  75                  80
```

```
Ile Leu Ile Phe Trp Ser Lys Asp Ile Gly Tyr Ser Phe Thr Val Gly
                85                  90                  95

Gly Ser Glu Ile Leu Phe Glu Val Pro Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
130                 135                 140

Val Gly Ala Glu Ala Ser Ile Ile Leu Gly Gln Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
    210                 215                 220
```

<210> SEQ ID NO 2
<211> LENGTH: 1805
<212> TYPE: DNA
<213> ORGANISM: homo sapiens

<400> SEQUENCE: 2

```
acagaaccca gaaaaacaac tcattcgctt tcatttcctc actgactata aagaataga      60 gaaggaaggg cttcagtgac cggctgcctg gctgacttac agcagtcaga ctctgacagg    120
atcatggcta tgatggaggt ccaggggga cccagcctgg acagacctg cgtgctgatc      180 gtgatcttca cagtgctcct gcagtctctc tgtgtggctg taacttacgt gtactttacc    240
aacgagctga agcagatgca ggacaagtac tccaaaagtg gcattgcttg tttcttaaaa    300
gaagatgaca gttattggga ccccaatgac gaagagagta tgaacagccc tgctggcaa    360 gtcaagtggc aactccgtca gctcgttaga aagactccaa gaatgaaaag gctctgggcc    420
gcaaaataaa ctcctgggaa tcatcaagga gtgggcattc attcctgagc aacttgcact    480
tgaggaatgg tgaactggtc atccatgaaa aaggttttta ctacatctat tcccaaacat    540
actttcgatt tcaggaggaa ataaagaaa acacaaagaa cgacaaacaa atggtccaat    600
atatttacaa atacacaagt tatcctgacc ctatattgtt gatgaaaagt gctagaaata    660
gttgttggtc taaagatgca gaatatggac tctattccat ctatcaaggg ggaatatttg    720
agcttaagga aaatgacaga attttttgttt ctgtaacaaa tgagcacttg atagacatgg    780
accatgaagc cagttttttt ggggcctttt tagttggcta actgacctgg aaagaaaaag    840
caataacctc aaagtgacta ttcagttttc aggatgatac actatgaaga tgtttcaaaa    900
aatctgacca aaacaaacaa acagaaaaca gaaaacaaaa aaacctctat gcaatctgag    960
tagagcagcc acaaccaaaa aattctacaa cacacactgt tctgaaagtg actcacttat   1020
cccaagagaa tgaaattgct gaaagatctt tcaggactct acctcatatc agtttgctag   1080
cagaaatcta gaagactgtc agcttccaaa cattaatgca atggttaaca tcttctgtct   1140
ttataatcta ctccttgtaa agactgtaga agaaagagca acaatccatc tctcaagtag   1200
tgtatcacag tagtagcctc caggtttcct taagggacaa catccttaag tcaaaagaga   1260
gaagaggcac cactaaaaga tcgcagtttg cctggtgcag tggctcacac ctgtaatccc   1320
```

```
aacattttgg gaacccaagg tgggtagatc acgagatcaa gagatcaaga ccatagtgac    1380
caacatagtg aaaccccatc tctactgaaa gtacaaaaat tagctgggtg tgttggcaca    1440
tgcctgtagt cccagctact tgagaggctg aggcaagaga attgtttgaa cccgggaggc    1500
agaggttgca gtgtggtgag atcatgccac tacactccag cctggcgaca gagcgagact    1560
tggtttcaaa aaaaaaaaa aaaaaaactt cagtaagtac gtgttatttt tttcaataaa    1620
attctattac agtatgtcat gtttgctgta gtgctcatat ttattgttgt ttttgtttta    1680
gtactcactt gtttcataat atcaagatta ctaaaaatgg gggaaaagac ttctaatctt    1740
tttttcataa tatctttgac acatattaca gaagaaataa atttcttact tttaatttaa    1800
tatga                                                                1805

<210> SEQ ID NO 3
<211> LENGTH: 1334
<212> TYPE: DNA
<213> ORGANISM: homo sapiens

<400> SEQUENCE: 3
atttcctcac tgactataaa agaatagaga aggaagggct tcagtgaccg gctgcctggc     60
tgacttacag cagtcagact ctgacaggat catggctatg atggaggtcc aggggggacc    120
cagcctggga cagacctgcg tgctgatcgt gatcttcaca gtgctcctgc agtctctctg    180
tgtggctgta acttacgtgt actttaccaa cgagctgaag cagtttgcag aaaatgattg    240
ccagagacta atgtctgggc agcagacagg gtcattgctg ccatcttgaa gtctaccttg    300
ctgagtctac cctgctgacc tcaagcccca tcaaggactg gttgaccctg gcctagacaa    360
ccaccgtgtt tgtaacagca ccaagagcag tcaccatgga aatccacttt tcagaaccaa    420
gggcttctgg agctgaagaa caggcaccca gtgcaagagc tttcttttca gaggcacgca    480
aatgaaaata tccccacac gctaccttct gcccccaatg cccaagtgtg ttagttaga    540 gaatatagcc tcagcctatg atatgctgca ggaaactcat attttgaagt ggaaaggatg    600
ggaggaggcg ggggagacgt atcgtattaa ttatcattct tggaataacc acagcacctc    660
acgtcaaccc gccatgtgtc tagtcaccag cattggccaa gttctatagg agaaactacc    720
aaaattcatg atgcaagaaa catgtgaggg tggagagagt gactggggct tcctctctgg    780
atttctattg ttcagaaatc aatatttatg cataaaaagg tctagaaaga gaaacaccaa    840
aatgacaatg tgatctctag atggtatgat tatgggtact tttttccttt tttatttttc    900 tatatttttac aaattttcta cagggaatgt tataaaaata tccatgctat ccatgtataa    960
ttttcataca gatttaaaga acacagcatt tttatatagt cttatgagaa acaaccata    1020 ctcaaaatta tgcacacaca cagtctgatc tcacccctgt aaacaagaga tatcatccaa    1080
aggttaagta ggaggtgaga atatagctgc tattagtggt tgttttgttt tgttttttgtg   1140 atttacttat ttagtttttg gagggttttt tttttctttt agaaaagtgt tctttacttt    1200
tccatgcttc cctgcttgcc tgtgtatcct gaatgtatcc aggctttata aactcctggg    1260
taataatgta gctacattaa cttgttaacc tcccatccac ttatacccag gaccttactc    1320
aattttccag gttc                                                      1334

<210> SEQ ID NO 4
<211> LENGTH: 281
<212> TYPE: PRT
<213> ORGANISM: homo sapiens
```

<400> SEQUENCE: 4

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280
```

<210> SEQ ID NO 5
<211> LENGTH: 101
<212> TYPE: PRT
<213> ORGANISM: homo sapiens

<400> SEQUENCE: 5

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80
```

```
Lys Trp Gln Leu Arg Gln Leu Val Arg Lys Thr Pro Arg Met Lys Arg
                85                  90                  95

Leu Trp Ala Ala Lys
            100

<210> SEQ ID NO 6
<211> LENGTH: 65
<212> TYPE: PRT
<213> ORGANISM: homo sapiens

<400> SEQUENCE: 6

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Phe Ala Glu Asn
            35                  40                  45

Asp Cys Gln Arg Leu Met Ser Gly Gln Gln Thr Gly Ser Leu Leu Pro
        50                  55                  60

Ser
65

<210> SEQ ID NO 7
<211> LENGTH: 223
<212> TYPE: PRT
<213> ORGANISM: homo sapiens

<400> SEQUENCE: 7

Gln Asp His Gly Tyr Asp Gly Pro Gly Thr Gln Pro Gly Thr
1               5                   10                  15

Asp Leu Arg Ala Asp Arg Asp Leu His Ser Ala Pro Val Ser Leu
                20                  25                  30

Cys Gly Cys Asn Leu Arg Val Leu Tyr Gln Arg Ala Glu Ala Glu Lys
            35                  40                  45

Gln Gln Asn Ile Ser Pro Leu Val Arg Glu Arg Gly Pro Gln Arg Val
        50                  55                  60

Ala Ala His Ile Thr Gly Thr Arg Gly Arg Ser Asn Thr Leu Ser Ser
65                  70                  75                  80

Pro Asn Ser Lys Asn Glu Lys Ala Leu Gly Arg Lys Ile Asn Ser Trp
                85                  90                  95

Glu Ser Ser Arg Ser Gly His Ser Phe Leu Ser Asn Leu His Leu Arg
            100                 105                 110

Asn Gly Glu Leu Val Ile His Glu Lys Gly Phe Tyr Tyr Ile Tyr Ser
        115                 120                 125

Gln Thr Tyr Phe Arg Phe Gln Glu Glu Ile Lys Glu Asn Thr Lys Asn
    130                 135                 140

Asp Lys Gln Met Val Gln Tyr Ile Tyr Lys Tyr Thr Ser Tyr Pro Asp
145                 150                 155                 160

Pro Ile Leu Leu Met Lys Ser Ala Arg Asn Ser Cys Trp Ser Lys Asp
                165                 170                 175

Ala Glu Tyr Gly Leu Tyr Ser Ile Tyr Gln Gly Gly Ile Phe Glu Leu
            180                 185                 190

Lys Glu Asn Asp Arg Ile Phe Val Ser Val Thr Asn Glu His Leu Ile
        195                 200                 205

Asp Met Asp His Glu Ala Ser Phe Phe Gly Ala Phe Leu Val Gly
    210                 215                 220
```

<210> SEQ ID NO 8
<211> LENGTH: 178
<212> TYPE: PRT
<213> ORGANISM: homo sapiens

<400> SEQUENCE: 8

Lys Glu Lys Gln Gln Asn Ile Ser Pro Leu Val Arg Glu Arg Gly Pro
1               5                   10                  15

Gln Arg Val Ala Ala His Ile Thr Gly Thr Arg Gly Arg Ser Asn Thr
            20                  25                  30

Leu Ser Ser Pro Asn Ser Lys Asn Glu Lys Ala Leu Gly Arg Lys Ile
        35                  40                  45

Asn Ser Trp Glu Ser Ser Arg Ser Gly His Ser Phe Leu Ser Asn Leu
    50                  55                  60

His Leu Arg Asn Gly Glu Leu Val Ile His Glu Lys Gly Phe Tyr Tyr
65                  70                  75                  80

Ile Tyr Ser Gln Thr Tyr Phe Arg Phe Gln Glu Glu Ile Lys Glu Asn
                85                  90                  95

Thr Lys Asn Asp Lys Gln Met Val Gln Tyr Ile Tyr Lys Tyr Thr Ser
            100                 105                 110

Tyr Pro Asp Pro Ile Leu Leu Met Lys Ser Ala Arg Asn Ser Cys Trp
        115                 120                 125

Ser Lys Asp Ala Glu Tyr Gly Leu Tyr Ser Ile Tyr Gln Gly Gly Ile
    130                 135                 140

Phe Glu Leu Lys Glu Asn Asp Arg Ile Phe Val Ser Val Thr Asn Glu
145                 150                 155                 160

His Leu Ile Asp Met Asp His Glu Ala Ser Phe Phe Gly Ala Phe Leu
                165                 170                 175

Val Gly

<210> SEQ ID NO 9
<211> LENGTH: 2301
<212> TYPE: DNA
<213> ORGANISM: homo sapiens

<400> SEQUENCE: 9
aaggcaagag atctaggact tctagccccct gaactttcag ccgaatacat ctttttccaaa     60 ggagtgaatt caggcccttg tatcactggc agcaggacgt gaccatggag aagctgttgt    120
gtttcttggt cttgaccagc ctctctcatg cttttggcca gacaggtaag ggccaccccca   180 ggctatggga gagatttgat ctgaggtatg ggggtgggggt ctaagactgc atgaacagtc    240 tcaaaaaaaaa aaaaaaaaga ctgtatgaac agaacagtgg agcatccttc atggtgtgtg   300
tgtgtgtgtg tgtgtgtgtg tgtgtgtgtg tggtgtgtaa ctggagaagg ggtcagtctg    360
tttctcaatc ttaaattcta tacgtaagtg aggggataga tctgtgtgat ctgagaaacc    420
tctcacattt gcttgtttttt ctggctcaca gacatgtcga ggaaggcttt tgtgtttccc    480
aaagagtcgg atacttccta tgtatccctc aaagcaccgt taacgaagcc tctcaaagcc    540
ttcactgtgt gcctccactt ctacacggaa ctgtcctcga cccgtgggta cagtattttc    600
tcgtatgcca ccaagagaca agacaatgag attctctatat tttggtctaa ggatatagga    660
tacagtttta cagtgggtgg gtctgaaata ttattcgagg ttcctgaagt cacagtagct    720
ccagtacaca tttgtacaag ctgggagtcc gcctcaggga tcgtgagagtt ctgggtagat    780 gggaagccca gggtgaggaa gagtctgaag aagggataca ctgtggggggc agaagcaagc    840

| | |
|---|---|
| atcatcttgg ggcaggagca ggattccttc ggtgggaact ttgaaggaag ccagtccctg | 900 |
| gtgggagaca ttggaaatgt gaacatgtgg gactttgtgc tgtcaccaga tgagattaac | 960 |
| accatctatc ttggcgggcc cttcagtcct aatgtcctga actggcgggc actgaagtat | 1020 |
| gaagtgcaag gcgaagtgtt caccaaaccc cagctgtggc cctgaggccc agctgtgggt | 1080 |
| cctgaaggta cctcccggtt ttttacaccg catgggcccc acgtctctgt ctctggtacc | 1140 |
| tcccgctttt ttacactgca tggttccac gtctctgtct ctgggccttt gttccctat | 1200 |
| atgcattgca ggcctgctcc accctcctca gcgcctgaga atggaggtaa agtgtctggt | 1260 |
| ctgggagctc gttaactatg ctgggaaacg gtccaaaaga atcagaattt gaggtgtttt | 1320 |
| gttttcattt ttatttcaag ttggacagat cttggagata atttcttacc tcacatagat | 1380 |
| gagaaaacta acacccagaa aggagaaatg atgttataaa aaactcataa ggcaagagct | 1440 |
| gagaaggaag cgctgatctt ctatttaatt ccccacccat gacccccaga aagcaggagg | 1500 |
| gcattgccca cattcacagg gctcttcagt ctcagaatca ggacactggc caggtgtctg | 1560 |
| gtttgggtcc agagtgctca tcatcatgtc atagaactgc tgggcccagg tctcctgaaa | 1620 |
| tgggaagccc agcaatacca cgcagtccct ccactttctc aaagcacact ggaaaggcca | 1680 |
| ttagaattgc cccagcagag cagatctgct ttttttccag agcaaaatga agcactaggt | 1740 |
| ataaatatgt tgttactgcc aagaacttaa atgactggtt tttgtttgct tgcagtgctt | 1800 |
| tcttaatttt atggctcttc tgggaaactc ctccccttt ccacacgaac cttgtggggc | 1860 |
| tgtgaattct ttcttcatcc ccgcattccc aatatatccca ggccacaaga gtggacgtga | 1920 |
| accacagggt gtcctgtcag aggagcccat ctcccatctc cccagctccc tatctggagg | 1980 |
| atagttggat agttacgtgt tcctagcagg accaactaca gtcttcccaa ggattgagtt | 2040 |
| atggactttg ggagtgagac atcttcttgc tgctggattt ccaagctgag aggacgtgaa | 2100 |
| cctgggacca ccagtagcca tcttgtttgc cacatggaga gagactgtga ggacagaagc | 2160 |
| caaactggaa gtggaggagc caagggattg acaaacaaca gagccttgac cacgtggagt | 2220 |
| ctctgaatca gccttgtctg gaaccagatc tacacctgga ctgcccaggt ctataagcca | 2280 |
| ataaagcccc tgtttacttg a | 2301 |

<210> SEQ ID NO 10
<211> LENGTH: 2301
<212> TYPE: DNA
<213> ORGANISM: homo sapiens

<400> SEQUENCE: 10

| | |
|---|---|
| aggaattgaa ctcagctctg ccccaagcgg acctaataga catctacaga actctccacc | 60 |
| ccaaatcaac agaatataca ttttttttcag caccacacca cacctattcc aaaattgatc | 120 |
| acatagttgg cagtaaagct ctcctcagca aatgtaaagg aacagaaatt ataacaaact | 180 |
| atctctcaga ccacagtgca atcaaattag aactcagaat taagaatctc actcaaaacc | 240 |
| gcacaactac atggaaactg aacaacctgc ttctgaatga ctactgggta cataatgaaa | 300 |
| tgaaggcaga aataaagatg ttctttgaaa tgaacaagaa caaacacaca acataccaga | 360 |
| atctctgggg cgcattcaaa gcagtgtgta gagggaaatt tatagcacta aatgcccaca | 420 |
| agagaaagca ggaaacatcc aaaattgaca tcctaacatc acagttaaaa gaactagaaa | 480 |
| agcaagagca aacacattca aaagctagca gaaggcaaga gataactaaa atcagagcag | 540 |
| aactgaagga aatagagaca caaaaaccct tcaaaaaatt aatgaatcca ggagctggtt | 600 |
| ttttgaaagg atcaacaaaa tagatagacc actagcaaga ctaataaaga aaaaagaga | 660 |

```
gaagaatcaa atagacacaa taaaaaaatg ataaaggggga tatcaccacc gatcccacgg      720
aaatacaaac taccatcaga gaatactaca aacacctcta cgcaaataaa ctagaaaatc      780
aagaagaaat ggataaattc ctcgacacat acactctccc aagactaaac caggaagaag      840
ttgaatctct gaatagacca ataacaggat atgaaattgt ggcaataatc aataccttac      900
caacaaaaaa gagtccagga ccagatggat tcacagccga attctaccag aggtacaagg      960
aggaactggt accattcctt ctgaaactat tccaatcaat agaaaagag ggaatcctcc      1020 ctaactcatt ttatgaggcc agcatcattc tgataccaaa gccgggcaga gacacaacca     1080
aaaaagagaa ttttagacca atcaatatcc ttgatgaaca ttgatgcaaa aatcctcaat     1140
aaaatactgc caaaccaaat ccagcagcac atcaaaaagc ttatccacca tgatcaagtg     1200
ggcttcatcc ctgggatgca aggctggttc aatatacgca aatcaataaa tgtaatccag     1260
catataaaca gagccaaaga caaaaccac atgattatct caatagatgc agaaaagacc      1320
tttgacaaaa ttcaacaacc cttcatgctc aaaactctca ataaattagg tattgatggg     1380
acgtatttca aaataataag agctatctat gacaaaccca cagccaatat catactgaat     1440
gggcaaaaac tggaagtatt cactttgaaa actggcacaa gacagggatg ccctctctca     1500
ccactcctat tcaacatagt gttggaagtt ctggccaggg caattaggca ggagaaggaa     1560
ataaagggta ttcaattagg aaaagaggaa gtcaaattgt ccctgtttgc agacgacatg     1620
attgtatatc tagaaaaccc cattgtctca gcccaaaatc tccttaagca gataagcaac     1680
ttcagcaaaa tctcaggata caaaatcaat gtacaaaaat cacaagcatt cttatacacc     1740
aacaacagac aaacagagag ccaaatcatg agtgaaatcc cattcacaat tgctttaaag     1800
agaataaaat acctaggaat ccaacttaca agggatgtga aggacctctt caaggagaac     1860
tacaaaccac tgctcaatga aataaaagag gataaaaaca aatggaagaa cattccatgc     1920
tcatgggtag gaagaatcaa tatcatgaaa atggccatac tgcccaaggt aatttacaga     1980
ttcaatgcca tccccatcaa gctaccaatg ccttcttca cagaattgga aaaaactatt      2040
tttagttcat atggaaccaa aaagagccc gcattgccaa gtcaatccta agccaaaaga     2100
acaaagctgg aggcatcaca ctacctgact tcaaactata ctacaaggct acagtaacca     2160
aaacagcatg gtactggaac caaaacagag atatagatca atggaacaga acagagccct     2220
caaaattaat gccacatatc tacaactatc tgatctttga caaacctgag aaaaaccagc     2280
aatggggaaa ggattcccca t                                               2301
```

<210> SEQ ID NO 11
<211> LENGTH: 2024
<212> TYPE: DNA
<213> ORGANISM: homo sapiens

<400> SEQUENCE: 11

```
aaggcaagag atctaggact tctagcccct gaactttcag ccgaatacat cttttccaaa       60
ggagtgaatt caggcccttg tatcactggc agcaggacgt gaccatggag aagctgttgt      120
gtttcttggt cttgaccagc ctctctcatg cttttggcca gacagacatg tcgaggaagg      180
cttttgtgtt tcccaaagag tcggatactt ccctatgtatc cctcaaagca ccgttaacga     240
agcctctcaa agccttcact gtgtgcctcc acttctacac ggaactgtcc tcgacccgtg      300
ggtacagtat tttctcgtat gccaccaaga gacaagacaa tgagattctc atattttggt     360
ctaaggatat aggatacagt tttacagtgg gtgggtctga aatattattc gaggttcctg     420
```

```
aagtcacagt agctccagta cacatttgta caagctggga gtccgcctca gggatcgtgg    480
agttctgggt agatgggaag cccagggtga ggaagagtct gaagaaggga tacactgtgg    540
gggcagaagc aagcatcatc ttggggcagg agcaggattc cttcggtggg aactttgaag    600
gaagccagtc cctggtggga gacattggaa atgtgaacat gtgggacttt gtgctgtcac    660
cagatgagat taacaccatc tatcttggcg ggcccttcag tcctaatgtc ctgaactggc    720
gggcactgaa gtatgaagtg caaggcgaag tgttcaccaa accccagctg tggccctgag    780
gcccagctgt gggtcctgaa ggtacctccc ggttttttac accgcatggg ccccacgtct    840
ctgtctctgg tacctcccgc ttttttacac tgcatggttc ccacgtctct gtctctgggc    900
ctttgttccc ctatatgcat tgcaggcctg ctccaccctc ctcagcgcct gagaatggag    960
gtaaagtgtc tggtctggga gctcgttaac tatgctggga acggtccaa aagaatcaga   1020 atttgaggtg ttttgttttc atttttattt caagttggac agatcttgga gataatttct   1080
tacctcacat agatgagaaa actaacaccc agaaaggaga atgatgtta taaaaaactc   1140 ataaggcaag agctgagaag gaagcgctga tcttctattt aattccccac ccatgacccc   1200
cagaaagcag gagggcattg cccacattca cagggctctt cagtctcaga atcaggacac   1260
tggccaggtg tctggtttgg gtccagagtg ctcatcatca tgtcatagaa ctgctgggcc   1320
caggtctcct gaaatgggaa gcccagcaat accacgcagt ccctccactt tctcaaagca   1380
cactggaaag gccattagaa ttgccccagc agagcagatc tgcttttttt ccagagcaaa   1440
atgaagcact aggtataaat atgttgttac tgccaagaac ttaaatgact ggtttttgtt   1500
tgcttgcagt gctttcttaa ttttatggct cttctgggaa actcctcccc ttttccacac   1560
gaaccttgtg gggctgtgaa ttctttcttc atcccgcat tcccaatata cccaggccac   1620
aagagtggac gtgaaccaca gggtgtcctg tcagaggagc ccatctccca tctcccagc   1680 tccctatctg gaggatagtt ggatagttac gtgttcctag caggaccaac tacagtcttc   1740
ccaaggattg agttatggac tttgggagtg agacatcttc ttgctgctgg atttccaagc   1800
tgagaggacg tgaacctggg accaccagta gccatcttgt ttgccacatg gagagagact   1860
gtgaggacag aagccaaact ggaagtggag gagccaaggg attgacaaac aacagagcct   1920
tgaccacgtg gagtctctga atcagccttg tctggaacca gatctacacc tggactgccc   1980
aggtctataa gccaataaag cccctgttta cttgaaaaaa aaaa                    2024
```

<210> SEQ ID NO 12
<211> LENGTH: 2421
<212> TYPE: DNA
<213> ORGANISM: homo sapiens

<400> SEQUENCE: 12

```
caccctcatg agccccgggt acgtttaact attgagggcc aggaaattgc cttcctcctg     60
gacactggcg cagccttctc agggttaatc tcctgtcctg gatgactgtc ttcaaggtcc    120
gttaccaccc gaggaatcct gggacagcct ataaccaggt atttctccca catcctcagt    180
tgtaattgag agactttaat ctttttcacat gccttttttg ttattcctga aagtcccaca    240
cccttattaa ggagggatat attagccaag gctggagcta ttatctacat gaatatgggg    300
aaaaagttac ccatttgctg tccccctactt gaggagggaa tcaaccctga agtctgggca    360
ttggaaggac aatttggaag ggcaaaaaat gcctgcccag tccaaatcag gttaaaagat    420
cccaccactt ttccgtatca aaggcaatat cccttaaggc ctgaagctca taaggatta    480 tagaatattg ttaaacattt aaaagctcaa ggcttagtga ggaaatgcag cagtccctgc    540
```

```
aacaccccag ttctaggagt acaaaaacca acagtcagt ggagactagt gcaagatctt    600
agactcatta atgaggcagt aattcctcta tatccagttg tacccaaccc ctataccctg    660
ctctctcaaa taccagggga agcagaatgg ttcacggttc tggacctcaa ggatgccttc    720
ttctttattc ccctgcactc tgactccag tttctctttg cttttgagga tcccacagac    780
cacacgtccc aacttacaca gatggtcttg ccccaagggt ttagggatag ccctcatctg    840
tttggtcagg cactggccca agatctatag gccacttctc aagtccaggc actctggtcc    900
ttcaatatgt ggatgattta cttttggcta ccagtttgga agcctcgtgc cagcaggcta    960
ctctggatct cttgaacttt ctggctaatc aagggtacaa ggtgtctagg tcgaaggccc   1020
agctttgcct acagcaggtt aaatatctaa gcctaatctt agccaaaggg accagggccc   1080
tcagcaagga atgaatacag cctatactgg cttatcctca ccctaagaca ttaaaacagt   1140
tgcggggatt ccttggaatt actggctttt gctgactatg atctccaga tacagcgaga   1200 cagccaggcc cctctatact ctaatcaagg aaacccagag ggcaaatact catctagtcg   1260
aaagggaacc agaggcagaa acagccttca aaagcttaaa gcaggctcta gtacaagctc   1320
cagctttaag ccttcccaca ggacagaact tctctttata catcacagag agagccaaga   1380
tagctcttgg agtccttaga ctcgtgggac aaccccacaa ccagtggcat acctaagtaa   1440
ggaaattgat gtagtagcaa aaggctggcc tcactgttta agggtagttg cagcagcggc   1500
cgtcttagcg tcagaggcta tcagaataat acaaggaaag gatctcactg tctggactac   1560
tcatgatgta aatggcatac taggtgccaa aggaagttta tggctatcag acaaccgcct   1620
cttagatgcc aggcactact ccttgaggga ctggtgctta aaatatgcac gtgcgtggcc   1680
ctcaaccctg ccacttttct cccagaggat ggggaaccaa ttgagcatga ctgccaacaa   1740
attatagtcc agacttatgc cgcccgagat gatctcttag aagtcccctt aactaatcct   1800
gaccttaacc tatataccga cggaagttca tttgtggaga atgggatacg aagggcaggt   1860
tacgccatag tgatgtaacc acacttgaaa gcaagcctct tccccagggg accagtgccc   1920
agttagcaga actagtggca cttacccgag ccttagaact gggaaaggga aaagaataa    1980 atgtgtatac agataacaag tatgcttatc taatcctaca tgcccatgct gcaatatgga   2040
aagaatggga gttcctaacc tctgggaacc cccgctggat gccacaggga agttatggag   2100
ttattgcaca tggtgcagga acccaaagag gtgggagtct acactacca aggccatcaa   2160 aatgggaagg agaggggaga acagcagcat aagcggctgg cagaggtagg gaaagaccag   2220
caagaaggaa agagagaaag agaaagtcag agaaagagac agagagagga agagacagag   2280
agacagaacg ttaaagaggg tgtcagaaac agagacaaac aaaaggagtc agaaagaagg   2340
acagacacag aaagtcaaag agagagttaa aagagagga agagacaaag aagtcgaaga   2400
gagaaagaga gagatggaag t                                              2421

<210> SEQ ID NO 13
<211> LENGTH: 2421
<212> TYPE: DNA
<213> ORGANISM: homo sapiens

<400> SEQUENCE: 13
ctttgcagat aaatatggca cactagcccc acgttttctg agacattcct caattgctta     60
gacatattct gagcctacag cagaggaacc tccagtctca gcaccatgaa tcaaactgcc    120
attctgattt gctgccttat ctttctgact ctaagtggca ttcaaggtaa ggaacatcaa    180
```

| | |
|---|---|
| aggatactta atttgtaaaa tgagaaatag gaataggtat aaattctaaa aatacagaaa | 240 |
| taatgtatt gtaaaagttt cactgcatgc ttataaataa gagggaaata aatagagatt | 300 |
| ccctcagatc ataaaactta tatgaattga agtgagagaa acaaatagaa taagagaaag | 360 |
| agaaggaaaa agggaaggag gacagaagag atggggaaga gggaggatag agagagaaaa | 420 |
| tgtgagggaa tgcggacaga gatgagatac agatacttcc ttacctaact aagctcaatg | 480 |
| aaccacatga actgtgctta agggtttgac tttataatca acaagctgca attcttttct | 540 |
| tccagataat caactcttta atcatttaca gttgtgttat gatgtgatcc attcctcctc | 600 |
| agattaagtg actatttgct gatatgggga tataggttct gctaaatacc accagtctac | 660 |
| attaaatgcc taaaatgaac actgtgctaa ccttctctgc tgttcctctt ttcctacagg | 720 |
| agtacctctc tctagaactg tacgctgtac ctgcatcagc attagtaatc aacctgttaa | 780 |
| tccaaggtct ttagaaaaac ttgaaattat tcctgcaagc caattttgtc cacgtgttga | 840 |
| gatcatgtga gtgaaatccc atctgattat cacttccctg ttgtaatta tatactgtat | 900 |
| taaatatgta atgataataa aaaaagatca gtaaggggtt tgtgatgatt ctaaaactaa | 960 |
| tgtacagcaa acaaaaacat gcagagtgaa acttaaatgt ctgacttcag aactgcgtat | 1020 |
| gccatctgtt ttattgaccc aacacagttt taaatatttt catccctatt tatttctaca | 1080 |
| gtgctacaat gaaaaagaag ggtgagaaga gatgtctgaa tccagaatcg aaggccatca | 1140 |
| agaatttact gaaagcagtt agcaaggaaa ggtaggtttg ctgttgcctg cagaagaatt | 1200 |
| gctctttagg aaacggcaat cttgggagtc agaaatactt gcattgtggt ttgctgtgca | 1260 |
| atcgctggtt taaagtatg ttaccaccac gccctcccct acctccattt atttaaatgc | 1320 |
| tgaggcacca tcttgtgtga taagtatcag aagttaccct gattaccagt caaccttgaa | 1380 |
| gtacagctat aactatctaa gcaaaactga caacattttc cccaagtctt tcatggttga | 1440 |
| aaaaagcaac ccctataatc cataatgaat gcatagcagc aggaaagctc agttatctat | 1500 |
| tctatgaact cggtactttc caaacacaac ccaatctgaa gccagagtca gactatcaca | 1560 |
| cttttatatc cccttctct tcttacaggt ctaaaagatc tccttaaaac cagaggggag | 1620 |
| caaaatcgat gcagtgcttc caaggatgga ccacacagag gctgcctctc ccatcacttc | 1680 |
| cctacatgga gtatatgtca agccataatt gttcttagtt tgcagttaca ctaaaaggtg | 1740 |
| accaatgatg gtcaccaaat cagctgctac tactcctgta ggaaggttaa tgttcatcat | 1800 |
| cctaagctat tcagtaataa ctctaccctg gcactataat gtaagctcta ctgaggtgct | 1860 |
| atgttcttag tggatgttct gaccctgctt caaatatttc cctcaccttt cccatcttcc | 1920 |
| aagggtacta aggaatcttt ctgctttggg gtttatcaga attctcagaa tctcaaataa | 1980 |
| ctaaaaggta tgcaatcaaa tctgcttttt aaagaatgct cttactttca tggacttcca | 2040 |
| ctgccatcct cccaaggggc ccaaattctt tcagtggcta cctacataca attccaaaca | 2100 |
| catacaggaa ggtagaaaata tctgaaaatg tatgtgtaag tattcttatt taatgaaga | 2160 |
| ctgtacaaag tagaagtctt agatgtatat atttcctata ttgttttcag tgtacatgga | 2220 |
| ataacatgta attaagtact atgtatcaat gagtaacagg aaaatttaa aaatacagat | 2280 |
| agatatatgc tctgcatgtt acataagata aatgtgctga atggttttca aaataaaaat | 2340 |
| gaggtactct cctggaaata ttaagaaaga ctatctaaat gttgaaagat caaaaggtta | 2400 |
| ataaagtaat tataactaag a | 2421 |

<210> SEQ ID NO 14
<211> LENGTH: 2421

<212> TYPE: DNA
<213> ORGANISM: homo sapiens

<400> SEQUENCE: 14

```
agatgacttt tttctattta tatttaataa gatgatgaac ccttcttgca ttcccgaaat    60
aaacctcaac tgttacagtg ttttattctt ttaatatgta cgaagtacat gttaagcaag   120
ttatttccta agcagcccca caaactgggc actactacca tcctgctctg cccctccctc   180
actctacttc agccacttca gccacaatgg cctctcctca ctgcccctct gatgcaccaa   240
gcttgttctc acctcaggaa tgtgcaacac ctgccagact tgctgttccc cggagcctcc   300
atccccagat atcctcatat atcatcctcc tcttcatttg tgtctctgct tacatatgac   360
ctatttacag aagcctttcc tgtctacccc ccatgaaata gaaatcgcat tccaatcttg   420
tctctacccc aatgctgttt cattttgtct gtagcaattg tcatcatctc atatatattc   480
acatgtggaa aatacacaaa atgtttaact tcttttaatt tacattccat ttccccatga   540
attgaagctc catgacagcg gagatttttc tctgctttcc ctgttgctca cttcccagca   600
ccaagagcag gcctggcaca tgggaagtac ttactattta ttgaatggat gaatgaacaa   660
atgaatgaat ggatacttat tttacacata agaaaactga agcttataga aattaagtaa   720
ctaaaatcac acagaagcac agctgaaact aaaacctacg tctaactttc aattcctgac   780
ccttaaccat taaaacaaat gacaggtgac tttaggccac tgaaaatgct catataatct   840
tatgaattct aaagcacaag ttaatcacac cattgattga aagtctgagg aatactgtat   900
agacaagccc ctgtacaagg taagcaaaag aatcagagga tggcctccaa agaattccct   960
ggacattatg ggaattacat tgttagcctt cctactgata cccataagcc tcacagcaag  1020
catcatgaag ctgtgacctt catctgcaca tgcccttgta tacccaaaag ataaaactgg  1080
atgcttcagg gccgaatggc caataaacac gtgtttatta ctggcatggg cagacacaca  1140
tactgaaagt accatttccc agcggactag ccatattatg atcagtacag acactaaaga  1200
tttagctttg aaaaaactat ttgctcttcc aaagctgaag aatcttctgt gatttcaaca  1260
ggcaagttac agtcaggtat tcttaatgtt cttttcctcc tctctcactg ggatactttc  1320
tttccttcag acaacgtcaa gcgaaaaaca aaatttcaca aatctccatt tctgacacta  1380
aacagtacag tatctttatt ttttttataa tttaatcaaa ccctgtattt tagaactgtg  1440
gggctgatcc aacattgcaa tgtgtcacat ttaattccat caatgtaaag cataatgagc  1500
aaagattaag gtagtgaggc ataactaaat gttttgaacc tgtgaatttc aaaagcaagg  1560
cccatttgtg ttatttttcta aatagtaaat aaaatcattt tccaacattt cactatcaaa  1620
ttacagtaat ttttccacca gtacacactt gaggaaagcc acaaaaagac ttttccaaca  1680
gttcattctg ttattgctca taccttcta aatacttctc ctcattggct tctattcaaa  1740
ggtaaatgga aagcagtaaa atttatggaa aatatattca actgcttaaa atacatcaac  1800
caaaaaaag attttagagc tgtattatga gttgtgaaat tgcattgcct tcacttacct  1860
ttcagtttca ctggtaggta acaaaactga cagactggtc aagttccaaa acatccccta  1920
tatagagcct gactcttcca tctcaaattc tcaccttggt caaggccaga gtaaacacct  1980
gtccttcaca tttttacaca acatcacttt gtatgctaca aatataagct ttcataccag  2040
ggaggaagca aattccagga cactggaaac atttctgctc tcttaaacca gtctgttgat  2100
tgttcccttg actttctcag ctgtcaggat agtgaaagga ggaaaactgc aaaactgtaa  2160
agtataacct gataagtttg cccctttaagc ttttcacaca gagagaggta aaataaaact  2220
```

```
caagtctaag gtttaaaatt gagctatgaa tattatattc tagcactaga caaaaatgtt      2280
gcaagatttt aataaaataa gattattaaa atcaattttt acatttcatg ggccaaggag      2340
agacatcaaa gaatgtttaa ctaacatttt aaagatacta tactttataa agttaagaag      2400
aaaaatgaca actgcaccag t                                                2421
```

<210> SEQ ID NO 15
<211> LENGTH: 1227
<212> TYPE: DNA
<213> ORGANISM: homo sapiens

<400> SEQUENCE: 15

```
ctttgcagat aaatatggca cactagcccc acgttttctg agacattcct caattgctta        60
gacatattct gagcctacag cagaggaacc tccagtctca gcaccatgaa tcaaactgcc       120
attctgattt gctgccttat ctttctgact ctaagtggca ttcaaggagt acctctctct       180
agaactgtac gctgtacctg catcagcatt agtaatcaac ctgttaatcc aaggtcttta       240
gaaaaacttg aaattattcc tgcaagccaa ttttgtccac gtgttgagat cattgctaca       300
atgaaaaaga agggtgagaa gagatgtctg aatccagaat cgaaggccat caagaattta       360
ctgaaagcag ttagcaagga aaggtctaaa agatctcctt aaaaccagag gggagcaaaa       420
tcgatgcagt gcttccaagg atggaccaca cagaggctgc ctctcccatc acttccctac       480
atggagtata tgtcaagcca taattgttct tagtttgcag ttacactaaa aggtgaccaa       540
tgatggtcac caaatcagct gctactactc ctgtaggaag gttaatgttc atcatcctaa       600
gctattcagt aataactcta ccctggcact ataatgtaag ctctactgag gtgctatgtt       660
cttagtggat gttctgaccc tgcttcaaat atttccctca cctttcccat cttccaaggg       720
tactaaggaa tctttctgct ttggggttta tcagaattct cagaatctca ataactaaa       780 aggtatgcaa tcaaatctgc tttttaaaga atgctcttta cttcatggac ttccactgcc       840
atcctcccaa ggggcccaaa ttctttcagt ggctacctac atacaattcc aaacacatac       900
aggaaggtag aaatatctga aaatgtatgt gtaagtattc ttatttaatg aaagactgta       960
caaagtagaa gtcttagatg tatatatttc ctatattgtt ttcagtgtac atggaataac      1020
atgtaattaa gtactatgta tcaatgagta acaggaaaat tttaaaaata cagatagata      1080
tatgctctgc atgttacata agataaaagt gctgaatggt tttcaaaata aaaatgaggt      1140
actctcctgg aaatattaag aaagactatc taaatgttga aagatcaaaa ggttaataaa      1200
gtaattataa ctaagaaaaa aaaaaaa                                          1227
```

<210> SEQ ID NO 16
<211> LENGTH: 98
<212> TYPE: PRT
<213> ORGANISM: homo sapiens

<400> SEQUENCE: 16

```
Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
```

| | 65 | | | 70 | | | 75 | | | 80 | |
|---|---|---|---|---|---|---|---|---|---|---|---|
Ala Ile Lys Asn Leu Leu Lys Ala Val Ser Lys Glu Arg Ser Lys Arg
                    85                  90                  95

Ser Pro

<210> SEQ ID NO 17
<211> LENGTH: 5687
<212> TYPE: DNA
<213> ORGANISM: homo sapiens

<400> SEQUENCE: 17

| | | | | | |
|---|---|---|---|---|---|
| ctctctggtt | gcccttaaca | ttttttcctt | catttcaact | ttggtgggtc | tgatgattat | 60 |
| gtgtcttggg | gttgctcttc | tcgaggagta | tcttagtagt | attctctgta | tttcctgaat | 120 |
| ttgaatgttg | gcctgtcttt | ctaggttggg | gaagttctcc | tggataatat | cctgaagagt | 180 |
| attttttcaac | ttggttctat | tctccttgtt | actttcaggt | acaccaatca | aacgtagatt | 240 |
| tggtcttgtc | acatagtccc | atatttcttg | gaggttttat | tcgttccttt | ttattctttt | 300 |
| ttctctagtt | ttgtcttctc | gctttatttc | actaagttga | tcttcaatct | ctgatatcct | 360 |
| tgcttctgct | tgattgattc | agctatcccc | cgctcgatat | tacaaaccat | gtcacgaggc | 420 |
| gtggacaccc | cccatgatat | ggggagtatt | atcacccccc | tcttcccca | ctggatatta | 480 |
| caaaccatgt | catagggagg | tggacatccc | ccacaatatg | aggagtaata | tcacccct | 540 |
| ttccccgcag | tggatattat | gaaccatgtc | acaggcggtt | aaacacccc | aacgatatgg | 600 |
| ggagtaatat | cacactcctc | tccccctgg | atattacgaa | ccatgtcatg | ggggtggac | 660 |
| acccttgca | atatggggag | taaaatcacc | ccctctccc | caactggat | attatgaacc | 720 |
| atgtcacagt | gggggaaaaa | tcctctgtga | tatgcagagt | aatatcaccc | cactctcacc | 780 |
| acctggatat | tacgaaccat | gtcacagggg | ggtggacacc | cccaagatg | ggggagtaat | 840 |
| atcacctcac | tctctgccac | cagatattac | aaactgtgtc | acaggggggt | gaacaacccc | 900 |
| cacaatatgg | ggagcactat | cacccccctc | ccccagggta | ttatgatcca | tgtcacaggg | 960 |
| gggtggatac | cacccactat | atggggagta | atatcacctt | tctctcccgc | cctggttttt | 1020 |
| atgaaccgtg | tcagggggg | gtggacaccc | cttgcgatat | ggggagtaat | atcaccccc | 1080 |
| tctccaccat | ctggatatta | cgaaccatgt | cacagggggg | tggacacccc | tgcgatatgg | 1140 |
| ggaggaatat | gcccctctcc | ccactggat | attacaaatc | atgtcacggg | ggacggacat | 1200 |
| cccccacaat | atgggagta | atatcaccac | actctcccct | gctggatatt | acgaaccata | 1260 |
| tcacaggcgg | ctggagacac | aaggcattaa | caatatttcg | agtaatatta | tctttccctt | 1320 |
| tgaacattat | gaacaatatg | acagaggggt | gtacacctcc | tgcgatattg | ggagtaatgt | 1380 |
| catcccctcc | cccactggat | attaggaacc | atattactgg | gggatgtatt | ccccttcta | 1440 |
| gattgggagg | aagatcatac | ttgccctccc | tgaatatttg | aaacaatatc | atagggttt | 1500 |
| gtacactttt | acgatattgg | gagtaatatc | atcctttctc | ccctggaaa | ttaggaacaa | 1560 |
| tatcacaggg | gtggtgtaca | cccctgcaat | atttagggta | atattattgt | cttctcccct | 1620 |
| cgatattagg | aacaatatta | caaggacggt | gtaaagtacc | tgccaaattg | ggaaaaatac | 1680 |
| tatcctctcc | ctcttgtata | ttagaaacaa | taacacaggg | gaatgtaca | cccactgcca | 1740 |
| tattgggagt | aatatcatac | tcgccccatc | ccccagatat | taggaacaat | atcacagcag | 1800 |
| gggtgtacac | ttttacgata | ttgggagtaa | tatcatactc | tctcccctg | gaaattagga | 1860 |
| ataatatcac | agagatggtg | tagaccctct | gcaatactta | ggataatatt | atcatctccc | 1920 |

```
ccctcgatat taggaacaat attacgggga gtgtaaatta cctgccaaat tggaggtaat    1980
cctctcctct ctctccctgt attttagaaa atataacaca caggaaatgt acaacactgc    2040
gatattcgga gtaatatctt cttctcccca cctggatatt aggaacaata acacggacgg    2100
ggcgtacacc cctcgcgata ttgaatgtaa tgtcatcctc tccctcccct tatattacga    2160
acaatatcac aggggggtgt acaaccctg caatattgga agtagtatca tccattctcc    2220
catgaatatt aggaacaata tcacaggggt agagtacacc ctctgcaatt cgggagtaa    2280
catcatcctc tcgttccctg gatattataa acaacaccac ggggggtgg gggtgtacac    2340
acccttcgat attgggagta atataatcct ttccctccct atatattaga agcaatatca    2400
caggggttgg tgtaaacttc ttgcgatatg gggattaata tcaccccct ctcctgccct    2460
ggatattatg aaccatatca cagggaggtg gacacactttt gcgatatggg gagtaatatc    2520
acgcccctct ccccccgat attacgaacc atatcacaag ggagtggacc ccccacga    2580
tatgggagt aatatcaccc ccctctcccg ccctggatat tacgaaccat atcacagggg    2640
gatggacacc ccccgcgatg cggggagtaa tgtcacccc ttctgccccc taggatatta    2700
cgaaccatat catggacacc ctccacgata ttggaaataa tatcatcctc tccccttgg    2760
atattaggaa caatatcaca ggggttgta cacctcctat gatattggaa gtaatatcat    2820
cctctccctc ctggatatta gcaacaatat cacagggagt gtgtacaacc ccagcgatat    2880
ttggagtaat atcaccctct caccccatgg atatgagaaa caatatcaca ggggaggtgt    2940
acatcccacg tgatattgtg tgtaatatca ttcttcccca acccctgcaa tattgtggtg    3000
taatataatt ctctcccttc ctggacatta tgaacaatat cactactagg tgatacatta    3060
ggagtaatgt atccatagga tattatgagg aatatcacag ggtgtacacc cactgtgata    3120
ttagaggtaa tatctcccta aaatattaag aagaatatct tacacccact gtgactttag    3180
aagtaatatc tccctaaaac gttacaaata acatcgcagg gtgtacactc acagtgatat    3240
taggagtaat atctccctag aatattacaa atacacatgg tgtaaaccca ctgtgacttt    3300
agaagaacta tctccctaaa ataatacaaa aatatcgcag tgtataccat aatatcccct    3360
agaatatcat aaataatatc acagggtgta cacccactgt gataatagga ataataccac    3420
cccaggatat tatgaataat gtcacaggct gtacacccac tatgacatta ggagtaatat    3480
ctccctagga cactatgaat aacatcacag attttacacc catggtgtgc acccactatg    3540
atattaggag taatatctgc acaggatata acaaataata gtacagggtg tacacatatg    3600
atatacaccc actgtgatat taggagaaat atatccctag gatattatga ataacctctc    3660
agagtacaca cacatggtat acaccctctg tggcattagg aacaataact ttctaaaaca    3720
ttacgaataa catcacagaa tgtacacaca tggtttacac ccactgtgac aggtgcaata    3780
tctcccttgg atattatgaa taacaacaaa ctatcactgt catattagga gtaatttctc    3840
cctagaatat tacaaataac atcacagggt gttcatttat ggtgcacacc cactgtgata    3900
ttaggagtaa tatctcccta ggatattact tttcatataa aagtgtgtac atccactgtg    3960
atattgggaa aaatatttct ctaggatatt atgaataata tcacagagcg tacacccact    4020
gtgatattag gagtaataat tccctgggtt attatgaata atatcacagg atgtacaacc    4080
actgtgatat taggagcaat atcttcctag gatattacaa ataatatcac agggtgtaca    4140
cccactgtga tattaaagta attttttaggt tattgtgaat aatatcacca agtgtacaaa    4200
catggtgtac actcactgtg atatcaggag taatatctca gtaaaatatt atgaataata    4260
tcacagggta tacacccact gtgatattag cagtagtatc tttgtaggat attacaaata    4320
```

```
atatcacagg gtgtatgccc actatgacat tagaagcaat atctccctag gatatcaaaa   4380
ataatatcac agggtgtaca acttctacat cccaggttct aagggattct cctgcttcag   4440
cctcctgagt ggctgggatt acagatgccc accaccacac ctggctaatt tcgtattttc   4500
agtagagatg gggtatcacc atgctggtca ggctggtctg gaacttctga cctcaggtga   4560
tccaccagcc tcggccttcc aaagtgctgg gaatacaggt gtgagccaac gtgcttggca   4620
gagagttata tattaaataa atctggaaac atagctccca tgtttgagtg tgcatttact   4680
tttatgaaga aattatgtca gaaaacctaa ggatgataat aaatatgaaa agtaactggc   4740
atgtaaaaag gtcttttgat taagaactat aaggttcgat ttcatttttta gataacgtga   4800 tcctagctct tgtatagtgc ttataaatat tctacatcaa aggaatttgt tgcacagtgt   4860
cagaataaaa taaagtgtat ttcactgctt cttaattttt aaattagact gagtttgttt   4920
tcctagagag agaagaacat ttttatttt ttctgaaaag agtaggccat atttttactga   4980 gatcttagat ttgttatata ttaggttttg gtcttctaac attctccagt ggattttctc   5040
taaagtaggt atgcacagaa agagttgaat agcaaaaaag taaatcatgt aataattctg   5100
agatttttgg gtttgtcaca actgagaaat attgctgagg gtgtatggtc ctcaagtgtg   5160
aaaatgttcc ttgtgaattg cttgtatccg aaatatacac acaacattaa gtcctggttt   5220 ttatcttta tttttccaa tcctttttc ttctcaaggt gtccaagtca cacagagcca   5280
cagaatctca caggtgtctc agaattcctc ctcctgggac tctcagagga tccagaactg   5340
cagccactcc ttgctgggct gttcctatcc atgtgcctgg tcacgatgct gggaacctg   5400 ctcatcatcc tggccgtcag ccctgactcc cacctccaca tccccatgta cttcttcctc   5460
tccaacctgt ccttgcctga cattggtttc accttggcca cggtccccaa gatgattgta   5520
gacatgcaat cacatagcag agtcatctcc catgcaggct gtctgacaca gatacctttc   5580
tttgtccttt ttgtatgtat agatgacatg ctcctgactg tgatggccta tgactgattt   5640
gtggccatct gtcaccccct gcactaccca gtcatcatga atcctca         5687
```

<210> SEQ ID NO 18
<211> LENGTH: 5687
<212> TYPE: DNA
<213> ORGANISM: homo sapiens

<400> SEQUENCE: 18

```
attgaatttt atctcagagc ccacatgaag caggatcaaa gtcagtacac atgaaaacta     60
gagcccaaag actataaagc atgaaataag gatttaagct aaccctatct tgtaaggggt    120
ttgtaaagcc cagcttgcat ctgagctaca ctagcaccag gacagccact cagtaatggg    180
gtttctcaag gttattgctt tcattcagt tgaaatgaga gtcatttctt acccttatgc    240
cctgtgagat ttcactggag gttgttcact gaaacatttt catatcattg catcaaccct    300
cttgaactca ctgtgcctgc ccccagttca gtctgtgact cacaagtacc ctgcagcaaa    360
agaaatccaa tagagggcaa atccctcacc ttaccttcct ttctaagacc tttgatgttc    420
tcatgtgtca tttcataatt gggattgtca attagtcgcc tcatctctgg tcctcacttt    480
cctctctccc agccaaactc aaccttcagc ccacacaatg gaattcaaca aaatgaggta    540
acagttttct gtgtgagtca ctctgggcaa ctctgttcac agagcactgt gaggtgagca    600
gccagaaccc aggcaagtgt ttcagccatc caagaactgg caggcagccc aagagacact    660
ctcacctgat gacagactag caggatgagt cctggaggaa atggttccca acagctgcag    720
```

```
aaggagtctc ttggctcatg cacagcaatg ctcttctcaa ttaaaaacgt tgtcattatt    780
gacactgcag tgtaaaatcc ttttacactg tgctcacatt tctacaggcc ttcacctgct    840
ctgcccatta agacaagac ccttccatga gatgatgaca tctctaagtt actgttccac     900
ccaaacagtc ctatataatg aagagaaaaa ttttgctggc cctcaaaagg caaacacaag    960
gagaaagatt tccacaagct gtttctcttt gctgagcact tagaggaaaa ctgtaagtgg   1020
ttggaagaag ctttgtttt ctacaagact tttagttatt cctcagaaat tttcctgctt    1080
attcccagag gaggtcatct cttagatgct gtcagtcaga tagggattgg cagccaagca   1140
gaggtgctca gagaggtttc caactaatgt ggccagcgga aaactgccaa gaagcaggg    1200 atccttagga caaataaact ggaagatatt ttggggataa aaataaatcc ttttgaaaat   1260
gaaagatgga gagatgctgt atatacaaat tgccctgttc tgaacaatgt tgtcactagg   1320
actggccctg gagaccaatg atacaaacca aaatgttctc agacatgctt tgatggtctt   1380
tttctccaaa gttatctatt ctgtttccat ttcattctca caggacttgc catggggttc   1440
tcataagatt tcacattggt cataatccag gtggccctgg actgcaacct ctgagttggc   1500
aacatcagaa taggaattac gaaaaaccaa tttaaagtta aatacagaca caggcaaaag   1560
agagatgggt tgtcgaagct agtgcctagg tggacactgc ctcacatttt taattccaga   1620
agccatcagt actgagtgtc agatctcatt agtcaaacac agtgatcagg aatcctgttt   1680
tcctggagga tttccttgag ggagggacca ctcaagagtc tgaaatattt cacgtcatag   1740
agtatggatc tcaccccaac acccaatcag aaaatagga gaactggaaa ccaaaattcc    1800
ccctcccgct gtgaaggat gaaaaccaga gtgttggagt tctgtcctga taatggagca    1860
gacagctagg cagcaatcaa tgagggccag tacaggaatt cagtgctaag tattgggtca   1920
taacagaagt agggaaggta ttaatccagt gctatatgag gatcctggga cactggctcc   1980
tagtaatcta gttataacta ttagcaaaaa agaaaaaaaa aatcagtgat gtgaagagat   2040
ggcctaaagg agctccagca atatagctaa gcagctggca agtggtctga ggagcattgc   2100
aattccaggc ctcctaaggt ggcagtacgg gcactggtaa gacattctgc tgtggtgaaa   2160
ctagtttacc atagaggatt cacaattaaa ataggcaaac aggaaatgca agacagaggc   2220
taacaaaggg tttttttttt ggtgggggg agttgtttgt ttgtttgttt gttttctgag    2280
acggagtctt cctctgttgc ccaggctgga atgcagtggc acgatctcag ctcactacaa   2340
cctctgcctc ccaggttcaa gcagttcttc tgcctcagcc tcccaggttc aagcagttct   2400
tctgcctcag cctcccaagt acctgggact atagctgtgt gccaccacat tgactaattt   2460
ttgtactttt agtacagact gggtttcacc atgttggcca ggctggtgtc gaactcctga   2520
cctcaagtaa tccccccgcc ttggcctccc aaagtgctgg aattacaggc atgagccacc   2580
acacctggcc agtttttggt aattcttaaa gaactcaatg agcaacactc aaacaaccat   2640
aaagactata gagctcatgg ttgaattta gatagctaaa cagacaggag ttttgtaag    2700 ttttgtaagt cttgctcatc cttccctctt ccatcctcta tctcaactat tctgtctacc   2760
attaaagcac cttagacctt gagtttggca atgcaacaag tgtgtgctca cacgaaata    2820 ggtaattcaa tagcaaagcc ctaaaacagc ctggcttgat tatttctcag ggcatgcagt   2880
tcctttgaag caggatcatt ttaataataa taataataga aataataata gaaattgaag   2940
acaattattt cacaatttcc atacacctaa gagctataca tatgaatgat aatgcataat   3000
tgtaaagcat gcatattaca ggtaataaat atgttagcta attataaaca atgcccattt   3060
tcatatagtt tatccttgcc aaataaaact gtaaaaaaaa gacacctttc aaatgctgct   3120
```

```
aaggagtaat acctgaatga ggttgattta atggagtctt agttcctgca tgtgttctaa    3180
ttgaatagac tatgtagtaa ttcccttaca tacccatcca tgtccaagaa cagtgaagat    3240
ctttatttaa tatgaattat tgcagatgat tagcacagtc tagccaaacc attccagtaa    3300
ttgtttttac ttgttatatt aatatataaa ttctcaaagg atataacagt gatgttgggt    3360
gaatttcact gaatgatagc tcaaacacct gaaatattga ctaagaaaac taatttatca    3420
atactgataa tcaattttaa tatgttaatt gattgtaata caggattctg tggttcaaaa    3480
aaaaagaaca agcaaaaaaa ctttcttcca tttccaaata ccaattaata gatctctact    3540
tccccttgga tttcttctta ccacctacca cctccaatct tcattctttc ctcacaaact    3600
aaacataaaa gttacctaca aagcatagaa tctgtgttaa aggatattct tgcttgtttt    3660
aagtccaaaa ttaaacagct ctgaattatt aaaaagcaca tgaattcaaa tgtcctattc    3720
taataagaaa atggtttaca tttctctatg ttcaaggaaa aaaatagtca agggtgtaca    3780
agtggggtaa aaattatttc cagtaggtta tgtgatttaa gttatagaaa cgaaccaggc    3840
aattcaatta aatgtcatgg aaagtaggtt ttttcttttc ctctttttt ctaatatgta    3900 cactttgtga aagataaat ccatagtgtg ataatttgtc cactgggtcc atcagacact    3960
ggagacagct tcctaagaat tataaggctt ctaaaggctt ctaaagccta aattgcctag    4020
agcattttgt gtgccaggca ctttgctagg tgccctaggg atgcaagaag tataaatgtt    4080
ttatgagaat acaggctgga aatgtattct tgattattcc tgtggaattt ctaggcagaa    4140
aagagtctaa tggggtatag gtatattttc tcaacacaat tttctgagcc tttaccagat    4200
gcagttctat ggtttgaatg tgtccctcag agtttgtgtg ttggaaactt aatccccaat    4260
gcaataatgt tggtgaggcc taatgaaagc ctaataatgt aggtgaggcc taatgagagc    4320
tgtttagacc atgaaggctc ttccctcatg gatggattaa tgctgttatg gtgggaatgg    4380
gttcattatt actggggtgg gttcataata aaaagatgag tttggcctgc tattctctct    4440 cttctcatc ctctcttcca ccatgggatg acacagcaag aaggcccctg caagatgccc    4500 tccccctcagt attggacttc acagcctcca ggaccataag ccaataaatt tttgttcatt    4560
ataaatttcc cagtctgtgg tattctgtta tagcaacact caatttatgc attacttcca    4620
gattcttatg gctataccta cttctcacag tttgtattca cccctccttc aaccaagtac    4680
ccttaacaca gttcccatag tcacaaagcc aggtcactga agctgccctc tctccaacca    4740
cacacatata gatcaaatga ccccagacat agagctgatt gagaaggagg gaccagtacg    4800
agctctgctt ccccagcagc ttcctggaaa gaagaggcaa tacaacccaa cccaaaagtg    4860
caagagaagt aacacctcat gggatgagct taattaatca atgggagagg acactagaag    4920
acactagagg atctccccttc ctcccttct ttcccacttc acccctcca gtctctgaac    4980 catgagctat ttcaaaggtg cagtaatgct atatttggct tctctgaaga tatcctatga    5040
ggccaagtca tcagctttgt tcattatcta agagtggtgg ccagctcacc agcacttccc    5100
atcatgtttg ccctccctct ttcccttgtg ttacttccca tttttccctta cttctgcttt    5160 cttggcatta aattctactc tgcaatgtta ggatataagt ttttgcctca gattctgttt    5220
tctaggaaac ccatgctaag acaacactgg cagtggccct ggaaaagtaa acctcatgat    5280
ggatttggag ttggattgtt cactgatctg aaggacagag gactccactt aagtggtaag    5340
cagtgtagct atgaactctg ccacgcaggc ctcacaatta ctgaggcttc ttttacctgt    5400
ggttaactgg gacacagaac agcaggaaat tgagtgtaga ggttatcaag tagctgcttc    5460
```

```
acttaattgg tataatttta tggagttaac ctggtttaga gtccagagaa cattccacat   5520
agcctagaaa gggtagttat ttgtccttac cataatcaag tcatactttg aatatgagtt   5580
ttccttccct gttcagcacc acttctctta gacttaagaa tgcctgatct gttgatatta   5640
tgtcccatgt aacattgcct gagacaaaga tatccatgta ccttaaa                 5687
```

<210> SEQ ID NO 19
<211> LENGTH: 140
<212> TYPE: PRT
<213> ORGANISM: homo sapiens

<400> SEQUENCE: 19

```
Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
        35                  40                  45

Leu Leu Leu Ala Ala Leu Val Gln Asp Tyr Val Gln Met Lys Ala Ser
    50                  55                  60

Glu Leu Glu Gln Glu Gln Glu Arg Glu Gly Ser Ser Leu Asp Ser Pro
65                  70                  75                  80

Arg Ser Lys Arg Cys Gly Asn Leu Ser Thr Cys Met Leu Gly Thr Tyr
                85                  90                  95

Thr Gln Asp Phe Asn Lys Phe His Thr Phe Pro Gln Thr Ala Ile Gly
            100                 105                 110

Val Gly Ala Pro Gly Lys Lys Arg Asp Met Ser Ser Asp Leu Glu Arg
        115                 120                 125

Asp His Arg Pro His Val Ser Met Pro Gln Asn Ala
    130                 135                 140
```

<210> SEQ ID NO 20
<211> LENGTH: 128
<212> TYPE: PRT
<213> ORGANISM: homo sapiens

<400> SEQUENCE: 20

```
Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
        35                  40                  45

Leu Leu Leu Ala Ala Leu Val Gln Asp Tyr Val Gln Met Lys Ala Ser
    50                  55                  60

Glu Leu Glu Gln Glu Gln Glu Arg Glu Gly Ser Arg Ile Ile Ala Gln
65                  70                  75                  80

Lys Arg Ala Cys Asp Thr Ala Thr Cys Val Thr His Arg Leu Ala Gly
                85                  90                  95

Leu Leu Ser Arg Ser Gly Gly Val Val Lys Asn Asn Phe Val Pro Thr
            100                 105                 110

Asn Val Gly Ser Lys Ala Phe Gly Arg Arg Arg Asp Leu Gln Ala
        115                 120                 125
```

<210> SEQ ID NO 21
<211> LENGTH: 141
<212> TYPE: PRT

<213> ORGANISM: homo sapiens

<400> SEQUENCE: 21

Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
        35                  40                  45

Leu Leu Leu Ala Ala Leu Val Gln Asp Tyr Val Gln Met Lys Ala Ser
    50                  55                  60

Glu Leu Glu Gln Glu Gln Glu Arg Glu Gly Ser Ser Leu Asp Ser Pro
65                  70                  75                  80

Arg Ser Lys Arg Cys Gly Asn Leu Ser Thr Cys Met Leu Gly Thr Tyr
                85                  90                  95

Thr Gln Asp Phe Asn Lys Phe His Thr Phe Pro Gln Thr Ala Ile Gly
            100                 105                 110

Val Gly Ala Pro Gly Lys Lys Arg Asp Met Ser Ser Asp Leu Glu Arg
        115                 120                 125

Asp His Arg Pro His Val Ser Met Pro Gln Asn Ala Asn
    130                 135                 140

<210> SEQ ID NO 22
<211> LENGTH: 116
<212> TYPE: PRT
<213> ORGANISM: homo sapiens

<400> SEQUENCE: 22

Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115

<210> SEQ ID NO 23
<211> LENGTH: 212
<212> TYPE: PRT
<213> ORGANISM: homo sapiens

<400> SEQUENCE: 23

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
50                   55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 24
<211> LENGTH: 136
<212> TYPE: PRT
<213> ORGANISM: homo sapiens

<400> SEQUENCE: 24

Met Cys Glu Ser Ser Lys Glu Ala Leu Ala Glu Asn Asn Leu Asn Leu
1               5                   10                  15

Pro Lys Met Ala Glu Lys Asp Gly Cys Phe Gln Ser Gly Phe Asn Glu
                20                  25                  30

Glu Thr Cys Leu Val Lys Ile Ile Thr Gly Leu Leu Glu Phe Glu Val
            35                  40                  45

Tyr Leu Glu Tyr Leu Gln Asn Arg Phe Glu Ser Ser Glu Glu Gln Ala
        50                  55                  60

Arg Ala Val Gln Met Ser Thr Lys Val Leu Ile Gln Phe Leu Gln Lys
65                  70                  75                  80

Lys Ala Lys Asn Leu Asp Ala Ile Thr Thr Pro Asp Pro Thr Thr Asn
                85                  90                  95

Ala Ser Leu Leu Thr Lys Leu Gln Ala Gln Asn Gln Trp Leu Gln Asp
            100                 105                 110

Met Thr Thr His Leu Ile Leu Arg Ser Phe Lys Glu Phe Leu Gln Ser
        115                 120                 125

Ser Leu Arg Ala Leu Arg Gln Met
    130                 135